US011155834B2

(12) United States Patent
Hooper

(10) Patent No.: US 11,155,834 B2
(45) Date of Patent: Oct. 26, 2021

(54) SIN NOMBRE VIRUS FULL-LENGTH M SEGMENT-BASED DNA VACCINES

(71) Applicant: The Government of the United States, as represented by the Secretary of the Army, Fort Detrick, MD (US)

(72) Inventor: Jay Hooper, New Market, MD (US)

(73) Assignee: The Government of the United States, as represented by the Secretary of the Army

( * ) Notice: Subject to any disclaimer, the term of this patent is extended or adjusted under 35 U.S.C. 154(b) by 0 days.

(21) Appl. No.: 16/553,556

(22) Filed: Aug. 28, 2019

(65) Prior Publication Data

US 2020/0102576 A1 Apr. 2, 2020

Related U.S. Application Data

(60) Division of application No. 15/081,218, filed on Mar. 25, 2016, now Pat. No. 10,443,073, which is a continuation of application No. 13/982,606, filed as application No. PCT/US2011/023098 on Jan. 31, 2011, now Pat. No. 9,315,826.

(51) Int. Cl.

| | |
|---|---|
| ***A61K 39/12*** | (2006.01) |
| ***C12N 15/86*** | (2006.01) |
| ***C07K 14/005*** | (2006.01) |
| ***C07K 16/10*** | (2006.01) |
| ***C12N 7/00*** | (2006.01) |
| *A61K 39/00* | (2006.01) |
| *C12N 15/10* | (2006.01) |

(52) U.S. Cl.

CPC .............. *C12N 15/86* (2013.01); *A61K 39/12* (2013.01); *C07K 14/005* (2013.01); *C07K 16/10* (2013.01); *C12N 7/00* (2013.01); *A61K 2039/53* (2013.01); *A61K 2039/575* (2013.01); *A61K 2039/70* (2013.01); *C12N 15/102* (2013.01); *C12N 2760/12111* (2013.01); *C12N 2760/12121* (2013.01); *C12N 2760/12122* (2013.01); *C12N 2760/12134* (2013.01); *C12N 2760/12143* (2013.01); *C12N 2760/12151* (2013.01); *C12N 2760/12171* (2013.01)

(58) Field of Classification Search

CPC .. A61K 39/12; A61K 2039/53; C12N 15/102; C12N 2760/12121; C12N 2760/12122; C12N 2760/12111; C12N 2760/12134

See application file for complete search history.

(56) References Cited

U.S. PATENT DOCUMENTS

| | | | |
|---|---|---|---|
| 4,945,050 | A | 7/1990 | Sanford |
| 5,853,980 | A | 12/1998 | Rollin |
| 5,916,754 | A | 6/1999 | Nichol |
| 5,945,277 | A | 8/1999 | Nichol |
| 6,316,250 | B1 | 11/2001 | Hjelle |
| 6,451,309 | B2 | 9/2002 | Hooper |
| 6,562,376 | B2 | 5/2003 | Hooper |
| 6,620,412 | B2 | 9/2003 | Hooper |
| 7,217,812 | B2 | 5/2007 | Hooper |
| 8,183,358 | B2 | 5/2012 | Hooper |
| 2002/0114818 | A1 | 8/2002 | Schmaljohn |
| 2004/0053216 | A1 | 3/2004 | Hooper |
| 2013/0273170 | A1 | 10/2013 | Hooper |

FOREIGN PATENT DOCUMENTS

| | | |
|---|---|---|
| WO | WO 95/19799 | 7/1995 |
| WO | WO 2004/058808 | 7/2004 |
| WO | WO 2008/100508 | 8/2008 |

OTHER PUBLICATIONS

Liu, R., et al., Jan. 2020, Vaccines and therapeutics against hantaviruses, Front. Microbiol. 10:article 2989, pp. 1-19.*

Szabó, R., 2017, Antiviral therapy and prevention against hantavirus infections, Acta virological 61:3-12; pp. 1-10.*

Maes, P., et al., 2009, Recent approaches in hantavirus vaccine development, Expert Rev. Vaccines 8(1):67-76.*

Schmaljohn, C., 2009, Vaccines for hantaviruses, Vaccine 27:D61-D64.*

Safronetz, D., et al., 2012, The Syrian hamster model of hantaivrus pulmonary syndrome, Antivir. Res. 95:282-292.*

Kruger, D. H., et al., Jun. 2011, Human pathogenic hantaviruses and prevention of infection, Human Vacc. 7:685-693.*

International Search Report, dated Jan. 7, 2013, issued in parallel application PCT US2011/023098, 4 pages.

International Preliminary Report on Patentability, dated Sep. 3, 2013, issued in parallel application PCT US2011/023098, 5 pages.

Bjaradway, et al. "Intramuscular inoculation of Sin Nombre hantavirus cDNAs induces . . . ", Vaccine 17 (1999), pp. 2836-2843.

Bharadway et al., "Genetic vaccines protect against Sin Nombre hantavirus challenge in the deer mouse . . . ", J. General Virology (2002) 83, pp. 1745-1751.

Custer et al.,"Active and Passive Vaccination against Hantavirus Pulmonary Syndrome with Andes Virus M Genome . . . ", J. Virology, Sep. 2003, vol. 77, No. 18, pp. 9894-9905.

Hooper et al., "DNA Vaccination with the Hantaan Virus M Gene Protects Hamsters . . . ", J. Virology, Sep. 2001, No. 75, No. 18, pp. 8469-8477.

(Continued)

*Primary Examiner* — Jeffrey S Parkin

(74) *Attorney, Agent, or Firm* — McBee Moore & Vanik IP, LLC

(57) ABSTRACT

The invention contemplates a new synthetic, codon-optimized Sin Nombre virus (SNV) full-length M gene open reading frame (ORF) that encodes a unique consensus amino acid sequence. The SNV ORF was cloned into a plasmid to form the first stable recombinant SNV full-length M gene that elicits neutralizing antibodies. The gene can be engineered into a vaccine system, and is useful to protect mammals against infection with Sin Nombre virus.

19 Claims, 14 Drawing Sheets

Specification includes a Sequence Listing.

(56) References Cited

OTHER PUBLICATIONS

Hooper et al., “Immuno Serum Produced by DNA Vaccination Protects Hamsters . . . ”, J. Virology, Feb. 2008, vol. 82, No. 3, pp. 1332-1338.
Wahl-Jensen et al., “Temporal Analysis of Andes Virus and Sin Nombre Virus . . . ”J. Virology, 81(4), May 2 2007, pp. 7449-7462.
Barry and Johnston, “Biological features of genetic immunization,” Vaccine, vol. 15, No. 8, 1997, pp. 788-791.
Gurunathan et al., “DNA Vaccines: Immunology, Application, and Optimization,” Annu.Rev.Immunol., 2000,18:927-974.
Klinman et al., “Contribution of Cells at the Site of DNA Vaccination to the Generation . . . ”, J. Immuno., 1998, 160:2388-2392.
Steele et al, “Cutaneous DNA Vaccination Against Ebola Virus”, Veterinary Pathology 2001, 38:203-215.
Yoshida et al., “Adavantage of gene gun-mediated over intramusculare inoculation of plasmid DNA . . . ”, Vaccine 18 (2000) pp. 1725-1729.
Fuller et al., “Preclinical and clinical progress of particle-mediated DNA vaccines . . . ”, Science Direct Methods 40 (2006), pp. 86-97.
Brocato et al., “Construction and Nonclinical Testing of a Pujmala Virus Synthetic M Gene-Based . . . ”, Clin. Vaccine Immunol. 2013, 20(2), 218 et seq.
Hammerbeck et al., Chap. 23—Hantavirus, in Vaccines for Biodefense and Emerging and Neglected Diseases, 2008, Elsevier Inc., pp. 377-409.
Hooper et al., “Hantaan/Andes virus DNA vaccine elecits a broadly cross-reactive . . . ”, Virology 347 (2006), pp. 208-216.
Jonsson et al., “Treatment of hantavirus pulmonary syndrome”, Science Direct Antiviral Research 78 (2008) pp. 162-169.
Hooper et al. “A novel Sin Nombre virus DNA vaccine and its inclusion in a candidate pan-hantavirus . . . ”, Vaccine 31 (2013), pp. 4314-4321.
Hooper et al., “DNA Vaccination with Hantavirus M Segment Elecits Neurtalizing Antibodies . . . ”, Virology 255 (1999), pp. 269-278.
McElroy et al., “Andes virus M genome segment is not sufficient to confer the virulence . . . ”, Science Direct Virology 326 (2004) pp. 130-139.
Brocato et al., “DNA Vaccine-Generated Duck Polyclonal Antibodies as a Postexposure . . . ”, PLoS ONE, vol. 7, No. 4, Apr. 2012, pp. 1-11.
Ray et al., “Study of Andes virus entry and neutralization using a pseudovirion system”, J. Virological Methods 163 (2010), pp. 416-423.
Schmaljohn and Hjelle, 1997, Emerg. Infect. Dis., vol. 3, pp. 95-104.
Schmaljohn et al., 1996, In the Bunyaviridae Ed. R. M. Elliott, New York Plenum Press, pp. 63-90.
Lee et al., 1990, Arch, Virol., Suppl 1, pp. 35-47.
Song et al., 1992, Vaccine 10, pp. 214-216.
Lu et al., 1996, J. Med. Virol., 49, pp. 333-335.
Schmaljohn et al., 1990, J. Virol. 64, pp. 3162-3170.
Schmaljohn et al., 1992, Vaccine 10, pp. 10-13.
Xu et al., 1992, Am. J. Trop. Med. Hyg., vol. 47, pp. 397-404.
Yoshimatsu et al., 1993, Arch. Virol., vol. 130, pp. 365-376.
Lundkvist et al., 1996, Virology 216, pp. 397-406.
Ulrich et al., 1998, Vaccine 16, pp. 272-280.
Schmaljohn and Nichols, 2001, Current Topics in Microbiology and Immunology, Hantaviruses, vol. 256, pp. 171-191.
Chu et al., 1995, J. Virol., vol. 69, pp. 6417-6423.
Arikawa et al., 1992, J. Gen. Virol., vol. 70, pp. 615-624.
Eisenbraun, et al., 1993, DNA Cell. Biol., vol. 12, pp. 791-797.
Fynan et al., 1993, PNAS USA, vol. 90, pp. 11478-11482.
Haynes et al., 1994, AIDS Res.Hum.Retrovirvses, vol. 10, Supple 2:S43.
Pertmer et al., 1995; Vaccine vol. 13, p. 1427 et seq.
Bos, J.D., 1997, Clin.Exp.Immunol., vol. 107, suppl. 1:3.
Labuda et al., 1996, Virology, 219:357.
Rambukkana et al., 1995, Lab. Invest. 73:521.
Stingl, G., 1993, Recent Results Cancer Res., 128:45.
Evans et al., Vaccine, 2009, vol. 27(18), pp. 2505-2512.
Yager et al., Expert Rev. Vaccines, 2009, vol. 8(9), pp. 1205-1220.
Robinson and Torres, 1997, Semin. Immunol. 9, pp. 271-283.
Gregoriadis, 1998, Pharm. Res. 15, pp. 661-670.
Van Drunen et al., Expert Rev. Vaccines, 2010, vol. 9(5), pp. 503-517.
Condon et al., DNA-based immunization by in vivo transfection of dendritic cells, Nat. Med., 1996, 10:1122-1128.
Monteiro-Riviere et al., The pig as a model for . . . , In: tumbleson MD, Schook, LB (eds). Advances in Swine in Biomedical Res., vol. 2, New York. Plemum Press. 1996,425-458.
Draize et al., Methods for the study of irritation . . . , J. Pharmacol. Exp. Ther., 1944, 82:377-390.
Charles River Lab., Arkansas Div., Assessment of the Local Skin Reactivity . . . , Final Study report for Protocol No. JTA00001 (2005).
Pertmer et al., Vaccine, 1995, 219:357.
Maes et al., Viral Immunology, 2008, 21(1):49-60.
Maes et al., Expert Review Vaccines, 2009, 8(1):67-76.
Xu et al., Am. J. Trop. Med. Hyg., 47(4), 1992, pp. 397-404.
Hammerbeck, C.D., et al.,Hantavirus. In: Vaccines for Biodefense and Emerging and Neglected Diseases (A.D.T. Barrett and L.R. Stanberry, Eds.), London, pp. 379-411 (2009).
Kwilas et al., A hantavirus pulmonary syndrome (HPS) DNA vaccine delivered . . . Curr.Gene Ther. 14(3):200-10 (2014).
Hooper et al., “DNA vaccine-derived human IgG produced in transchrornosomal bovines protect in lethal models . . . ” Sci Transl. Med. 6(264):264ra162 (2014).
Haese et al., “Antiviral biologic produced in DNA vaccine/goose platform . . . ” PLoS Negl Trop Dis 9(6):e0003803 (2015).
Safronetz et al., “Pathophysiology of hantavirus pulmonary syndrome in rhesus macaques”, PNAS vol. 111, No. 19 (2014).

* cited by examiner

| | Group 1 | Group 2 | Group 3 |
|---|---|---|---|
| **Vaccine:** | HFRS mix | HPS mix | HFRS/HPS mix |
| **Plasmids:** | pWRG/HTN-M(x) | pWRG/SN-M(opt) | pWRG/HTN-M(x) |
| | pWRG/PUU-M(s2) | pWRG/AND-M | pWRG/PUU-M(s2) |
| | | | pWRG/SN-M(opt) |
| | | | pWRG/AND-M |
| **Dose** | 2 mg | 2 mg | 4 mg |

Pseudovirons made with pWRG/SN-M(opt) are neutralized by SNV immune sera

— Naive rabbit sera
— anti-VSV-G
— anti-SNV rabbit sera

Pseudovirion prep 1

Pseudovirion prep 2

Reciprocal Antibody Dilution

SIN NOMBRE VIRUS FULL-LENGTH M SEGMENT-BASED DNA VACCINES

This application is a divisional of Ser. No. 15/081,218, filed Mar. 28, 2016 (now U.S. Pat. No. 10,443,073), which is a continuation of Ser. No. 13/982,606, filed Jul. 30, 2013 (now U.S. Pat. No. 9,315,816), which is a 371 national phase application based on PCT/US11/023,098, filed Jan. 31, 2011. This application claims priority from each of these prior applications, and each is incorporated herein in its entirety by reference.

BACKGROUND OF THE INVENTION

Hantaviruses are considered Category A Priority Pathogens by the National Institute of Allergies and Infectious Disease. These viruses cause a spectrum of vascular-leak syndromes including hantavirus pulmonary syndrome (HPS) and hemorrhagic fever with renal syndrome (HFRS). Many HPS and HFRS hantaviruses pose a natural threat to persons working, living or traveling in endemic regions, including military personnel. There is one hantavirus (Andes virus) that has unique properties that make amenable to use as a biological weapon.

Andes virus (ANDV) and Sin Nombre virus (SNV) are the predominant causes of HPS in South and North America, respectively. These rodent-borne viruses were discovered in the early 1990's and have caused severe disease in several hundred persons.

Since the discovery of SNV in 1993, it has caused severe disease in ~500 persons in the United States and Canada, resulting in ~200 deaths (35% case-fatality rate). SNV is carried by the deer mouse and transmitted via inhalation or ingestion of contaminated secreta/excreta, or by rodent bite. Most of the fatalities occurred in previously healthy working-age males. HPS is a disease with rapid onset, and rapid progression from mild to severe disease (i.e., can occur over the weekend). The disease begins as an influenza-like illness including fever, headache, nausea, cough, and can progress rapidly to respiratory failure and cardiogenic shock. There is no specific therapeutic or vaccine to treat or prevent HPS. Hammerbeck, C. D., Wahl-Jensen, V., Hooper, J. W. Hantavirus. In: Vaccines for Biodefense and Emerging and Neglected Diseases (A. D. T. Barrett and L. R. Stanberry, Eds.), pp. 379-411. London: Academic Press, 2009; Jonsson C. B, J. Hooper, and G. Mertz (2008). Treatment of hantavirus pulmonary syndrome. Antiviral Res. Antiviral Res. 78:162-169.

There is no population with pre-existing immunity to SNV or ANDV and this virus is lethal in 35-40% of the people it infects. Note that this 35-40% case-fatality rate occurs despite treatment in modern intensive care units. All ages and both sexes are susceptible to ANDV and SNV. Most cases occur in previously healthy working-age males. The incubation period is approximately two weeks. Disease onset-to-death is rapid (over the weekend). In an animal model of HPS (Syrian hamsters), ANDV is highly lethal by all routes tested including the oral route. SNV is highly infectious (infectious dose 50% is 2 plaque forming units in Syrian hamsters but does cause lethal disease (Hooper et al., 2001). Thus, an infection model, rather than a lethal disease model, is used to evaluate medical countermeasures to prevent SNV infection.

New-World hantaviruses have been associated with outbreaks of a highly lethal disease, hantavirus pulmonary syndrome (HPS), in the Americas (reviewed in Schmaljohn and Hjelle, 1997, Emerg. Infect Dis. 3, 95-104). The disease is characterized by fever and vascular leakage resulting in non-cardiogenic pulmonary edema followed by shock. Case-fatality for HPS caused by the most prevalent North American and South American hantaviruses, Sin Nombre virus (SNV) and Andes virus (ANDV), respectively is 30-50%.

Currently, there are four known hantaviruses associated with hemorrhagic fever with renal syndrome (HFRS): Hantaan virus (HTNV), Dobrava-Belgrade virus (DOBV), Puumala virus (PUUV), and Seoul virus (SEOV). Because distinct hantaviruses are usually carried by only one principal rodent host species, their distribution is generally limited to the range of that host (reviewed in Schmaljohn and Hjelle, 1997, Emerg. Infect. Dis. 3, 95-104). HTNV, carried by *Apodemus agrarius*, is found in Asia; DOBV, carried by *Apodemus flavicollis*, and PUUV, carried by *Clethrionomys glareolus*, are found in Europe. SEOV is more widely disseminated than any other recognized hantaviruses because its host, the common urban rat (*Rattus norvegicus*), is found throughout the world.

There is an alarming paucity of existing medical countermeasures to prevent or treat HPS. There is no vaccine against SNV, ANDY or any other HPS-associated hantavirus. Moreover, aside from basic research, there are no funded HPS vaccine development efforts. There is no specific drug to prevent or treat HPS. The treatment for HPS is extracorporeal membrane oxygenation therapy (ECMO) with costs as much as $500,000 per patient. Expertise at performing adult ECMO resides at only a few hospitals in the world. Thus, we are poorly prepared to deal with naturally occurring HPS cases (there have been ~2500 cases including ~500 in the US since 1993), or the use of hantaviruses as biological weapons.

Viruses in the Hantavirus genus (family Bunyaviridae) are enveloped and contain a genome comprised of three single-stranded RNA segments designated large (L), medium (M), and small (S) based on size (reviewed in Schmaljohn, 1996, In *The Bunyaviridae* Ed. R. M. Elliott. New York, Plenum Press p. 63-90). The hantavirus L segment encodes the RNA dependent RNA polymerase, M encodes two envelope glycoproteins (G1 and G2, also known as $G_n$ and $G_c$), and S encodes the nucleocapsid protein (N).

A number of inactivated HFRS vaccines derived from cell culture or rodent brain were developed and tested in Asia (Lee et al., 1990, *Arch. Virol., Suppl.* 1, 35-47; Song et al., 1992, *Vaccine* 10, 214-216; Lu et al., 1996, *J. Med. Virol.* 49, 333-335). Drawbacks of these traditional killed-virus vaccines include a requirement for appropriate containment for the growth and manipulation of virus, and the necessity to ensure complete inactivation of infectivity without destroying epitopes on the virion important for protective immunity. In order to overcome these drawbacks, vaccine approaches involving recombinant DNA technology were developed including: vaccinia-vectored vaccines (Schmaljohn et al. 1990, *J. Virol.* 64, 3162-3170; Schmaljohn et al. 1992, *Vaccine* 10, 10-13; Xu et al. 1992, *Am. J. Trop. Med. Hyg.* 47, 397-404), protein subunit vaccines expressed in bacteria or insect cells (Schmaljohn et al. 1990, supra; Yoshimatsu et al., 1993, *Arch. Virol.* 130, 365-376; Lundkvist et al., 1996, *Virology* 216, 397-406), and a hepatitis core antigen-based recombinant vaccine (Ulrich et al., 1998, *Vaccine* 16, 272-280). For a review of hantavirus vaccine efforts see the review by Hooper and Li (Hooper and Li, 2001). ; Hammerbeck, C. D., Wahl-Jensen, V., Hooper, J. W. Hantavirus. In: Vaccines for Biodefense and Emerging and Neglected Diseases (A. D. T. Barrett and L. R. Stanberry, Eds.), pp. 379-411).

Vaccination with vaccinia recombinants expressing the M segment of either HTNV or SEOV elicited neutralizing antibodies and protected rodents against infection with both HTNV and SEOV, suggesting that an immune response to Gn-Gc alone can confer protection (Schmaljohn et al. 1990, supra; Xu et al. 1992, supra; Chu et al. 1995, *J. Virol.* 69, 6417-6423). Similarly, vaccination with Gn-Gc protein expressed in insect cells (baculovirus recombinant virus system) elicited neutralizing antibodies and protected hamsters from infection with HTNV (Schmaljohn et al. 1990, supra). In both the vaccinia and baculovirus systems, vaccination with Gn-Gc provided more complete protection than Gn or Gc alone (Schmaljohn et al. 1990, supra). There are reports that candidate DNA vaccines comprised of around 500 nucleotide stretches of the Sin Nombre virus (SNV) M gene, or the full-length S gene, are immunogenic in mice (Bharadwaj, et al., 1999, Vaccine 17, 2836,43) and conferred some protection against infection with SNV in a deer mouse infection model (Bharadwaj, et al., 2002, J. Gen. Virol. 83, 1745-1751). The protection was surmised to be cell-mediated because there was no convincing evidence that these constructs elicited a neutralizing, or otherwise protective, antibody response.

There have been several publications reporting the successful use of plasmid DNA vaccines containing the full-length M gene of SEOV, HTNV, ANDV, including the following reports:

1. Hooper, J. W., K. I. Kamrud, F. Elgh, D. Custer, and C. S. Schmaljohn (1999). DNA vaccination with hantavirus M segment elicits neutralizing antibodies and protects against Seoul virus infection. Virology, 255:269-278.
2. Hooper, J. W., D. Custer, E. Thompson, and C. S. Schmaljohn (2001). DNA Vaccination with the Hantaan virus M gene protects hamsters against three of four HFRS hantaviruses and elicits a high-titer neutralizing antibody response in rhesus monkeys. Journal of Virology 75:8469-8477.
3. Custer, D. M., E. Thompson, C. S. Schmaljohn, T. G. Ksiazek, and J. W. Hooper (2003). Active and passive vaccination against hantavirus pulmonary syndrome using Andes virus M genome segment-based DNA vaccine. Journal of Virology 79:9894:9905.
4. Hooper, J. W., D. M. Custer, J. Smith, and Victoria Wahl-Jensen. Hantaan/Andes virus DNA vaccine elicits a broadly cross-reactive neutralizing antibody response in nonhuman primates (2006). Virology 347:208-216.

In all cases high titer neutralizing antibodies were detected in animals (including nonhuman primates) vaccinated with the full-length M gene DNA vaccines, and protection from infection was achieved in rodent models. Neutralizing antibody responses to Gn-Gc in the aforementioned vaccine studies correlated with protection, suggesting that neutralizing antibodies not only play an important role in preventing hantavirus infection, but also might be sufficient to confer protection. Passive transfer of neutralizing monoclonal antibodies (MAbs) specific to either Gn or Gc protected hamsters against HTNV infection (Schmaljohn et al., 1990, supra; Arikawa et al., 1992, *J. Gen. Virol.* 70, 615-624), supporting the idea that neutralizing antibodies alone can confer protection. This is further supported by the finding that serum from nonhuman primates vaccinated using a gene gun with DNA vaccines containing the HTNV or ANDY full-length M genes protected hamsters from infection with HTNV or lethal disease caused by ANDY Custer, D. M., E. Thompson, C. S. Schmaljohn, T. G. Ksiazek, and J. W. Hooper (2003). Active and passive vaccination against hantavirus pulmonary syndrome using Andes virus M genome segment-based DNA vaccine. Journal of Virology 79:9894:9905). Similarly, sera from rabbits vaccinated with the ANDY M gene-based DNA vaccine using electroporation protected hamsters from a lethal challenge with ANDY (Hooper J. W., A. M. Ferro, and V. Wahl-Jensen Immune Serum Produced by DNA Vaccination Protects Hamsters Against Lethal Respiratory Challenge with Andes Virus (2008). Journal of Virology 82:1332-1338.)

Hitherto, attempts to produce vaccines that produce neutralizing antibodies against SNV have been unsuccessful. For instance, Hjelle et al. (U.S. Pat. No. 6,316,250) attempted to vaccinate with the entire SNV Gn or fragments of G1 to generated antibodies. However, their vaccine did not produce high titer neutralizing antibodies. There are currently no serious efforts to develop an HPS vaccine anywhere in the world, including SNV vaccine. (refs 17, 18 below) NIH is currently funding a handful of academic laboratories working on hantavirus basic research.

The inventors have produced DNA vaccines against other hantaviruses including Seoul virus (SEOV), Hantaan virus, (HTNV) Puumala virus (PUUV) and Andes virus (ANDY) (refs 1, 5 and 6 below). There are a number of issued and pending patents related to these vaccines (refs 23-26 below). SEOV, HTNV, and PUUV cause hemorrhagic fever with renal syndrome (HFRS). All of these DNA vaccines are based on the full-length M gene open reading frame that encodes the Gn and Gc proteins, and all of these vaccines elicit neutralizing antibodies in animal models. Neutralizing antibodies produced by DNA vaccination have been shown to protect against infection and disease in passive transfer studies (refs 3,4 below). In addition, the Hantaan and Puumala DNA vaccines have been tested in a phase 1 clinical trial (ongoing). The immunogenicity data generated in this phase 1 trial demonstrates that DNA vaccines against hantaviruses were capable of eliciting neutralizing antibodies in humans. This was the first time hantavirus neutralizing antibodies have been produced in humans using plasmid DNA. The overall seroconversion rate in this phase 1 trial was 43% (12 of 28). One of the most notable findings was that very high titers of neutralizing antibodies were achievable. Two of the peak anti-Hantaan virus titers were >1,000 and four of the peak anti-Puumala virus titers were >1,000. Neutralizing antibody titers as high as 10,240 were achieved for both Hantaan virus and Puumala virus.

The antibody response elicited by the hantavirus M gene-based DNA vaccines have been shown to cross-neutralize some, but not other hantaviruses. For example, the HTNV DNA vaccine was shown to elicit neutralizing antibodies against Seoul virus and Dobrava virus (a major cause of HFRS in the Balkans) (ref 1 below). In some cases the cross-neutralizing antibody response is produced in certain species using certain delivery technologies, but not others. This was the case with our ANDY DNA vaccine. When nonhuman primates were vaccinated with the ANDY DNA vaccine using a gene gun the sera contained antibodies that not only neutralized ANDY but also neutralized SNV and Black Creek Canal virus (ref. 3 below). Based on those results we concluded that the development of a SNV-specific DNA vaccine was unnecessary. However, recently we found that when rabbits were vaccinated with the ANDY DNA vaccine using muscle electroporation the sera was unable to neutralize SNV despite exhibiting very high titer ANDY-neutralizing activity (ref 4 below). It is speculated that this could be due to antibody specificity differences, antibody avidity differences, or antibody isotype differences.

This finding prompted us to reinitiate the development of a SNV M gene-based DNA vaccine rather than depend on the ANDY DNA vaccine to cross-protect against SNV.

The inventor is named as an inventor on other U.S. patents and publications, related to vaccines for hantaviruses and poxviruses, namely U.S. Pat. Nos. 6,451,309; 6,620,412;

6,562,376, 7,217,812, and U.S. Patent application publication US-2010-03203024 A1. The entire contents of these patents are incorporated herein by reference.

SUMMARY OF THE INVENTION

Key to the invention is a novel synthetic, codon-optimized Sin Nombre virus full-length M gene open reading frame (ORF). To date, there are no reports of a full-length M gene, or SNV M gene ORF, being successfully engineered into a DNA vaccine plasmid or other mammalian expression vector. This SNV M gene DNA sequence has been altered (or optimized) in such a way as to increase the stability of the mRNA and to, theoretically, eliminate sequences that destabilize the plasmid in E. col. In addition, four amino acids that were unique to our full-length clone were changed to consensus amino acids based on alignments with five hantavirus M gene sequences from GeneBank. The ORF nucleic acid sequence was changed without altering the coded amino acid sequence of the Sin Nombre M gene product, other than the four aforementioned amino acids. This was accomplished by codon optimizing the ORF. The process of codon optimization not only changed the nucleic sequence, but also it was intended to allow more efficient codon usage and increased stability of the mRNA produced by the plasmid. An algorithm called GeneOptimizer (patent pending), owned by GeneArt was used to allow more efficient codon usage and stabilization of the mRNA. It is noted that, while the ORF was codon optimized, the flanking sequence was unchanged.

This synthetic M gene has been engineered into a plasmid-based vaccine system, (i.e., pWRG/SN-M(opt)), and is believed could be subcloned into a virus-vectored vaccine. The preferred DNA plasmid containing this sequence is designated pWRG/SN-M(opt), and its DNA sequence is described in detail below. pWRG/SN-M(opt) is capable of eliciting good neutralizing antibody responses against Sin Nombre virus. In fact, pWRG/SN-M(opt), as a DNA vaccine delivered by gene gun, is the first vaccine of any kind that has elicited convincing levels of neutralizing antibodies against Sin Nombre virus in animals.

The development of this novel SNV full-length M segment and its use as a vaccine can be summarized as follows. As mentioned above, it had been hoped that an Andes virus M gene-based DNA vaccine would cross-neutralize with the other HPS virus, Sin Nombre virus. In fact, early results gave indication that this would be the case. When nonhuman primates were vaccinated with the ANDY DNA vaccine using a gene gun the sera contained antibodies that not only neutralized ANDY but also neutralized SNV and Black Creek Canal virus (6). Based on those results the inventor concluded that the development of a SNV-specific DNA vaccine was unnecessary. However, recently the inventor found that when rabbits were vaccinated with the ANDY DNA vaccine using muscle electroporation the sera was unable to neutralize SNV despite exhibiting very high titer ANDY-neutralizing activity (11). The data is published in Hooper J. W., A. M. Ferro, and V. Wahl-Jensen Immune Serum Produced by DNA Vaccination Protects Hamsters Against Lethal Respiratory Challenge with Andes Virus (2008). Journal of Virology 82:1332-1338. The inventor realized that the ANDY DNA vaccine would not be suitable as a vaccine to cross-protect against SNV, so sought a vaccine specifically for SNV.

The inventor cloned the full-length M gene from SNV, strain CC107 into a DNA vaccine vector, producing a plasmid with an intact open reading frame—pWRG/SN-M (2a). pWRG/SNV-M(2a) was tested for immunogenicity in rabbits, and it was discovered that high-titer neutralizing antibodies were produced after 4 vaccinations. This represented the first time high-titer SNV neutralizing antibodies were ever produced by any vaccine.

However, it required more vaccinations than the inventor would have preferred, so pWRG/SNV-M(2a) was re-designed for optimization. It was found that the M gene sequence in pWRG/SNV-M(2a) produced amino acids that were unique to our clone (i.e., not in published GeneBank SNV M sequences). This is shown in the Table 1 below, by identifying possible cloning errors in pWRG/SN-M(2a) M gene ORF and determining consensus amino acid sequence. In Table 1, SN-M(2a) is the amino acid sequence of the SNV M open reading frame (ORF) cloned into pWRG/SN-M(2a). This sequence as aligned with several SNV M gene ORFs from Genebank: AAA68036 (SNV strain CC107), AAA68036 (SNV strain CC107 isolate 74), NP_941974 (SNV strain NMH10), 083887 (New York virus), AAC54561 (NY-2 virus), and AC54559 (Rhode Island 1 virus). The four amino acids so identified were changed to the consensus amino acids in the synthetic gene cloned into pWRG/SN-N(opt), see below.

These consensus amino acids were identified at these positions and then an optimized version of this gene was synthesized. Next, we cloned the synthetic M gene (SN-M (2a)) into a DNA vaccine vector and named the plasmid pWRG/SN-M(opt). This plasmid pWRG/SN-M(opt) was deposited on Jan. 26, 2011 in the American Type Culture Collection, located at 10801 University Blvd. Manassas, Va. 20110. The deposit was made under the terms of the Budapest Treaty.

Table 2 shows the nucleic acid differences between the original cloned M gene (SN-M[2a]) and the optimized M gene (SN-M[opt]).

TABLE 1

The amino acid sequence encoded by the ORF cloned into pWRG/SN-M(2a) (SEQ ID NO: 15) was aligned with six SNV M sequences (SEQ ID NOS: 16-21, respectively, in order of appearance) from genebank (accession numbers are shown). There were four positions (the first "Q" in line 1; the first "A" in the line beginning with nucleic acid 241; the first "G" in the line beginning with nucleic acid 421; and the third "P" in the line beginning with nucleic acid 481) that were unique to the cloned ORF (highlighted in bold type and underlined). These amino acids were changed to the consensus amino acids when the new gene was synthesized to produce pWRG/SN-M(opt).

```
SN-M(2a)   1  MVGWVCIFLVVLTTATAGLTRNLYELQIECPHTVGLGQGYVTGSVETTPILLTQVADLKI

AAA6800    1  ..........................K.................................
AAA68036   1  ..........................K.................................
NP_941974  1  ..........................K...................I.............
Q83887     1  .......S.....A.T..........K............................T....
```

TABLE 1-continued

The amino acid sequence encoded by the ORF cloned into pWRG/SN-M(2a) (SEQ ID NO: 15) was aligned with six SNV M sequences (SEQ ID NOS: 16-21, respectively, in order of appearance) from genebank (accession numbers are shown). There were four positions (the first "Q" in line 1; the first "A" in the line beginning with nucleic acid 241; the first "G" in the line beginning with nucleic acid 421; and the third "P" in the line beginning with nucleic acid 481) that were unique to the cloned ORF (highlighted in bold type and underlined). These amino acids were changed to the consensus amino acids when the new gene was synthesized to produce pWRG/SN-M(opt).

| | | |
|---|---|---|
| AAC54561 | 1 | ...F........A.T...........K..................G.........T.... |
| AAC54559 | 1 | ............A.T...........K............................T.... |
| consensus | 1 | ***.***.****.*.***********.******************..********.**** |
| SN-M(2a) | 61 | ESSCNFDLHVPATTTQKYNQVDWTKKSSTTESTNAGATTFEAKTKEVNLKGTCNIPPTTF |
| AAA6800 | 61 | ............................................................ |
| AAA68036 | 61 | ............................................................ |
| NP_941974 | 61 | ..............................................I............. |
| Q83887 | 61 | ...........S.SI......E.A.........S.............S........V... |
| AAC54561 | 61 | ...........S.SI......E.A.........S.............S........V... |
| AAC54559 | 61 | ...........S.SI......E.A.........S.............S........V... |
| consensus | 61 | ***********.*..******.*.*********.************..********.*** |
| SN-M(2a) | 121 | EAAYKSRKTVICYDLACNQTHCLPTVHLIAPVQTCMSVRSCMIGLLSSRIQVIYEKTYCV |
| AAA6800 | 121 | ............................................................ |
| AAA68036 | 121 | ...F........................................................ |
| NP_941974 | 121 | ............................................................ |
| Q83887 | 121 | ............................................................ |
| AAC54561 | 121 | ............................................................ |
| AAC54559 | 121 | ....................Y....................................... |
| consensus | 121 | ***.****************.*************************************** |
| SN-M(2a) | 181 | TGQLIEGLCFIPTHTIALTQPGHTYDTMTLPVTCFLVAKKLGTQLKLAVELEKLITGVSC |
| AAA6800 | 181 | ............................................................ |
| AAA68036 | 181 | ............................................................ |
| NP_941974 | 181 | ............................................................ |
| Q83887 | 181 | ....V..........................I..............I.........ASG. |
| AAC54561 | 181 | ....V..........................I..............I.........ASG. |
| AAC54559 | 181 | ....V..........................I..............I.........ASG. |
| consensus | 181 | ****.**************************.**************.*********...* |
| SN-M(2a) | 241 | **A**ENSFQGYYICFIGKHSEPLFVPTMEDYRSAELFTRMVLNPRGEDHDPDQNGQGLMRIAG |
| AAA6800 | 241 | T........................................................... |
| AAA68036 | 241 | T........................................................... |
| NP_941974 | 241 | T........................................................... |
| Q83887 | 241 | T...........L..........M.D.................................. |
| AAC54561 | 241 | T...........L..........M.D.................................. |
| AAC54559 | 241 | T...........L.......S..M.D.................................. |
| consensus | 241 | .***********.*******.**.*.********************************** |
| SN-M(2a) | 301 | PVTAKVPSTETTETMQGIAFAGAPMYSSFSTLVRKADPEYVFSPGIIAESNHSVCDKKTV |
| AAA6800 | 301 | ............................................................ |
| AAA68036 | 301 | ............................................................ |
| NP_941974 | 301 | ............................................................ |
| Q83887 | 301 | .I....................................D....................I |
| AAC54561 | 301 | .I...........A........................D....................I |
| AAC54559 | 301 | .I......................T.............D...................AI |
| consensus | 301 | *.***********.**********.*************.*******************.. |
| SN-M(2a) | 361 | PLTWTGFLAVSGEIERITGCTVFCTLAGPGASCEAYSETGIFNISSPTCLVNKVQKFRGS |
| AAA6800 | 361 | ............................................................ |
| AAA68036 | 361 | ............................................................ |
| NP_941974 | 361 | ...............K............................................ |
| Q83887 | 361 | ...............K..........V................................. |
| AAC54561 | 361 | ...............K..........V................................. |
| AAC54559 | 361 | ...............K..........V......K.......................... |
| consensus | 361 | ***************.**********.******.************************** |
| SN-M(2a) | 421 | EQRINFMCQRVDQ**G**VVVYCNGQKKVILTKTLVIGQCIYTFTSLFSLIPGVAHSLAVELCV |
| AAA6800 | 421 | .............D.............................................. |
| AAA68036 | 421 | .............D.............................................. |
| NP_941974 | 421 | .............D.............................................. |
| Q83887 | 421 | .............D.I............................................ |
| AAC54561 | 421 | .............D.I............................................ |

TABLE 1-continued

The amino acid sequence encoded by the ORF cloned into pWRG/SN-M(2a) (SEQ ID NO: 15) was aligned with six SNV M sequences (SEQ ID NOS: 16-21, respectively, in order of appearance) from genebank (accession numbers are shown). There were four positions (the first "Q" in line 1; the first "A" in the line beginning with nucleic acid 241; the first "G" in the line beginning with nucleic acid 421; and the third "P" in the line beginning with nucleic acid 481) that were unique to the cloned ORF (highlighted in bold type and underlined). These amino acids were changed to the consensus amino acids when the new gene was synthesized to produce pWRG/SN-M(opt).

| | | |
|---|---|---|
| AAC54559 | 421 | .............D.I...............I............................ |
| consensus | 421 | *************.*.***************.**************************** |
| | | |
| SN-M(2a) | 481 | PGLHGWATTALLITFCFGWLLIPTVTLIILKILRLLTF**P**CSHYSTESKFKVILERVKVEY |
| AAA6800 | 481 | .......................................S.................... |
| AAA68036 | 481 | .......................................S.................... |
| NP_941974 | 481 | .........................A.............S.................... |
| Q83887 | 481 | ..........................I.M..........S...........A........ |
| AAC54561 | 481 | ..........................I.M..........S...........A........ |
| AAC54559 | 481 | ........A.................I.M..........S...........A........ |
| consensus | 481 | ********.****************..*.**********.***********.******** |
| | | |
| SN-M(2a) | 541 | QKTMGSMVCDICHHECETAKELETHKKSCPEGQCPYCMTITESTESALQAHFSICKLTNR |
| AAA6800 | 541 | ............................................................ |
| AAA68036 | 541 | ............................................................ |
| NP_941974 | 541 | ....................................................A....... |
| Q83887 | 541 | ..........V............................M.................... |
| AAC54561 | 541 | ..........V............................M.................... |
| AAC54559 | 541 | ..........A............................M........L........... |
| consensus | 541 | **********.****************************.********.***.******* |
| | | |
| SN-M(2a) | 601 | FQENLKKSLKRPEVRKGCYRTLGVFRYKSRCYVGLVWGILLTTELIIWAASADTPLMESG |
| AAA6800 | 601 | ...I........................................................ |
| AAA68036 | 601 | ...I........................................................ |
| NP_941974 | 601 | ............................................................ |
| Q83887 | 601 | ..............KQ......................V.......V............. |
| AAC54561 | 601 | ..............KQ......................V.......V............. |
| AAC54559 | 601 | ..............KQ.R....................V.......V............. |
| consensus | 601 | ***.**********..*.********************.*******.************* |
| | | |
| SN-M(2a) | 661 | WSDTAHGVGIVPMKTDLELDFALASSSSYSYRRKLVNPANQEETLPFHFQLDKQVVHAEI |
| AAA6800 | 661 | ............................................................ |
| AAA68036 | 661 | ............................................................ |
| NP_941974 | 661 | ..........I................................................. |
| Q83887 | 661 | ........................................K................... |
| AAC54561 | 661 | ....................................D...K................... |
| AAC54559 | 661 | ........................................K................... |
| consensus | 661 | **********.*************************.***.******************* |
| | | |
| SN-M(2a) | 721 | QNLGHWMDGTFNIKTAFHCYGECKKYAYPWQTAKCFFEKDYQYETSWGCNPPDCPGVGTG |
| AAA6800 | 721 | ............................................................ |
| AAA68036 | 721 | ............................................................ |
| NP_941974 | 721 | ............................................................ |
| Q83887 | 721 | ............................................................ |
| AAC54561 | 721 | ............................................................ |
| AAC54559 | 721 | ............................................................ |
| consensus | 721 | ************************************************************ |
| | | |
| SN-M(2a) | 781 | CTACGVYLDKLRSVGKAYKIVSLKYTRKVCIQLGTEQTCKHIDVNDCLVTPSVKVCMIGT |
| AAA6800 | 781 | ............................................................ |
| AAA68036 | 781 | ............................................................ |
| NP_941974 | 781 | ............................................................ |
| Q83887 | 781 | ........................F...............................L... |
| AAC54561 | 781 | ........................F...............................L... |
| AAC54559 | 781 | .............G..........F...............................L... |
| consensus | 781 | *************.**********.*******************************.*** |
| | | |
| SN-M(2a) | 841 | ISKLQPGDTLLFLGPLEQGGIILKQWCTTSCVFGDPGDIMSTTSGMRCPEHTGSFRKICG |
| AAA6800 | 841 | ............................................................ |
| AAA68036 | 841 | ............................................................ |
| NP_941974 | 841 | ............................................................ |
| Q83887 | 841 | ...........................................T..K............. |
| AAC54561 | 841 | ...........................................T..K............. |
| AAC54559 | 841 | ...........................................T..K............. |
| consensus | 841 | *******************************************.**.************* |

TABLE 1-continued

The amino acid sequence encoded by the ORF cloned into pWRG/SN-M(2a) (SEQ ID NO: 15) was aligned with six SNV M sequences (SEQ ID NOS: 16-21, respectively, in order of appearance) from genebank (accession numbers are shown). There were four positions (the first "Q" in line 1; the first "A" in the line beginning with nucleic acid 241; the first "G" in the line beginning with nucleic acid 421; and the third "P" in the line beginning with nucleic acid 481) that were unique to the cloned ORF (highlighted in bold type and underlined). These amino acids were changed to the consensus amino acids when the new gene was synthesized to produce pWRG/SN-M(opt).

```
SN-M(2a)    901 FATTPTCEYQGNTVSGFQRMMATRDSFQSFNVTEPHITSNRLEWIDPDSSIKDHINMVLN
AAA6800     901 ............................................................
AAA68036    901 ............................................................
NP_941974   901 ............................................................
Q83887      901 .............I..............................................
AAC54561    901 .............I..............................................
AAC54559    901 .............I..............................................
consensus   901 *************.**********************************************

SN-M(2a)    961 RDVSFQDLSDNPCKVDLHTQSIDGAWGSGVGFTLVCTVGLTECANFITSIKACDSAMCYG
AAA6800     961 ............................................................
AAA68036    961 ............................................................
NP_941974   961 ............................................................
Q83887      961 ............................................................
AAC54561    961 ............................................................
AAC54559    961 ............................................................
consensus   961 ************************************************************

SN-M(2a)   1021 ATVTNLLRGSNTVKVVGKGGHSGSLFKCCHDTDCTEEGLAASPPHLDRVIGYNQIDSDKV
AAA6800    1021 ............................................................
AAA68036   1021 ............................................................
NP_941974  1021 ............................................................
Q83887     1021 ............................................................
AAC54561   1021 ............................................................
AAC54559   1021 ......................S.....................................
consensus  1021 **********************.*************************************

SN-M(2a)   1081 YDDGAPPCTIKCWFTKSGEWLLGILNGNWVVVAVLIVILILSILLFSFFCPVRNRKNKAN
AAA6800    1081 ...............R............................................
AAA68036   1081 ............................................................
NP_941974  1081 .....................................................S......
Q83887     1081 ...................................................I.G....S.
AAC54561   1081 ...................................................I.G....S.
AAC54559   1081 ...................................................I.G....S.
consensus  1081 ***************.***********************************.*.****.*
```

TABLE 2

The sequence starts at the NotI site and ends at the BstB1 or BglII site depending on the construct (BstB1 for SN-M(2a) (SEQ ID NO: 22) and BglII for SN-M(opt) (SEQ ID NO: 2).

```
SN-M(2a)      1 GCGGCCGCGGATCTGCAGGAATTCGGCACGAGAGTAGTAGACTCCGCACGAAGAAGCAAA
SN-M(opt)     1 ............................................................

SN-M(2a)     61 CACTGAATAAAGGATATACAGAATGGTAGGGTGGGTTTGCATCTTCCTCGTGGTCCTTAC
SN-M(opt)    61 ...........................G..C.....G...........G.....G..G..

SN-M(2a)    121 TACTGCAACTGCTGGATTGACACGGAATCTCTATGAATTACAGATAGAATGTCCACATAC
SN-M(opt)   121 C..C..C..A..C..CC....C.....C..G..C..GC.GA....C..G..C..C..C..

SN-M(2a)    181 TGTGGGTCTAGGTCAAGGTTATGTGACAGGTTCTGTAGAAACTACACCTATTCTCTTAAC
SN-M(opt)   181 C.....C..G..C..G..C..C.....C..CAGC..G..G..A..C..C..C..GC.G..

SN-M(2a)    241 ACAGGTAGCTGACCTCAAGATTGAGAGTTCTTGCAATTTTGACTTGCATGTCCCAGCCAC
SN-M(opt)   241 C.....G..C.....G...........CAGC.....C..C...C....C..G..C.....

SN-M(2a)    301 TACTACTCAGAAATACAATCAAGTTGACTGGACTAAAAAAAGTTCTACTACAGAAAGCAC
SN-M(opt)   301 C..C..C...........C..G..G........C..G..G..CAGC..C..C..G.....

SN-M(2a)    361 GAATGCAGGTGCAACTACATTTGAGGCTAAAACAAAAGAGGTAAATTTAAAAGGCACATG
SN-M(opt)   361 C..C..C..A..C..C..C..C.....C..G..C.....A..G..CC.G..G.....C..

SN-M(2a)    421 TAATATTCCTCCAACTACGTTTGAGGCTGCATACAAGTCAAGGAAGACAGTGATTTGTTA
```

TABLE 2-continued

The sequence starts at the NotI site and ends at the BstB1 or BglII site depending on the construct (BstB1 for SN-M(2a) (SEQ ID NO: 22) and BglII for SN-M(opt) (SEQ ID NO: 2).

```
SN-M(opt)    421 C..C..C..C..C..C..A........C..C......AGC..A.....C.....C..C..

SN-M(2a)     481 TGATTTGGCCTGTAATCAAACACATTGTCTTCCTACAGTCCATCTGATTGCTCCTGTTCA
SN-M(opt)    481 C..CC......C..C..G..C..C..C..G..C..C..G..C.....C..C..C..G..

SN-M(2a)     541 AACATGTATGTCTGTACGGAGCTGTATGATAGGTCTGTTATCTAGCAGGATCCAGGTTAT
SN-M(opt)    541 G..C..C...AGC..G........C.....C..C...C.G..C...C..........G..

SN-M(2a)     601 CTACGAGAAGACATATTGTGTCACGGGTCAGTTAATAGAAGGGCTATGTTTCATTCCAAC
SN-M(opt)    601 .........A..C..C..C..G..C..C...C.G..C..G..C..G..C.....C..C..

SN-M(2a)     661 ACATACAATTGCACTTACACAGCCTGGTCATACTTATGATACTATGACATTGCCTGTGAC
SN-M(opt)    661 C..C.....C..C..G..C.....C..C..C..C..C..C..C.....CC....C.....

SN-M(2a)     721 TTGTTTTTTAGTAGCCAAAAAGTTGGGGACGCAGCTTAAGCTGGCTGTTGAGTTAGAGAA
SN-M(opt)    721 C..C...C.G..G.....G...C....C..C.....G........C..G...C.G..A..

SN-M(2a)     781 ATTGATTACTGGTGTGAGCTGCGCAGAGAATAGCTTCCAAGGTTATTACATCTGTTTTAT
SN-M(opt)    781 GC....C..C..C.........A.C.....C........G..C..C........C..C..

SN-M(2a)     841 TGGAAAACATTCAGAGCCCTTATTTGTACCAACAATGGAAGATTATAGATCAGCTGAGTT
SN-M(opt)    841 C..C..G..CAGC......C.G..C..G..C..C...........C...AGC..C...C.

SN-M(2a)     901 ATTTACTCGTATGGTTTTAAATCCAAGAGGTGAAGATCATGACCCTGATCAAAATGGACA
SN-M(opt)    901 G..C..C..G.....GC.G..C..C..G..C..G..C..C.....C..C..G..C..C..

SN-M(2a)     961 AGGGTTGATGAGAATAGCTGGACCTGTTACTGCCAAGGTACCATCTACAGAAACGACTGA
SN-M(opt)    961 G..CC.....C.G..C..C.....C..G..C........G..CAGC..C..G..A..C..

SN-M(2a)    1021 AACAATGCAAGGAATTGCATTTGCTGGGGCACCAATGTATAGTTCATTCTCAACTCTTGT
SN-M(opt)   1021 ...C.....G..C.....C..C..C..A..C..C.....C..CAGC...AGC..C..G..

SN-M(2a)    1081 GAGAAAAGCTGATCCTGAATATGTCTTTTCTCCAGGTATAATTGCAGAATCAAATCATAG
SN-M(opt)   1081 .C.G..G..C..C..C..G..C..G..CAGC..C..C..C.....C..GAGC..C..C..

SN-M(2a)    1141 TGTTTGTGATAAAAAGACAGTGCCCCTAACATGGACTGGGTTTCTAGCAGTTTCAGGAGA
SN-M(opt)   1141 C..G..C..C..G..A..C........G..C.....C..C..C..G..C..GAGC..C..

SN-M(2a)    1201 GATAGAAAGGATAACAGGCTGTACAGTTTTCTGTACATTGGCTGGACCTGGTGCCAGTTG
SN-M(opt)   1201 ...C..GC....C..C.....C..C..G.....C..CC....C........C.....C..

SN-M(2a)    1261 TGAAGCATACTCAGAAACAGGAATCTTCAACATAAGCTCCCCAACTTGCTTGGTAAATAA
SN-M(opt)   1261 C..G..C...AGC..G.....C...........C...AG...C..C...C....G..C..

SN-M(2a)    1321 AGTCCAAAAATTTAGAGGTTCAGAACAAAGAATTAATTTTATGTGTCAAAGGGTTGATCA
SN-M(opt)   1321 G..G..G..G..CC.G..CAGC..G..GC.G..C..C..C.....C..GC....G..C..

SN-M(2a)    1381 AGGTGTTGTGGTTTACTGTAATGGACAGAAGAAAGTCATTCTTACCAAAACCCTAGTAAT
SN-M(opt)   1381 G.AC..G.....G.....C..C..C.....A.....G..C..G.....G.....G..G..

SN-M(2a)    1441 AGGTCAATGTATCTACACATTTACTAGTCTGTTTTCACTGATCCCTGGAGTTGCTCATTC
SN-M(opt)   1441 C..C..G..C........C..C..C..C.....CAGC...........C..G......AG

SN-M(2a)    1501 CCTTGCTGTGGAGTTATGTGTTCCAGGTCTTCATGGCTGGGCTACAACAGCACTACTTAT
SN-M(opt)   1501 ...G..A..C..AC.G..C..G..T..C..G..C..A.....C..C..C..C..G..G..

SN-M(2a)    1561 TACTTTCTGCTTTGGCTGGCTTCTCATACCAACAGTTACTTTAATTATACTAAAAATCTT
SN-M(opt)   1561 C..C........C........G..G..C..C.....G..CC.G..C..C..G..G...C.

SN-M(2a)    1621 AAGGCTATTGACCTTCCCATGCTCGCACTATTCTACAGAATCAAAATTCAAAGTCATTTT
SN-M(opt)   1621 GC....GC........AGC...AGC.....CAGC..C..G..C..G........G...C.

SN-M(2a)    1681 AGAAAGAGTCAAGGTGGAGTATCAAAAGACAATGGGTTCAATGGTGTGTGACATTTGTCA
SN-M(opt)   1681 G...C.C..G...........C..G..A..C.....CAGC........C.....C..C..

SN-M(2a)    1741 CCATGAATGTGAGACGGCAAAAGAGCTCGAAACACATAAGAAAAGTTGCCCAGAAGGTCA
SN-M(opt)   1741 ...C..G..C.....A..C........G.....C..C.....G..C.....C..G..C..

SN-M(2a)    1801 ATGCCCATACTGCATGACAATAACTGAGTCCACTGAGAGTGCATTACAAGCTCATTTTTC
SN-M(opt)   1801 G.....C...........C..C..A...AG...C.....C..CC.G..G..C..C..CAG

SN-M(2a)    1861 AATCTGTAAGCTAACGAACAGGTTCCAGGAAAATCTAAAAAAATCATTAAAACGTCCAGA
SN-M(opt)   1861 C.....C.....G..C...C.............C..G..G..GAGCC.G..G..G..C..

SN-M(2a)    1921 AGTAAGGAAAGGTTGTTACAGGACATTAGGAGTATTCCGCTACAAGAGCAGGTGCTATGT
SN-M(opt)   1921 ...GC....G..C..C...C....CC.G..C..G.....G.........C..........
```

TABLE 2-continued

The sequence starts at the NotI site and ends at the BstBl or BglII site depending on the construct (BstB1 for SN-M(2a) (SEQ ID NO: 22) and BglII for SN-M(opt) (SEQ ID NO: 2).

| | | |
|---|---|---|
| SN-M(2a) | 1981 | TGGCTTAGTATGGGGGATCCTCTTGACGACAGAGCTGATTATATGGGCTGCTAGTGCAGA |
| SN-M(opt) | 1981 | G...C.G..G.....C..T..GC....C...........C..C.....C..C..C..C.. |
| SN-M(2a) | 2041 | TACCCCTCTAATGGAGTCTGGTTGGTCAGATACAGCACATGGTGTAGGTATAGTCCCTAT |
| SN-M(opt) | 2041 | C.....C..G.....AAGC..G...AGC..C..C..T.....C..G..A..C..G..C.. |
| SN-M(2a) | 2101 | GAAAACAGATTTAGAGCTTGACTTTGCCTTGGCCTCATCATCTTCTTATAGTTATAGAAG |
| SN-M(opt) | 2101 | ......CAACC.G..A..G.....C...C.....AGCAGCAGCAGC..C..C..CC.GC. |
| SN-M(2a) | 2161 | AAAGCTTGTAAACCCTGCCAATCAAGAGGAGACACTCCCTTTTCATTTCCAGTTAGATAA |
| SN-M(opt) | 2161 | G.....G..G.....C.....C..G..A........G..C..C..C.....AC.G..C.. |
| SN-M(2a) | 2221 | GCAAGTAGTGCATGCAGAAATACAGAACCTAGGGCATTGGATGGATGGCACATTCAACAT |
| SN-M(opt) | 2221 | ...G..G.....C..C..G..C........G..C..C........C.....C.....T.. |
| SN-M(2a) | 2281 | AAAGACTGCTTTCCATTGCTATGGAGAATGTAAAAAATATGCCTATCCTTGGCAGACAGC |
| SN-M(opt) | 2281 | C.....C..C.....C.....C..C..G..C..G..G..C.....C..C........C.. |
| SN-M(2a) | 2341 | CAAGTGTTTCTTTGAAAAAGATTATCAGTATGAAACAAGCTGGGGCTGTAACCCACCAGA |
| SN-M(opt) | 2341 | ......C.....C..G..G..C..C.....C..G..............C.....C..C.. |
| SN-M(2a) | 2401 | TTGCCCAGGAGTAGGGACAGGTTGTACAGCCTGTGGGGTATACTTAGACAAGCTCCGTTC |
| SN-M(opt) | 2401 | C..T..T..C..G..C..C..C.....C.....C..C..G...C.G........G..GAG |
| SN-M(2a) | 2461 | AGTTGGGAAAGCCTATAAAATTGTATCACTCAAATACACGCGAAAGGTGTGTATTCAATT |
| SN-M(opt) | 2461 | C..G..C..G.....C..G..C..G..C..G..G.....C..G..A.....C..C..GC. |
| SN-M(2a) | 2521 | GGGGACAGAACAAACCTGTAAACATATAGATGTTAATGATTGTTTGGTCACCCCGTCTGT |
| SN-M(opt) | 2521 | ...C.....G..G..A..C..G..C..C..C..G..C.....CC....G.....CAGC.. |
| SN-M(2a) | 2581 | TAAAGTTTGCATGATAGGTACCATCTCGAAGCTTCAGCCAGGTGACACCTTATTGTTTTT |
| SN-M(opt) | 2581 | G.....C..T.....T..C......AGC.....G.....C..C..T...C.GC....CC. |
| SN-M(2a) | 2641 | GGGCCCTTTAGAGCAAGGTGGGATTATTCTAAAACAATGGTGCACAACATCATGTGTGTT |
| SN-M(opt) | 2641 | ......CC.G..A..G..C..C..C.....G..G..G.....T..C..C..C..C..... |
| SN-M(2a) | 2701 | TGGAGACCCTGGTGATATCATGTCAACAACAAGTGGGATGAGATGCCCTGAGCACACAGG |
| SN-M(opt) | 2701 | C..C.....C..C..C......AGC..C..CTCC..C...C.G.....C........C.. |
| SN-M(2a) | 2761 | GTCTTTTAGAAAAATCTGTGGATTTGCTACAACACCTACATGTGAATATCAAGGTAATAC |
| SN-M(opt) | 2761 | CAGC..CC.G..G..T.....C..C..C..C..C.....C..C..G..C..G..C..C.. |
| SN-M(2a) | 2821 | AGTGTCTGGATTCCAACGCATGATGGCAACTCGAGATTCTTTTCAATCATTCAATGTGAC |
| SN-M(opt) | 2821 | C.....C..C.....G..G........C..C..G...AGC..C..GAGC.....C..... |
| SN-M(2a) | 2881 | AGAACCACATATTACCAGCAATCGACTGGAATGGATTGATCCAGATAGTAGTATTAAAGA |
| SN-M(opt) | 2881 | C..G..C..C..C........C..G...........C..C..C..C..C..C..C..G.. |
| SN-M(2a) | 2941 | CCATATCAACATGGTTTTGAATAGAGATGTTTCCTTCCAAGATCTAAGTGATAATCCATG |
| SN-M(opt) | 2941 | ...C...........GC.C...C.G..C..GAG......G..C..G..C..C..C..C.. |
| SN-M(2a) | 3001 | TAAGGTTGATTTGCATACACAATCTATTGATGGGGCTTGGGGATCAGGAGTGGGCTTTAC |
| SN-M(opt) | 3001 | C.....G..CC....C..C..GAGC..C..C..C..C.....CAGC..C........C.. |
| SN-M(2a) | 3061 | ATTAGTATGTACTGTAGGTCTTACAGAGTGTGCAAATTTCATAACTTCAATTAAGGCGTG |
| SN-M(opt) | 3061 | .C.G..G..C..A..G..C..G..C.....C..C..C.....C..C..C..C.....C.. |
| SN-M(2a) | 3121 | TGATTCTGCTATGTGTTATGGGGCCACAGTTACAAATCTACTCAGAGGGTCTAACACAGT |
| SN-M(opt) | 3121 | C..CAGC..C.....C..C..C.....C..G..C..C..G..GC.G..C..C........ |
| SN-M(2a) | 3181 | TAAAGTTGTCGGTAAAGGTGGGCATTCTGGGTCCTTGTTCAAGTGCTGCCATGATACTGA |
| SN-M(opt) | 3181 | G..G..G..G..C..G..C..C..CAGC..CAG.C....T...........C..C..C.. |
| SN-M(2a) | 3241 | CTGTACTGAAGAAGGTTTAGCAGCATCACCACCTCATTTAGATAGGGTTACTGGTTACAA |
| SN-M(opt) | 3241 | ...C..C..G.....CC.G..C..CAGC..C.....CC.G..C..A..G..C..C..... |
| SN-M(2a) | 3301 | TCAAATAGATTCTGATAAGGTTTATGATGACGGTGCACCGCCCTGTACAATTAAATGTTG |
| SN-M(opt) | 3301 | C..G..C..CAGC..C.....G..C..C..T..C..C..T.....C..C..C..G..C.. |
| SN-M(2a) | 3361 | GTTCACAAAGTCAGGTGAGTGGTTGCTAGGAATTCTTAATGGCAATTGGGTAGTAGTTGC |
| SN-M(opt) | 3361 | ......C...AGC..C......C....G..C..C..G..C.....C.....C..C..G.. |
| SN-M(2a) | 3421 | TGTTTTGATTGTAATTTTGATACTATCAATACTCCTGTTCAGCTTCTTTTGTCCTGTTAG |
| SN-M(opt) | 3421 | C..GC....C..G..CC....C..G..T..C..G..............C..C..C..GC. |

TABLE 2-continued

The sequence starts at the NotI site and ends at the BstB1 or BglII site depending on the construct (BstB1 for SN-M(2a) (SEQ ID NO: 22) and BglII for SN-M(opt) (SEQ ID NO: 2).

| | | |
|---|---|---|
| SN-M(2a) | 3481 | AAATAGAAAAAATAAGGCCAATTAGCAAACATATATGTAAGTAAGGGTATGATCATATTA |
| SN-M(opt) | 3481 | G..CC.G..G..C........T...................................... |
| SN-M(2a) | 3541 | TATCATTATGCGTATACTCTTATATCTATAATATCTATGTATCCTTATACTCTAACTATT |
| SN-M(opt) | 3541 | ............................................................ |
| SN-M(2a) | 3601 | TATATTAATTTTTACTTTTATACAAGTATTAACTAACCCATTACCAGCTAAAAAAAACAA |
| SN-M(opt) | 3601 | ............................................................ |
| SN-M(2a) | 3661 | ACCCTTAACACCTATATAATCCCATTTGCTTATTACGAGGCTTTTGTTCCTGCGGAGTCT |
| SN-M(opt) | 3661 | ............................................................ |
| SN-M(2a) | 3721 | ACTACTATTCGAA |
| SN-M(opt) | 3721 | .......AGATCT |

This new SNV vaccine was tested for a capacity to elicit neutralizing antibodies by vaccinating rabbits with the pWRG/SN-M(opt) using muscle electroporation. Very high titers of SNV neutralizing antibodies were produced after only a single vaccination.

The term "antibody" is art-recognized terminology and is intended to include molecules or active fragments of molecules that bind to known antigens. These active fragments can be derived from an antibody of the present invention by a number of techniques. For further description of general techniques for the isolation of active fragments of antibodies, see for example, Khaw, B. A. et al. *J. Nucl. Med.* 23:1011-1019 (1982). The term "antibody" also includes bispecific and chimeric antibodies and antibodies in non-mammalian species.

By neutralizing antibodies, or NAb, it is meant an antibody which defends a cell from an antigen or infectious body by inhibiting or neutralizing any effect it has biologically. For instance, a neutralizing antibody for SNV is an antibody which can inhibit or reduce the biological effects of SNV infection, that is, it binds to the virus and interferes with its ability to infect a cell.

By "high titer" it is meant meant neutralizing antibody titers similar to those produced in individuals that were infected with the virus and survived. As described in greater detail in the examples, the present inventors have found that serum from a vaccine immunized with a DNA vaccine comprising the M segment of Sin Nombre virus contains antibodies able to neutralize Sin Nombre virus.

As used herein the term "immunogenically active" designates the ability to stimulate an immune response, i.e., to stimulate the production of antibodies, particularly humoral antibodies, or to stimulate a cell-mediated response. For example, the ability to stimulate the production of circulating or secretory antibodies or the production of a cell-mediated response in local mucosal regions, (e.g., intestinal mucosa), peripheral blood, cerebral spinal fluid or the like. The effective immunizing amount of the immunogenically active component(s) of this invention may vary and may be any amount sufficient to evoke an immune response and provide immunological protection against Sin Nombre virus infection. Amounts where a dosage unit comprises at least about 5 micrograms to about 5 milligrams of plasmid DNA are contemplated. At least one dosage unit per patient is contemplated herein as a vaccination regimen. In some embodiments, two or more dosage units may be especially useful. The skilled artisan will quickly recognize that a particular quantity of vaccine composition per dosage unit, as well as the total number of dosage units per vaccination regimen, may be optimized, so long as an effective immunizing amount of the virus or a component thereof is ultimately delivered to the animal.

We next combined the SNV DNA vaccine with an Andes virus construct, pWRG/AND-M, and a mixture of the two plasmids was used to vaccinate rabbits using muscle electroporation. High titer neutralizing antibodies against both SNV and ANDY were produced after 1 or 2 vaccinations. The SNV neutralizing activity was especially potent (titers>10,000 after 1 vaccination). Thus, the combination of the pWRG/SN-M(opt) DNA vaccine and pWRG/AND-M DNA vaccine effectively elicited high-titer neutralizing antibodies against the most prevalent and lethal hantavirus in North and South America. The novelty and potency of this SNV DNA vaccine and its utility in alone or in combination with other hantavirus DNA vaccine plasmids is a main focus of this application.

The amino acid one letter code is defined as the following: A=Alanine (Ala), I=Isoleucine (He), L=Leucine (Leu), M=Methionine (Met), F=Phenylalanine (Phe), P=Proline (Pro), W=Tryptophan (Trp), V=Valine (Val), N=Asparagine (Asn), C=Cysteine (Cys), Q=Glutamine (Q), G=Glycine (Gly), S=Serine (Ser), T=Threonine (Thr), Y=Tyrosine (Tyr), R=Arginine (Arg), H=Histidine (His), K=Lysine (Lys), D=Aspartic acid (Asp), and E=Glutamic acid (Glu).

As would be understood by someone having skill in this art, this invention covers sequences that are not necessarily physically derived from the nucleotide sequence itself, but may be generated in any manner, including for example, chemical synthesis or DNA replication or reverse transcription or transcription, which are based on the information provided by the sequence bases in the region(s) from which the polynucleotide is derived. In addition, combinations of regions corresponding to that of the designated sequence may be modified in ways known in the art to be consistent with an intended use.

It is also understood in the art that certain changes to the nucleotide sequence employed in a genetic construct have little or no bearing on the proteins encoded by the construct, for example due to the degeneracy of the genetic code. Such changes result either from silent point mutations or point mutations that encode different amino acids that do not appreciably alter the behavior of the encoded protein. It is understood that portions of the coding region can be eliminated without affecting the ability of the construct to achieve the desired effect, namely induction of a protective immune response against Sin Nombre virus. It is further understood in the art that certain advantageous steps can be taken to increase the antigenicity of an encoded protein by modifying its amino acid composition. Such changes in amino acid composition can be introduced by modifying the genetic sequence encoding the protein. It is contemplated that all such modifications and variations of the M segment of Sin Nombre virus are equivalents within the scope of the present invention.

The DNA encoding the desired antigen can be introduced into the cell in any suitable form including, a linearized plasmid, a circular plasmid, a plasmid capable of replication, an episome, RNA, etc. Preferably, the gene is contained in a plasmid. In a particularly preferred embodiment, the plasmid is an expression vector, such as pWRG7077. In another embodiment, the DNA encoding the desired antigen can be introduced into virus-based vaccine vectors such as recombinant adenovirus, recombinant vesicular stomatitis virus, or alphavirus replicons. Individual expression vectors capable of expressing the genetic material can be produced using standard recombinant techniques.

This invention entails new recombinant SNV DNA sequences which are useful to elicit neutralizing antibodies against SNV. The DNA sequences include the codon-optimized full-length M segment [designated SN-M(opt)] (SEQ ID NO:1), the optimized ORF plus M gene flanking sequences (SEQ ID NO:2), and the optimized open reading frame (ORF) (SEQ ID NO:3).

Thus in one embodiment the invention entails an isolated nucleic acid sequence set forth in SEQ ID NO:1, which is as follows. The Sin Nombre virus M gene (optimized) open reading frame is underlined. The synthetic open reading frame and flanking sequence was cloned into the Not I, Bgl II site of pWRG7077 (published). The Not 1 cloning site (GCGGCCGCGG) (SEQ ID NO:7) and the Bgl II cloning site (GATCT) (SEQ ID NO:8) are in bold. An extraneous sequence having the sequence "ATCTGCAGGAATTCGGCACGAG" (SEQ ID NO:9) is in italics. The flanking sequences include 5' and 3' non-translated sequence from the SNV M genome segment, and a 24-base sequence (the extraneous sequence) between the Not I site and position +2 of the M gene (not +1 because the first nucleotide is missing). This sequence was found to be essential for expression of the Gn protein from the Hantaan virus and Seoul virus full-length M gene-based DNA vaccine plasmids, pWRG/HTN-M(x) and pWRG/SEO-M, respectably. (See U.S. Pat. No. 7,217,812) It is noted that experiments demonstrated that this 24-base sequence was not essential for expression of Gn from the Puumala M gene-based DNA vaccine plasmid or the Andes M gene-based DNA vaccine plasmid, but was retained in those constructs (See US Patent Application Publication No. 20100323024 and U.S. Pat. No. 7,217,812, respectively).

Two SNV M segment nontranslated regions are indicated by wavy underline, and are between the extraneous sequence and the beginning of the ORF, and between the end of the ORF and the Bgl II cloning site.

```
GGGGGGGGGGGGCGCTGAGGTCTGCCTCGTGAAGAAGGTGTTGCT

GACTCATACCAGGCCTGAATCGCCCCATCATCCAGCCAGAAAGTG

AGGGAGCCACGGTTGATGAGAGCTTTGTTGTAGGTGGACCAGTTG

GTGATTTTGAACTTTTGCTTTGCCACGGAACGGTCTGCGTTGTCG

GGAAGATGCGTGATCTGATCCTTCAACTCAGCAAAAGTTCGATTT
```

-continued

```
ATTCAACAAAGCCGCCGTCCCGTCAAGTCAGCGTAATGCTCTGCC

AGTGTTACAACCAATTAACCAATTCTGATTAGAAAAACTCATCGA

GCATCAAATGAAACTGCAATTTATTCATATCAGGATTATCAATAC

CATATTTTTGAAAAAGCCGTTTCTGTAATGAAGGAGAAAACTCAC

CGAGGCAGTTCCATAGGATGGCAAGATCCTGGTATCGGTCTGCGA

TTCCGACTCGTCCAACATCAATACAACCTATTAATTTCCCCTCGT

CAAAAATAAGGTTATCAAGTGAGAAATCACCATGAGTGACGACTG

AATCCGGTGAGAATGGCAAAAGCTTATGCATTTCTTTCCAGACTT

GTTCAACAGGCCAGCCATTACGCTCGTCATCAAAATCACTCGCAT

CAACCAAACCGTTATTCATTCGTGATTGCGCCTGAGCGAGACGAA

ATACGCGATCGCTGTTAAAAGGACAATTACAAACAGGAATCGAAT

GCAACCGGCGCAGGAACACTGCCAGCGCATCAACAATATTTTCAC

CTGAATCAGGATATTCTTCTAATACCTGGAATGCTGTTTTCCCGG

GGATCGCAGTGGTGAGTAACCATGCATCATCAGGAGTACGGATAA

AATGCTTGATGGTCGGAAGAGGCATAAATTCCGTCAGCCAGTTTA

GTCTGACCATCTCATCTGTAACATCATTGGCAACGCTACCTTTGC

CATGTTTCAGAAACAACTCTGGCGCATCGGGCTTCCCATACAATC

GATAGATTGTCGCACCTGATTGCCCGACATTATCGCGAGCCCATT

TATACCCATATAAATCAGCATCCATGTTGGAATTTAATCGCGGCC

TCGAGCAAGACGTTTCCCGTTGAATATGGCTCATAACACCCCTTG

TATTACTGTTTATGTAAGCAGACAGTTTTATTGTTCATGATGATA

TATTTTTATCTTGTGCAATGTAACATCAGAGATTTTGAGACACAA

CGTGGCTTTCCCCCCCCCCCCGGCATGCCTGCAGGTCGACAATAT

TGGCTATTGGCCATTGCATACGTTGTATCTATATCATAATATGTA

CATTTATATTGGCTCATGTCCAATATGACCGCCATGTTGACATTG

ATTATTGACTAGTTATTAATAGTAATCAATTACGGGGTCATTAGT

TCATAGCCCATATATGGAGTTCCGCGTTACATAACTTACGGTAAA

TGGCCCGCCTGGCTGACCGCCCAACGACCCCCGCCCATTGACGTC

AATAATGACGTATGTTCCCATAGTAACGCCAATAGGGACTTTCCA

TTGACGTCAATGGGTGGAGTATTTACGGTAAACTGCCCACTTGGC

AGTACATCAAGTGTATCATATGCCAAGTCCGCCCCCTATTGACGT

CAATGACGGTAAATGGCCCGCCTGGCATTATGCCCAGTACATGAC

CTTACGGGACTTTCCTACTTGGCAGTACATCTACGTATTAGTCAT

CGCTATTACCATGGTGATGCGGTTTTGGCAGTACACCAATGGGCG

TGGATAGCGGTTTGACTCACGGGGATTTCCAAGTCTCCACCCCAT

TGACGTCAATGGGAGTTTGTTTTGGCACCAAAATCAACGGGACTT

TCCAAAATGTCGTAATAACCCCGCCCCGTTGACGCAAATGGGCGG

TAGGCGTGTACGGTGGGAGGTCTATATAAGCAGAGCTCGTTTAGT

GAACCGTCAGATCGCCTGGAGACGCCATCCACGCTGTTTTGACCT

CCATAGAAGACACCGGGACCGATCCAGCCTCCGCGGCCGGGAACG
```

-continued

GTGCATTGGAACGCGGATTCCCCGTGCCAAGAGTGACGTAAGTAC

CGCCTATAGACTCTATAGGCACACCCCTTTGGCTCTTATGCATGC

TATACTGTTTTTGGCTTGGGGCCTATACACCCCCGCTTCCTTATG

CTATAGGTGATGGTATAGCTTAGCCTATAGGTGTGGGTTATTGAC

CATTATTGACCACTCCCCTATTGGTGACGATACTTTCCATTACTA

ATCCATAACATGGCTCTTTGCCACAACTATCTCTATTGGCTATAT

GCCAATACTCTGTCCTTCAGAGACTGACACGGACTCTGTATTTTT

ACAGGATGGGGTCCCATTTATTATTTACAAATTCACATATACAAC

AACGCCGTCCCCCGTGCCCGCAGTTTTTATTAAACATAGCGTGGG

ATCTCCACGCGAATCTCGGGTACGTGTTCCGGACATGGGCTCTTC

TCCGGTAGCGGCGGAGCTTCCACATCCGAGCCCTGGTCCCATGCC

TCCAGCGGCTCATGGTCGCTCGGCAGCTCCTTGCTCCTAACAGTG

GAGGCCAGACTTAGGCACAGCACAATGCCCACCACCACCAGTGTG

CCGCACAAGGCCGTGGCGGTAGGGTATGTGTCTGAAAATGAGCTC

GGAGATTGGGCTCGCACCGCTGACGCAGATGGAAGACTTAAGGCA

GCGGCAGAAGAAGATGCAGGCAGCTGAGTTGTTGTATTCTGATAA

GAGTCAGAGGTAACTCCCGTTGCGGTGCTGTTAACGGTGGAGGGC

AGTGTAGTCTGAGCAGTACTCGTTGCTGCCGCGCGCGCCACCAGA

CATAATAGCTGACAGACTAACAGACTGTTCCTTTCCATGGGTCTT

TTCTGCAGTCACCGTCCAAGCTT

GCGGCCGCGG*ATCTGCAGGAATTCGGCACGAG*AGTAGTAGACTCC

GCACGAAGAAGCAAACACTGAATAAAGGATATACAGAATGGTGGG

CTGGGTGTGCATCTTCCTGGTGGTGCTGACCACCGCCACAGCCGG

CCTGACCCGGAACCTGTACGAGCTGAAGATCGAGTGCCCCCACAC

CGTGGGCCTGGGCCAGGGCTACGTGACCGGCAGCGTGGAGACAAC

CCCCATCCTGCTGACCCAGGTGGCCGACCTGAAGATTGAGAGCAG

CTGCAACTTCGACCTGCACGTGCCCGCCACCACCACCCAGAAATA

CAACCAGGTGGACTGGACCAAGAAGAGCAGCACCACCGAGAGCAC

CAACGCCGGAGCCACCACCTTCGAGGCCAAGACCAAAGAAGTGAA

CCTGAAGGGCACCTGCAACATCCCCCCCACCACATTTGAGGCCGC

CTACAAGAGCAGAAAGACCGTGATCTGCTACGACCTGGCCTGCAA

CCAGACCCACTGCCTGCCCACCGTGCACCTGATCGCCCCCGTGCA

GACCTGCATGAGCGTGCGGAGCTGCATGATCGGCCTGCTGTCCAG

CCGGATCCAGGTGATCTACGAGAAAACCTACTGCGTGACCGGCCA

-continued

GCTGATCGAGGGCCTGTGCTTCATCCCCACCCACACAATCGCCCT

GACCCAGCCCGGCCACACCTACGACACCATGACCCTGCCCGTGAC

CTGCTTTCTGGTGGCCAAGAAGCTGGGCACCCAGCTGAAGCTGGC

CGTGGAGCTGGAAAAGCTGATCACCGGCGTGAGCTGCACCGAGAA

CAGCTTCCAGGGCTACTACATCTGCTTCATCGGCAAGCACAGCGA

GCCCCTGTTCGTGCCCACCATGGAAGATTACAGAAGCGCCGAGCT

GTTCACCCGGATGCCCTGAAGTACACCCGGAAAGTGTGCATCCAG

CTGGGCACAGAGCAGACATGCAAGCACATCGACGTGAACGATTGC

CTGGTGACCCCCAGCGTGAAAGTCTGTATGATTGGCACCATCAGC

AAGCTGCAGCCCGGCGATACCCTGCTGTTCCTGGGCCCCCTGGAA

CAGGGCGGCATCATTCTGAAGCAGTGGTGTACCACCTCCTGCGTG

TTCGGCGACCCCGGCGACATCATGAGCACCACCTCCGGCATGCGG

TGCCCCGAGCACACCGGCAGCTTCCGGAAGATTTGTGGCTTCGCC

ACCACCCCTACCTGCGAGTACCAGGGCAACACCGTGTCCGGCTTC

CAGCGGATGATGGCCACCCGGGATAGCTTCCAGAGCTTCAACGTG

ACCGAGCCCCACATCACCAGCAACCGGCTGGAATGGATCGACCCC

GACAGCAGCATCAAGGACCACATCAACATGGTGCTCAATCGGGAC

GTGAGCTTCCAGGACCTGAGCGACAACCCCTGCAAGGTGGACCTG

CACACCCAGAGCATCGACGGCGCCTGGGGCAGCGGCGTGGGCTTC

ACACTGGTGTGCACAGTGGGCCTGACCGAGTGCGCCAACTTCATC

ACCTCCATCAAGGCCTGCGACAGCGCCATGTGCTACGGCGCCACC

GTGACCAACCTGCTGCGGGGCTCCAACACAGTGAAGGTGGTGGGC

AAGGGCGGCCACAGCGGCAGCCTGTTTAAGTGCTGCCACGACACC

GACTGCACCGAGGAAGGCCTGGCCGCCAGCCCCCCTCACCTGGAC

AGAGTGACCGGCTACAACCAGATCGACAGCGACAAGGTGTACGAC

GATGGCGCCCCTCCCTGCACCATCAAGTGCTGGTTCACCAAGAGC

GGCGAGTGGCTGCTGGGCATCCTGAACGGCAACTGGGTCGTCGTG

GCCGTGCTGATCGTGATCCTGATCCTGTCTATCCTGCTGTTCAGC

TTCTTCTGCCCCGTGCGGAACCGGAAGAACAAGGCCAACTAGCAA

ACATATATGTAAGTAAGGGTATGATCATATTATATCATTATGCGT

-continued

ATACTCTTATATCTATAATATCTATGTATCCTTATACTCTAACTA
TTTATATTAATTTTTACTTTTATACAAGTATTAACTAACCCATTA
CCAGCTAAAAAAAACAAACCCTTAACACCTATATAATCCCATTTG
CTTATTACGAGGCTTTTGTTCCTGCGGAGTCTACTACTAAGATCT
ACGTATGATCAGCCTCGACTGTGCCTTCTAGTTGCCAGCCATCTG
TTGTTTGCCCCTCCCCCGTGCCTTCCTTGACCCTGGAAGGTGCCA
CTCCCACTGTCCTTTCCTAATAAAATGAGGAAATTGCATCGCATT
GTCTGAGTAGGTGTCATTCTATTCTGGGGGGTGGGGTGGGGCAGG
ACAGCAAGGGGGAGGATTGGGAAGACAATAGCAGGCATGCTGGGG
ATGCGGTGGGCTCTATGGCTTCTGAGGCGGAAAGAACCAGCTGGG
GCTCGACAGCTCGACTCTAGAATTGCTTCCTCGCTCACTGACTCG
CTGCGCTCGGTCGTTCGGCTGCGGCGAGCGGTATCAGCTCACTCA
AAGGCGGTAATACGGTTATCCACAGAATCAGGGGATAACGCAGGA
AAGAACATGTGAGCAAAAGGCCAGCAAAAGGCCAGGAACCGTAAA
AAGGCCGCGTTGCTGGCGTTTTTCCATAGGCTCCGCCCCCCTGAC
GAGCATCACAAAAATCGACGCTCAAGTCAGAGGTGGCGAAACCCG
ACAGGACTATAAAGATACCAGGCGTTTCCCCCTGGAAGCTCCCTC
GTGCGCTCTCCTGTTCCGACCCTGCCGCTTACCGGATACCTGTCC
GCCTTTCTCCCTTCGGGAAGCGTGGCGCTTTCTCATAGCTCACGC
TGTAGGTATCTCAGTTCGGTGTAGGTCGTTCGCTCCAAGCTGGGC
TGTGTGCACGAACCCCCCGTTCAGCCCGACCGCTGCGCCTTATCC
GGTAACTATCGTCTTGAGTCCAACCCGGTAAGACACGACTTATCG
CCACTGGCAGCAGCCACTGGTAACAGGATTAGCAGAGCGAGGTAT
GTAGGCGGTGCTACAGAGTTCTTGAAGTGGTGGCCTAACTACGGC
TACACTAGAAGAACAGTATTTGGTATCTGCGCTCTGCTGAAGCCA
GTTACCTTCGGAAAAAGAGTTGGTAGCTCTTGATCCGGCAAACAA
ACCACCGCTGGTAGCGGTGGTTTTTTTGTTTGCAAGCAGCAGATT
ACGCGCAGAAAAAAAGGATCTCAAGAAGATCCTTTGATCTTTTCT
ACGGGGTCTGACGCTCAGTGGAACGAAAACTCACGTTAAGGGATT
TTGGTCATGAGATTATCAAAAAGGATCTTCACCTAGATCCTTTTA
AATTAAAAATGAAGTTTTAAATCAATCTAAAGTATATATGAGTAA
ACTTGGTCTGACAGTTACCAATGCTTAATCAGTGAGGCACCTATC
TCAGCGATCTGTCTATTTCGTTCATCCATAGTTGCCTGACTC

This is the full-length optimized SNV M gene of pWRG/SN-M(opt). The nucleic acids outside the Not 1 and Bgl II cloning sites are not considered significant to the use of the SNV M gene.

Another valuable sequence is the isolated nucleic acid sequence of the SNV M gene (optimized) open reading frame plus the flanking sequence, as shown in SEQ ID NO:2, as follows:

GCGGCCGCGGATCTGCAGGAATTCGGCACGAGAGTAGTAGACTCCGCACG
AAGAAGCAAACACTGAATAAAGGATATACAGAATGGTGGGCTGGGTGTGC
ATCTTCCTGGTGGTGCTGACCACCGCCACAGCCGGCCTGACCCGGAACCT
GTACGAGCTGAAGATCGAGTGCCCCCACACCGTGGGCCTGGGCCAGGGCT
ACGTGACCGGCAGCGTGGAGACAACCCCCATCCTGCTGACCCAGGTGGCC
GACCTGAAGATTGAGAGCAGCTGCAACTTCGACCTGCACGTGCCCGCCAC
CACCACCCAGAAATACAACCAGGTGGACTGGACCAAGAAGAGCAGCACCA
CCGAGAGCACCAACGCCGGAGCCACCACCTTCGAGGCCAAGACCAAAGAA
GTGAACCTGAAGGGCACCTGCAACATCCCCCCCACCACATTTGAGGCCGC
CTACAAGAGCAGAAAGACCGTGATCTGCTACGACCTGGCCTGCAACCAGA
CCCACTGCCTGCCCACCGTGCACCTGATCGCCCCCGTGCAGACCTGCATG
AGCGTGCGGAGCTGCATGATCGGCCTGCTGTCCAGCCGGATCCAGGTGAT
CTACGAGAAAACCTACTGCGTGACCGGCCAGCTGATCGAGGGCCTGTGCT
TCATCCCCACCCACACAATCGCCCTGACCCAGCCCGGCCACACCTACGAC
ACCATGACCCTGCCCGTGACCTGCTTTCTGGTGGCCAAGAAGCTGGGCAC
CCAGCTGAAGCTGGCCGTGGAGCTGGAAAAGCTGATCACCGGCGTGAGCT
GCACCGAGAACAGCTTCCAGGGCTACTACATCTGCTTCATCGGCAAGCAC
AGCGAGCCCCTGTTCGTGCCCACCATGGAAGATTACAGAAGCGCCGAGCT
GTTCACCCGGATGGTGCTGAACCCCAGGGGCGAGGACCACGACCCCGACC
AGAACGGCCAGGGCCTGATGCGGATCGCCGGACCCGTGACCGCCAAGGTG
CCCAGCACCGAGACAACCGAAACCATGCAGGGCATTGCCTTCGCCGGAGC
CCCCATGTACAGCAGCTTCAGCACCCTGGTGCGGAAGGCCGACCCCGAGT
ACGTGTTCAGCCCCGGCATCATTGCCGAGAGCAACCACAGCGTGTGCGAC
AAGAAAACCGTGCCCCTGACCTGGACCGGCTTCCTGGCCGTGAGCGGCGA
GATCGAGCGGATCACCGGCTGCACCGTGTTCTGCACCCTGGCCGGACCTG
GCGCCAGCTGCGAGGCCTACAGCGAGACAGGCATCTTCAACATCAGCAGC
CCCACCTGCCTGGTGAACAAGGTGCAGAAGTTCCGGGGCAGCGAGCAGCG
GATCAACTTCATGTGCCAGCGGGTGGACCAGGACGTGGTGGTGTACTGCA
ACGGCCAGAAAAAAGTGATCCTGACCAAGACCCTGGTGATCGGCCAGTGC
ATCTACACCTTCACCAGCCTGTTCAGCCTGATCCCTGGCGTGGCTCATAG
CCTGGCAGTCGAACTGTGCGTGCCTGGCCTGCACGGATGGGCCACCACCG
CCCTGCTGATCACCTTCTGCTTCGGCTGGCTGCTGATCCCCACAGTGACC
CTGATCATCCTGAAGATCCTGCGGCTGCTGACCTTCAGCTGCAGCCACTA
CAGCACCGAGTCCAAGTTCAAAGTGATTCTGGAACGCGTGAAGGTGGAGT
ACCAGAAAACCATGGGCAGCATGGTGTGCGACATCTGCCACCACGAGTGC
GAGACAGCCAAAGAGCTGGAAACCCACAAGAAGAGCTGCCCCGAGGGCCA
GTGCCCCTACTGCATGACCATCACAGAGAGCACCGAGAGCGCCCTGCAGG
CCCACTTCAGCATCTGCAAGCTGACCAACCGGTTCCAGGAAAACCTGAAG
AAGAGCCTGAAGCGGCCCGAAGTGCGGAAGGGCTGCTACCGGACCCTGGG

-continued

CGTGTTCCGGTACAAGAGCCGGTGCTATGTGGGCCTGGTGTGGGGCATTC

TGCTGACCACAGAGCTGATCATCTGGGCCGCCAGCGCCGACACCCCCCTG

ATGGAAAGCGGGTGGAGCGACACCGCTCATGGCGTGGGAATCGTGCCCAT

GAAAACCGACCTGGAACTGGACTTCGCCCTGGCCAGCAGCAGCAGCTACA

GCTACCGGCGGAAGCTGGTGAACCCCGCCAACCAGGAAGAGACACTGCCC

TTCCACTTCCAACTGGACAAGCAGGTGGTGCACGCCGAGATCCAGAACCT

GGGCCACTGGATGGACGGCACCTTCAATATCAAGACCGCCTTCCACTGCT

ACGGCGAGTGCAAGAAGTACGCCTACCCCTGGCAGACCGCCAAGTGCTTC

TTCGAGAAGGACTACCAGTACGAGACAAGCTGGGGCTGCAACCCCCCCGA

CTGTCCTGGCGTGGGCACCGGCTGTACCGCCTGCGGCGTGTACCTGGACA

AGCTGCGGAGCGTGGGCAAGGCCTACAAGATCGTGTCCCTGAAGTACACC

CGGAAAGTGTGCATCCAGCTGGGCACAGAGCAGACATGCAAGCACATCGA

CGTGAACGATTGCCTGGTGACCCCCAGCGTGAAAGTCTGTATGATTGGCA

CCATCAGCAAGCTGCAGCCCGGCGATACCCTGCTGTTCCTGGGCCCCCTG

GAACAGGGCGGCATCATTCTGAAGCAGTGGTGTACCACCTCCTGCGTGTT

CGGCGACCCCGGCGACATCATGAGCACCACCTCCGGCATGCGGTGCCCCG

AGCACACCGGCAGCTTCCGGAAGATTTGTGGCTTCGCCACCACCCCTACC

TGCGAGTACCAGGGCAACACCGTGTCCGGCTTCCAGCGGATGATGGCCAC

CCGGGATAGCTTCCAGAGCTTCAACGTGACCGAGCCCCACATCACCAGCA

ACCGGCTGGAATGGATCGACCCCGACAGCAGCATCAAGGACCACATCAAC

ATGGTGCTCAATCGGGACGTGAGCTTCCAGGACCTGAGCGACAACCCCTG

CAAGGTGGACCTGCACACCCAGAGCATCGACGGCGCCTGGGGCAGCGGCG

TGGGCTTCACACTGGTGTGCACAGTGGGCCTGACCGAGTGCGCCAACTTC

ATCACCTCCATCAAGGCCTGCGACAGCGCCATGTGCTACGGCGCCACCGT

GACCAACCTGCTGCGGGGCTCCAACACAGTGAAGGTGGTGGGCAAGGGCG

GCCACAGCGGCAGCCTGTTTAAGTGCTGCCACGACACCGACTGCACCGAG

GAAGGCCTGGCCGCCAGCCCCCCTCACCTGGACAGAGTGACCGGCTACAA

CCAGATCGACAGCGACAAGGTGTACGACGATGGCGCCCCTCCCTGCACCA

TCAAGTGCTGGTTCACCAAGAGCGGCGAGTGGCTGCTGGGCATCCTGAAC

GGCAACTGGGTCGTCGTGGCCGTGCTGATCGTGATCCTGATCCTGTCTAT

CCTGCTGTTCAGCTTCTTCTGCCCCGTGCGGAACCGGAAGAACAAGGCCA

ACTAGCAAACATATATGTAAGTAAGGGTATGATCATATTATATCATTATG

CGTATACTCTTATATCTATAATATCTATGTATCCTTATACTCTAACTATT

TATATTAATTTTTACTTTTATACAAGTATTAACTAACCCATTACCAGCTA

AAAAAAACAAACCCTTAACACCTATATAATCCCATTTGCTTATTACGAGG

CTTTTGTTCCTGCGGAGTCTACTACTAAGATCT

The flanking sequences are the cloning sites plus the SNV M segment non-translated regions of SEQ ID NO:1, and also includes the "extraneous sequence" at the 5' end. The first flanking sequence is:

(SEQ ID:NO 5)

ATCTGCAGGAATTCGGCACGAGAGTAGTAGACTCCGCACGAAGAAGCAAA

-continued

CACTGAATAAAGGATATACAGA; the second flanking sequence is (SEQ ID NO: 6)

CAAACATATATGTAAGTAAGGGTATGATCATATTATATCATTATGCGTAT

ACTCTTATATCTATAATATCTATGTATCCTTATACTCTAACTATTTATAT

TAATTTTTACTTTTATACAAGTATTAACTAACCCATTACCAGCTAAAAAA

AACAAACCCTTAACACCTATATAATCCCATTTGCTTATTACGAGGCTTTT

GTTCCTGCGGAGTCTACTACTAA

Another valuable sequence is the isolated nucleic acid sequence of the SNV M gene (optimized) open reading frame by itself, as shown in SEQ ID NO:3. As a point of reference, the ORF begins with the ATG start codon and ends with the TAG stop codon. SEQ ID NO:3 is as follows:

ATGGTGGGCTGGGTGTGCATCTTCCTGGTGGTGCTGACCACCGCCACAGC

CGGCCTGACCCGGAACCTGTACGAGCTGAAGATCGAGTGCCCCCACACCG

TGGGCCTGGGCCAGGGCTACGTGACCGGCAGCGTGGAGACAACCCCCATC

CTGCTGACCCAGGTGGCCGACCTGAAGATTGAGAGCAGCTGCAACTTCGA

CCTGCACGTGCCCGCCACCACCACCCAGAAATACAACCAGGTGGACTGGA

CCAAGAAGAGCAGCACCACCGAGAGCACCAACGCCGGAGCCACCACCTTC

GAGGCCAAGACCAAAGAAGTGAACCTGAAGGGCACCTGCAACATCCCCCC

CACCACATTTGAGGCCGCCTACAAGAGCAGAAAGACCGTGATCTGCTACG

ACCTGGCCTGCAACCAGACCCACTGCCTGCCCACCGTGCACCTGATCGCC

CCCGTGCAGACCTGCATGAGCGTGCGGAGCTGCATGATCGGCCTGCTGTC

CAGCCGGATCCAGGTGATCTACGAGAAAACCTACTGCGTGACCGGCCAGC

TGATCGAGGGCCTGTGCTTCATCCCCACCCACACAATCGCCCTGACCCAG

CCCGGCCACACCTACGACACCATGACCCTGCCCGTGACCTGCTTTCTGGT

GGCCAAGAAGCTGGGCACCCAGCTGAAGCTGGCCGTGGAGCTGGAAAAGC

TGATCACCGGCGTGAGCTGCACCGAGAACAGCTTCCAGGGCTACTACATC

TGCTTCATCGGCAAGCACAGCGAGCCCCTGTTCGTGCCCACCATGGAAGA

TTACAGAAGCGCCGAGCTGTTCACCCGGATGGTGCTGAACCCCAGGGGCG

AGGACCACGACCCCGACCAGAACGGCCAGGGCCTGATGCGGATCGCCGGA

CCCGTGACCGCCAAGGTGCCCAGCACCGAGACAACCGAAACCATGCAGGG

CATTGCCTTCGCCGGAGCCCCCATGTACAGCAGCTTCAGCACCCTGGTGC

GGAAGGCCGACCCCGAGTACGTGTTCAGCCCCGGCATCATTGCCGAGAGC

AACCACAGCGTGTGCGACAAGAAAACCGTGCCCCTGACCTGGACCGGCTT

CCTGGCCGTGAGCGGCGAGATCGAGCGGATCACCGGCTGCACCGTGTTCT

GCACCCTGGCCGGACCTGGCGCCAGCTGCGAGGCCTACAGCGAGACAGGC

ATCTTCAACATCAGCAGCCCCACCTGCCTGGTGAACAAGGTGCAGAAGTT

CCGGGGCAGCGAGCAGCGGATCAACTTCATGTGCCAGCGGGTGGACCAGG

ACGTGGTGGTGTACTGCAACGGCCAGAAAAAAGTGATCCTGACCAAGACC

CTGGTGATCGGCCAGTGCATCTACACCTTCACCAGCCTGTTCAGCCTGAT

CCCTGGCGTGGCTCATAGCCTGGCAGTCGAACTGTGCGTGCCTGGCCTGC

-continued

```
ACGGATGGGCCACCACCGCCCTGCTGATCACCTTCTGCTTCGGCTGGCTG
CTGATCCCCACAGTGACCCTGATCATCCTGAAGATCCTGCGGCTGCTGAC
CTTCAGCTGCAGCCACTACAGCACCGAGTCCAAGTTCAAAGTGATTCTGG
AACGCGTGAAGGTGGAGTACCAGAAAACCATGGGCAGCATGGTGTGCGAC
ATCTGCCACCACGAGTGCGAGACAGCCAAAGAGCTGGAAACCCACAAGAA
GAGCTGCCCCGAGGGCCAGTGCCCCTACTGCATGACCATCACAGAGAGCA
CCGAGAGCGCCCTGCAGGCCCACTTCAGCATCTGCAAGCTGACCAACCGG
TTCCAGGAAAACCTGAAGAAGAGCCTGAAGCGGCCCGAAGTGCGGAAGGG
CTGCTACCGGACCCTGGGCGTGTTCCGGTACAAGAGCCGGTGCTATGTGG
GCCTGGTGTGGGGCATTCTGCTGACCACAGAGCTGATCATCTGGGCCGCC
AGCGCCGACACCCCCCTGATGGAAAGCGGGTGGAGCGACACCGCTCATGG
CGTGGGAATCGTGCCCATGAAAACCGACCTGGAACTGGACTTCGCCCTGG
CCAGCAGCAGCAGCTACAGCTACCGGCGGAAGCTGGTGAACCCCGCCAAC
CAGGAAGAGACACTGCCCTTCCACTTCCAACTGGACAAGCAGGTGGTGCA
CGCCGAGATCCAGAACCTGGGCCACTGGATGGACGGCACCTTCAATATCA
AGACCGCCTTCCACTGCTACGGCGAGTGCAAGAAGTACGCCTACCCCTGG
CAGACCGCCAAGTGCTTCTTCGAGAAGGACTACCAGTACGAGACAAGCTG
GGGCTGCAACCCCCCCGACTGTCCTGGCGTGGGCACCGGCTGTACCGCCT
GCGGCGTGTACCTGGACAAGCTGCGGAGCGTGGGCAAGGCCTACAAGATC
GTGTCCCTGAAGTACACCCGGAAAGTGTGCATCCAGCTGGGCACAGAGCA
GACATGCAAGCACATCGACGTGAACGATTGCCTGGTGACCCCCAGCGTGA
AAGTCTGTATGATTGGCACCATCAGCAAGCTGCAGCCCGGCGATACCCTG
CTGTTCCTGGGCCCCCTGGAACAGGGCGGCATCATTCTGAAGCAGTGGTG
TACCACCTCCTGCGTGTTCGGCGACCCCGGCGACATCATGAGCACCACCT
CCGGCATGCGGTGCCCCGAGCACACCGGCAGCTTCCGGAAGATTTGTGGC
TTCGCCACCACCCCTACCTGCGAGTACCAGGGCAACACCGTGTCCGGCTT
CCAGCGGATGATGGCCACCCGGGATAGCTTCCAGAGCTTCAACGTGACCG
AGCCCCACATCACCAGCAACCGGCTGGAATGGATCGACCCCGACAGCAGC
ATCAAGGACCACATCAACATGGTGCTCAATCGGGACGTGAGCTTCCAGGA
CCTGAGCGACAACCCCTGCAAGGTGGACCTGCACACCCAGAGCATCGACG
GCGCCTGGGGCAGCGGCGTGGGCTTCACACTGGTGTGCACAGTGGGCCTG
ACCGAGTGCGCCAACTTCATCACCTCCATCAAGGCCTGCGACAGCGCCAT
GTGCTACGGCGCCACCGTGACCAACCTGCTGCGGGGCTCCAACACAGTGA
AGGTGGTGGGCAAGGGCGGCCACAGCGGCAGCCTGTTTAAGTGCTGCCAC
GACACCGACTGCACCGAGGAAGGCCTGGCCGCCAGCCCCCCTCACCTGGA
CAGAGTGACCGGCTACAACCAGATCGACAGCGACAAGGTGTACGACGATG
GCGCCCCTCCCTGCACCATCAAGTGCTGGTTCACCAAGAGCGGCGAGTGG
CTGCTGGGCATCCTGAACGGCAACTGGGTCGTCGTGGCCGTGCTGATCGT
GATCCTGATCCTGTCTATCCTGCTGTTCAGCTTCTTCTGCCCCGTGCGGA
ACCGGAAGAACAAGGCCAACTAG
```

SEQ ID NO:2 and SEQ ID NO:3 are especially useful as a DNA cassette. The preferred cassette is the SNV optimized M gene cassette in the SNV-M (opt) (preferably taken from the Not 1 site to the BglII site, or minimally the ORF (SEQ ID NO:3) operably linked to a promoter) which can be subcloned into any other vaccine/expression system available, and used to generate active or passive immunity against SN virus. The DNA cassette specifically includes at least SEQ ID NO:2 linked to a promoter operable in a eukaryotic expression system. Alternatively, the DNA cassette includes the sequence in SEQ ID NO:3 (within pWRG/SN-M(opt)) from the ATG start codon to the TAG stop codon.

The peptide encoded by DNA sequence SEQ ID NO:3 is as follows: SN-M(opt) amino acid sequence (SEQ ID NO:4)

```
SN-M(opt) amino acid sequence
MVGWVCIFLVVLTTATAGLTRNLYELKIECPHTVGLGQGYVTGSVETTP
ILLTQVADLKIESSCNFDLHVPATTTQKYNQVDWTKKSSTTESTNAGAT
TFEAKTKEVNLKGTCNIPPTTFEAAYKSRKTVICYDLACNQTHCLPTVH
LIAPVQTCMSVRSCMIGLLSSRIQVIYEKTYCVTGQLIEGLCFIPTHTI
ALTQPGHTYDTMTLPVTCFLVAKKLGTQLKLAVELEKLITGVSCTENSF
QGYYICFIGKHSEPLFVPTMEDYRSAELFTRMVLNPRGEDHDPDQNGQG
LMRIAGPVTAKVPSTETTETMQGIAFAGAPMYSSFSTLVRKADPEYVFS
PGIIAESNHSVCDKKTVPLTWTGFLAVSGEIERITGCTVFCTLAGPGAS
CEAYSETGIFNISSPTCLVNKVQKFRGSEQRINFMCQRVDQDVVVYCNG
QKKVILTKTLVIGQCIYTFTSLFSLIPGVAHSLAVELCVPGLHGWATTA
LLITFCFGWLLIPTVTLIILKILRLLTFSCSHYSTESKFKVILERVKVE
YQKTMGSMVCDICHHECETAKELETHKKSCPEGQCPYCMTITESTESAL
QAHFSICKLTNRFQENLKKSLKRPEVRKGCYRTLGVFRYKSRCYVGLVW
GILLTTELIIWAASADTPLMESGWSDTAHGVGIVPMKTDLELDFALASS
SSYSYRRKLVNPANQEETLPFHFQLDKQVVHAEIQNLGHWMDGTFNIKT
AFHCYGECKKYAYPWQTAKCFFEKDYQYETSWGCNPPDCPGVGTGCTAC
GVYLDKLRSVGKAYKIVSLKYTRKVCIQLGTEQTCKHIDVNDCLVTPSV
KVCMIGTISKLQPGDTLLFLGPLEQGGIILKQWCTTSCVFGDPGDIMST
TSGMRCPEHTGSFRKICGFATTPTCEYQGNTVSGFQRMMATRDSFQSFN
VTEPHITSNRLEWIDPDSSIKDHINMVLNRDVSFQDLSDNPCKVDLHTQ
SIDGAWGSGVGFTLVCTVGLTECANFITSIKACDSAMCYGATVTNLLRG
SNTVKVVGKGGHSGSLFKCCHDTDCTEEGLAASPPHLDRVTGYNQIDSD
KVYDDGAPPCTIKCWFTKSGEWLLGILNGNWVVVAVLIVILILSILLFS
FFCPVRNRKNKAN
```

There are four residues that are altered in the M(opt) from the M(2a): K at position 27, T at position 241, D at position 434, and S at position 519. The enhanced immunogenicity of pWRG/SN-M(opt) vs pWRG/SN-M(2a) is speculated to be due to the nucleic acid changes, one or more of the four amino acid changes, or a combination thereof.

In another embodiment, the invention entails a recombinant DNA construct comprising:

(i) a vector, and (ii) the DNA fragment comprising the nucleic acid sequence set forth in SEQ ID NO:1, SEQ ID NO:2 or SEQ ID NO:3, or a DNA fragment comprising a nucleic acid sequence that encodes the amino acid sequence set forth in SEQ ID NO:4, operably linked to a promoter sequence.

As would be understood by someone having skill in this art, the DNA constructs of our invention will have all necessary structural components for expression of the DNA fragment of interest (e.g., promoters functional in mammals, and the like). The vector can take the form of a plasmid such as pCRR (Invitrogen) or pJW4303 (Konishi, E. et al., 1992, *Virology* 188:714), or any expression vector such as viral vectors e.g. adenovirus or Venezuelan equine encephalitis virus and others known in the art. Preferably the vector is a recombinant adenovirus or recombinant vesicular stomatitis virus, or alphavirus replicon. Preferably, a promoter sequence operable in the target cell is operably linked to the DNA sequence. Several such promoters are known for mammalian systems which may be joined 5', or upstream, of the coding sequence for the encoded protein to be expressed. A suitable and preferred promoter is the human cytomegalovirus immediate early promoter, preferably operably linked to intron A. Another preferred promoter is the beta-actin promoter or the SV40 promoter. A downstream transcriptional terminator, or polyadenylation sequence, such as the polyA addition sequence of the bovine growth hormone gene, may also be added 3' to the protein coding sequence.

Preferably, the construct is the pWRG/SN-M(opt) DNA vaccine plasmid, whose sequence is set forth above and referred to as SEQ ID NO:1.

In a further embodiment, the present invention relates to host cells stably transformed or transfected with the above-described recombinant DNA constructs. The host cell can be prokaryotic such as *Bacillus* or *E. coli*, or eukaryotic such a *Saccharomyces* or *Pichia*, or mammalian cells or insect cells. The vector containing the Sin Nombre virus M gene sequence is expressed in the bacteria and the expressed product used for diagnostic procedures or as a vaccine. Please see e.g., Maniatis et al., 1985 *Molecular Cloning: A Laboratory Manual* or *DNA Cloning*, Vol. I and II (D. N. Glover, ed., 1985) for general cloning methods. The DNA sequence can be present in the vector operably linked to a highly purified IgG molecule, an adjuvant, a carrier, or an agent for aid in purification of Sin Nombre virus proteins or peptides. The transformed or transfected host cells can be used as a source of DNA sequences described above. When the recombinant molecule takes the form of an expression system, the transformed or transfected cells can be used as a source of the protein or peptide encoded by the DNA. The DNA can be used as circular or linear, or linearized plasmid as long as the Sin Nombre virus sequences are operably linked to a promoter which can be expressed in the transfected cell.

In another embodiment, the invention entails vaccines against infection with Sin Nombre virus. In a method for eliciting in a subject an immune response against Sin Nombre virus, the method comprises administering to a subject a DNA fragment comprising a genome segment of hantavirus. In one preferred embodiment, the vaccine composition comprises an effective immunizing amount of SNV plasmid DNA, which plasmid DNA comprises one or more of the recombinant DNA constructs described above, and a pharmacologically acceptable carrier. That is, the recombinant DNA construct should minimally include (i) a vector, and (ii) the DNA fragment comprising the nucleic acid sequence set forth in SEQ ID NO:1, SEQ ID NO:2 or SEQ ID NO:3, or a DNA fragment comprising a nucleic acid sequence that encodes the amino acid sequence set forth in SEQ ID NO:4. The DNA fragment is operably linked to a promoter sequence. The pharmacologically acceptable carrier may be any carrier that is known in the art, which is safe and effective for a SNV DNA vaccine. Examples of such carriers include PBS, water, saline, Tris-EDTA, and mixtures of these.

The vaccine composition may which further comprise an adjuvant. The adjuvant may be any one that is known in the art, which is safe and effective for a SNV DNA vaccine. As used herein the term "adjuvant" refers to any component which improves the body's response to a vaccine. The adjuvant will typically comprise about 0.1 to 50% vol/vol of the vaccine formulation of the invention, more preferably about 1 to 50% of the vaccine, and even more desirably about 1 to 20% thereof. Examples of such adjuvants include CpG (cystein-phosphate-guanine) oligodeoxynucleic acid, or plasmid DNA-encoded heat labile enterotoxins, or alum.

The immunizing amount of SNV plasmid DNA is preferably between about 5 micrograms (e.g., with gene gun administration) and about 5 milligrams (e.g., electroporation or other forms of administration). By "immunizing amount", it is meant the amount of vaccine or immunogenic composition that is needed to raise high titers of neutralizing antibodies in response to the composition.

One unique aspect of our invention is that it can further comprise one or more additional vaccine components of other hantaviruses, to make a bi-valent, tri-valent, multivalent or pan-virus vaccine. In one embodiment, a DNA vaccine is contemplated that elicits an immune response against multiple HPS-associated hantaviruses and protects against more than one HPS virus. Such a DNA vaccine comprises one of the SNV sequences described above (SEQ ID NO:1, SEQ ID NO:2 or SEQ ID NO:3), in combination with an HPS hantavirus M gene DNA vaccine (such as M gene DNA vaccine from one or more of Black Creek Canal virus, Bayou virus, New York virus, Andes virus and Laguna Negra virus) such that each M gene is expressed in the subject. The respective M gene DNA sequences may each be part of respective recombinant constructs that each include (i) a vector and (ii) the desired DNA fragment that is operably linked to a promoter sequence. A preferred HPS virus is Andes virus.

In another embodiment, a DNA vaccine elicits an immune response against both HFRS and HPS hantavirus and protects against all the hantaviruses causing severe disease by providing to a subject a DNA vaccine comprising one of the SNV sequences described above (SEQ ID NO:1, SEQ ID NO:2 or SEQ ID NO:3), in combination with at least one HFRS hantavirus M gene DNA vaccine (such as Hantaan M gene DNA vaccine, Puumala M gene DNA vaccine, Seoul M gene DNA vaccine and Dobrava M gene DNA) such that each M gene is expressed in the subject. Furthermore, the M gene DNA vaccine from one or more of another HPS-associated virus (such as Black Creek Canal virus, Bayou virus, New York virus, Andes virus and Laguna Negra virus) may be included, to strengthen the HPS component. The respective M gene DNA sequences may each be part of respective recombinant constructs that each include (i) a vector and (ii) the desired DNA fragment that is operably linked to a promoter sequence.

The SNV M gene or the other HPS or HFRS M gene may be administered separately, i.e. on separate vectors, or may be combined on the same vector as is described in one aspect of this invention. For instance, a pan-HPS virus vaccine can include any of SEQ ID NO:1, SEQ ID NO:2, or SEQ ID NO:3, and a suitable Andes M gene sequence (in whole, or an ORF with flanking sequences, or simply the ORF). A preferred Andes M gene sequence is SEQ ID NO:10, which is the full-length ANDY M gene described in U.S. Pat. No. 7,217,812 (and the sequence is referred to as SEQ ID NO:8 therein).

A preferred Puumala M gene sequence is SEQ ID NO:11, which is the full-length PUUV M gene described in U.S. patent publication number 20100323024 (and the sequence is referred to as SEQ ID NO: 1 therein). A preferred Hantaan M gene sequence is SEQ ID NO:12, which is the full-length HNTV M gene described in U.S. Pat. No. 7,217,812 (and the sequence is referred to as SEQ ID NO:7 therein). A preferred Seoul M gene sequence is SEQ ID NO:13, which is the full-length Seoul M gene described in U.S. Pat. No. 7,217, 812 (and the sequence is referred to as SEQ ID NO:3 therein). The preferred HPS/HFRS vaccine combination includes Hantaan, Puumala, Andes, and Sin Nombre DNA vaccines, although Seoul DNA vaccine is also a good component for the combined vaccine. Any of these M genes can be used in full-length, or just the ORF with flanking sequences, or simply the ORF. As someone skilled in this art would understand, this invention entailing the combination of hantavirus M genes is not limited at all to these specific M genes—these are merely examples, and any M gene isolated or derived or improved or otherwise altered from the hantavirus (e.g., an altered Seoul M gene, or a non-optimized Puumala M gene).

The vaccine may involve the delivery of pWRG/SN-M (opt) DNA (SEQ ID NO:1), or the DNA of SEQ ID NO:2 or SEQ ID NO:3 (or, if a multivalent vaccine is employed, one or more of the above-described sequences of the other HPS- or HI-RS-associated viruses) by any of several platforms used to deliver gene-based vaccines. For example, the vaccine could comprise a composition comprising inert particles and a nucleic acid coated onto the inert particles producing nucleic acid coated particles. The nucleic acid will comprise a promoter operative in the cells of a mammal and further comprise (or even consist essentially of or consist of) SEQ ID NO:1, SEQ ID NO:2 or SEQ ID NO:3. As would be understood by someone having skill in this art, the ORF sequence (SEQ ID NO:3) is essential (and for the other HPS- or HFRS-associated viruses, the ORF of the respective M gene). The flanking region between the cloning sites and the ORF are preferably included, as they may be helpful for efficient expression. The inert particle may be gold particles, silver particles, platinum particles, tungsten particles, polystyrene particles, polypropylene particles, polycarbonate particles, and the like, as would be understood by someone having ordinary skill in this art. In particular, it is preferred that the inert particle is suitable for use in a gene gun.

The invention further encompasses a method for inducing a protective immune response against Sin Nombre virus infection in a mammal, comprising the step of accelerating into epidermal cells of the mammal in vivo a composition comprising inert particles and a nucleic acid coated onto the inert particles producing nucleic acid coated particles, such that said nucleic acid is expressed (e.g., gene gun administration). The nucleic acid will comprise a promoter effective and functional in the cells of a mammal and SEQ ID NO:1, SEQ ID NO:2 or SEQ ID NO:3.

Electroporation is another method of administration. Electroporation involves injecting plasmid DNA into a tissue (e.g. muscle or skin) and then applying micropulses of an electric field causing transient permeability of the cells of the vaccinee. This transient permeability allows for a more efficient take-up of the DNA vaccine plasmid.

In a more general method for inducing a protective immune response against Sin Nombre virus infection in a mammal, a composition is administered to a mammal comprising a nucleic acid comprising a promoter operative in the cells of a mammal and one of SEQ ID NO: 1, SEQ ID NO:2 or SEQ ID NO:3. It is generally preferred that the chosen sequence be inserted into a plasmid, and the plasmid administered. To that end, preferably the nucleic acid is a component of one of the above-referenced DNA constructs. However, it is known that a linear piece of DNA consisting of only a promoter and the gene-of-interest can elicit an immune response. Thus, one option for the composition is that it comprises SEQ ID NO: 1, SEQ ID NO:2 or SEQ ID NO:3 plus an appropriate promoter. One preferred method comprises the step of administering a composition comprising an effective immunizing amount of SNV plasmid DNA, which plasmid DNA comprises one of the recombinant DNA construct described above; and a pharmacologically acceptable carrier. Another preferred method comprises the step of administering a composition comprising an effective immunizing amount of EQ ID NO: 1, SEQ ID NO:2 or SEQ ID NO:3 operably linked to a promoter operative in the cells of a mammal plus an appropriate promoter; and a pharmacologically acceptable carrier. Appropriate pharmacologically acceptable carriers are discussed elsewhere in this document. Preferably, the immunizing amount of SNV plasmid DNA is between about 5 micrograms and about 5 milligrams.

In another embodiment, this invention provides a method for raising high titers of neutralizing antibodies against Sin Nombre virus in a mammal or a bird. The method comprises the step of administering a composition comprising a SNV plasmid DNA which comprises one or more of the recombinant DNA constructs described above (including SEQ ID NO:1, SEQ ID NO:2 or SEQ ID NOT:3); and a pharmacologically acceptable carrier. Preferably, the titers are at least 100, and more preferably are at least 10,000. As someone having ordinary skill in this art would recognize, in the context of hantavirus infection, titers with a level of at least 100 are significant, and considered "high" because they are 10 times higher than the minimal titer of 10 that has been used to evaluate vaccines against HFRS (a titer of 10 indicates there was a 50% reduction in plaque forming units when virus was combined with serum for a final dilution of 1:10). Titers of >10,000 are similar to those produced in person who have developed HPS and survived.

High titers are obtained even with only one dose or administration of the composition, although additional doses or vaccinations can boost titers even higher. The pharmacologically acceptable carrier can be any such carrier known in the art which is safe and does not hamper effectiveness of the composition. Examples are mentioned above, and throughout this document. The amount of the composition required for raising high titers of neutralizing antibodies is between about 5 micrograms and about 5 milligrams. The inventors discovered that the composition was effective in both mammals and birds.

The invention also encompasses post-exposure prophylactics, or passive vaccines, for treating or preventing Sin Nombre virus infections, for someone who has already been exposed to Sin Nombre virus and may be infected. Polyclonal antibodies may be obtained using methods known in the art, from a population of vaccinees (human or animal) vaccinated with a Sin Nombre virus DNA vaccine comprised of a plasmid expressing SEQ ID NO:1, SEQ ID NO:2 or SEQ ID NO;3, such as pWRG/SN-M(opt). Alternatively, polyclonal or monoclonal antibodies could be produced in animals using the pWRG/ SN-M(opt) plasmid, or a plasmid containing SEQ ID NO:2 or SEQ ID NO:3, operably associated with a promoter and any other elements needed for expression of the sequence. The methods entail administration of a therapeutically or prophylactically effective amount of the antibodies which protect against Sin Nombre virus disease in combination with a pharmaceutically acceptable carrier or excipient. For instance, a therapeutic composition for ameliorating symptoms of Sin Nombre virus infection may comprise a composition comprising these polyclonal antibodies, and a pharmaceutically acceptable excipient. For instance, pWRG/ SN-M(opt) may be used to vaccinate ducks, sheep, or transgenic cows or rabbits to produce polyclonal neutralizing antibodies for use in humans.

The invention also entails a method for diagnosis of Sin Nombre virus infection by assaying for the presence of Sin Nombre virus in a sample using the above-described antibodies. For instance, a method for the diagnosis of Sin Nombre virus infection may comprise the steps of:

(i) contacting a sample from an individual suspected of having Sin Nombre virus infection with a composition comprising the polyclonal antibodies (e.g., the pWRG/SN-M(opt) plasmid could be used to produce diagnostic antibodies in any of several species of animals- goats, rabbits, etc.); and (ii) detecting the presence or absence of Sin Nombre virus infection by detecting the presence or absence of a complex formed between Sin Nombre virus antigens and antibodies specific therefor.

In addition, the invention encompasses novel immunoprobes and test kits for detection of Sin Nombre virus infection comprising antibodies according to the present invention. For immunoprobes, the antibodies are directly or indirectly attached to a suitable reporter molecule, e.g., and enzyme or a radionuclide. The test kit includes a container holding one or more antibodies according to the present invention and instructions for using the antibodies for the purpose of binding to Sin Nombre virus to form an immunological complex and detecting the formation of the immunological complex such that presence or absence of the immunological complex correlates with presence or absence of Sin Nombre virus. For instance, the kit may include kit may include a container holding one or more polyclonal antibodies of the present invention which binds a Sin Nombre virus antigen, and ancillary reagents suitable for use in detecting Sin Nombre virus antigens, and instructions for using any of the antibodies or polyclonal antibodies described herein for the purpose of binding to SNV antigen to form an immunological complex and detecting the formation of the immunological complex such that the presence or absence of the immunological complex correlates with presence or absence of Sin Nombre virus antigens in the sample. Examples of containers include multiwell plates which allow simultaneous detection of Sin Nombre virus in multiple samples.

Further, the invention contemplates a method for producing pseudotyped viruses for use in serologic assays or delivery of gene therapies to endothelial cells targeted by hantavirus glycoproteins. The invention as used for this purpose would comprise the following steps. The plasmid pWRG/SN-M(opt) or derivative thereof would be used to transfect cells or stably transform cells. Cells expressing the Sin Nombre glycoproteins could then be infected with viruses engineered to produce progeny that incorporate the Sin Nombre glycoproteins into progeny virus surface envelopes. Pseudotype virus systems include retrovirus systems and vesicular stomatitis virus systems. Pseudotypes have been produced using the hantavirus full-length M gene plasmids, including pWRG/SN-M(opt). The pseudotypes can be used for testing for neutralizing antibodies. They also may be used to deliver genes to endothelial cells in a clinical setting. For example, gene therapy viruses containing the Sin Nombre glycoproteins on their surface will target to certain endothelial cells.

The invention also entails a therapeutic composition for ameliorating symptoms of Sin Nombre virus infection. The composition includes polyclonal or monoclonal antibodies specifically raised against one of SEQ ID NO:1, SEQ ID NO:2 or SEQ ID NO:3. The composition may be combined with a pharmaceutically acceptable carrier and/or an adjuvant, such as the examples as described herein.

Other embodiments are discussed below. The invention is described in further detail by the non-limiting examples and text below.

BRIEF DESCRIPTION OF THE FIGURES

FIG. 1. Hantavirus neutralizing antibodies produced in rabbits vaccinated with full-length hantavirus M gene-based DNA vaccines using muscle electroporation.

FIG. 2. Neutralizing antibody data from rabbits vaccinated with pWRG/SN-M(opt) (also designated as pWRG/SN-M(opt)). Rabbits were vaccinated on days 0, 28, 56 and 84. Sera collected on days 0, 56, and 70 where tested for Sin Nombre virus neutralizing antibodies by plaque reduction neutralization test (PRNT). The neutralizing antibody titers are shown.

FIG. 4. Mixed hantavirus DNA vaccines are feasible. Three mixtures of hantavirus DNA vaccine plasmids delivered by muscle electroporation were tested in rabbits.

FIG. 6. pWRG/SN-M(opt) DNA vaccine is immunogenic and protective in hamsters. Groups of 7-8 hamsters received 2 vaccinations (week 0, 3), or three vaccinations (week 0, 3, 6) with pWRG/SN-M(opt), or 3 vaccinations with a negative control DNA vaccine, or no vaccine. Vaccinations were performed using a gene gun.

DETAILED DESCRIPTION OF THE INVENTION

Supplemental to the previous description of the invention, the following further details are provided.

The inventor has created a novel, synthetic codon optimized Sin Nombre virus full-length M gene, ORF plus flanking sequences, and ORF, that are each stably maintained in a DNA vaccine plasmid, and elicit good neutralizing antibodies in animal models. Heretofore, there was no full length Sin Nombre M gene clone stably inserted it on an expression plasmid, which could be successfully expressed. Likewise, this is the first time any vaccine, of any kind, has been shown to elicit high titer neutralizing antibodies and protect against SNV infection in an animal model.

The inventor cloned the full-length M gene from SNV, strain CC107 into a DNA vaccine vector (i.e., RNA was purified, reverse transcribed to cDNA, PCR amplified, and cloned into a DNA vaccine plasmid [pWRG7077]). Ultimately, the inventor was able to produce a unique plasmid with an intact open reading frame (designated pWRG/SN-M(2a) or "M(2a)"). It was confirmed that this plasmid could produce the Gn and Gc protein in cell culture. pWRG/SN-M(2a) was tested for immunogenicity in rabbits using muscle electroporation technology. Three rabbits were vaccinated on weeks 0, 2, 4, 6 with 0.4 mg of DNA per vaccination. Sera were collected on weeks 0, 4, and 8. PRNT were performed to detect SNV neutralizing antibodies. The data demonstrated that high-titer neutralizing antibody were produced after 4 vaccinations (FIG. 1). The titers reached were over 10,000, which is considered are similar to those produced in person who have developed HPS and survived. In the art of immunology, and especially regarding hantaviruses, any titer over 100 would be considered good, and useful for vaccine purposes. This was the first time high-titer SNV neutralizing antibodies were ever produced by any vaccine, confirming the uniqueness of the M(2a) plasmid. Nevertheless, one undesirable result was that the M(2a) required more vaccinations to raise high-titers than the inventor's previous hantavirus vaccines, namely the HTNV, PUUV, or ANDY M gene-based DNA vaccines.

Figure 1A:
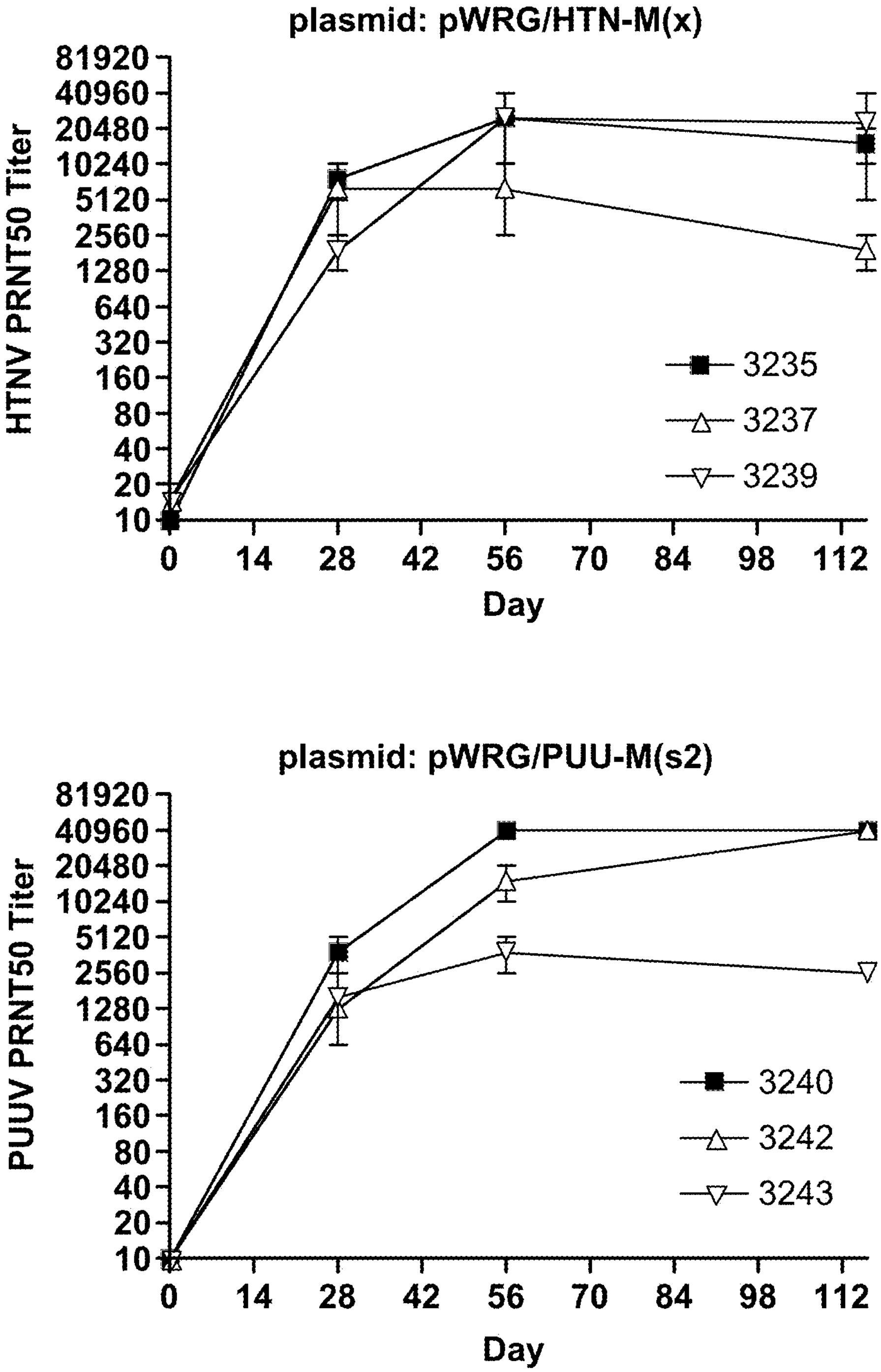
FIG. 1A) Hantaan, Puumala, and Andes DNA vaccines. Groups of 3 rabbits were vaccinated with either the Hantaan DNA vaccine, pWRG/HTN-M(x) (described in U.S. Pat. No. 7,217,812), or the Puumala DNA vaccine, pWRG/PUU-M(s2) (described in U.S. Patent Publication No. 20100323024) on days 0, 14, 28, and 32 by muscle electroporation (Invoio Elgen device, dose was 0.4 mg of DNA per injection. Sera were collected on weeks 0, 28, 56, and 116 and tested in homotypic PRNT. Symbols represent the mean of two separate PRNT±SE.
Figure 1B:
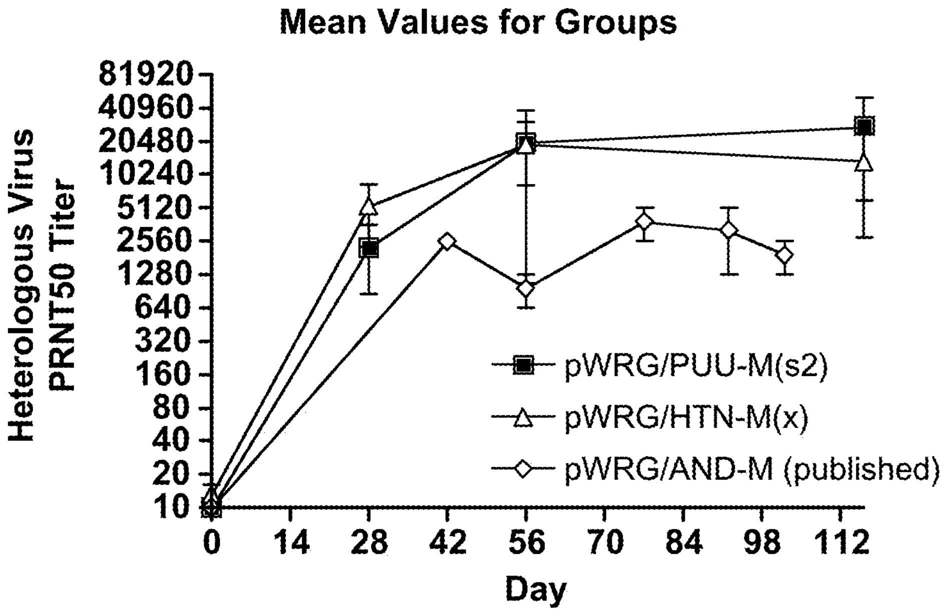
FIG. 1B) The same data from panel A were combined to show mean titers for the groups. In addition, published data from rabbits vaccinated with the Andes DNA vaccine, pWRG/AND-M, are included. Note the vaccination days were different for the Andes DNA vaccine (shown in grey arrows).
Figure 1C:
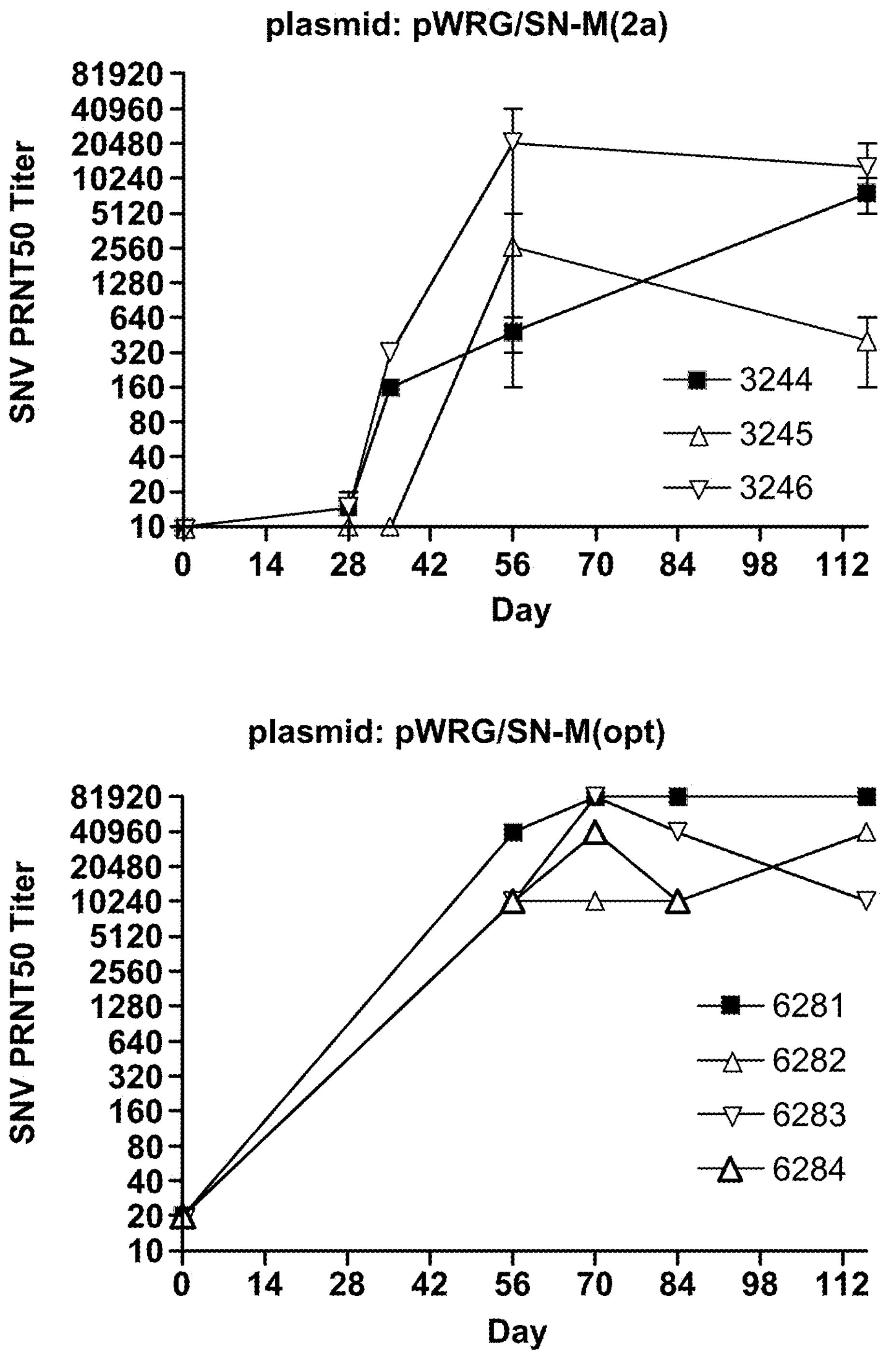
FIG. 1C) Sin Nombre DNA vaccines. The first generation SNV full-length M gene based DNA vaccine, pWRG/SNV-M(2a), was tested in three rabbits. The animals were vaccinated four times (arrows) and sera were tested for SNV neutralizing antibodies. High-titer neutralizing antibody could be produced after multiple vaccinations. The second generation plasmid, pWRG/SN-M(opt), was tested in rabbits. Rabbits were vaccinated on days 0, 28, 56 and 84. Sera collected on the indicated days were tested for SNV neutralizing antibodies. High-titers were achieved after 2, or fewer, vaccinations (sera from day 28 was not collected).
Figure 1D:
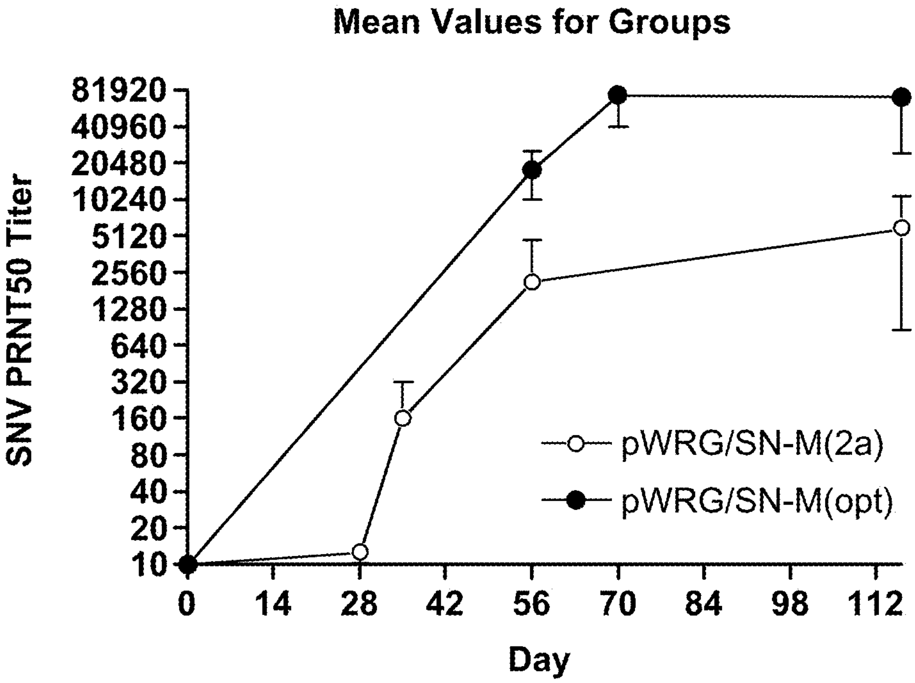
FIG. 1D) The same data from panel C were combined to show mean titers for the groups±SE.
Figure 2A:
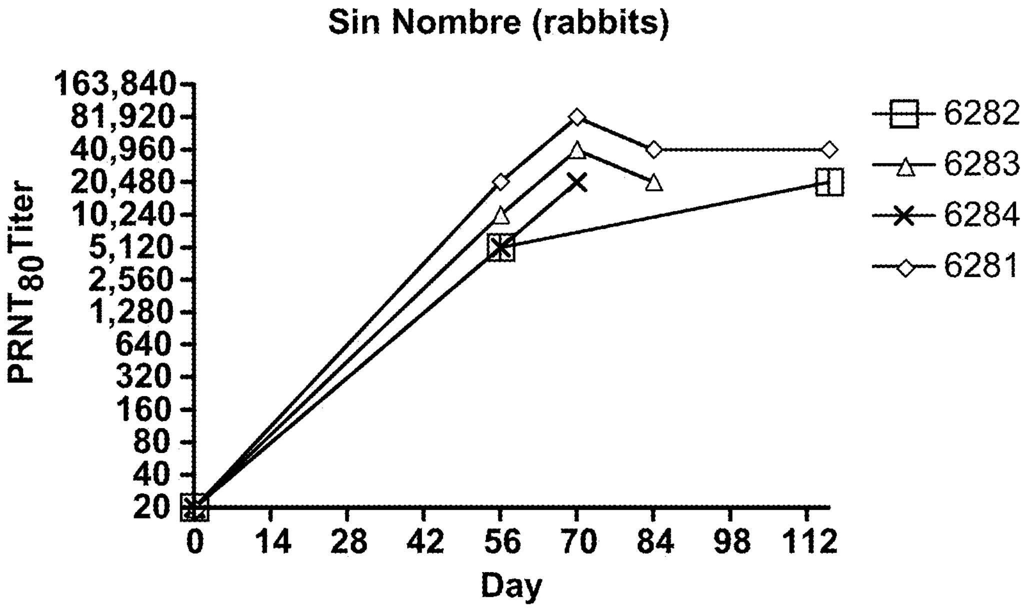
FIG. 2A. The titers are the reciprocal of the highest dilution reducing the number of plaques in the media alone wells by 80%.
Figure 2B:
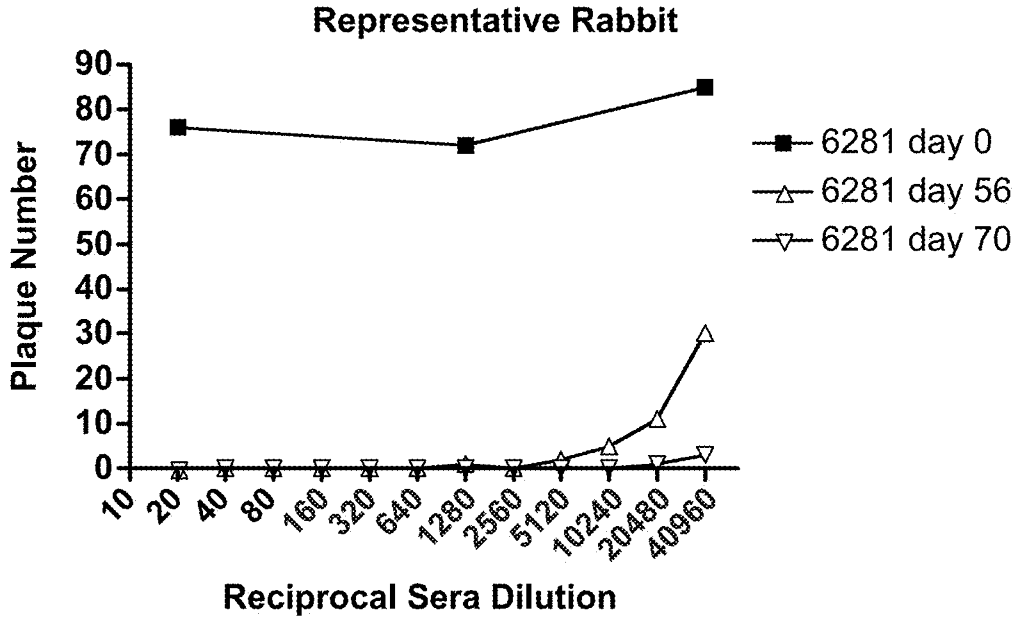
FIG. 2B. Raw plaque for one representative rabbit are shown before vaccination, after 2 (day 56) and after 3 (day 70). Note that there is 100% neutralization out to a 1:10,240 dilution for the day 70 serum. The numbers 6281, 6282, 6283, and 5284 are designations for the different rabbits vaccinated.

In an attempt to improve immunogenicity and potency, the M(2a) plasmid was refined by (1) first determining any possible flaws in the open reading frame and (2) obtaining the synthesis of a codon-optimized version of the SNV M gene. The inventor analyzed the M gene sequence in pWRG/SN-M(2a) and discovered amino acids that were unique to the clone (i.e., not in published GeneBank SNV M sequences) (Table 1). He identified consensus amino acids at these positions and then had an optimized version of this gene synthesized (work contracted to GeneArt) (Table 2). Next, the synthetic M gene was cloned into a DNA vaccine vector and the resultant plasmid was named pWRG/SN-M(opt) (or "M(opt)"). The sequence of the pWRG/SN-M(opt) plasmid is given in SEQ ID NO:1. M(opt) was tested for a capacity to elicit neutralizing antibodies by vaccinating rabbits with the pWRG/SN-(opt) using muscle electroporation. Four rabbits were vaccinated on weeks 0, 4, and 8 with 1 mg of DNA per vaccination. Sera were collected on weeks 0, 8 and 10. PRNT were performed to detect SNV neutralizing antibodies. Very high titers of SNV neutralizing antibodies were produced after only 2 vaccinations (week 8 sera) with pWRG/SN-M(opt) (FIG. 2) After 3 vaccinations (week 10 sera) there was 100% neutralization in all four rabbits even when the sera was diluted≥1:5,000. This was a significant improvement over the M(2a) results—2 vaccinations is considered acceptable to be convenient enough for human or animal use.

Figure 3A:
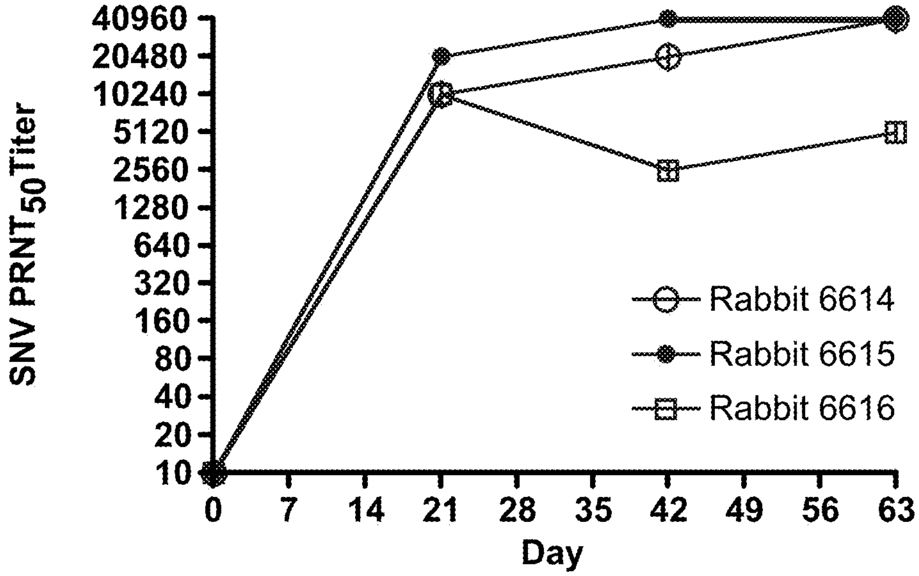
FIG. 3. HPS vaccine. Plasmid mixtures were tested in rabbits using muscle electroporation (EP). Three rabbits were vaccinated by muscle EP on day 0, 21, and 42 with a 1:1 mixture of the pWRG/SN-M(opt) and pWRG/AND-M DNA (described in U.S. Pat. No. 7,217,812) vaccine plasmids. Sera were collected at the indicated time points and plaque reduction neutralization tests (PRNT) were performed. Neutralizing antibodies were produced against both SNV and ANDY after a single vaccination. Overall, the neutralizing antibody titers were greater against SNV (FIG. 3A) than ANDY (FIG. 3B). Device=Ichor Tri-grid device; Dose=2.0 mg mixed DNA/injection, 1 injection per vaccination. (Unpublished) The numbers 6214, 6215, and 6216 are designations for the different rabbits vaccinated.
Figure 3B:
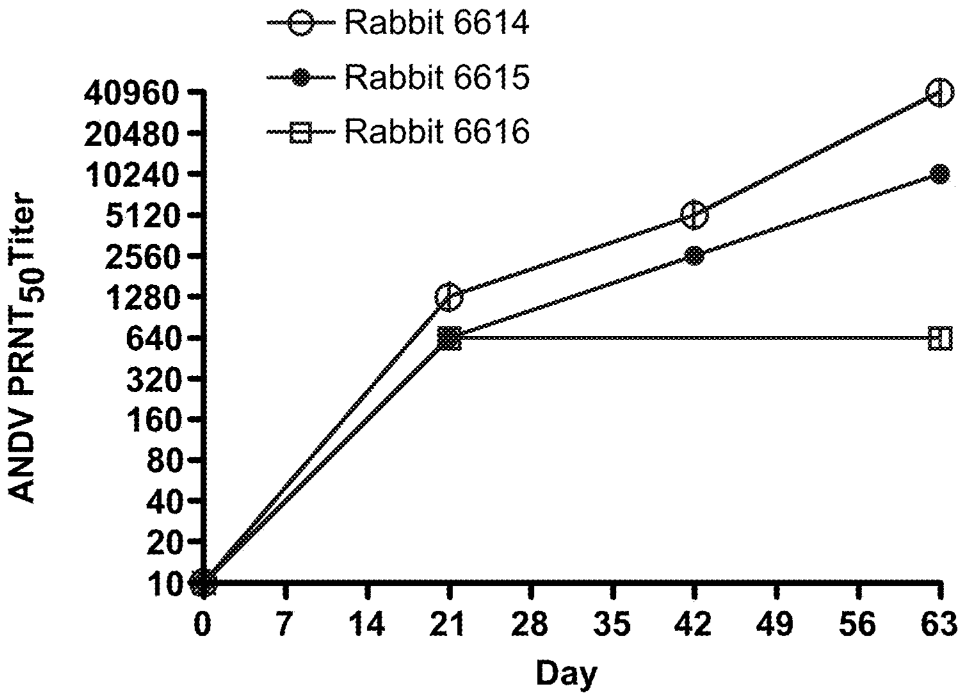
Figure 4A:
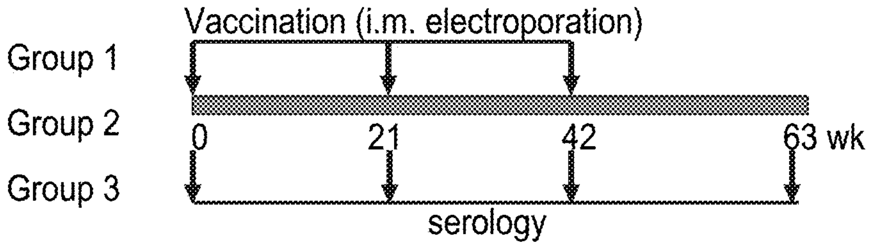
FIG. 4A) Experimental design. Groups of three rabbits were vaccinated three times by muscle electroporation using the Ichor Tri-grid at three-week intervals. The HFRS mixture was comprised of equal volumes of Hantaan and Puumala DNA vaccine plasmids, pWRG/HTN-M(x) and pWRG/PUU-M(52), respectively. The HPS mixture was comprised of equal volumes of Andes and Sin Nombre DNA vaccine plasmids, pWRG/AND-M and pWRG/SN-M(opt), respectively. The HFRS/HPS mixture was comprised of equal volumes of the Hantaan, Puumala, Andes, and Sin Nombre DNA vaccine plasmids. The mixtures contained 1 mg of each plasmid per dose.
Figure 4B:
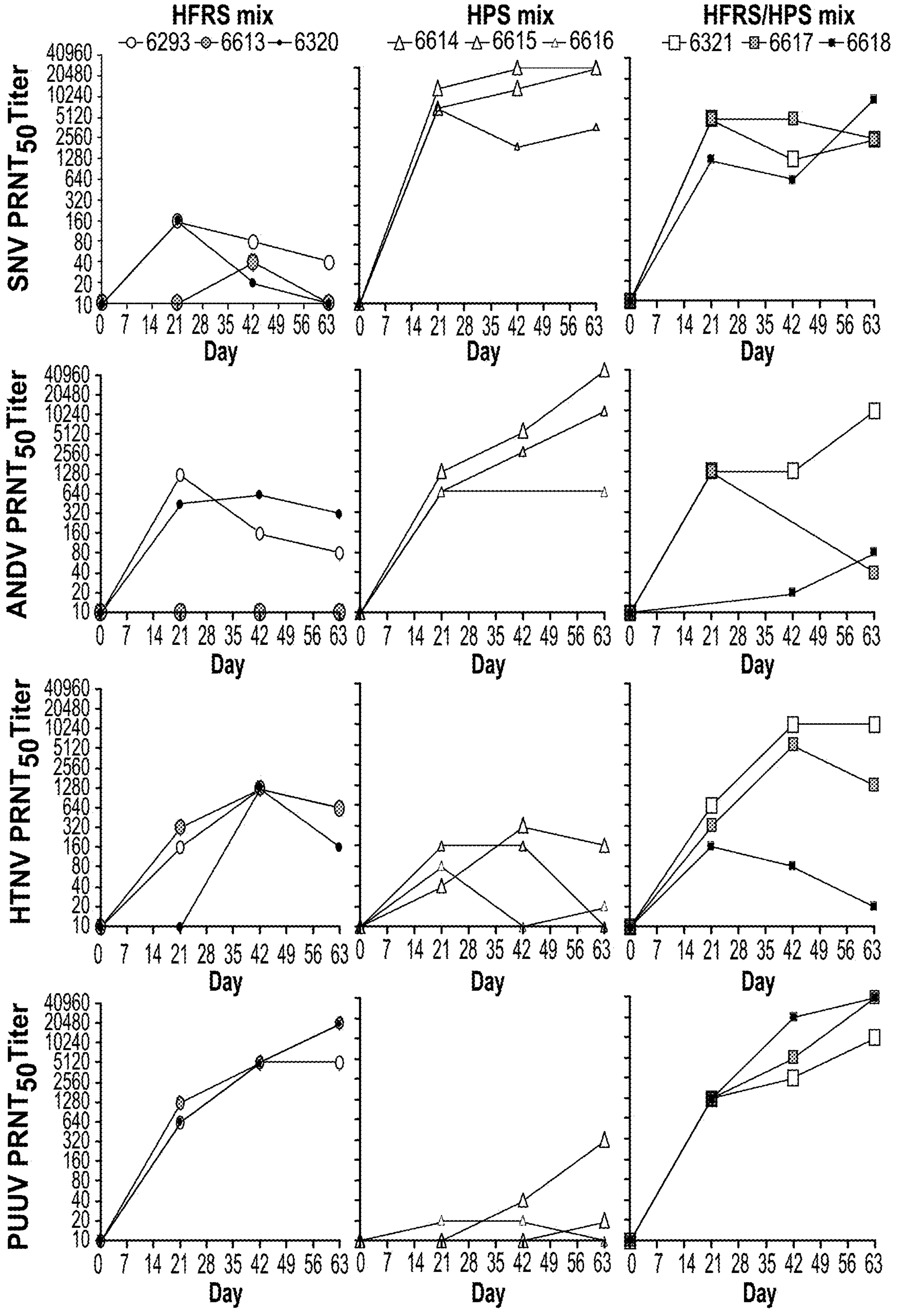
FIG. 4B) Neutralizing antibody titers for individual rabbits are shown. The virus used in the neutralization test is shown on the y-axis. Sera from days 0, 21, 42, and 63 were tested.
Figure 4C:
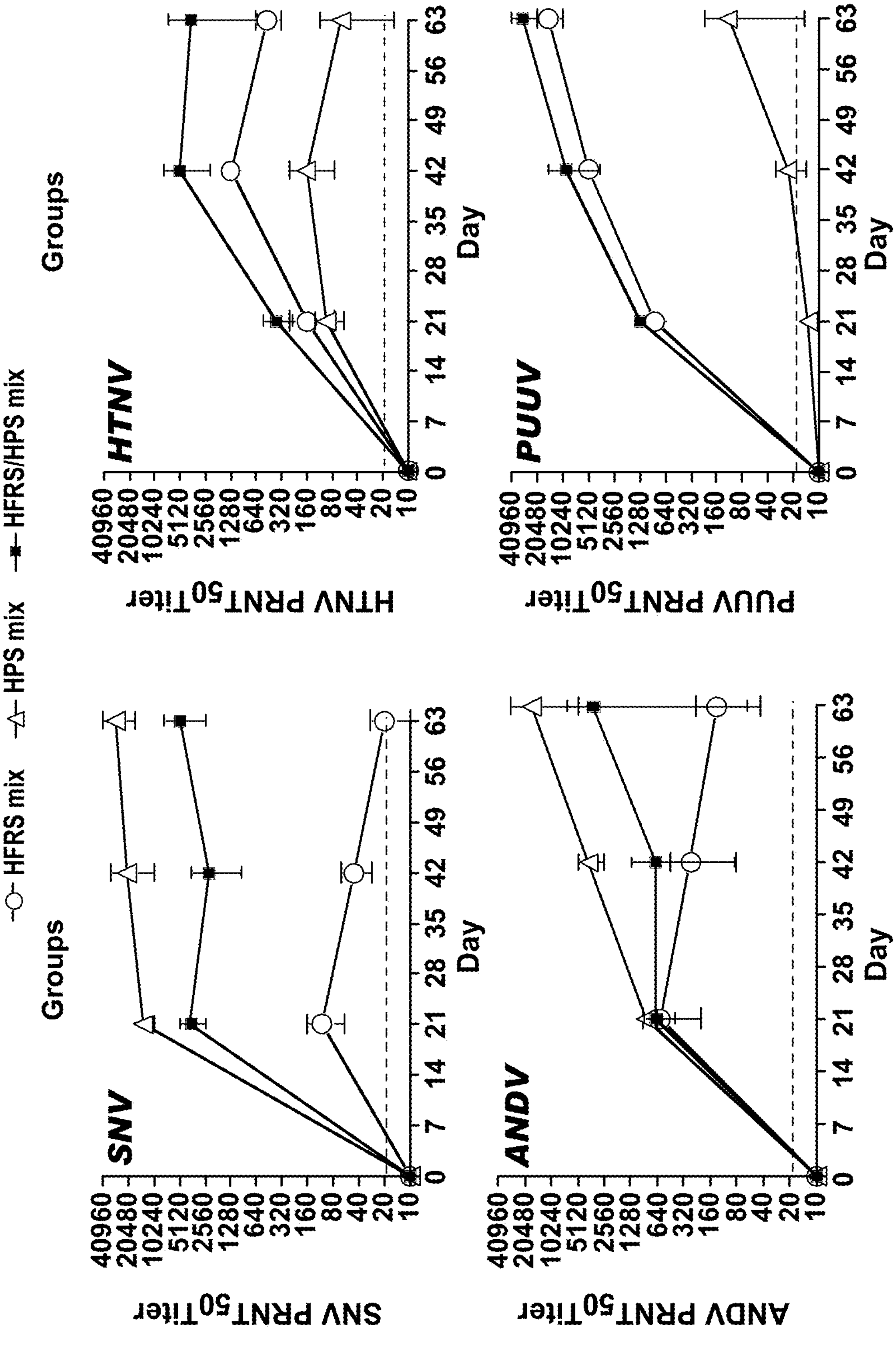
FIG. 4C) Mean neutralizing titers for each group plus/minus standard error. The data demonstrate that it is possible to mix hantavirus DNA vaccines into a single-injection vaccine and produce neutralizing antibodies against multiple hantaviruses. The HFRS DNA vaccine was more effective at neutralizing Puumala virus and Hantaan virus and the HPS DNA vaccine was more effective at neutralizing Andes virus and Sin Nombre virus. The HFRS/HPS DNA vaccine elicited neutralizing antibodies against all four hantaviruses after a single vaccination for all but one rabbit.
Figure 5:
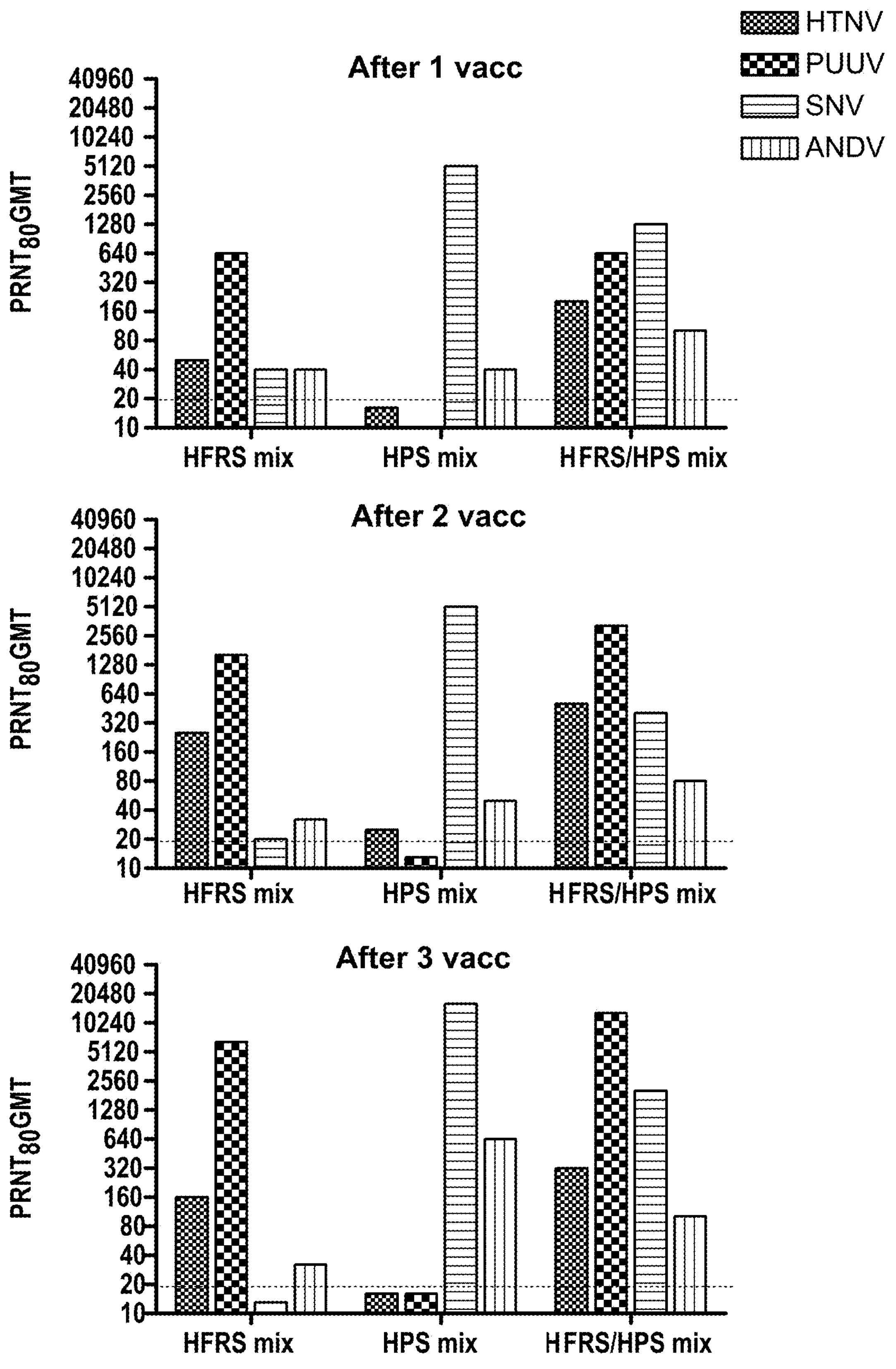
FIG. 5. PRNT80 GMT against HTNV, PUUV, SNV, and ANDY for each DNA vaccine formulation after 1, 2, or 3 vaccinations are shown. These data are from the same experiment shown in FIG. 2; however PRNT80 GMT are shown here. PRNT80 titers are a more stringent measure of neutralizing antibodies that PRNT50. The HFRS mix (pWRG/HTN-M[x] and pWRG/PUU-M[s2]) produced GMTs>100 against HTNV and PUUV. The HPS mix (pWRG/SN-M[opt] and pWRG/AND-M) produced GMTs>100 against SNV and ANDY. And the HFRS/HPS mix "pan-hantavirus" produced GMTs>100 against all four hantaviruses. PUUV PRNT endpoints after 1 vaccination were not determined beyond 640 (indicated by ≥). <indicates GMT was below detection. These data demonstrate the utility of using the SN DNA vaccine as part of HPS vaccine or a pan-hantavirus DNA vaccine.
Figure 6A:
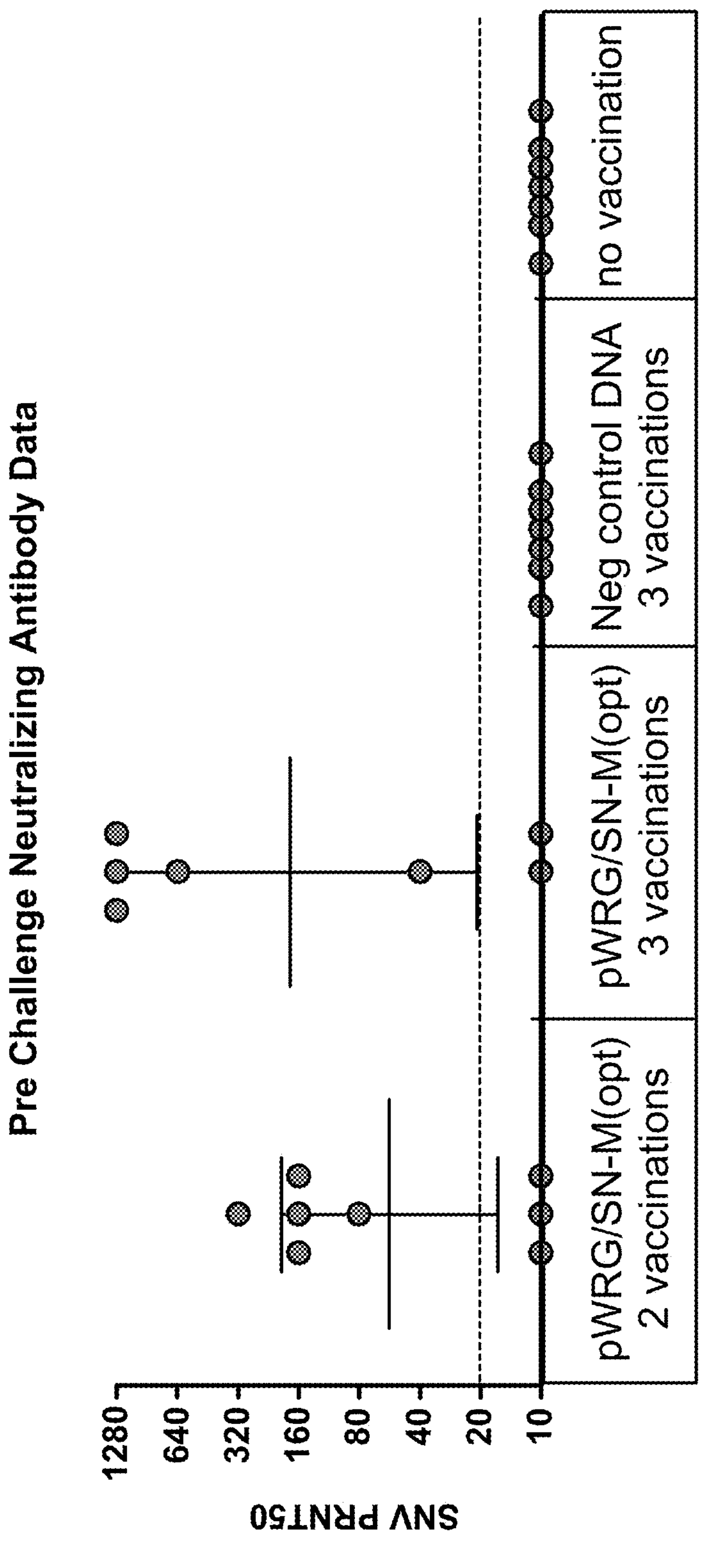
FIG. 6A) Sera collected on week 9 were tested for SNV neutralizing antibody by SNV PRNT. Each symbol represents the $PRNT_{50}$ titer of an individual hamster. The geometric mean titer and 95% confidence interval for each group are shown. The limit of detection was a titer of 20 (dashed line). Seroconversion rates after 2 or 3 vaccinations were 62.5% (5 of 8) and 71.4% (5 of 7), respectively. The immune response was lower than what we observed in rabbits using electroporation, but was nevertheless evidence that the pWRG/SN-M(opt) plasmid was immunogenic in hamsters.
Figure 6B:
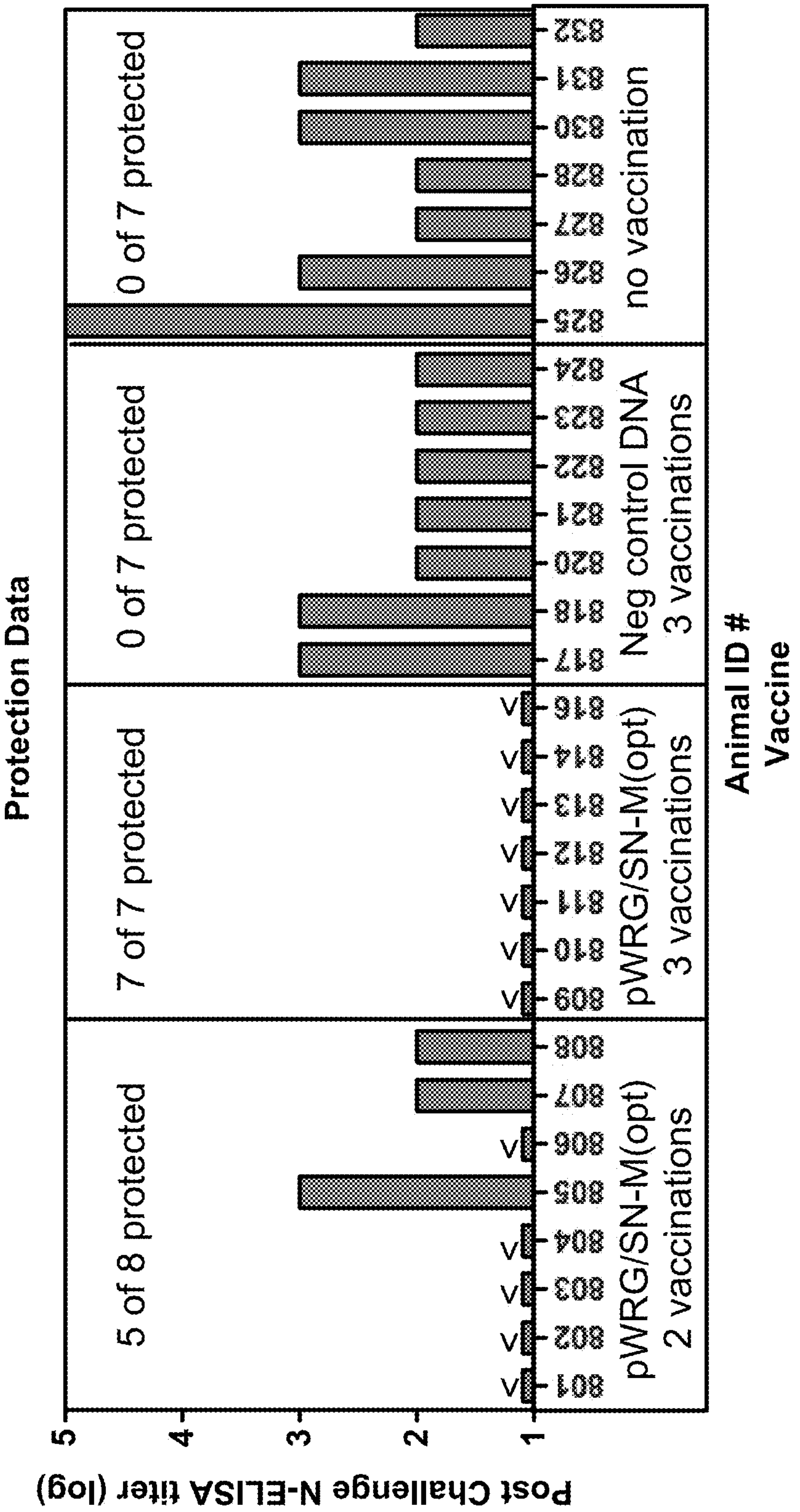
FIG. 6B) The hamsters were challenged with 200 pfu of SNV by the intramuscular route on week 11. Sera were collected on week 16 and tested by ELISA for evidence of SNV infection (note that SNV infects hamsters but is not lethal). A positive ELISA indicates the hamsters were infected with SNV (i.e., not protected). 2 vaccinations with pWRG/SN-M(opt) protected 62.5% of the hamsters and 3 vaccinations protected 100% of the hamsters. All of the negative control hamsters were infected. <indicates titer was below level of detection.
Figure 7:
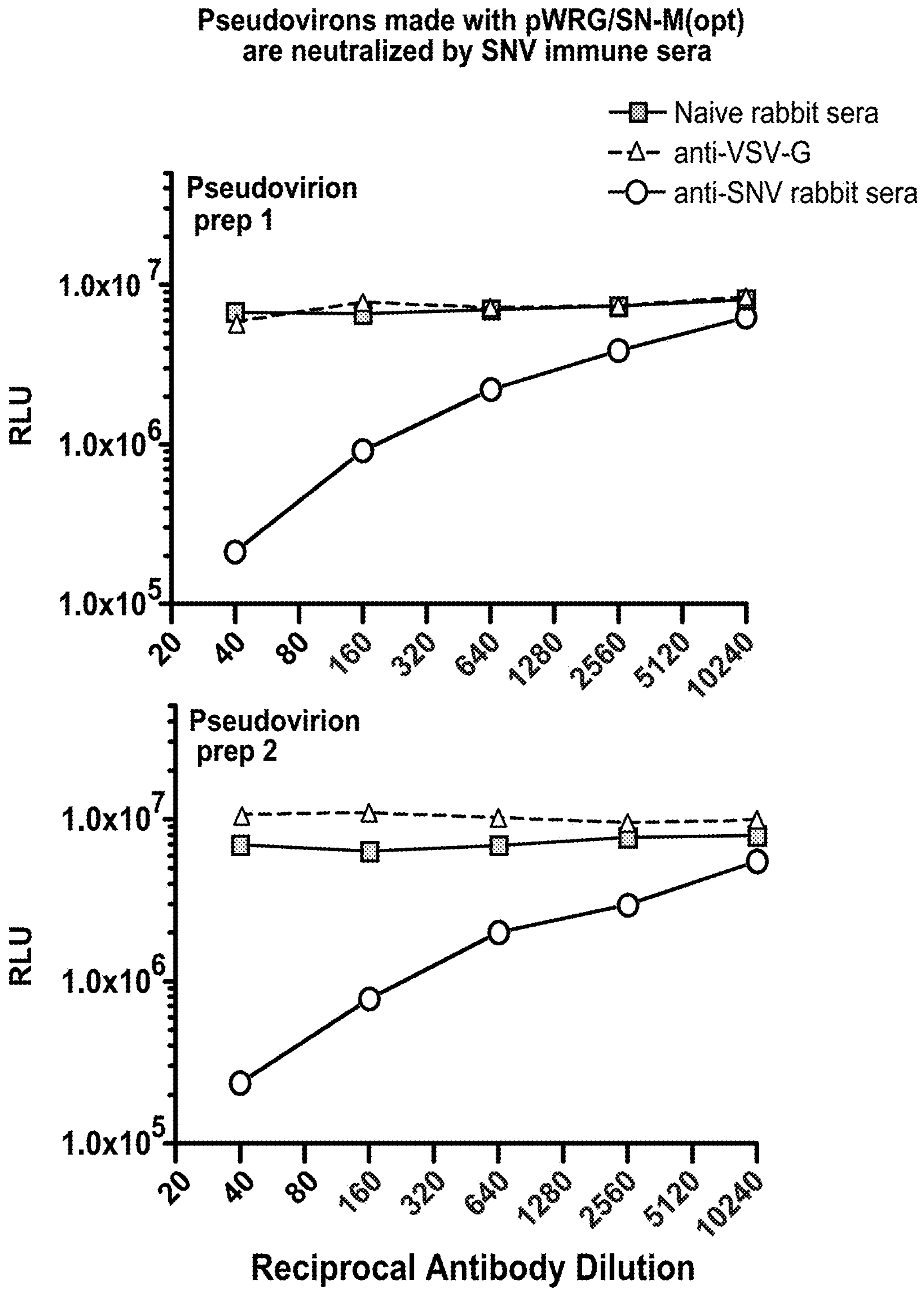
FIG. 7. The pWRG/SN-M(opt) plasmid was used to make pseudovirions that were specifically neutralized by rabbit sera containing SNV neutralizing antibodies. 293T cells were transfected with pWRG/SN-M(opt) and then, after 24 hr, were "infected" with recombinant vesicular stomatitis virus (VSV) that had the G protein deleted and replaced with the Renilla luciferase gene (VSV deltaG luciferase reporter core virus system was provided by Robert Doms, University of Pennsylvania). After 48 hr at 37 C, the supernatant was harvested and pseudovirion particles were purified on a sucrose gradient. Two different preparations of pseudovirions (prep 1, top panel; prep 2, bottom panel) where then mixed with serial dilutions of naïve rabbit sera, anti-SNV rabbit sera, or anti-VSV-G antibody (as control) and incubated for 1 hr at 37 C. The mixtures were then used to infect BHK cells in a 96-well format for 24 hours. Cell lysates were harvested, combined with luciferase substrate, and the luciferase reporter activity in Relative Luminescent Units (RLU) was measured using a luminometer. Symbols represent the average value of duplicates. The data demonstrate that the anti-SNV rabbit sera, but not the other sera, reduced the RLU activity (neutralized the pseudovirions) in a dose dependent manor. This assay can be used to measure SNV neutralizing antibodies in any sera including humans vaccinated with candidate HPS vaccines, or naturally infected with hantaviruses FIG. 8. The nonoptimized version of the Sin Nombre DNA vaccine, pWRG/SN-M(2a), was tested for the capacity to produce neutralizing antibodies in an avian species. Ducks were vaccinated with 0.4 mg of plasmid DNA using muscle electroporation on days 0, 14, and 42. Sera was collected on days 0, 28, and 56 and tested for SNV neutralizing antibodies by PRNT. Higher titers are expected using the optimized pWRG/SN-M(opt) plasmid. These data demonstrate that the Sin Nombre DNA vaccine can be used to produce high titer neutralizing antibodies in avian species. This antibody is reasonably expected to be purified from eggs and may be used in humans or other mammals as post-exposure prophylactics or therapeutics, or as diagnostic reagents. The duck IgY naturally loses the Fc fragment of the antibody and this, it is believed, will make the molecule less reactogenic when used in a human as a therapeutic or post-exposure prophylactic.
Figure 8:
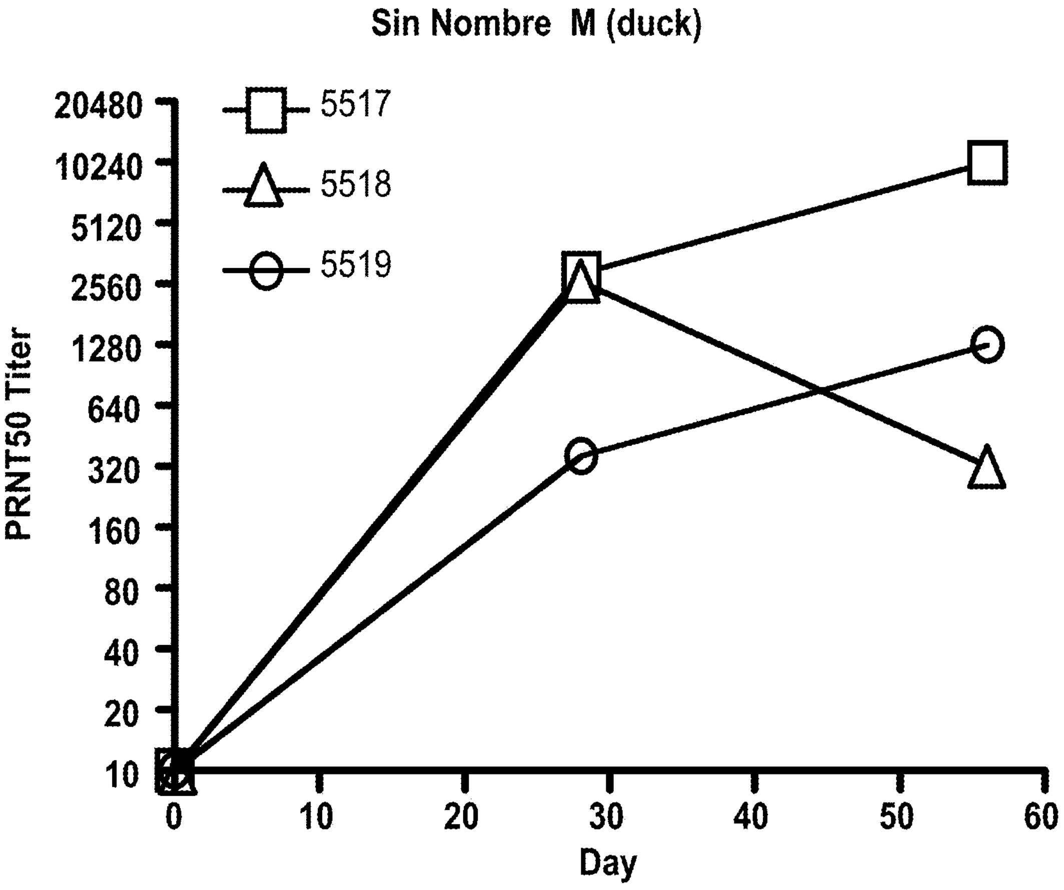

Having found the pWRG/SN-M(opt) to be a potent DNA vaccine, the inventor next combined the SNV DNA vaccine with the pWRG/AND-M. A mixture of the two plasmids was used to vaccinate rabbits using muscle electroporation. High titer neutralizing antibodies against both SNV and ANDY were produced after 1 or 2 vaccinations (FIG. 3). The SNV neutralizing activity was especially potent (titers>10,000 after 1 vaccination). Thus, the combination of the pWRG/SN-M(opt) DNA vaccine and pWRG/AND-M DNA vaccine effectively elicited high-titer neutralizing antibodies against the most prevalent and lethal hantavirus in North and South America. The novelty and potency of this SNV DNA vaccine was surprising and unexpected.

In summary, the inventor produced two plasmids that elicited high titer neutralizing antibodies against SNV in animal models. Thus, one point of novelty of the invention is that it elicits Sin Nombre virus neutralizing antibodies, and with significantly high titers. To the best of the inventor's knowledge, there is no other SNV vaccine that elicits antibodies that directly neutralize Sin Nombre virus.

Vaccines and Immunogenic Compositions

To summarize, the vaccines and immunogenic compositions comtemplated by this invention include: (1) Sin Nombre virus vaccines and immunogenic compositions; (2) Sin Nombre virus +other HPS viruses (e.g., Andes virus) vaccines and immunogenic compositions; (3) Sin Nombre virus vaccines and immunogenic compositions +HFRS viruses (e.g., Puumula and Hantaan viruses) vaccines and immunogenic compositions; and (4) Sin Nombre virus+other HPS viruses (e.g., Andes virus) vaccines and immunogenic compositions+HFRS viruses (e.g., Puumula and Hantaan viruses) vaccines and immunogenic compositions. These vaccines and immunogenic compositions, when transfected into mammalian cells, result in the expression of proteins that mimic the Gn and Gc surface glycoproteins of SNV and the other hantaviruses targeted. When these DNA vaccines or immunogenic compositions are introduced into the cells of a vaccinee, the vaccinee produces a neutralizing antibody response against SNV, and, if relevant, the other hantavirus (es). Neutralizing antibody responses are sufficient to confer protection against SNV and the other hantaviruses. Thus, SEQ ID NO:1, SEQ ID NO:2 and SEQ ID NO:3, and derivatives thereof, represent a candidate vaccine for the prevention of HPS caused by SNV. Moreover, these novel sequences, and derivatives thereof, can be used to generate anti-SNV immunotherapeutics and diagnostic antibodies in animals (The term transfected is used herein to refer to cells which have incorporated the delivered foreign DNA vaccine, whichever delivery technique is used.)

As noted above, there is no vaccine or drug to prevent or treat HPS. One of the embodiments of the invention described herein is a DNA vaccine based on the M-gene segment of Sin Nombre virus. The M genome segment encodes the two proteins found on the virus surface.

One embodiment of the invention encompasses DNA vaccines. DNA vaccination involves administering antigen-encoding polynucleotides in vivo to induce the production of a correctly folded antigen(s) within the target cells. The introduction of the DNA vaccine will cause to be expressed within those cells the structural protein determinants associated with the pathogen protein or proteins. The processed structural proteins will be displayed on the cellular surface of the transfected cells in conjunction with the Major Histocompatibility Complex (MHC) antigens of the normal cell. Even when cell-mediated immunity is not the primary means of preventing infection, it is likely important for resolving established infections. Furthermore, the structural proteins released by the expressing transfected cells can also be picked up by antigen-presenting cells to trigger systemic humoral antibody responses.

The DNA vaccine according to the present invention is inherently safe, is not painful to administer, and should not result in adverse side effects to the vaccinated individual. In addition, the invention does not require growth or use of Sin Nombre virus, which is a biosafety level 3 (BSL-3) virus, and is a BSL-4 virus if the virus is grown to high levels or used in animals.

In order to achieve the immune response sought, a DNA vaccine construct capable of causing transfected cells of the vaccinated individual to express one or more major viral antigenic determinant is necessary. This can be done by identifying regions of the viral genome which code for viral glycoproteins or capsid components, and joining such coding sequences to promoters capable of expressing the sequences in cells of the vaccinee. Alternatively, the viral genome itself, or parts of the genome, can be used.

In a preferred embodiment, the vaccine is a plasmid based codon-optimized Sin Nombre virus (SNV) M gene open reading frame. The M gene encodes for two proteins that form a part of the viral capsid. In nature these are glycosylated during synthesis in mammalian cells which would occur after vaccination. SNV is one of several viruses that cause Hantavirus Pulmonary Syndrome, a disease with high mortality (20-50%). There have been several hundred cases in the Americas over the past several years. This vaccine has been shown to induce high neutralizing antibody titers in animals and therefore would be useful for a human vaccine. Two hantavirus DNA vaccines—Hantaan and Puumala—have been shown to induce neutralizing antibodies in human clinical trials. (Presentation given: "Preclinical and Phase 1 Clinical Studies of a DNA Vaccine for HI-RS Caused by Hantaviruses" J. Hooper, to the American Society of Microbiology Biodefense Meeting, held in Baltimore, February, 2010)

As noted above, attempts to produce SNV vaccine that produce neutralizing antibodies against SNV have been unsuccessful. Here, for the first time, the inventor has synthesized a codon-optimized full-length M gene open reading frame and cloned it into a DNA vaccine expression vector (e.g., pWRG-SN-M(opt)). The nucleotide sequences are completely unique because the ORF has been optimized. Regarding the preferred embodiment pWRG/SN-M(opt), hamsters and rabbits vaccinated with pWRG/SN-M(opt) using a gene gun developed neutralizing antibodies as measured by plaque reduction neutralization test (PRNT) with $PRNT_{50}$ titers ranging from 10,240—over 81,920 in rabbits by electroporation; in hamsters, less than 20-1,280 by gene gun. This is believed to be the first candidate SNV vaccine that successfully elicits neutralizing antibodies against SNV.

In its preferred vaccine embodiment, the SNV virus M gene-based DNA vaccine is a plasmid that consists of a well-characterized backbone that enables expression of the above-described synthentic, codon-optimized, SNV virus full-length M gene, or the ORF with or without flanking sequences. Preferred examples are SEQ ID NO:1, SEQ ID NO:2 and SEQ ID NO:3. It can be used in other vaccine systems and systems for generating SNV neutralizing antibodies.

In this application we describe the elicitation of protective immunity to SNV alone or with other hantaviruses by DNA vaccines. The gene(s) of interest, in our case, a synthetic Sin Nombre virus M gene having at least one of the sequences identified herein as SEQ ID NO:1, SEQ ID NO:2, and SEQ ID NO:3, is controlled by a mammalian or virus promoter (e.g., the cytomegalovirus immediate early promoter followed by intron A) that facilitates expression of the naked DNA gene product(s) within the vaccinee's cells. Preferably, Intron A is included. It is preferred even to use pWRG/SN-M(opt) as the DNA vaccine plasmid. This intracellular expression can elicit both humoral and cell-mediated immune responses (Robinson and Torres, 1997, supra; and Gregoriadis, 1998, supra). Methods of DNA delivery include needle inoculation, needle-free jet injection, oral or pulmonary delivery, and inoculation by particle bombardment (i.e., gene gun) and electroporation—by well-known methods for each. Needle inoculation and needle-free jet injection may be made with or without electroporation. Delivery may be intramuscular or intradermal, as appropriate.

A suitable construct for use in the method of the present invention is pWRG7077 (4326 bp) (PowderJect Vaccines, Inc., Madison, Wis.). pWRG7077 includes a human cytomegalovirus (hCMV) immediate early promoter (IE) and a bovine growth hormone polyA addition site. Between the promoter and the polyA addition site is Intron A, a sequence that naturally occurs in conjunction with the hCMV IE promoter that has been demonstrated to increase transcription when present on an expression plasmid. Downstream from Intron A, and between Intron A and the polyA addition sequence, are unique cloning sites into which the hantavirus M DNA can be cloned. Also provided on pWRG7077 is a gene that confers bacterial host-cell resistance to kanamycin. Any of the fragments that encode hantavirus Gn and/or Gc or nucleocapsid peptides can be cloned into one of the cloning sites in pWRG7077, using methods known to the art.

The DNA can be delivered by injection into the tissue of the recipient, oral or pulmonary delivery and inoculation by particle bombardment (i.e., gene gun). Any of these methods can be used to deliver DNA as long as the DNA is expressed and the desired antigen is made in the cell. Two methods are exemplified in this application, both shown to be successful in eliciting a protective immune response in the vaccinee.

In one aspect of the invention, the DNA vaccine is delivered by coating a small carrier particle with the DNA vaccine and delivering the DNA-coated particle into an animal's epidermal tissue via particle bombardment. This method may be adapted for delivery to either epidermal or mucosal tissue, or delivery into peripheral blood cells, and thus may be used to induce humoral, cell-mediated, and secretory immune Reponses in the vaccinated individual.

To deliver DNA vaccines by particle bombardment, we chose to use the PowderJect-XR™ gene gun device described in WO 95/19799, 27 Jul. 1995. Other instruments are available and known to people in the art. This instrument, which delivers DNA-coated gold beads directly into epidermal cells by high-velocity particle bombardment, was shown to more efficiently induce both humoral and cell-mediated immune responses, with smaller quantities of DNA, than inoculation of the same DNAs by other parenteral routes (Eisenbraun, M. et al., 1993, DNA Cell. Biol. 12: 791; Fynan, E. F. et al., 1993, Proc. Natl. Acad. Sci. USA 90: 11478; Haynes, J. R. et al., 1994, AIDS Res. Hum. Retroviruses 10: Suppl. 2:S43; Pertmer, T. M. et al., 1995, Vaccine 13: 1427). Epidermal inoculation of the DNA candidate vaccines also offers the advantages of gene expression in an immunologically active tissue that is generally exfoliated within 15 to 30 days, and which is an important natural focus of viral replication after tick-bite (Bos, J. D., 1997, Clin. Exp. Immunol. 107 Suppl. 1:3; Labuda, M. et al., 1996, Virology 219:357; Rambukkana, A. et al., 1995, Lab. Invest. 73:521; Stingl, G., 1993, Recent Results Cancer Res. 128: 45; Evans et al., Vaccine, 2009, Vol. 27(18), pp. 2506-2512; Yager et al., Expert Rev. Vaccines, 2009, Vol. 8(9), pp. 1205-1220).

The technique of accelerated particles gene delivery or particle bombardment is based on the coating of DNA to be delivered into cells onto extremely small carrier particles, which are designed to be small in relation to the cells sought to be transformed by the process. The DNA sequence containing the desired gene can be simply dried onto a small inert particle. The particle may be made of any inert material such as an inert metal (gold, silver, platinum, tungsten, etc.) or inert plastic (polystyrene, polypropylene, polycarbonate, etc.). Preferably, the particle is made of gold, platinum or tungsten. Most preferably, the particle is made of gold. suitably, the particle is spherical and has a diameter of 0.5 to 5 microns, preferably 1 to 3 microns.

The DNA sequence containing the desired gene prepared in the form suitable for gene introduction can be simply dried onto naked gold or tungsten pellets. However, DNA molecules in such a form may have a relatively short period of stability and may tend to degrade rather rapidly due to chemical reactions with the metallic or oxide substrate of the particle itself. Thus, if the carrier particles are first coated with an encapsulating agent, the DNA strands have greatly improved stability and do not degrade significantly even over a time period of several weeks. A suitable encapsulating agent is polylysine (molecular weight 200,000) which can be applied to the carrier particles before the DNA molecules are applied. Other encapsulating agents, polymeric or otherwise, may also be useful as similar encapsulating agents, including spermidine. The polylysine is applied to the particles by rinsing the gold particles in a solution of 0.02% polylysine and then air drying or heat drying the particles thus coated. Once the metallic particles coated with polylysine were properly dried, DNA strands are then loaded onto the particles.

The DNA is loaded onto the particles at a rate of between 0.5 and 30 micrograms of DNA per milligram of gold bead spheres. A preferable ratio of DNA to gold is 0.5 5.0 ug of DNA per milligram of gold. A sample procedure begins with gamma irradiated (preferably about 30 kGy) tefzel tubing. The gold is weighed out into a microfuge tube, spermidine (free base) at about 0.05 M is added and mixed, and then the DNA is added. A 10% CaCl solution is incubated along with the DNA for about 10 minutes to provide a fine calcium precipitate. The precipitate carries the DNA with it onto the beads. The tubes are microfuged and the pellet resuspended and washed in 100% ethanol and the final product resuspeded in 100% ethanol at 0.0025 mg/ml PVP. The gold with the DNA is then applied onto the tubing and dried.

The general approach of accelerated particle gene transfection technology is described in U.S. Pat. No. 4,945,050 to Sanford. An instrument based on an improved variant of that approach is available commercially from PowderJect Vaccines, Inc., Madison Wis., and is described in WO 95/19799. All documents cited herein supra and infra are hereby incorporated in their entirety by reference thereto. Briefly, the DNA-coated particles are deposited onto the interior surface of plastic tubing which is cut to a suitable length to form sample cartridges. A sample cartridge is placed in the path of a compressed gas (e.g., helium at a pressure sufficient to dislodge the particles from the cartridge e.g., 350 400 psi). The particles are entrained in the gas stream and are delivered with sufficient force toward the target tissue to enter the cells of the tissue. Further details are available in the published apparatus application.

The coated carrier particles are physically accelerated toward the cells to be transformed such that the carrier particles lodge in the interior of the target cells. This technique can be used either with cells in vitro or in vivo. At some frequency, the DNA which has been previously coated onto the carrier particles is expressed in the target cells. This gene expression technique has been demonstrated to work in prokaryotes and eukaryotes, from bacteria and yeasts to higher plants and animals. Thus, the accelerated particle method provides a convenient methodology for delivering genes into the cells of a wide variety of tissue types, and offers the capability of delivering those genes to cells in situ and in vivo without any adverse impact or effect on the treated individual. Therefore, the accelerated particle method is also preferred in that it allows a DNA vaccine capable of eliciting an immune response to be directed both to a particular tissue, and to a particular cell layer in a tissue, by varying the delivery site and the force with which the particles are accelerated, respectively. This technique is thus particularly suited for delivery of genes for antigenic proteins into the epidermis.

A DNA vaccine can be delivered in a non-invasive manner to a variety of susceptible tissue types in order to achieve the desired antigenic response in the individual. Most advantageously, the genetic vaccine can be introduced into the epidermis. Such delivery, it has been found, will produce a systemic humoral immune response.

To obtain additional effectiveness from this technique, it may also be desirable that the genes be delivered to a mucosal tissue surface, in order to ensure that mucosal, humoral and cellular immune responses are produced in the vaccinated individual. There are a variety of suitable delivery sites available including any number of sites on the epidermis, peripheral blood cells, i.e. lymphocytes, which could be treated in vitro and placed back into the individual, and a variety of oral, upper respiratory, and genital mucosal surfaces.

Gene gun-based DNA immunization achieves direct, intracellular delivery of DNA, elicits higher levels of protective immunity, and requires approximately three orders of magnitude less DNA than methods employing standard inoculation.

Moreover, gene gun delivery allows for precise control over the level and form of antigen production in a given epidermal site because intracellular DNA delivery can be controlled by systematically varying the number of particles delivered and the amount of DNA per particle. This precise control over the level and form of antigen production may allow for control over the nature of the resultant immune response.

The invention further covers passive vaccines for treating or preventing Sin Nombre virus infections comprising a therapeutically or prophylactically effective amount of the antibodies of the present invention which protect against Sin Nombre virus disease in combination with a pharmaceutically acceptable carrier or excipient. As described in greater detail herein, the present inventor has found that serum from a vaccinee immunized with a DNA vaccine comprising the Sin Nombre virus M segment described above contains antibodies able to neutralize Sin Nombre virus and display in vitro and in vivo Sin Nombre virus neutralization properties.

The invention also contemplates a new recombinant DNA vaccine approach that involves vaccination with naked DNA expressing individual Sin Nombre virus genome segment cDNAs. Naked DNA vaccination involves delivery of plasmid DNA constructs with a gene(s) of interest into the tissue of the vaccinee (reviewed in Robinson and Torres, 1997, *Semin. Immunol.* 9, 271-283; and Gregoriadis, 1998, *Pharm. Res.* 15, 661-670). DNA vaccination mimicks the de novo antigen production and MHC class I-restricted antigen presentation obtainable with live vaccines, without the risks of pathogenic infection. Also, this DNA vaccine approach allows delivery to mucosal tissues which may aid in conferring resistance to viral introduction since entry of the virus may be through mucosal tissues.

This vaccine was also tested for a capacity to elicit neutralizing antibodies in rabbits using muscle electroporation as the means of vaccine delivery. The electroporation device and dose of DNA delivered is compatible with human use (Ichor Tri-grid device). Well-known methods of electroporation are effective for this DNA vaccine. For instance, Hooper et al. (Feb. 2008), describes methods useful for this. (Hooper et al, "Immune Serum Produced by DNA Vaccination Protects Hamsters against Lethal Respiratory Challenge with Andes Virus", J. Virology, Feb. 2008, Vol. 82, No. 3, pp.1332-1338; also see, van Drunen, et al., Expert Rev. Vaccines, 2010, Vol. 9(5), pp.503-517). In addition, mammals such as rabbits can be vaccinated by muscle electroporation with a DNA vaccine plasmid such as pWRG/SN-M (opt) to rapidly generate sera containing high-titer SNV neutralizing antibodies. Sera can be collected and tested for neutralizing antibodies by PRNT.

Vaccination with the SNV M gene-based DNA vaccine, called pWRG/SN-M(opt), elicits high-titer neutralizing antibodies. It is widely believed in the field that neutralizing antibodies are surrogate endpoints of protective immunity, so any vaccine that elicits high-titer neutralizing antibodies has utility as a vaccine. This vaccine could be used to immunize against North American HPS. In addition, it could be combined with other hantavirus DNA vaccines to create a pan-hantavirus vaccine. In short, the plasmid containing the synthetic codon-optimized SNV M gene is exceedingly effective at eliciting neutralizing antibodies.

For a HPS vaccine composition or immunogenic composition, the composition will have at least one of the above-described SNV sequences (SEQ ID NO:1, SEQ ID NO:2 or SEQ ID NO:3), plus at least one other M-gene (e.g., whole full-length or ORF or ORF plus flanking sequences) from a different (non-SNV) HPS. Examples of other HPS viruses include Black Creek Canal virus, Bayou virus, New York virus, Andes virus, and Laguna Negra virus. A preferred HPS vaccine or immunogenic composition comprises at least one of the above-described SNV sequences, and the Andes M-gene—preferably plasmid pWRG/AND-M(x) (SEQ ID NO:10), below:

gggggggggg ggcgctgagg tctgcctcgt gaagaaggtg 40
ttgctgactc ataccaggcc tgaatcgccc catcatccag 80
ccagaaagtg agggagccac ggttgatgag agctttgttg 120
taggtggacc agttggtgat tttgaacttt tgctttgcca 160
cggaacggtc tgcgttgtcg ggaagatgcg tgatctgatc 200
cttcaactca gcaaaagttc gatttattca acaaagccgc 240
cgtcccgtca agtcagcgta atgctctgcc agtgttacaa 280
ccaattaacc aattctgatt agaaaaactc atcgagcatc 320
aaatgaaact gcaatttatt catatcagga ttatcaatac 360
catatttttg aaaaagccgt ttctgtaatg aaggagaaaa 400
ctcaccgagg cagttccata ggatggcaag atcctggtat 440
cggtctgcga ttccgactcg tccaacatca atacaaccta 480

-continued ttaatttccc ctcgtcaaaa ataaggttat caagtgagaa 520
atcaccatga gtgacgactg aatccggtga gaatggcaaa 560
agcttatgca tttctttcca gacttgttca acaggccagc 600
cattacgctc gtcatcaaaa tcactcgcat caaccaaacc 640
gttattcatt cgtgattgcg cctgagcgag acgaaatacg 680
cgatcgctgt taaaaggaca attacaaaca ggaatcgaat 720
gcaaccggcg caggaacact gccagcgcat caacaatatt 760
ttcacctgaa tcaggatatt cttctaatac ctggaatgct 800
gttttcccgg ggatcgcagt ggtgagtaac catgcatcat 840
caggagtacg gataaaatgc ttgatggtcg gaagaggcat 880
aaattccgtc agccagttta gtctgaccat ctcatctgta 920
acatcattgg caacgctacc tttgccatgt ttcagaaaca 960
actctggcgc atcgggcttc ccatacaatc gatagattgt 1000
cgcacctgat tgcccgacat tatcgcgagc ccatttatac 1040
ccatataaat cagcatccat gttggaattt aatcgcggcc 1080
tcgagcaaga cgtttcccgt tgaatatggc tcataacacc 1120
ccttgtatta ctgtttatgt aagcagacag ttttattgtt 1160
catgatgata tatttttatc ttgtgcaatg taacatcaga 1200
gattttgaga cacaacgtgg ctttcccccc ccccccggca 1240
tgcctgcagg tcgacaatat tggctattgg ccattgcata 1280
cgttgtatct atatcataat atgtacattt atattggctc 1320
atgtccaata tgaccgccat gttgacattg attattgact 1360
agttattaat agtaatcaat tacggggtca ttagttcata 1400
gcccatatat ggagttccgc gttacataac ttacggtaaa 1440
tggcccgcct ggctgaccgc ccaacgaccc ccgcccattg 1480
acgtcaataa tgacgtatgt tcccatagta acgccaatag 1520
ggactttcca ttgacgtcaa tgggtggagt atttacggta 1560
aactgcccac ttggcagtac atcaagtgta tcatatgcca 1600
agtccgcccc ctattgacgt caatgacggt aaatggcccg 1640
cctggcatta tgcccagtac atgaccttac gggactttcc 1680
tacttggcag tacatctacg tattagtcat cgctattacc 1720
atggtgatgc ggttttggca gtacaccaat gggcgtggat 1760
agcggtttga ctcacgggga tttccaagtc tccaccccat 1800
tgacgtcaat gggagtttgt tttggcacca aaatcaacgg 1840
gactttccaa aatgtcgtaa taaccccgcc ccgttgacgc 1880
aaatgggcgg taggcgtgta cggtgggagg tctatataag 1920
cagagctcgt ttagtgaacc gtcagatcgc ctggagacgc 1960
catccacgct gttttgacct ccatagaaga caccgggacc 2000
gatccagcct ccgcggccgg gaacggtgca ttggaacgcg 2040
gattccccgt gccaagagtg acgtaagtac cgcctataga 2080

-continued

```
ctctataggc acaccccttt ggctcttatg catgctatac     2120
tgtttttggc ttggggccta tacacccccg cttccttatg     2160
ctataggtga tggtatagct tagcctatag gtgtgggtta     2200
ttgaccatta ttgaccactc ccctattggt gacgatactt     2240
tccattacta atccataaca tggctctttg ccacaactat     2280
ctctattggc tatatgccaa tactctgtcc ttcagagact     2320
gacacggact ctgtattttt acaggatggg gtcccattta     2360
ttatttacaa attcacatat acaacaacgc cgtcccccgt     2400
gcccgcagtt tttattaaac atagcgtggg atctccacgc     2440
gaatctcggg tacgtgttcc ggacatgggc tcttctccgg     2480
tagcggcgga gcttccacat ccgagccctg gtcccatgcc     2520
tccagcggct catggtcgct cggcagctcc ttgctcctaa     2560
cagtggaggc cagacttagg cacagcacaa tgcccaccac     2600
caccagtgtg ccgcacaagg ccgtggcggt agggtatgtg     2640
tctgaaaatg agctcggaga ttgggctcgc accgctgacg     2680
cagatggaag acttaaggca gcggcagaag aagatgcagg     2720
cagctgagtt gttgtattct gataagagtc agaggtaact     2760
cccgttgcgg tgctgttaac ggtggagggc agtgtagtct     2800
gagcagtact cgttgctgcc gcgcgcgcca ccagacataa     2840
tagctgacag actaacagac tgttcctttc catgggtctt     2880
ttctgcagtc agggtccaag cttgcggccg cggatctgca     2920
ggaattcggc acgagagtag tagactccgc acgaagaagc     2960
aaaaaattaa agaagtgagt ttaaaatgga agggtggtat     3000
ctggttgttc ttggagtctg ctatacgctg acactggcaa     3040
tgcccaagac catttatgag cttaaaatgg aatgcccgca     3080
cactgtgggt ctcggtcaag gttacatcat tggctcaaca     3120
gaactaggtt tgatctcaat tgaggctgca tctgatataa     3160
agctcgagag ctcttgcaat tttgatcttc atacaacatc     3200
tatggcccag aagagtttca cccaagttga atggagaaag     3240
aaaagtgaca caactgatac cacaaatgct gcgtccacta     3280
cctttgaagc acaaactaaa actgttaacc ttagagggac     3320
ttgtatactg gcacctgaac tctatgatac attgaagaaa     3360
gtaaaaaaga cagtcctgtg ctatgatcta acatgtaatc     3400
aaacacattg tcagccaact gtctatctga ttgcacctgt     3440
attgacatgc atgtcaataa gaagttgtat ggctagtgtg     3480
tttacaagca ggattcaggt gatttatgaa aagacacatt     3520
gtgtaacagg tcagctgatt gagggtcagt gtttcaaccc     3560
agcacacaca ttgacattat ctcagcctgc tcacacttat     3600
gatactgtca cccttcctat ctcttgtttt ttcacaccaa     3640
agaagtcgga gcaactaaaa gttataaaaa catttgaagg     3680
aattctgacg aagacaggtt gcacggagaa tgcattgcag     3720
```

-continued

```
ggttattatg tgtgtttttt agggagtcat tcagaacctt     3760
taattgttcc gagtttggag gacatacggt ctgctgaagt     3800
tgttagtagg atgcttgtac accctagggg agaagaccat     3840
gatgccatac agaattcaca aagtcactta agaatagtgg     3880
gacctatcac agcaaaagtg ccatcaacta gttccacaga     3920
taccctaaag gggacagcct ttgcaggcgt cccaatgtat     3960
agctctttat ctacactagt cagaaatgca gacccagaat     4000
ttgtattttc tccaggtata gtacctgaat ctaatcacag     4040
tacatgtgat aagaagacag tacctatcac atggacaggc     4080
tacctaccaa tatcaggtga gatggaaaaa gtgactggat     4120
gtacagtttt ttgtacacta gcaggacctg gtgctagttg     4160
tgaggcctat tctgaaaatg gtatatttaa catcagttct     4200
ccaacatgtc ttgtaaacaa agtccaaaga tttcgtggat     4240
ctgaacagaa aataaatttt atctgtcagc gggtagatca     4280
ggatgttgtt gtatactgca atgggcaaaa gaaagtcata     4320
ttaaccaaaa ctttggttat tgggcagtgt atttatacat     4360
tcacaagcct attttcattg atgcctgatg tagcccactc     4400
attggctgta gaattatgtg tcccgggatt acatgggtgg     4440
gccactgtca tgcttctatc aacattctgc tttgggtggg     4480
tcttgattcc tgcggtcaca ttaataatat taaagtgtct     4520
aagggttttg acgttttctt gttcccatta cactaatgag     4560
tcaaaattta aattcatcct ggaaaaagtt aaaattgaat     4600
accaaaagac tatgggatca atggtgtgcg atgtatgtca     4640
tcatgagtgt gaaacagcaa aagaacttga atcacataga     4680
cagagttgta tcaatggaca atgtccttat tgcatgacaa     4720
taactgaagc aactgaaagt gccttgcaag cccattattc     4760
catttgtaaa ttggcaggaa gatttcagga ggcactgaaa     4800
aagtcactta aaaagccaga ggtaaaaaaa ggttgttaca     4840
gaacactcgg ggtatttaga tataaaagta gatgttatgt     4880
gggtttggta tggtgcctat tgttgacatg tgaaattgtt     4920
atttgggccg caagtgcaga gactccacta atggagtcag     4960
gctggtcaga tacggctcat ggtgttggtg agattccaat     5000
gaagacagac ctcgagctgg acttttcact gccttcttca     5040
tcctcttaca gttataggag aaagctcaca aacccagcca     5080
ataaagaaga gtctattccc ttccacttcc agatggaaaa     5120
acaagtaatt catgctgaaa tccaacccct gggtcattgg     5160
atggatgcga catttaatat taagactgca tttcattgtt     5200
atggtgcatg ccagaaatac tcttatccat ggcagacatc     5240
taagtgcttc tttgaaaagg actaccagta tgaaacaggc     5280
tggggctgta atcctggtga ctgcccaggg gttgggactg     5320
```

-continued

```
gatgcactgc ttgtggtgtt tatctcgata aactaaaatc     5360
tgttgggaag gcctataaga taatttcttt aaaatatacc     5400
agaaaggttt gtattcagtt aggaacagaa caaacttgca     5440
agcatattga tgcaaatgat tgtttagtga caccatctgt     5480
gaaagtttgc atagtgggca cagtttcaaa acttcaacca     5520
tctgatactc ttttgttctt aggtccacta gaacaagggg     5560
gaatcattct taagcaatgg tgcacaacat catgtgcatt     5600
tggggaccct ggtgatatca tgtccactcc cagtggtatg     5640
aggtgtccag agcacactgg atcatttagg aaaatttgcg     5680
gttttgctac tacaccagtt tgtgaatatc aaggaaatac     5720
catttctgga tataaaagaa tgatggcaac aaaagattca     5760
ttccaatcat ttaacttaac agaacctcac atcacaacaa     5800
acaagcttga atggatcgac ccagatggga atacaagaga     5840
ccacgtaaac cttgtcttaa atagagatgt ctcatttcag     5880
gatttaagtg ataacccctg taaagtagac ctacacacac     5920
aagcaataga aggggcatgg ggttctggtg tagggtttac     5960
actcacatgt actgtcggat taacagagtg cccaagtttt     6000
atgacatcaa ttaaggcatg tgacctagct atgtgttatg     6040
gatcaacagt aacaaacctt gccaggggct ctaatacagt     6080
gaaagtagtt ggtaaaggag gccattcagg gtcctcattt     6120
aaatgctgtc atgatacaga ttgctcctct gaaggtttac     6160
ttgcatcagc ccctcatctt gagagggtaa caggattcaa     6200
tcaaattgat tcagataagg tttatgatga tggtgcacca     6240
ccttgcacat tcaaatgctg gttcactaag tcaggtgagt     6280
ggcttcttgg gatcttaaac gggaattgga ttgttgttgt     6320
agtgcttgtt gtgatactca ttctctctat cataatgttc     6360
agtgttttgt gtcccaggag agggcacaag aaaactgtct     6400
aagcattgac ctcaactcct acattagatc atatacattt     6440
atgcacttcc tcatatttag ctgcactaag atattaataa     6480
actctagtta ttgactttat aagattatta tggaactaac     6520
ctcacttaaa aaaaacaaat actttactca tatataactc     6560
catattctct taccgaggat tttgttcctg cggagcatac     6600
tactaggatc tacgtatgat cagcctcgac tgtgccttct     6640
agttgccagc catctgttgt ttgcccctcc cccgtgcctt     6680
ccttgaccct ggaaggtgcc actcccactg tcctttccta     6720
ataaaatgag gaaattgcat cgcattgtct gagtaggtgt     6760
cattctattc tggggggtgg ggtggggcag gacagcaagg     6800
gggaggattg ggaagacaat agcaggcatg ctggggatgc     6840
ggtgggctct atggcttctg aggcggaaag aaccagctgg     6880
ggctcgacag ctcgactcta gaattgcttc ctcgctcact     6920
gactcgctgc gctcggtcgt tcggctgcgg cgagcggtat     6960
```

-continued

```
cagctcactc aaaggcggta atacggttat ccacagaatc     7000
aggggataac gcaggaaaga acatgtgagc aaaaggccag     7040
caaaaggcca ggaaccgtaa aaaggccgcg ttgctggcgt     7080
ttttccatag gctccgcccc cctgacgagc atcacaaaaa     7120
tcgacgctca agtcagaggt ggcgaaaccc gacaggacta     7160
taaagatacc aggcgtttcc ccctggaagc tccctcgtgc     7200
gctctcctgt tccgaccctg ccgcttaccg gatacctgtc     7240
cgcctttctc ccttcgggaa gcgtggcgct ttctcatagc     7280
tcacgctgta ggtatctcag ttcggtgtag gtcgttcgct     7320
ccaagctggg ctgtgtgcac gaaccccccg ttcagcccga     7360
ccgctgcgcc ttatccggta actatcgtct tgagtccaac     7400
ccggtaagac acgacttatc gccactggca gcagccactg     7440
gtaacaggat tagcagagcg aggtatgtag gcggtgctac     7480
agagttcttg aagtggtggc ctaactacgg ctacactaga     7520
agaacagtat ttggtatctg cgctctgctg aagccagtta     7560
ccttcgaaaa aagagttggt agctcttgat ccggcaaaca     7600
aaccaccgct ggtagcggtg gtttttttgt ttgcaagcag     7640
cagattacgc gcagaaaaaa aggatctcaa gaagatcctt     7680
tgatcttttc tacggggtct gacgctcagt ggaacgaaaa     7720
ctcacgttaa gggattttgg tcatgagatt atcaaaaagg     7760
atcttcacct agatcctttt aaattaaaaa tgaagtttta     7800
aatcaatcta aagtatatat gagtaaactt ggtctgacag     7840
ttaccaatgc ttaatcagtg aggcacctat ctcagcgatc     7880
tgtctatttc gttcatccat agttgcctga ctc            7913
```

For a HPS+HFRS, or pan-hantavirus, vaccine composition or immunogenic composition, the composition will have at least one of the above-described SNV sequences (SEQ ID NO:1, SEQ ID NO:2 or SEQ ID NO:3), plus at least one other M-gene (e.g., whole full-length or ORF or ORF plus flanking sequences) from an HFRS virus. Examples of HFRS viruses include Seoul virus, Hantaan virus, Pumuula virus, and Dobrava virus. In addition, the vaccine composition or immunogenic composition may further include one or more of the above-described other HPS M-genes (e.g., whole full-length or ORF or ORF plus flanking sequences). A preferred HPS+HFRS vaccine or immunogenic composition comprises at least one of the above-described SNV sequences, and one or more of Puumala M-gene plasmid (preferably plasmid pWRG/PUU-M (s2) shown below as SEQ ID NO:11 or the ORF shown below as SEQ ID NO:14), Hantaan M-gene plasmid (preferably plasmid pWRG/HTN-M(x) shown below as SEQ ID NO:12), and Seoul (preferably plasmid pWRG-SEO-M which is Seoul hantavirus M segment, strain SR-11, subcloned into DNA vector pWRG7077, and shown below as SEQ ID NO:13).

pWRG/PUU-M(s2) DNA vaccine plasmid
(the underlined section indicates the ORF)

(SEQ ID NO: 11)

GGGGGGGGGGGGCGCTGAGGTCTGCCTCGTGAAGAAGGTGTTGCTGAC

TCATACCAGGCCTGAATCGCCCCATCATCCAGCCAGAAAGTGAGGGAG

CCACGGTTGATGAGAGCTTTGTTGTAGGTGGACCAGTTGGTGATTTTG

AACTTTTGCTTTGCCACGGAACGGTCTGCGTTGTCGGGAAGATGCGTG

ATCTGATCCTTCAACTCAGCAAAAGTTCGATTTATTCAACAAAGCCGC

CGTCCCGTCAAGTCAGCGTAATGCTCTGCCAGTGTTACAACCAATTAA

CCAATTCTGATTAGAAAAACTCATCGAGCATCAAATGAAACTGCAATT

TATTCATATCAGGATTATCAATACCATATTTTTGAAAAAGCCGTTTCT

GTAATGAAGGAGAAAACTCACCGAGGCAGTTCCATAGGATGGCAAGAT

CCTGGTATCGGTCTGCGATTCCGACTCGTCCAACATCAATACAACCTA

TTAATTTCCCCTCGTCAAAAATAAGGTTATCAAGTGAGAAATCACCAT

GAGTGACGACTGAATCCGGTGAGAATGGCAAAAGCTTATGCATTTCTT

TCCAGACTTGTTCAACAGGCCAGCCATTACGCTCGTCATCAAAATCAC

TCGCATCAACCAAACCGTTATTCATTCGTGATTGCGCCTGAGCGAGAC

GAAATACGCGATCGCTGTTAAAAGGACAATTACAAACAGGAATCGAAT

GCAACCGGCGCAGGAACACTGCCAGCGCATCAACAATATTTTCACCTG

AATCAGGATATTCTTCTAATACCTGGAATGCTGTTTTCCCGGGGATCG

CAGTGGTGAGTAACCATGCATCATCAGGAGTACGGATAAAATGCTTGA

TGGTCGGAAGAGGCATAAATTCCGTCAGCCAGTTTAGTCTGACCATCT

CATCTGTAACATCATTGGCAACGCTACCTTTGCCATGTTTCAGAAACA

ACTCTGGCGCATCGGGCTTCCCATACAATCGATAGATTGTCGCACCTG

ATTGCCCGACATTATCGCGAGCCCATTTATACCCATATAAATCAGCAT

CCATGTTGGAATTTAATCGCGGCCTCGAGCAAGACGTTTCCCGTTGAA

TATGGCTCATAACACCCCTTGTATTACTGTTTATGTAAGCAGACAGTT

TTATTGTTCATGATGATATATTTTTATCTTGTGCAATGTAACATCAGA

GATTTTGAGACACAACGTGGCTTTCCCCCCCCCCCCGGCATGCCTGCA

GGTCGACAATATTGGCTATTGGCCATTGCATACGTTGTATCTATATCA

TAATATGTACATTTATATTGGCTCATGTCCAATATGACCGCCATGTTG

ACATTGATTATTGACTAGTTATTAATAGTAATCAATTACGGGGTCATT

AGTTCATAGCCCATATATGGAGTTCCGCGTTACATAACTTACGGTAAA

TGGCCCGCCTGGCTGACCGCCCAACGACCCCCGCCCATTGACGTCAAT

AATGACGTATGTTCCCATAGTAACGCCAATAGGGACTTTCCATTGACG

TCAATGGGTGGAGTATTTACGGTAAACTGCCCACTTGGCAGTACATCA

AGTGTATCATATGCCAAGTCCGCCCCCTATTGACGTCAATGACGGTAA

ATGGCCCGCCTGGCATTATGCCCAGTACATGACCTTACGGGACTTTCC

TACTTGGCAGTACATCTACGTATTAGTCATCGCTATTACCATGGTGAT

GCGGTTTTGGCAGTACACCAATGGGCGTGGATAGCGGTTTGACTCACG

GGGATTTCCAAGTCTCCACCCCATTGACGTCAATGGGAGTTTGTTTTG

GCACCAAAATCAACGGGACTTTCCAAAATGTCGTAATAACCCCGCCCC

-continued

GTTGACGCAAATGGGCGGTAGGCGTGTACGGTGGGAGGTCTATATAAG

CAGAGCTCGTTTAGTGAACCGTCAGATCGCCTGGAGACGCCATCCACG

CTGTTTTGACCTCCATAGAAGACACCGGGACCGATCCAGCCTCCGCGG

CCGGGAACGGTGCATTGGAACGCGGATTCCCCGTGCCAAGAGTGACGT

AAGTACCGCCTATAGACTCTATAGGCACACCCCTTTGGCTCTTATGCA

TGCTATACTGTTTTTGGCTTGGGGCCTATACACCCCCGCTTCCTTATG

CTATAGGTGATGGTATAGCTTAGCCTATAGGTGTGGGTTATTGACCAT

TATTGACCACTCCCCTATTGGTGACGATACTTTCCATTACTAATCCAT

AACATGGCTCTTTGCCACAACTATCTCTATTGGCTATATGCCAATACT

CTGTCCTTCAGAGACTGACACGGACTCTGTATTTTTACAGGATGGGGT

CCCATTTATTATTTACAAATTCACATATACAACAACGCCGTCCCCCGT

GCCCGCAGTTTTTATTAAACATAGCGTGGGATCTCCACGCGAATCTCG

GGTACGTGTTCCGGACATGGGCTCTTCTCCGGTAGCGGCGGAGCTTCC

ACATCCGAGCCCTGGTCCCATGCCTCCAGCGGCTCATGGTCGCTCGGC

AGCTCCTTGCTCCTAACAGTGGAGGCCAGACTTAGGCACAGCACAATG

CCCACCACCACCAGTGTGCCGCACAAGGCCGTGGCGGTAGGGTATGTG

TCTGAAAATGAGCTCGGAGATTGGGCTCGCACCGCTGACGCAGATGGA

AGACTTAAGGCAGCGGCAGAAGAAGATGCAGGCAGCTGAGTTGTTGTA

TTCTGATAAGAGTCAGAGGTAACTCCCGTTGCGGTGCTGTTAACGGTG

GAGGGCAGTGTAGTCTGAGCAGTACTCGTTGCTGCCGCGCGCGCCACC

AGACATAATAGCTGACAGACTAACAGACTGTTCCTTTCCATGGGTCTT

TTCTGCAGTCACCGTCCAAGCTTGCGGCCGCGGATCTGCAGGAATTCG

GCACGAGAGTAGTAGACTCCGCAAGAAACAGCAAACACAGATAAATAT

GGGCGAGCTGTCCCCTGTGTGCCTGTACCTGCTGCTGCAGGGCCTGCT

GCTGTGTAACACCGGAGCCGCCAGGAACCTGAACGAGCTGAAGATGGA

GTGCCCCCACACCATCAGACTGGGCCAGGGCCTGGTGGTGGGCAGCGT

GGAGCTGCCCAGCCTGCCCATCCAGCAGGTGGAGACCCTGAAGCTGGA

GAGCAGCTGTAACTTCGACCTGCACACCAGCACAGCCGGCCAGCAGAG

CTTCACCAAGTGGACCTGGGAGATCAAGGGCGACCTGGCCGAGAACAC

CCAGGCCAGCAGCACCAGCTTCCAGACCAAGAGCAGCGAGGTGAACCT

GAGAGGCCTGTGCCTGATCCCCACACTGGTGGTGGAGACCGCCGCCAG

AATGAGAAAGACCATCGCCTGCTACGACCTGAGCTGTAACCAGACCGT

GTGTCAGCCTACCGTGTACCTGATGGGCCCTATCCAGACCTGTATCAC

CACCAAGAGCTGCCTGCTGTCCCTGGGCGATCAGAGAATCCAGGTGAA

CTACGAGAAAACCTACTGTGTGAGCGGCCAGCTGGTGGAGGGCATCTG

CTTCAACCCCATCCACACCATGGCCCTGAGCCAGCCTAGCCACACCTA

CGACATCATGACCATGATGGTGAGATGCTTTCTGGTGATCAAGAAGGT

GACCAGCGGCGACAGCATGAAGATCGAGAAGAACTTCGAGACCCTGGT

GCAGAAGAATGGCTGTACCGCCAACAACTTCCAGGGCTACTACATCTG

CCTGATCGGCAGCAGCAGCGAGCCCCTGTACGTGCCCGCCCTGGACGA

CTACAGAAGCGCCGAGGTGCTGTCCAGAATGGCCTTCGCCCCCCACGG

-continued

CGAGGACCACGACATCGAGAAAAACGCCGTGTCCGCCATGAGAATCGC

CGGCAAGGTGACCGGCAAGGCCCCCAGCACCGAGTCCAGCGACACCGT

GCAGGGCATCGCCTTCAGCGGCAGCCCCCTGTACACCTCCACCGGCGT

GCTGACCAGCAAGGACGACCCCGTGTACATCTGGGCCCCTGGCATCAT

CATGGAGGGCAACCACAGCATCTGTGAGAAGAAAACCCTGCCCCTGAC

CTGGACCGGCTTCATCAGCCTGCCCGGCGAGATCGAGAAAACCACCCA

GTGTACCGTGTTCTGTACCCTGGCCGGACCTGGCGCCGACTGTGAGGC

CTACAGCGAGACCGGCATCTTCAACATCAGCAGCCCCACCTGCCTGAT

CAACCGGGTGCAGAGGTTCAGAGGCAGCGAGCAGCAGATCAAGTTTGT

GTGCCAGCGGGTGGACATGGACATCACCGTGTACTGTAACGGCATGAA

GAAGGTGATCCTGACCAAGACACTGGTGATCGGCCAGTGTATCTACAC

CTTCACCAGCATCTTCTCCCTGATCCCCGGCGTGGCCCACAGCCTGGC

CGTGGAGCTGTGTGTGCCCGGCCTGCACGGCTGGGCCACCATGCTGCT

GCTGCTGACCTTCTGCTTCGGCTGGGTGCTGATCCCTACCATCACCAT

GATCCTGCTGAAGATCCTGATCGCCTTCGCCTACCTGTGCTCCAAGTA

CAACACCGACAGCAAGTTCAGAATCCTGATCGAGAAAGTGAAGCGGGA

GTACCAGAAAACCATGGGCAGCATGGTGTGTGAAGTGTGCCAGTACGA

GTGTGAGACCGCCAAGGAGCTGGAGTCCCACAGAAAGAGCTGCTCCAT

CGGCAGCTGCCCCTACTGCCTGAACCCCAGCGAGGCCACCACCTCCGC

CCTGCAGGCCCACTTCAAAGTGTGTAAGCTGACCAGCCGGTTCCAGGA

GAACCTGAGGAAGTCCCTGACCGTGTACGAGCCCATGCAGGGCTGCTA

CAGAACCCTGAGCCTGTTCCGGTACAGGAGCCGGTTCTTTGTGGGCCT

GGTGTGGTGTGTGCTGCTGGTGCTGGAGCTGATTGTGTGGGCCGCCAG

CGCCGAGACCCAGAACCTGAATGCCGGCTGGACCGACACCGCCCACGG

CAGCGGCATCATCCCCATGAAAACCGACCTGGAGCTGGACTTCAGCCT

GCCTAGCAGCGCCTCCTACACCTACAGGCGGCAGCTGCAGAATCCTGC

CAACGAGCAGGAGAAGATCCCCTTCCACCTGCAGCTGTCCAAGCAGGT

GATCCACGCCGAGATTCAGCACCTGGGCCACTGGATGGACGCCACCTT

CAACCTGAAAACCGCCTTCCACTGCTACGGCAGCTGTGAGAAGTACGC

CTACCCTTGGCAGACCGCCGGCTGCTTCATCGAGAAGGACTACGAGTA

CGAGACCGGCTGGGGCTGTAATCCTCCTGATTGCCCCGGAGTGGGCAC

CGGCTGTACTGCATGTGGCGTGTACCTGGACAAGCTGAAGTCTGTGGG

CAAGGTGTTCAAGATCGTGTCCCTGAGGTACACCCGGAAAGTGTGTAT

CCAGCTGGGCACCGAGCAGACCTGTAAGACCGTGGACAGCAACGATTG

CCTGATCACAACCAGCGTGAAAGTGTGTCTGATCGGCACCATCAGCAA

GTTCCAGCCCAGCGATACCCTGCTGTTTCTGGGCCCCCTGCAGCAGGG

CGGCCTGATCTTCAAGCAGTGGTGTACCACCACCTGCCAGTTCGGCGA

TCCCGGCGATATCATGAGCACCCCCACCGGCATGAAGTGCCCTGAGCT

GAACGGCAGCTTCCGGAAGAAGTGTGCCTTCGCCACCACCCCTGTGTG

TCAGTTCGACGGCAACACCATCAGCGGCTACAAGCGGATGATCGCCAC

-continued

CAAGGACAGCTTCCAGTCCTTCAACGTGACCGAGCCCCACATCAGCAC

CAGCGCCCTGGAGTGGATCGATCCCGACAGCAGCCTGAGGGACCACAT

CAACGTGATCGTGTCCAGGGACCTGAGCTTCCAGGACCTGAGCGAGAC

CCCCTGCCAGATCGACCTGGCCACCGCCAGCATCGATGGCGCCTGGGG

CAGCGGAGTGGGCTTCAACCTGGTGTGTACAGTGAGCCTGACCGAGTG

TAGCGCCTTCCTGACCAGCATCAAAGCCTGTGACGCCGCCATGTGTTA

CGGCAGCACCACCGCCAACCTGGTGAGAGGCCAGAACACCATCCACAT

TGTGGGCAAAGGCGGCCACAGCGGCAGCAAGTTTATGTGCTGCCACGA

CACCAAGTGTAGCAGCACCGGCCTGGTGGCCGCTGCCCCCCACCTGGA

CAGAGTGACCGGCTACAACCAGGCCGACAGCGACAAGATTTTCGACGA

CGGAGCCCCTGAGTGTGGCATGAGTTGCTGGTTCAAGAAGAGCGGCGA

GTGGATTCTGGGCGTGCTGAACGGGAATTGGATGGTGGTGGCCGTGCT

GGTCGTGCTGCTGATCCTGAGCATCCTGCTGTTCACCCTGTGCTGCCC

TAGGAGACCCAGCTACCGGAAGGAGCACAAGCCCTGAGTTTTGCTTAC

TAACATAATTATTGTATTCTGTTTATTGACACAATTACCATATGATTA

ACTGTATTCCCCCATCTTATATCTTATATAATATTCTTTATTTAATCA

CTATATAGAAAAAAAACTAGCACTTTACTAATTAAATTACCCCATACC

GATTATGCCTGGACTTTTGTTCCTGCGGAGCATACTACTAGGATCTAC

GTATGATCAGCCTCGACTGTGCCTTCTAGTTGCCAGCCATCTGTTGTT

TGCCCCTCCCCCGTGCCTTCCTTGACCCTGGAAGGTGCCACTCCCACT

GTCCTTTCCTAATAAAATGAGGAAATTGCATCGCATTGTCTGAGTAGG

TGTCATTCTATTCTGGGGGGTGGGGTGGGGCAGGACAGCAAGGGGGAG

GATTGGGAAGACAATAGCAGGCATGCTGGGGATGCGGTGGGCTCTATG

GCTTCTGAGGCGGAAAGAACCAGCTGGGGCTCGACAGCTCGACTCTAG

AATTGCTTCCTCGCTCACTGACTCGCTGCGCTCGGTCGTTCGGCTGCG

GCGAGCGGTATCAGCTCACTCAAAGGCGGTAATACGGTTATCCACAGA

ATCAGGGGATAACGCAGGAAAGAACATGTGAGCAAAAGGCCAGCAAAA

GGCCAGGAACCGTAAAAAGGCCGCGTTGCTGGCGTTTTTCCATAGGCT

CCGCCCCCCTGACGAGCATCACAAAAATCGACGCTCAAGTCAGAGGTG

GCGAAACCCGACAGGACTATAAAGATACCAGGCGTTTCCCCCTGGAAG

CTCCCTCGTGCGCTCTCCTGTTCCGACCCTGCCGCTTACCGGATACCT

GTCCGCCTTTCTCCCTTCGGGAAGCGTGGCGCTTTCTCATAGCTCACG

CTGTAGGTATCTCAGTTCGGTGTAGGTCGTTCGCTCCAAGCTGGGCTG

TGTGCACGAACCCCCCGTTCAGCCCGACCGCTGCGCCTTATCCGGTAA

CTATCGTCTTGAGTCCAACCCGGTAAGACACGACTTATCGCCACTGGC

AGCAGCCACTGGTAACAGGATTAGCAGAGCGAGGTATGTAGGCGGTGC

TACAGAGTTCTTGAAGTGGTGGCCTAACTACGGCTACACTAGAAGAAC

AGTATTTGGTATCTGCGCTCTGCTGAAGCCAGTTACCTTCGGAAAAAG

AGTTGGTAGCTCTTGATCCGGCAAACAAACCACCGCTGGTAGCGGTGG

TTTTTTTGTTTGCAAGCAGCAGATTACGCGCAGAAAAAAAGGATCTCA

AGAAGATCCTTTGATCTTTTCTACGGGGTCTGACGCTCAGTGGAACGA

-continued

AAACTCACGTTAAGGGATTTTGGTCATGAGATTATCAAAAAGGATCTT

CACCTAGATCCTTTTAAATTAAAAATGAAGTTTTAAATCAATCTAAAG

TATATATGAGTAAACTTGGTCTGACAGTTACCAATGCTTAATCAGTGA

GGCACCTATCTCAGCGATCTGTCTATTTCGTTCATCCATAGTTGCCTG

ACTC

Puumala synthetic full-length M-segment ORF

SEQ ID NO: 14

ATGGGCGAGCTGTCCCCTGTGTGCCTGTACCTGCTGCTGCAGGGCCTG

CTGCTGTGTAACACCGGAGCCGCCAGGAACCTGAACGAGCTGAAGATG

GAGTGCCCCCACACCATCAGACTGGGCCAGGGCCTGGTGGTGGGCAGC

GTGGAGCTGCCCAGCCTGCCCATCCAGCAGGTGGAGACCCTGAAGCTG

GAGAGCAGCTGTAACTTCGACCTGCACACCAGCACAGCCGGCCAGCAG

AGCTTCACCAAGTGGACCTGGGAGATCAAGGGCGACCTGGCCGAGAAC

ACCCAGGCCAGCAGCACCAGCTTCCAGACCAAGAGCAGCGAGGTGAAC

CTGAGAGGCCTGTGCCTGATCCCCACACTGGTGGTGGAGACCGCCGCC

AGAATGAGAAAGACCATCGCCTGCTACGACCTGAGCTGTAACCAGACC

GTGTGTCAGCCTACCGTGTACCTGATGGGCCCTATCCAGACCTGTATC

ACCACCAAGAGCTGCCTGCTGTCCCTGGGCGATCAGAGAATCCAGGTG

AACTACGAGAAAACCTACTGTGTGAGCGGCCAGCTGGTGGAGGGCATC

TGCTTCAACCCCATCCACACCATGGCCCTGAGCCAGCCTAGCCACACC

TACGACATCATGACCATGATGGTGAGATGCTTTCTGGTGATCAAGAAG

GTGACCAGCGGCGACAGCATGAAGATCGAGAAGAACTTCGAGACCCTG

GTGCAGAAGAATGGCTGTACCGCCAACAACTTCCAGGGCTACTACATC

TGCCTGATCGGCAGCAGCAGCGAGCCCCTGTACGTGCCCGCCCTGGAC

GACTACAGAAGCGCCGAGGTGCTGTCCAGAATGGCCTTCGCCCCCCAC

GGCGAGGACCACGACATCGAGAAAAACGCCGTGTCCGCCATGAGAATC

GCCGGCAAGGTGACCGGCAAGGCCCCCAGCACCGAGTCCAGCGACACC

GTGCAGGGCATCGCCTTCAGCGGCAGCCCCCTGTACACCTCCACCGGC

GTGCTGACCAGCAAGGACGACCCCGTGTACATCTGGGCCCCTGGCATC

ATCATGGAGGGCAACCACAGCATCTGTGAGAAGAAAACCCTGCCCCTG

ACCTGGACCGGCTTCATCAGCCTGCCCGGCGAGATCGAGAAAACCACC

CAGTGTACCGTGTTCTGTACCCTGGCCGGACCTGGCGCCGACTGTGAG

GCCTACAGCGAGACCGGCATCTTCAACATCAGCAGCCCCACCTGCCTG

ATCAACCGGGTGCAGAGGTTCAGAGGCAGCGAGCAGCAGATCAAGTTT

GTGTGCCAGCGGGTGGACATGGACATCACCGTGTACTGTAACGGCATG

AAGAAGGTGATCCTGACCAAGACACTGGTGATCGGCCAGTGTATCTAC

ACCTTCACCAGCATCTTCTCCCTGATCCCCGGCGTGGCCCACAGCCTG

GCCGTGGAGCTGTGTGTGCCCGGCCTGCACGGCTGGGCCACCATGCTG

CTGCTGCTGACCTTCTGCTTCGGCTGGGTGCTGATCCCTACCATCACC

ATGATCCTGCTGAAGATCCTGATCGCCTTCGCCTACCTGTGCTCCAAG

TACAACACCGACAGCAAGTTCAGAATCCTGATCGAGAAAGTGAAGCGG

-continued

GAGTACCAGAAAACCATGGGCAGCATGGTGTGTGAAGTGTGCCAGTAC

GAGTGTGAGACCGCCAAGGAGCTGGAGTCCCACAGAAAGAGCTGCTCC

ATCGGCAGCTGCCCCTACTGCCTGAACCCCAGCGAGGCCACCACCTCC

GCCCTGCAGGCCCACTTCAAAGTGTGTAAGCTGACCAGCCGGTTCCAG

GAGAACCTGAGGAAGTCCCTGACCGTGTACGAGCCCATGCAGGGCTGC

TACAGAACCCTGAGCCTGTTCCGGTACAGGAGCCGGTTCTTTGTGGGC

CTGGTGTGGTGTGTGCTGCTGGTGCTGGAGCTGATTGTGTGGGCCGCC

AGCGCCGAGACCCAGAACCTGAATGCCGGCTGGACCGACACCGCCCAC

GGCAGCGGCATCATCCCCATGAAAACCGACCTGGAGCTGGACTTCAGC

CTGCCTAGCAGCGCCTCCTACACCTACAGGCGGCAGCTGCAGAATCCT

GCCAACGAGCAGGAGAAGATCCCCTTCCACCTGCAGCTGTCCAAGCAG

GTGATCCACGCCGAGATTCAGCACCTGGGCCACTGGATGGACGCCACC

TTCAACCTGAAAACCGCCTTCCACTGCTACGGCAGCTGTGAGAAGTAC

GCCTACCCTTGGCAGACCGCCGGCTGCTTCATCGAGAAGGACTACGAG

TACGAGACCGGCTGGGGCTGTAATCCTCCTGATTGCCCCGGAGTGGGC

ACCGGCTGTACTGCATGTGGCGTGTACCTGGACAAGCTGAAGTCTGTG

GGCAAGGTGTTCAAGATCGTGTCCCTGAGGTACACCCGGAAAGTGTGT

ATCCAGCTGGGCACCGAGCAGACCTGTAAGACCGTGGACAGCAACGAT

TGCCTGATCACAACCAGCGTGAAAGTGTGTCTGATCGGCACCATCAGC

AAGTTCCAGCCCAGCGATACCCTGCTGTTTCTGGGCCCCCTGCAGCAG

GGGCGGCCTGATCTTCAAGCAGTGGTGTACCACCACCTGCCAGTTCGG

CGATCCCGGCGATATCATGAGCACCCCCACCGGCATGAAGTGCCCTGA

GCTGAACGGCAGCTTCCGGAAGAAGTGTGCCTTCGCCACCACCCCTGT

GTGTCAGTTCGACGGCAACACCATCAGCGGCTACAAGCGGATGATCGC

CACCAAGGACAGCTTCCAGTCCTTCAACGTGACCGAGCCCCACATCAG

CACCAGCGCCCTGGAGTGGATCGATCCCGACAGCAGCCTGAGGGACCA

CATCAACGTGATCGTGTCCAGGGACCTGAGCTTCCAGGACCTGAGCGA

GACCCCCTGCCAGATCGACCTGGCCACCGCCAGCATCGATGGCGCCTG

GGGCAGCGGAGTGGGCTTCAACCTGGTGTGTACAGTGAGCCTGACCGA

GTGTAGCGCCTTCCTGACCAGCATCAAAGCCTGTGACGCCGCCATGTG

TTACGGCAGCACCACCGCCAACCTGGTGAGAGGCCAGAACACCATCCA

CATTGTGGGCAAAGGCGGCCACAGCGGCAGCAAGTTTATGTGCTGCCA

CGACACCAAGTGTAGCAGCACCGGCCTGGTGGCCGCTGCCCCCCACCT

GGACAGAGTGACCGGCTACAACCAGGCCGACAGCGACAAGATTTTCGA

CGACGGAGCCCCTGAGTGTGGCATGAGTTGCTGGTTCAAGAAGAGCGG

CGAGTGGATTCTGGGCGTGCTGAACGGGAATTGGATGGTGGTGGCCGT

GCTGGTCGTGCTGCTGATCCTGAGCATCCTGCTGTTCACCCTGTGCTG

CCCTAGGAGACCCAGCTACCGGAAGGAGCACAAGCCCTGA

Plasmid pWRG/HTN-M(x)

SEQ ID NO: 12 gggggggggg ggcgctgagg tctgcctcgt gaagaaggtg 40
ttgctgactc ataccaggcc tgaatcgccc catcatccag 80

-continued

```
ccagaaagtg agggagccac ggttgatgag agctttgttg  120
taggtggacc agttggtgat tttgaacttt tgctttgcca  160
cggaacggtc tgcgttgtcg ggaagatgcg tgatctgatc  200
cttcaactca gcaaaagttc gatttattca acaaagccgc  240
cgtcccgtca agtcagcgta atgctctgcc agtgttacaa  280
ccaattaacc aattctgatt agaaaaactc atcgagcatc  320
aaatgaaact gcaatttatt catatcagga ttatcaatac  360
catatttttg aaaaagccgt ttctgtaatg aaggagaaaa  400
ctcaccgagg cagttccata ggatggcaag atcctggtat  440
cggtctgcga ttccgactcg tccaacatca atacaaccta  480
ttaatttccc ctcgtcaaaa ataaggttat caagtgagaa  520
atcaccatga gtgacgactg aatccggtga gaatggcaaa  560
agcttatgca tttctttcca gacttgttca acaggccagc  600
cattacgctc gtcatcaaaa tcactcgcat caaccaaacc  640
gttattcatt cgtgattgcg cctgagcgag acgaaatacg  680
cgatcgctgt taaaaggaca attacaaaca ggaatcgaat  720
gcaaccggcg caggaacact gccagcgcat caacaatatt  760
ttcacctgaa tcaggatatt cttctaatac ctggaatgct  800
gttttcccgg ggatcgcagt ggtgagtaac catgcatcat  840
caggagtacg gataaaatgc ttgatggtcg gaagaggcat  880
aaattccgtc agccagttta gtctgaccat ctcatctgta  920
acatcattgg caacgctacc tttgccatgt ttcagaaaca  960
actctggcgc atcgggcttc ccatacaatc gatagattgt 1000
cgcacctgat tgcccgacat tatcgcgagc ccatttatac 1040
ccatataaat cagcatccat gttggaattt aatcgcggcc 1080
tcgagcaaga cgtttcccgt tgaatatggc tcataacacc 1120
ccttgtatta ctgtttatgt aagcagacag ttttattgtt 1160
catgatgata tatttttatc ttgtgcaatg taacatcaga 1200
gattttgaga cacaacgtgg ctttcccccc ccccccggca 1240
tgcctgcagg tcgacaatat tggctattgg ccattgcata 1280
cgttgtatct atatcataat atgtacattt atattggctc 1320
atgtccaata tgaccgccat gttgacattg attattgact 1360
agttattaat agtaatcaat tacggggtca ttagttcata 1400
gcccatatat ggagttccgc gttacataac ttacggtaaa 1440
tggcccgcct ggctgaccgc ccaacgaccc ccgcccattg 1480
acgtcaataa tgacgtatgt tcccatagta acgccaatag 1520
ggactttcca ttgacgtcaa tgggtggagt atttacggta 1560
aactgcccac ttggcagtac atcaagtgta tcatatgcca 1600
agtccgcccc ctattgacgt caatgacggt aaatggcccg 1640
cctggcatta tgcccagtac atgaccttac gggactttcc 1680
```

-continued

```
tacttggcag tacatctacg tattagtcat cgctattacc 1720

atggtgatgc ggttttggca gtacaccaat gggcgtggat 1760

agcggtttga ctcacgggga tttccaagtc tccaccccat 1800

tgacgtcaat gggagtttgt tttggcacca aaatcaacgg 1840

gactttccaa aatgtcgtaa taaccccgcc ccgttgacgc 1880

aaatgggcgg taggcgtgta cggtgggagg tctatataag 1920

cagagctcgt ttagtgaacc gtcagatcgc ctggagacgc 1960

catccacgct gttttgacct gcatcgaaga caccgggacc 2000

gatccagcct ccgcggccgg gaacggtgca ttggaacgcg 2040

gattccccgt gccaagagtg acgtaagtac cgcctataga 2080

ctctataggc acacccottt ggctcttatg catgctatac 2120

tgtttttggc ttggggccta tacacccccg cttccttatg 2160

ctataggtga tggtatagct tagcctatag gtgtgggtta 2200

ttgaccatta ttgaccactc ccctattggt gacgatactt 2240

tccattacta atccataaca tggctctttg ccacaactat 2280

ctctattggc tatatgccaa tactctgtcc ttcagagact 2320

gacacggact ctgtattttt acaggatggg gtcccattta 2360

ttatttacaa attcacatat acaacaacgc cgtcccccgt 2400

gcccgcagtt tttattaaac atagcgtggg atctccacgc 2440

gaatctcggg tacgtgttcc ggacatgggc tcttctccgg 2480

tagcggcgga gcttccacat ccgagccctg gtcccatgcc 2520

tccagcggct catggtcgct cggcagctcc ttgctcctaa 2560

cagtggaggc cagacttagg cacagcacaa tgcccaccac 2600

caccagtgtg ccgcacaagg ccgtggcggt agggtatgtg 2640

tctgaaaatg agctcggaga ttgggctcgc accgctgacg 2680

cagatggaag acttaaggca gcggcagaag aagatgcagg 2720

cagctgagtt gttgtattct gataagagtc agaggtaact 2760

cccgttgcgg tgctgttaac ggtggagggc agtgtagtct 2800

gagcagtact cgttgctgcc gcgcgcgcca ccagacataa 2840

tagctgacag actaacagac tgttcctttc catgggtctt 2880

ttctgcagtc accgtccaag cttgcggccg cggatctgca 2920

ggaattcggc acgagagtag tagactccgc aagaaacagc 2960

agtcaatcag caacatgggg atatggaagt ggctagtgat 3000

ggccagttta gtatggcctg ttttgacact gagaaatgtc 3040

tatgacatga aaattgagtg cccccataca gtaagttttg 3080

gggaaaacag tgtgataggt tatgtagaat taccccccgt 3120

gccattggcc gacacagcac agatggtgcc tgagagttct 3160

tgtagcatgg ataatcacca atcgttgaat acaataacaa 3200

aatataccca agtaagttgg agaggaaagg ctgatcagtc 3240

acagtctagt caaaattcat ttgagacagt gtccactgaa 3280

gttgacttga aaggaacatg tgctctaaaa cacaaaatgg 3320
```

-continued

```
tggaagaatc ataccgtagt aggaaatcag taacctgtta 3360
cgacctgtct tgcaatagca cttactgcaa gccaacacta 3400
tacatgattg taccaattca tgcatgcaat atgatgaaaa 3440
gctgtttgat tgcattggga ccatacagag tacaggtggt 3480
ttatgagaga tcttattgca tgacaggagt cctgattgaa 3520
gggaaatgct ttgtcccaga tcaaagtgtg gtcagtatta 3560
tcaagcatgg gatctttgat attgcaagtg ttcatattgt 3600
atgtttcttt gttgcagtta aagggaatac ttataaaatt 3640
tttgaacagg ttaagaaatc ctttgaatca acatgcaatg 3680
atacagagaa taaagtgcaa ggatattata tttgtattgt 3720
agggggaaac tctgcaccaa tatatgttcc aacacttgat 3760
gatttcagat ccatggaagc atttacagga atcttcagat 3800
caccacatgg ggaagatcat gatctggctg gagaagaaat 3840
tgcatcttat tctatagtcg gacctgccaa tgcaaaagtt 3880
cctcatagtg ctagctcaga tacattgagc ttgattgcct 3920
attcaggtat accatcttat tcttccctta gcatcctaac 3960
aagttcaaca gaagctaagc atgtattcag ccctgggttg 4000
ttcccaaaac ttaatcacac aaattgtgat aaaagtgcca 4040
taccactcat atggactggg atgattgatt tacctggata 4080
ctacgaagct gtccaccctt gtacagtttt ttgcgtatta 4120
tcaggtcctg gggcatcatg tgaagccttt tctgaaggcg 4160
ggattttcaa cataacctct cccatgtgct tagtgtcaaa 4200
acaaaatcga ttccggttaa cagaacagca agtgaatttt 4240
gtgtgtcagc gagtggacat ggacattgtt gtgtactgca 4280
acgggcagag gaaagtaata ttaacaaaaa ctctagttat 4320
tggacagtgt atatatacta taacaagctt attctcatta 4360
ctacctggag tagcacattc tattgctgtt gaattgtgtg 4400
tacctgggtt ccatggttgg gccacagctg ctctgcttgt 4440
tacattctgt ttcggatggg ttcttatacc agcaattaca 4480
tttatcatac taacagtcct aaagttcatt gctaatattt 4520
ttcacacaag taatcaagag aataggctaa aatcagtact 4560
tagaaagata aaggaagagt ttgaaaaaac aaaaggctca 4600
atggtatgtg atgtctgcaa gtatgagtgt gaaacctata 4640
aagaattaaa ggcacacggg gtatcatgcc cccaatctca 4680
atgtccttac tgttttactc attgtgaacc cacagaagca 4720
gcattccaag ctcattacaa ggtatgccaa gttactcaca 4760
gattcaggga tgatctaaag aaaactgtta ctcctcaaaa 4800
ttttacacca ggatgttacc ggacactaaa tttatttaga 4840
tacaaaagca ggtgctacat ctttacaatg tggatatttc 4880
ttcttgtctt agaatccata ctgtgggctg caagtgcatc 4920
```

-continued

```
agagacacca ttaactcctg tctggaatga caatgcccat 4960
ggggtaggtt ctgttcctat gcatacagat ttagagcttg 5000
atttctcttt aacatccagt tccaagtata cataccgtag 5040
gaggttaaca aacccacttg aggaagcaca atccattgac 5080
ctacatattg aaatagaaga acagacaatt ggtgttgatg 5120
tgcatgctct aggacactgg tttgatggtc gtcttaacct 5160
taaaacatcc tttcactgtt atggtgcttg tacaaagtat 5200
gaataccctt ggcatactgc aaagtgccac tatgaaagag 5240
attaccaata tgagacgagc tggggttgta atccatcaga 5280
ttgtcctggg gtgggcacag gctgtacagc atgtggttta 5320
tacctagatc aactgaaacc agttggtagt gcttataaaa 5360
ttatcacaat aaggtacagc aggagagtct gtgttcagtt 5400
tggggaggaa aacctttgta agataataga catgaatgat 5440
tgttttgtat ctaggcatgt taaggtctgc ataattggta 5480
cagtatctaa attctctcag ggtgatacct tattgttttt 5520
tggaccgctt gaaggtggtg gtctaatatt taaacactgg 5560
tgtacatcca catgtcaatt tggtgaccca ggagatatca 5600
tgagtccaag agacaaaggt tttttatgcc ctgagtttcc 5640
aggtagtttc aggaagaaat gcaactttgc tactacccct 5680
atttgtgagt atgatggaaa tatggtctca ggttacaaga 5720
aagtgatggc cacaattgat tccttccaat cttttaatac 5760
aagcactatg cacttcactg atgaaaggat agagtggaaa 5800
gaccctgatg gaatgctaag ggaccatata aacattttag 5840
taacgaagga cattgacttt gataaccttg gtgaaaatcc 5880
ttgcaaaatt ggcctacaaa catcttctat tgagggggcc 5920
tggggttctg gtgtggggtt cacattaaca tgtctggtat 5960
cactaacaga atgtcctacc tttttgacct caataaaggc 6000
ttgtgataag gctatctgtt atggtgcaga gagtgtaaca 6040
ttgacaagag gacaaaatac agtcaaggta tcagggaaag 6080
gtggccatag tggttcaaca tttaggtgtt gccatgggga 6120
ggactgttca caaattggac tccatgctgc tgcacctcac 6160
cttgacaagg taaatgggat ttctgagata gaaaatagta 6200
aagtatatga tgatggggca ccgcaatgtg ggataaaatg 6240
ttggtttgtt aaatcagggg aatggatttc agggatattc 6280
agtggtaatt ggattgtact cattgtcctc tgtgtatttc 6320
tattgttctc cttggtttta ctaagcattc tctgtcccgt 6360
aaggaagcat aaaaaatcat agctaaattc tgtgactatc 6400
ctgttcttat gtatagcttt aacatatata ctaattttta 6440
tattccagta tactctatct aacacactaa aaaaaatagt 6480
agctttctaa ccacaaaacg gatctacgta tgatcagcct 6520
cgactgtgcc ttctagttgc cagccatctg ttgtttgccc 6560
```

-continued ctcccccgtg ccttccttga ccctggaagg tgccactccc 6600
actgtccttt cctaataaaa tgaggaaatt gcatcgcatt 6640
gtctgagtag gtgtcattct attctggggg gtggggtggg 6680
gcaggacagc aagggggagg attgggaaga caatagcagg 6720
catgctgggg atgcggtggg ctctatggct tctgaggcgg 6760
aaagaaccag ctggggctcg acagctcgac tctagaattg 6800
cttcctcgct cactgactcg ctgcgctcgg tcgttcggct 6840
gcggcgagcg gtatcagctc actcaaaggc ggtaatacgg 6880
ttatccacag aatcagggga taacgcagga aagaacatgt 6920
gagcaaaagg ccagcaaaag gccaggaacc gtaaaaaggc 6960
cgcgttgctg gcgtttttcc ataggctccg cccccctgac 7000
gagcatcaca aaaatcgacg ctcaagtcag aggtggcgaa 7040
acccgacagg actataaaga taccaggcgt ttccccctgg 7080
aagctccctc gtgcgctctc ctgttccgac cctgccgctt 7120
accggatacc tgtccgcctt tctcccttcg ggaagcgtgg 7160
cgctttctca tagctcacgc tgtaggtatc tcagttcggt 7200
gtaggtcgtt cgctccaagc tgggctgtgt gcacgaaccc 7240
cccgttcagc ccgaccgctg cgccttatcc ggtaactatc 7280
gtcttgagtc caacccggta agacacgact tatcgccact 7320
ggcagcagcc actggtaaca ggattagcag agcgaggtat 7360
gtaggcggtg ctacagagtt cttgaagtgg tggcctaact 7400
acggctacac tagaagaaca gtatttggta tctgcgctct 7440
gctgaagcca gttaccttcg gaaaaagagt tggtagctct 7480
tgatccggca aacaaaccac cgctggtagc ggtggttttt 7520
ttgtttgcaa gcagcagatt acgcgcagaa aaaaaggatc 7560
tcaagaagat cctttgatct tttctacggg gtctgacgct 7600
cagtggaacg aaaactcacg ttaagggatt ttggtcatga 7640
gattatcaaa aaggatcttc acctagatcc ttttaaatta 7680
aaaatgaagt tttaaatcaa tctaaagtat atatgagtaa 7720
acttggtctg acagttacca atgcttaatc agtgaggcac 7760
ctatctcagc gatctgtcta tttcgttcat ccatagttgc 7800 pWRG-SEO-M (Seoul hantavirus M segment, strain SR-11, subcloned into DNA vector pWRG7077)

SEQ ID NO: 13 gggggggggg ggcgctgagg tctgcctcgt gaagaaggtg 40
ttgctgactc ataccaggcc tgaatcgccc catcatccag 80
ccagaaagtg agggagccac ggttgatgag agctttgttg 120
taggtggacc agttggtgat tttgaacttt tgctttgcca 160
cggaacggtc tgcgttgtcg ggaagatgcg tgatctgatc 200
cttcaactca gcaaaagttc gatttattca acaaagccga 240
cgtcccgtca agtcagcgta atgctctgcc agtgttacaa 280
ccaattaacc aattctgatt agaaaaactc atcgagcatc 320

-continued

```
aaatgaaact gcaatttatt catatcagga ttatcaatac  360
catatttttg aaaaagccgt ttctgtaatg aaggagaaaa  400
ctcaccgagg cagttccata ggatggcaag atcctggtat  440
cggtctgcga ttccgactcg tccaacatca atacaaccta  480
ttaatttccc ctcgtcaaaa ataaggttat caagtgagaa  520
atcaccatga gtgacgactg aatccggtga gaatggcaaa  560
agcttatgca tttctttcca gacttgttca acaggccagc  600
cattacgctc gtcatcaaaa tcactcgcat caaccaaacc  640
gttattcatt cgtgattgcg cctgagcgag acgaaatacg  680
cgatcgctgt taaaaggaca attacaaaca ggaatcgaat  720
gcaaccggcg caggaacact gccagcgcat caacaatatt  760
ttcacctgaa tcaggatatt cttctaatac ctggaatgct  800
gttttcccgg ggatcgcagt ggtgagtaac catgcatcat  840
caggagtacg gataaaatgc ttgatggtcg gaagaggcat  880
aaattccgtc agccagttta gtctgaccat ctcatctgta  920
acatcattgg caacgctacc tttgccatgt ttcagaaaca  960
actctggcgc atcgggcttc ccatacaatc gatagattgt 1000
cgcacctgat tgccccacat tatcgcgagc ccatttatac 1040
ccatataaat cagcatccat gttggaattt aatcgcggcc 1080
tcgagcaaga cgtttcccgt tgaatatggc tcataacacc 1120
ccttgtatta ctgtttatgt aagcagacag ttttattgtt 1160
catgatgata tatttttatc ttgtgcaatg taacatcaga 1200
gattttgaga cacaacgtgg ctttcccccc ccccccggca 1240
tgcctgcagg tcgacataaa tcaatattgg ctattggcca 1280
ttgcatacgt tgtatctata tcataatatg tacatttata 1320
ttggctcatg tccaatatga ccgccatgtt gacattgatt 1360
attgactagt tattaatagt aatcaattac ggggtcatta 1400
gttcatagcc catatatgga gttccgcgtt acataactta 1440
cggtaaatgg cccgcctcgt gaccgcccaa cgacccccgc 1480
ccattgacgt caataatgac gtatgttccc atagtaacgc 1520
caatagggac tttccattga cgtcaatggg tggagtattt 1560
acggtaaact gcccacttgg cagtacatca agtgtatcat 1600
atgccaagtc cggcccccta ttgacgtcaa tgacggtaaa 1640
tggcccgcct ggcattatgc ccagtacatg accttacggg 1680
actttcctac ttggcagtac atctacgtat tagtcatcgc 1720
tattaccatg gtgatgcggt tttggcagta caccaatggg 1760
cgtggatagc ggtttgactc acggggattt ccaagtctcc 1800
accccattga cgtcaatggg agtttgtttt ggcaccaaaa 1840
tcaacgggac tttccaaaat gtcgtaataa ccccgccccg 1880
ttgacgcaaa tgggcggtag gcgtgtacgg tgggaggtct 1920
```

-continued atataagcag agctcgttta gtgaaccgtc agatcgcctg 1960
gagacgccat ccacgctgtt ttgacctcca tagaagacac 2000
cgggaccgat ccagcctccg cggccgggaa cggtgcattg 2040
gaacgcggat tccccgtgcc aagagtgacg taagtaccgc 2080
ctatagactc tataggcaca cccctttggc tcttatgcat 2120
gctatactgt ttttggcttg gggcctatac acccccgctc 2160
cttatgctat aggtgatggt atagcttagc ctataggtgt 2200
gggttattga ccattattga ccactcccct attggtgacg 2240
atactttcca ttactaatcc ataacatggc tctttgccac 2280
aactatctct attggctata tgccaatact ctgtccttca 2320
gagactgaca cggactctgt atttttacag gatggggtcc 2360
catttattat ttacaaattc acatatacaa caacgccgtc 2400
ccccgtgccc gcagttttta ttaaacatag cgtgggatct 2440
ccacgcgaat ctcgggtacg tgttccggac atgggctctt 2480
ctccggtagc ggcggagctt ccacatccga gccctggtcc 2520
catgcctcca gcggctcatg gtcgctcggc agctccttgc 2560
tcctaacagt ggaggccaga cttaggcaca gcacaatgcc 2600
caccaccacc agtgtgccgc acaaggccgt ggcggtaggg 2640
tatgtgtctg aaaatgagct cggagattgg gctcgcaccg 2680
tgacgcagat ggaagactta aggcagcggc agaagaagat 2720
gcaggcagct gagttgttgt attctgataa gagtcagagg 2760
taactcccgt tgcggtgctg ttaacggtgg agggcagtgt 2800
agtctgagca gtactcgttg ctgccgcgcg cgccaccaga 2840
cataatagct gacagactaa cagactgttc ctttccatgg 2880
gtcttttctg cagtcaccgt ccaagcttgc ggccgcggat 2920
ctgcaggaat tcggcacgag agtagtagac tccgcaagaa 2960
acagcagtta aagaacaata ggatcatgtg gagtttgcta 3000
ttactggccg ctttagttgg ccaaggcttt gcattaaaaa 3040
atgtatttga catgagaatt cagttgcccc actcagtcaa 3080
ctttggggaa acaagtgtgt caggctatac agaatttccc 3120
ccactctcat tacaggaggc agaacagcta gtgccagaga 3160
gctcatgcaa catggacaac caccagtcac tctcaacaat 3200
aaataaatta accaaggtca tatggcggaa aaaagcaaat 3240
caggaatcag caaaccagaa ttcatttgaa gttgtggaaa 3280
gtgaagtcag ctttaaaggg ttgtgtatgt taaagcatag 3320
aatggttgaa gaatcatata gaaataggag atcagtaatc 3360
tgttatgatc tagcctgtaa tagtacattc tgtaaaccaa 3400
ctgtttatat gattgttcct atacatgctt gcaacatgat 3440
gaaaagctgt ttgattggcc ttggccccta cagaatccag 3480
gttgtctatg aaaggacata ctgcactacg ggtatattga 3520
cagaaggaaa atgctttgtc cctgacaagg ctgttgtcag 3560

-continued

```
tgcattgaaa agaggcatgt atgctatagc aagcatagag 3600
acaatctgct tttttattca tcagaaaggg aatacatata 3640
agatagtgac tgccattaca tcagcaatgg gctccaaatg 3680
taataataca gatactaaag ttcaaggata ttatatctgt 3720
attattggtg gaaactccgc ccctgtatat gcccctgctg 3760
gtgaagactt cagagcaatg gaggtttttt ctgggattat 3800
tacatcacca catggagaag accatgacct acccggcgaa 3840
gaaatcgcaa cgtaccagat ttcagggcag atagaggcaa 3880
aaatccctca tacagtgagc tccaaaaact taaaattgac 3920
tgcttttgca ggtattccat catactcatc aactagtata 3960
ttggctgctt cagaagatgg tcgtttcata tttagtcctg 4000
gtttatttcc taacctaaat cagtcagtct gtgacaacaa 4040
tgcactccct ttaatctgga ggggcctaat tgatttaacg 4080
ggatactatg aggcagtcca cccttgcaat gtgttctgtg 4120
tcttatcagg accaggtgct tcatgtgagg ccttttcaga 4160
aggaggtatt ttcaatatta cttctccaat gtgtctggtg 4200
tctaagcaaa atagatttag agcagctgag cagcagatta 4240
gctttgtctg ccaaagagtt gatatggata ttatagtgta 4280
ctgtaatggt cagaaaaaaa caatcctaac aaaaacatta 4320
gttataggcc aatgtattta tactattaca agtctctttt 4360
cactgttacc aggggttgcc cattctattg ctattgagtt 4400
gtgtgttcca gggtttcatg gctgggccac agctgcactt 4440
ttgattacat tctgcttcgg ctgggtattg attcctgcat 4480
gtacattagc tattctttta gtccttaagt tctttgcaaa 4520
tatccttcat acaagcaatc aagagaaccg attcaaagcc 4560
attctacgga aaataaagga ggagtttgaa aaaacaaagg 4600
gttccatggt ttgtgagatc tgtaagtatg agtgtgaaac 4640
attaaaggaa ttgaaggcac ataacctatc atgtgttcaa 4680
ggagagtgcc catattgctt tacccactgt gaaccgacag 4720
aaactgcaat tcaggcacat tacaaagttt gtcaagccac 4760
ccaccgattc agagaagatt taaaaaagac tgtaactcct 4800
caaaatattg ggccaggctg ttaccgaaca ctaaatcttt 4840
ttaggtataa aagtaggtgt tatattctga caatgtggac 4880
tcttcttctc attattgaat ccatcctctg ggcagcaagt 4920
gcagcagaaa tccccccttgt ccctctctgg acagataatg 4960
ctcatggcgt tgggagtgtt cctatgcata cggatcttga 5000
attagacttc tctttgccat ccagttctaa gtacacatac 5040
aaaagacatc tcacaaaccc agttaatgac caacagagtg 5080
tctcattgca tatagaaatt gaaagtcaag gcattggtgc 5120
tgctgttcat catcttggac attggtatga tgcaagattg 5160
```

-continued aatctaaaaa cctcatttca ttgttatggt gcctgcacaa 5200
aatatcaata cccatggcac actgcaaaat gccattttga 5240
gaaagattat gagtatgaaa atagctgggc ttgcaacccc 5280
ccagattgcc caggggttgg tacaggttgt actgcttgtg 5320
gattatatct agatcaattg aagccggtag gaacagcctt 5360
taaaattata agtgtaagat acagtagaaa agtgtgcgtg 5400
cagtttggtg aagaacacct ttgtaaaaca attgatatga 5440
atgattgctt tgtgactagg catgccaaaa tatgtataat 5480
tgggactgta tctaagtttt ctcaaggtga cactctacta 5520
tttctggggc ccatggaagg aggtggtata atctttaaac 5560
actggtgtac atctacctgt cactttggag accctggtga 5600
tgtcatgggt ccaaaagata aaccatttat ttgccctgaa 5640
ttcccagggc aatttaggaa aaaatgtaac tttgccacaa 5680
ctccagtttg tgaatatgat ggaaacatta tatcaggcta 5720
taagaaagta cttgcaacaa ttgattcttt ccaatcattt 5760
aacacaagca atatacactt cactgatgag agaattgaat 5800
ggagagaccc tgatggcatg cttcgggatc atattaatat 5840
tgttatttct aaagatattg attttgaaaa tttggctgag 5880
aatccttgta aagtagggct ccaggcagca aacatagaag 5920
gtgcctgggg ttcaggtgtc gggtttacac tcacatgcaa 5960
ggtgtctctc acagaatgcc caacatttct tacatcaata 6000
aaggcctgtg acatggcaat ttgttatggt gcagaaagtg 6040
tgacactctc acgaggacaa aatactgtca aaattaccgg 6080
gaaaggtggc catagtggtt cttcattcaa atgctgtcat 6120
gggaaagaat gttcatcaac tggcctccaa gccagtgcac 6160
cacatctgga taaggtaaat ggtatctctg agttagaaaa 6200
cgagaaagtt tatgatgacg gtgcacctga atgtggcatt 6240
acttgttggt ttaaaaaatc aggtgaatgg gttatgggta 6280
taatcaatgg gaactgggtt gtcctaattg tcttgtgtgt 6320
actgctgctc ttttctctta tcctgttgag catcttgtgt 6360
cctgttagaa agcataaaaa atcataaatc ccacctaaca 6400
atcttcacat catgtatcga ttttcaaaca ctttatcatt 6440
tagaacttaa cttggcacta ctatctgata actgactttc 6480
atttttattt ttatatggat taattactaa aaaaaatact 6520
ctctcgtgcc gaattcgata tcaagcttat cgataccgtc 6560
gacctcgagg gggggcccgg tacccgggat cctcgcaatc 6600
cctaggagga ttaggcaagg gcttgagctc acgctcttgt 6640
gagggacaga aatacaatca ggggcagtat atgaatactc 6680
catggagaaa cccagatcta cgtatgatca gcctcgactg 6720
tgccttctag ttgccagcca tctgttgttt gcccctcccc 6760
cgtgccttcc ttgaccctgg aaggtgccac tcccactgtc 6800

-continued

```
ctttcctaat aaaatgagga aattgcatcg cattgtctga 6840

gtaggtgtca ttctattctg gggggtgggg tggggcagga 6880

cagcaagggg gaggattggg aagacaatag caggcatgct 6920

ggggatgcgg tgggctctat ggcttctgag gcggaaagaa 6960

ccagctgggg ctcgacagct cgactctaga attgcttcct 7000

cgctcactga ctcgctgcgc tcggtcgttc ggctgcggcg 7040

agcggtatca gctcactcaa aggcggtaat acggttatcc 7080

acagaatcag gggataacgc aggaaagaac atgtgagcaa 7120

aaggccagca aaaggccagg aaccgtaaaa aggccgcgtt 7160

gctggcgttt ttccataggc tccgcccccc tgacgagcat 7200

cacaaaaatc gacgctcaag tcagaggtgg cgaaacccga 7240

caggactata aagataccag gcgtttcccc ctggaagctc 7280

cctcgtgcgc tctcctgttc cgaccctgcc gcttaccgga 7320

tacctgtccg cctttctccc ttcgggaagc gtggcgcttt 7360

ctcaatgctc acgctgtagg tatctcagtt cggtgtaggt 7400

cgttcgctcc aagctgggct gtgtgcacga accccccgtt 7440

cagcccgacc gctgcgcctt atccggtaac tatcgtcttg 7480

agtccaaccc ggtaagacac gacttatcgc cactggcagc 7520

agccactggt aacaggatta gcagagcgag gtatgtaggc 7560

ggtgctacag agttcttgaa gtggtggcct aactacggct 7600

acactagaag gacagtattt ggtatctgcg ctctgctgaa 7640

gccagttacc ttcggaaaaa gagttggtag ctcttgatcc 7680

ggcaaacaaa ccaccgctgg tagcggtggt ttttttgttt 7720

gcaagcagca gattacgcgc agaaaaaaag gatctcaaga 7760

agatcctttg atcttttcta cggggtctga cgctcagtgg 7800

aacgaaaact cacgttaagg gattttggtc atcagattat 7840

caaaaaggat cttcacctag atccttttaa attaaaaatg 7880

aagttttaaa tcaatctaaa gtatatatga gtaaacttgg 7920

tctgacagtt accaatgctt aatcagtgag gcacctatct 7960

cagcgatctg tctatttcgt tcatccatag ttgcctgact 8000

c                                           8001
```

More preferably, it further includes the Andes M-gene construct pWRG/AND-M(x) (SEQ ID NO:10), which strengthens the HPS component.

Where gene-gun delivery is contemplated, the DNA segments from different viruses can be on different particles or on the same particle, whichever results in the desired immune response. The vaccine is designed to protect against pathologies resulting from exposure to one or several hantaviruses. The vaccine can also be combined with reagents which increase the antigenicity of the vaccine, or reduce its side effects. As shown above, the delivery of a combination of vaccines by electroporation involves mixtures of DNA. This demonstrates that plasmids can be mixed and any interference from the respective DNA with each other can be overcome—another advantage of this invention.

For DNA vaccinations described here, as appropriate, when inducing cellular, humoral, and protective immune responses after DNA vaccination the preferred target cells are epidermal cells, rather than cells of deeper skin layers such as the dermis. Epidermal cells are preferred recipients of DNA vaccines because they are the most accessible cells of the body and may, therefore, be immunized non-invasively. Secondly, in addition to eliciting a humoral immune response, DNA immunized epidermal cells also elicit a cytotoxic immune response that is stronger than that generated in sub-epidermal cells. Delivery to epidermis also has the advantages of being less invasive and delivering to cells which are ultimately sloughed by the body.

Although it can be desirable to induce an immune response by delivering genetic material to a target animal, merely demonstrating an immune response is not necessarily sufficient to confer protective advantage on the animal. What is important is to achieve a protective immune response that manifests itself in a clinical difference. That is, a method is effective only if it prevents infection or reduces the severity of the disease symptoms. It is preferred that the immunization method be at least 20% effective in preventing death in an immunized population after challenge with SNV or, if a multivalent vaccine is used, at least one of the other targeted hantaviruses. More preferably, the vaccination method is 50% or more effective, and most preferably 70 100% effective, in preventing death in an immunized population. The vaccination method is shown herein to be 100% effective in the hamster models for hantavirus. Hamsters have been used extensively as the laboratory models of choice for assessment of protective immune responses to hantaviruses. In contrast, unimmunized animals are uniformly infected by challenge with hantavirus. The inventor's results indicate that vaccination with our SNV vaccines protects against infection with SNV. As is well known, high titer antibody such as achieved by the inventor is predictive of protection.

Generally, the DNA vaccine administered may be in an amount of about 5 ug-5 mg of DNA per dose and will depend on the delivery technology, subject to be treated, capacity of the subject's immune system to develop the desired immune response, and the degree of protection desired. Precise amounts of the vaccine to be administered may depend on the judgement of the practitioner and may be peculiar to each subject and antigen. Delivery technology plays an important role in determining dosage—e.g., an adjuvant may change the dosage or number of vaccinations needed.

The vaccine for eliciting an immune response against one or more viruses, may be given in a single dose schedule, or if deemed necessary or desirable, a multiple dose schedule in which a primary course of vaccination may be with 1-8 separate doses, followed by other doses given at subsequent time intervals required to maintain and or reinforce the immune response, for example, at 14 months for a second dose, and if needed, a subsequent dose(s) after several months. Examples of suitable immunization schedules include: (i) 0, 1 months and 6 months, (ii) 0, 7 days and 1 month, (iii) 0 and 1 month, (iv) 0 and 6 months, or other schedules sufficient to elicit the desired immune responses expected to confer protective immunity, or reduce disease symptoms, or reduce severity of disease.

In a related embodiment, this invention provides a method for raising high titers of neutralizing antibodies against Sin Nombre virus in a mammal or a bird. The method comprises the step of administering a composition comprising a SNV plasmid DNA which comprises one or more of the recombinant DNA constructs described above (including SEQ ID NO:1, SEQ ID NO:2 or SEQ ID NOT:3); and a pharmacologically acceptable carrier. The step of administering may need to be repeated as desired in order to achieve the level of titer targeted. Preferably the titer is measured to be between 100 and 10,000.

Therapeutic Use of Polyclonal and Monoclonal Antibodies

In another embodiment, the present invention relates to polyclonal antibodies from vaccinees receiving the DNA vaccines described above. A composition comprising the polyclonal antibodies can be used as a prophylactic or therapeutic effective in preventing onset of Sin Nombre virus infection after exposure to it, and/or in treating Sin Nombre virus disease. For example, the composition of the present invention is composed of polyclonal antiserum from a population of animals or humans vaccinated with a DNA vaccine comprised of a plasmid expressing the above-described synthetic Sin Nombre virus M gene. The polyclonal serum would contain neutralizing antibodies against Sin Nombre virus. Unlike conventional polyclonal immune serum products, the process used to make this invention (DNA vaccination to produce antibody in vaccinees) does not involve live virus and does not require the identification of patients who have survived Sin Nombre virus disease.

Similarly, animals or humans vaccinated with one of the above-described DNA vaccines can produce SNV-neutralizing monoclonal antibodies (Mab), which Mab can then be engineered into expression systems.

In one embodiment of this method, the invention contemplates a method to treat or prevent or ameliorate symptoms after onset of Sin Nombre virus infection by administering a therapeutically or prophylactically effective amount of serum of the present invention or a mixture of antibodies of the present invention to a subject in need of such treatment. The antibodies are specific for peptides encoded by the nucleic acids described herein—e.g., where the Gn and Gc are encoded by the nucleic acid of one of SEQ ID NO:1, SEQ ID NO:2 and/or SEQ ID NO:3.

The polyclonal antibodies described herein are characterized in that the antibody binds to the appropriate immunogen, i.e. Gn and Gc, as measured by assays such as ELISA, immunoprecipitation, or immunofluorescence. Also, the antibodies must neutralize Sin Nombre virus as measured by plaque reduction neutralization test (PRNT). Any antibody retaining these characteristics is related to the present invention. The polyclonal antibody may be concentrated, irradiated, and tested for a capacity to neutralize Sin Nombre virus. Serum lots with sufficiently high neutralizing antibody titers, i.e., high enough to give a detectable response in the recipient after transfer, can be pooled. The product can then be lyophilized for storage and reconstituted for use.

As described in greater detail in the examples, the present inventor has found that serum from a vaccinee immunized with a DNA vaccine comprising one of the above-described SNV sequences, contains antibodies able to neutralize hantavirus.

Given these results, polyclonal antibodies according to the present invention are suitable both as therapeutic and prophylactic agents for treating or preventing SNV infection or disease in susceptible SNV-exposed subjects. Subjects include rodents such as mice or guinea pigs, avian, and mammals (including transgenic animals), including humans Any active form of the antibodies can be administered. Antibodies of the present invention can be produced in any system, including insect cells, baculovirus expression systems, chickens, rabbits, goats, cows, or plants such as tomato, potato, banana or strawberry. Methods for the production of antibodies in these systems are known to a person with ordinary skill in the art. Preferably, the antibodies used are compatible with the recipient species such that the immune response to the antibodies does not result in clearance of the antibodies before virus can be controlled, and the induced immune response to the antibodies in the subject does not induce "serum sickness" in the subject.

Treatment of individuals having SNV infection may comprise the administration of a therapeutically effective amount of anti-SNV antibodies of the present invention. The antibodies can be provided in a kit as described below. In providing a patient with antibodies, or fragments thereof, capable of binding to SNV, or an antibody capable of protecting against SNV in a recipient patient, the dosage of administered agent will vary depending upon such factors as the patient's age, weight, height, sex, general medical condition, previous medical history, etc. In general, it is desirable to provide the recipient with a dosage of antibody which is in the range of from about 1 pg/kg 100 pg/kg, 100 pg/kg 500 pg/kg, 500 pg/kg 1 ng/kg, 1 ng/kg 100 ng/kg, 100 ng/kg 500 ng/kg, 500 ng/kg 1 ug/kg, 1 ug/kg 100 ug/kg, 100 ug/kg 500 ug/kg, 500 ug/kg 1 mg/kg, 1 mg/kg 50 mg/kg, 50 mg/kg 100 mg/kg, 100 mg/kg 500 mg/kg, 500 mg/kg 1 g/kg, 1 g/kg 5 g/kg, 5 g/kg 10 g/kg (body weight of recipient), although a lower or higher dosage may be administered.

The antibodies capable of protecting against hantavirus are intended to be provided to recipient subjects in an amount sufficient to effect a reduction in the SNV infection symptoms. An amount is said to be sufficient to "effect" the reduction of infection symptoms if the dosage, route of administration, etc. of the agent are sufficient to influence such a response. Responses to antibody administration can be measured by analysis of subject's vital signs.

A composition is said to be "pharmacologically acceptable" if its administration can be tolerated by a recipient patient. Such an agent is said to be administered in a "therapeutically effective amount" if the amount administered is physiologically significant. An agent is physiologically significant if its presence results in a detectable change in the physiology of a recipient patient.

The compounds of the present invention can be formulated according to known methods to prepare pharmaceutically useful compositions, whereby these materials, or their functional derivatives, are combined in admixture with a pharmaceutically acceptable carrier vehicle. Suitable vehicles and their formulation, inclusive of other human proteins, e.g., human serum albumin, are described, for example, in Remington's Pharmaceutical Sciences (16th ed., Osol, A. ed., Mack Easton Pa. (1980)). In order to form a pharmaceutically acceptable composition suitable for effective administration, such compositions will contain an effective amount of the above-described compounds together with a suitable amount of carrier vehicle.

Additional pharmaceutical methods may be employed to control the duration of action. Control release preparations may be achieved through the use of polymers to complex or absorb the compounds. The controlled delivery may be exercised by selecting appropriate macromolecules (for example polyesters, polyamino acids, polyvinyl, pyrrolidone, ethylenevinylacetate, methylcellulose, carboxymethylcellulose, or protamine sulfate) and the concentration of macromolecules as well as the method of incorporation in order to control release. Another possible method to control the duration of action by controlled release preparations is to incorporate the compounds of the present invention into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, interfacial polymerization, for example, hydroxymethylcellulose or gelatin-microcapsules and poly (methylmethacylate)-microcapsules, respectively, or in colloidal drug delivery systems, for example, liposomes, albumin microspheres, microemulsions, nanoparticles, and nanocapsules or in macroemulsions. Such techniques are disclosed in Remington's Pharmaceutical Sciences (1980).

Administration of the antibodies disclosed herein may be carried out by any suitable means, including parenteral injection (such as intraperitoneal, subcutaneous, or intramuscular injection), in ovo injection of birds, orally, or by topical application of the antibodies (typically carried in a pharmaceutical formulation) to an airway surface. Topical application of the antibodies to an airway surface can be carried out by intranasal administration (e.g., by use of dropper, swab, or inhaler which deposits a pharmaceutical formulation intranasally). Topical application of the antibodies to an airway surface can also be carried out by inhalation administration, such as by creating respirable particles of a pharmaceutical formulation (including both solid particles and liquid particles) containing the antibodies as an aerosol suspension, and then causing the subject to inhale the respirable particles. Methods and apparatus for administering respirable particles of pharmaceutical formulations are well known, and any conventional technique can be employed. Oral administration may be in the form of an ingestible liquid or solid formulation.

The treatment may be given in a single dose schedule, or preferably a multiple dose schedule in which a primary course of treatment may be with 1-10 separate doses, followed by other doses given at subsequent time intervals required to maintain and or reinforce the response, for example, at 1-4 months for a second dose, and if needed, a subsequent dose(s) after several months. Examples of suitable treatment schedules include: (i) 0, 1 month and 6 months, (ii) 0, 7 days and 1 month, (iii) 0 and 1 month, (iv) 0 and 6 months, or other schedules sufficient to elicit the desired responses expected to reduce disease symptoms, or reduce severity of disease.

Diagnostic Methods

The present invention still further pertains to a method for detecting SNV in a sample suspected of containing SNV. The method includes contacting the sample with polyclonal antibodies of the present invention which bind SNV antigens, allowing the antibody to bind to the SNV antigen(s) to form an immunological complex, detecting the formation of the immunological complex and correlating the presence or absence of the immunological complex with the presence or absence of SNV antigen in the sample. The sample can be biological, environmental or a food sample.

The language "detecting the formation of the immunological complex" is intended to include discovery of the presence or absence of SNV antigen in a sample. The presence or absence of SNV antigen can be detected using an immunoassay. A number of immunoassays used to detect and/or quantitate antigens are well known to those of ordinary skill in the art. See Harlow and Lane, Antibodies: A Laboratory Manual (Cold Spring Harbor Laboratory, New York 1988 555 612). Such immunoassays include antibody capture assays, antigen capture assays, and two-antibody sandwich assays. These assays are commonly used by those of ordinary skill in the art.

In an antibody capture assay, the antigen is attached to solid support, and labeled antibody is allowed to bind. After washing, the assay is quantitated by measuring the amount of antibody retained on the solid support. A variation of this assay is a competitive ELISA wherein the antigen is bound to the solid support and two solutions containing antibodies which bind the antigen, for example, serum from a SNV virus vaccinee and the polyclonal antibodies of the present invention, are allowed to compete for binding of the antigen. The amount of polyclonal antibody bound is then measured, and a determination is made as to whether the serum contains anti SNV antigen antibodies. This competitive ELISA can be used to indicate immunity to known protective epitopes in a vaccinee following vaccination.

In an antigen capture assay, the antibody is attached to a solid support, and labeled antigen is allowed to bind. The unbound proteins are removed by washing, and the assay is quantitated by measuring the amount of antigen that is bound. In a two-antibody sandwich assay, one antibody is bound to a solid support, and the antigen is allowed to bind to this first antibody. The assay is quantitated by measuring the amount of a labeled second antibody that can bind to the antigen.

These immunoassays typically rely on labeled antigens, antibodies, or secondary reagents for detection. These proteins can be labeled with radioactive compounds, enzymes, biotin, or fluorochromes of these, radioactive labeling can be used for almost all types of assays and with most variations. Enzyme-conjugated labels are particularly useful when radioactivity must be avoided or when quick results are needed. Biotin-coupled reagents usually are detected with labeled streptavidin. Streptavidin binds tightly and quickly to biotin and can be labeled with radioisotopes or enzymes. Fluorochromes, although requiring expensive equipment for their use, provide a very sensitive method of detection. Antibodies useful in these assays include monoclonal antibodies, polyclonal antibodies, and affinity purified polyclonal antibodies. Those of ordinary skill in the art will know of other suitable labels which may be employed in accordance with the present invention. The binding of these labels to antibodies or fragments thereof can be accomplished using standard techniques commonly known to those of ordinary skill in the art. Typical techniques are described by Kennedy, J. H., et al., 1976 (Clin. Chim Acta 70:1 31), and Schurs, A. H. W. M., et al. 1977 (Clin. Chim Acta 81:1 40). Coupling techniques mentioned in the latter are the glutaraldehyde method, the periodate method, the dimaleimide method, and others, all of which are incorporated by reference herein.

The language "biological sample" is intended to include biological material, e.g. cells, tissues, or biological fluid. By "environmental sample" is meant a sample such as soil and water. Food samples include canned goods, meats, and others.

Yet another aspect of the present invention is a kit for detecting hantavirus in a biological sample. The kit includes a container holding one or more polyclonal antibodies of the present invention which binds a SNV antigen and instructions for using the antibody for the purpose of binding to SNV antigen to form an immunological complex and detecting the formation of the immunological complex such that the presence or absence of the immunological complex correlates with presence or absence of SNV in the sample. Examples of containers include multiwell plates which allow simultaneous detection of SNV in multiple samples.

Production of Pseudotyped Virions

Another use of the invention is a method for producing pseudotyped virions. One of the above-described DNA constructs is used to transfect cells, under conditions that pseudotyped virions or SNV glycoprotein is produced. The pseudotyped viruses are useful in serologic assays or delivery of gene therapies to endothelial cells targeted by hantavirus glycoproteins.

REFERENCES

1. Hooper J W, Custer D M, Thompson E, Schmaljohn C S. DNA vaccination with the hantaan virus m gene protects hamsters against three of four HFRS hantaviruses and elicits a high-titer neutralizing antibody response in rhesus monkeys. *J Virol* 2001; 75(18): 8469-8477.
2. Fuller D H, Loudon P, Schmaljohn C. Preclinical and clinical progress of particle-mediated DNA vaccines for infectious diseases. *Methods* 2006:40:86-97.
3. Custer D M, Thompson E, Schmaljohn C S, et al. Active and passive vaccination against hantavirus pulmonary syndrome with Andes virus M genome segment-based DNA vaccine. *J Virol* 2003; 77(18):9894-9905.
4. Hooper J W, Ferro A M, and Wahl-Jensen V Immune Serum Produced by DNA Vaccination Protects Hamsters Against Lethal Respiratory Challenge with Andes Virus. *Journal of Virology* 2008 82:1332-1338.
5. Hooper J W, Kamrud K I, Elgh F, et al. DNA vaccination with hantavirus M segment elicits neutralizing antibodies and protects against Seoul virus infection. *Virology* 1999; 255:269-278.
6. Hooper J W, Custer D M, Smith J., and Wahl-Jensen W. Hantaan/Andes virus DNA vaccine elicits a broadly cross-reactive neutralizing antibody response in nonhuman primates. *Virology* 2006; 347:208-216.
7. Condon C, Watkins SC, Celluzzi C M, et al. DNA-based immunization by in vivo transfection of dendritic cells. *Nat Med* 1996; 10:1122-1128.
8. Barry M A, Johnston S A. Biological features of genetic immunization. *Vaccine* 1997; 15:788-791.
9. Yoshida A, Nagata T, Uchijima M, et al. Advantage of gene gun-mediated over intramuscular inoculation of plasmid DNA vaccine in reproducible induction of specific immune responses. *Vaccine* 2000; 18:1725-1729.
10. Steele K E, Stabler K, VanderZanden L. Cutaneous DNA vaccination against Ebola virus by particle bombardment: histopathology and alteration of CD3-positive dendritic epidermal cells. *Vet Path* 2001; 38:203-215.
11. Monteiro-Riviere N A, Riviere J. The pig as a model for cutaneous pharmacology and toxicology research. In: Tumbleson M E, Schook L B (eds). *Advances in Swine in Biomedical Research*, Vol. 2, New York, Plenum Press, 1996, pp. 425-458.
12. Draize J H, Woodward G, Calvery H O. Methods for the study of irritation and toxicity of substances applied topically to the skin and mucous membranes. *J Pharmacol Exp Ther* 1944; 82,377-390.
13. Klinman D M, Sechler J M G, Conover J, et al. Contribution of cells at the site of DNA vaccination to the generation of antigen-specific immunity and memory. *J Immunol* 1998; 160: 2388-2392.
14. Gurunathan S, Klinman D, Seder R. DNA vaccines. 2000 *Ann Rev Immunol* 2000; 7-74.
15. McElroy A K, Smith J M, Hooper J W, Schmaljohn C S. Andes virus M genome segment is not sufficient to confer the virulence associated with Andes virus in Syrian hamsters. Virology 2004; 326(1):130-139.
16. Charles River Laboratories—Arkansas Division. Assessment of the Local Skin Reactivity and Systemic Toxicity of Hantaan Virus DNA Vaccine pWRG/HTN-M(x) following PowderJect® Delivery to Syrian Hamster Skin. Final Study Report for Protocol Number JTA00001. 2005.
17. Hammerbeck, C. D., Wahl-Jensen, V., Hooper, J.W. Hantavirus. In: Vaccines for Biodefense and Emerging and Neglected Diseases (A. D. T. Barrett and L. R. Stanberry, Eds.), pp. 379-411. London: Academic Press, 2009.
18. Jonsson C. B, J. Hooper, and G. Mertz (2008). Treatment of hantavirus pulmonary syndrome. Antiviral Res. Antiviral Res. 78:162-169.
23. Schmaljohn, C. S., and J. W. Hooper (January, 27 2000). U.S. patent application Ser. No. 09/491,974; publication number 2002/0114818, published Aug. 22, 2002, entitled "DNA vaccines against hantavirus infections"
24. Hooper, J. W., C. S. Schmaljohn and M. Custer. "Extraneous DNA sequence that facilitates hantavirus gene expression. U.S. Pat. No. 7,217,812. Issued May 15, 2007.
25. Hooper, J. W., C. S. Schmaljohn. DNA Vaccines Against Hantavirus. Korean Patent 660040. Issued December 2006, and European Patent EPO 00908388.2, issued January 2007

26. Hooper, J. W. Puumala virus full-length M segment-based DNA vaccines. U.S. application Ser. No. 12/449,504, filed Aug. 11, 2009; PCT/US2008/001847, published Jan. 15, 2009

The contents of all cited references (including literature references, issued patents, published patent applications, and co-pending patent applications) cited throughout this application are hereby expressly incorporated by reference.

What is claimed is:

1. A method for inducing an immune response against Sin Nombre virus (SNV) infection in a mammal or a bird, the method comprising administering to the mammal or the bird a composition comprising a pharmacologically acceptable carrier and an effective amount to elicit the immune response of a first plasmid comprising a first recombinant DNA construct comprising:

(i) a first vector, (ii) a first promoter, and (iii) a first nucleic acid comprising SEQ ID NO:2 or SEQ ID NO:3, the first nucleic acid encoding SNV Gc and Gn glycoproteins, the expression of the SNV Gc and Gn glycoproteins being operably linked to the first promoter;

the administering resulting in the expression of the SNV Gc and Gn glycoproteins.

2. The method of claim 1, the administering comprising needle inoculation or needle-free jet injection.

3. The method of claim 1, the administering raising a titer of neutralizing antibodies against SNV in the mammal or the bird, wherein the titer is at least 100, wherein the titer is the reciprocal of the final dilution of serum to produce a 50% reduction in plaque forming units when combined with SNV.

4. The method of claim 3, wherein the titer is at least 10,000.

5. The method of claim 1, wherein the first promoter is a cytomegalovirus promoter, a beta-actin promoter, or a SV40 promoter.

6. The method of claim 1, wherein the first nucleic acid comprises SEQ ID NO: 2.

7. The method of claim 1, wherein the first plasmid comprises SEQ ID NO: 1.

8. The method of claim 1, wherein the effective amount is from about 5 micrograms to about 5 milligrams.

9. The method of claim 1 further comprising administering a second plasmid comprising a second recombinant DNA construct comprising:

(i) a second vector, (ii) a second promoter, and (iii) a second nucleic acid encoding Andes virus Gc and Gn glycoproteins, the expression of the Andes virus Gc and Gn glycoproteins being operably linked to the second promoter; and the administering resulting in the expression of the Andes virus Gc and Gn glycoproteins.

10. The method of claim 9, wherein the second plasmid comprises SEQ ID NO:10.

11. The method of claim 1 further comprising administering a third plasmid comprising a third recombinant DNA construct comprising:

(i) a third vector, (ii) a third promoter, and (iii) a third nucleic acid encoding at least one first Gn glycoprotein and at least one first Gc glycoprotein, the at least one first Gn glycoprotein and the at least one first Gc glycoprotein being from at least one hantavirus selected from Hantaan virus, Puumala virus, and Seoul virus, the at least one first Gn glycoprotein and the at least one first Gc glycoprotein being operably linked to the third promoter;

the administering resulting in the expression of the at least one first Gc glycoprotein and the at least one first Gn glycoprotein.

12. The method of claim 11, wherein:

(a) the hantavirus is Puumala virus and the third plasmid comprises SEQ ID NO:11, (b) the hantavirus is Hantaan virus and the third plasmid comprises SEQ ID NO:12, (c) the hantavirus is Seoul virus and the third plasmid comprises SEQ ID NO:13, or (d) a combination of (a)-(c).

13. The method of claim 11, wherein the hantavirus is Puumala virus and the third nucleic acid comprises SEQ ID NO: 14.

14. The method of claim 9 further comprising administering a third plasmid comprising a third recombinant DNA construct comprising:

(i) a third vector, (ii) a third promoter, and (iii) a third nucleic acid encoding at least one first Gn glycoprotein and at least one first Gc glycoprotein, the at least one first Gn glycoprotein and the at least one first Gc glycoprotein being from at least one hantavirus selected from Hantaan virus, Puumala virus, and Seoul virus, the at least one first Gn glycoprotein and the at least one first Gc glycoprotein being operably linked to the third promoter;

the administering resulting in the expression of the at least one first Gc glycoprotein and the at least one first Gn glycoprotein.

15. The method of claim 14, wherein:

(a) the hantavirus is Puumala virus and the third plasmid comprises SEQ ID NO:11, (b) the hantavirus is Hantaan virus and the third plasmid comprises SEQ ID NO:12, (c) the hantavirus is Seoul virus and the third plasmid comprises SEQ ID NO:13, or (d) a combination of (a)-(c).

16. The method of claim 14, wherein the hantavirus is Puumala virus and the third nucleic acid comprises SEQ ID NO: 14.

17. The method of claim 2, the administering further comprising electroporation.

18. The method of claim 5, wherein the promoter is the cytomegalovirus promoter, the recombinant DNA construct further comprises Intron A, the cytomegalovirus promoter is operably linked to Intron A, and Intron A is upstream of the nucleic acid.

19. The method of claim 9, wherein the second plasmid is administered in the composition.

* * * * *

SEQUENCE LISTING

```
<160> NUMBER OF SEQ ID NOS: 22

<210> SEQ ID NO 1
<211> LENGTH: 7938
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

gggggggggg ggcgctgagg tctgcctcgt gaagaaggtg ttgctgactc ataccaggcc     60

tgaatcgccc catcatccag ccagaaagtg agggagccac ggttgatgag agctttgttg    120

taggtggacc agttggtgat tttgaacttt tgctttgcca cggaacggtc tgcgttgtcg    180

ggaagatgcg tgatctgatc cttcaactca gcaaaagttc gatttattca acaaagccgc    240

cgtcccgtca agtcagcgta atgctctgcc agtgttacaa ccaattaacc aattctgatt    300

agaaaaactc atcgagcatc aaatgaaact gcaatttatt catatcagga ttatcaatac    360

catatttttg aaaaagccgt ttctgtaatg aaggagaaaa ctcaccgagg cagttccata    420

ggatggcaag atcctggtat cggtctgcga ttccgactcg tccaacatca atacaaccta    480

ttaatttccc ctcgtcaaaa ataaggttat caagtgagaa atcaccatga gtgacgactg    540

aatccggtga gaatggcaaa agcttatgca tttctttcca gacttgttca acaggccagc    600

cattacgctc gtcatcaaaa tcactcgcat caaccaaacc gttattcatt cgtgattgcg    660

cctgagcgag acgaaatacg cgatcgctgt taaaaggaca attacaaaca ggaatcgaat    720

gcaaccggcg caggaacact gccagcgcat caacaatatt ttcacctgaa tcaggatatt    780

cttctaatac ctggaatgct gttttcccgg ggatcgcagt ggtgagtaac catgcatcat    840

caggagtacg gataaaatgc ttgatggtcg gaagaggcat aaattccgtc agccagttta    900

gtctgaccat ctcatctgta acatcattgg caacgctacc tttgccatgt ttcagaaaca    960

actctggcgc atcgggcttc ccatacaatc gatagattgt cgcacctgat tgcccgacat   1020

tatcgcgagc ccatttatac ccatataaat cagcatccat gttggaattt aatcgcggcc   1080

tcgagcaaga cgtttcccgt tgaatatggc tcataacacc ccttgtatta ctgtttatgt   1140

aagcagacag ttttattgtt catgatgata tatttttatc ttgtgcaatg taacatcaga   1200

gattttgaga cacaacgtgg ctttcccccc ccccccggca tgcctgcagg tcgacaatat   1260

tggctattgg ccattgcata cgttgtatct atatcataat atgtacattt atattggctc   1320

atgtccaata tgaccgccat gttgacattg attattgact agttattaat agtaatcaat   1380

tacggggtca ttagttcata gcccatatat ggagttccgc gttacataac ttacggtaaa   1440

tggcccgcct ggctgaccgc ccaacgaccc ccgcccattg acgtcaataa tgacgtatgt   1500

tcccatagta acgccaatag ggactttcca ttgacgtcaa tgggtggagt atttacggta   1560

aactgcccac ttggcagtac atcaagtgta tcatatgcca agtccgcccc ctattgacgt   1620

caatgacggt aaatggcccg cctggcatta tgcccagtac atgaccttac gggactttcc   1680

tacttggcag tacatctacg tattagtcat cgctattacc atggtgatgc ggttttggca   1740

gtacaccaat gggcgtggat agcggtttga ctcacgggga tttccaagtc tccaccccat   1800
```

```
tgacgtcaat gggagtttgt tttggcacca aaatcaacgg gactttccaa aatgtcgtaa   1860
taaccccgcc ccgttgacgc aaatgggcgg taggcgtgta cggtgggagg tctatataag   1920
cagagctcgt ttagtgaacc gtcagatcgc ctggagacgc catccacgct gttttgacct   1980
ccatagaaga caccgggacc gatccagcct ccgcggccgg gaacggtgca ttggaacgcg   2040
gattccccgt gccaagagtg acgtaagtac cgcctataga ctctataggc acacccettt   2100
ggctcttatg catgctatac tgtttttggc ttggggccta tacacccccg cttccttatg   2160
ctataggtga tggtatagct tagcctatag gtgtgggtta ttgaccatta ttgaccactc   2220
ccctattggt gacgatactt tccattacta atccataaca tggctctttg ccacaactat   2280
ctctattggc tatatgccaa tactctgtcc ttcagagact gacacggact ctgtattttt   2340
acaggatggg gtcccattta ttatttacaa attcacatat acaacaacgc cgtcccccgt   2400
gcccgcagtt tttattaaac atagcgtggg atctccacgc gaatctcggg tacgtgttcc   2460
ggacatgggc tcttctccgg tagcggcgga gcttccacat ccgagccctg gtcccatgcc   2520
tccagcggct catggtcgct cggcagctcc ttgctcctaa cagtggaggc cagacttagg   2580
cacagcacaa tgcccaccac caccagtgtg ccgcacaagg ccgtggcggt agggtatgtg   2640
tctgaaaatg agctcggaga ttgggctcgc accgctgacg cagatggaag acttaaggca   2700
gcggcagaag aagatgcagg cagctgagtt gttgtattct gataagagtc agaggtaact   2760
cccgttgcgg tgctgttaac ggtggagggc agtgtagtct gagcagtact cgttgctgcc   2820
gcgcgcgcca ccagacataa tagctgacag actaacagac tgttcctttc catgggtctt   2880
ttctgcagtc accgtccaag cttgcggccg cggatctgca ggaattcggc acgagagtag   2940
tagactccgc acgaagaagc aaacactgaa taaaggatat acagaatggt gggctgggtg   3000
tgcatcttcc tggtggtgct gaccaccgcc acagccggcc tgacccggaa cctgtacgag   3060
ctgaagatcg agtgccccca caccgtgggc ctgggccagg gctacgtgac cggcagcgtg   3120
gagacaaccc ccatcctgct gacccaggtg gccgacctga agattgagag cagctgcaac   3180
ttcgacctgc acgtgcccgc caccaccacc cagaaataca accaggtgga ctggaccaag   3240
aagagcagca ccaccgagag caccaacgcc ggagccacca ccttcgaggc caagaccaaa   3300
gaagtgaacc tgaagggcac ctgcaacatc ccccccacca catttgaggc cgcctacaag   3360
agcagaaaga ccgtgatctg ctacgacctg gcctgcaacc agacccactg cctgcccacc   3420
gtgcacctga tcgcccccgt gcagacctgc atgagcgtgc ggagctgcat gatcggcctg   3480
ctgtccagcc ggatccaggt gatctacgag aaaacctact gcgtgaccgg ccagctgatc   3540
gagggcctgt gcttcatccc cacccacaca atcgccctga cccagcccgg ccacacctac   3600
gacaccatga ccctgcccgt gacctgcttt ctggtggcca agaagctggg cacccagctg   3660
aagctggccg tggagctgga aaagctgatc accggcgtga gctgcaccga gaacagcttc   3720
cagggctact acatctgctt catcggcaag cacagcgagc ccctgttcgt gcccaccatg   3780
gaagattaca gaagcgccga gctgttcacc cggatggtgc tgaaccccag gggcgaggac   3840
cacgaccccg accagaacgg ccagggcctg atgcggatcg ccggacccgt gaccgccaag   3900
gtgcccagca ccgagacaac cgaaaccatg cagggcattg ccttcgccgg agcccccatg   3960
tacagcagct tcagcaccct ggtgcggaag gccgaccccg agtacgtgtt cagccccggc   4020
atcattgccg agagcaacca cagcgtgtgc gacaagaaaa ccgtgcccct gacctggacc   4080
ggcttcctgg ccgtgagcgg cgagatcgag cggatcaccg gctgcaccgt gttctgcacc   4140
ctggccggac ctggcgccag ctgcgaggcc tacagcgaga caggcatctt caacatcagc   4200
```

-continued

```
agccccacct gcctggtgaa caaggtgcag aagttccggg gcagcgagca gcggatcaac   4260
ttcatgtgcc agcgggtgga ccaggacgtg gtggtgtact gcaacggcca gaaaaaagtg   4320
atcctgacca agaccctggt gatcggccag tgcatctaca ccttcaccag cctgttcagc   4380
ctgatccctg gcgtggctca tagcctggca gtcgaactgt gcgtgcctgg cctgcacgga   4440
tgggccacca ccgccctgct gatcaccttc tgcttcggct ggctgctgat ccccacagtg   4500
accctgatca tcctgaagat cctgcggctg ctgaccttca gctgcagcca ctacagcacc   4560
gagtccaagt tcaaagtgat tctggaacgc gtgaaggtgg agtaccagaa aaccatgggc   4620
agcatggtgt gcgacatctg ccaccacgag tgcgagacag ccaaagagct ggaaacccac   4680
aagaagagct gccccgaggg ccagtgcccc tactgcatga ccatcacaga gagcaccgag   4740
agcgccctgc aggcccactt cagcatctgc aagctgacca accggttcca ggaaaacctg   4800
aagaagagcc tgaagcggcc cgaagtgcgg aagggctgct accggaccct gggcgtgttc   4860
cggtacaaga gccggtgcta tgtgggcctg gtgtggggca ttctgctgac cacagagctg   4920
atcatctggg ccgccagcgc cgacaccccc ctgatggaaa gcgggtggag cgacaccgct   4980
catggcgtgg gaatcgtgcc catgaaaacc gacctggaac tggacttcgc cctggccagc   5040
agcagcagct acagctaccg gcggaagctg gtgaaccccg ccaaccagga agagacactg   5100
cccttccact tccaactgga caagcaggtg gtgcacgccg agatccagaa cctgggccac   5160
tggatggacg gcaccttcaa tatcaagacc gccttccact gctacggcga gtgcaagaag   5220
tacgcctacc cctggcagac cgccaagtgc ttcttcgaga aggactacca gtacgagaca   5280
agctggggct gcaacccccc cgactgtcct ggcgtgggca ccggctgtac cgcctgcggc   5340
gtgtacctgg acaagctgcg gagcgtgggc aaggcctaca agatcgtgtc cctgaagtac   5400
acccggaaag tgtgcatcca gctgggcaca gagcagacat gcaagcacat cgacgtgaac   5460
gattgcctgg tgacccccag cgtgaaagtc tgtatgattg gcaccatcag caagctgcag   5520
cccggcgata ccctgctgtt cctgggcccc ctggaacagg gcggcatcat tctgaagcag   5580
tggtgtacca cctcctgcgt gttcggcgac cccggcgaca tcatgagcac cacctccggc   5640
atgcggtgcc ccgagcacac cggcagcttc cggaagattt gtggcttcgc caccaccccct   5700
acctgcgagt accagggcaa caccgtgtcc ggcttccagc ggatgatggc cacccgggat   5760
agcttccaga gcttcaacgt gaccgagccc cacatcacca gcaaccggct ggaatggatc   5820
gaccccgaca gcagcatcaa ggaccacatc aacatggtgc tcaatcggga cgtgagcttc   5880
caggacctga gcgacaaccc ctgcaaggtg gacctgcaca cccagagcat cgacggcgcc   5940
tggggcagcg gcgtgggctt cacactggtg tgcacagtgg gcctgaccga gtgcgccaac   6000
ttcatcacct ccatcaaggc ctgcgacagc gccatgtgct acggcgccac cgtgaccaac   6060
ctgctgcggg gctccaacac agtgaaggtg gtgggcaagg gcggccacag cggcagcctg   6120
tttaagtgct gccacgacac cgactgcacc gaggaaggcc tggccgccag ccccccctcac   6180
ctggacagag tgaccggcta caaccagatc gacagcgaca aggtgtacga cgatggcgcc   6240
cctccctgca ccatcaagtg ctggttcacc aagagcggcg agtggctgct gggcatcctg   6300
aacggcaact gggtcgtcgt ggccgtgctg atcgtgatcc tgatcctgtc tatcctgctg   6360
ttcagcttct tctgccccgt gcggaaccgg aagaacaagg ccaactagca aacatatatg   6420
taagtaaggg tatgatcata ttatatcatt atgcgtatac tcttatatct ataatatcta   6480
tgtatcctta tactctaact atttatatta atttttactt ttatacaagt attaactaac   6540
```

-continued

```
ccattaccag ctaaaaaaaa caaaccctta acacctatat aatcccattt gcttattacg   6600

aggcttttgt tcctgcggag tctactacta agatctacgt atgatcagcc tcgactgtgc   6660

cttctagttg ccagccatct gttgtttgcc cctcccccgt gccttccttg accctggaag   6720

gtgccactcc cactgtcctt tcctaataaa atgaggaaat tgcatcgcat tgtctgagta   6780

ggtgtcattc tattctgggg ggtggggtgg ggcaggacag caagggggag gattgggaag   6840

acaatagcag gcatgctggg gatgcggtgg gctctatggc ttctgaggcg gaaagaacca   6900

gctggggctc gacagctcga ctctagaatt gcttcctcgc tcactgactc gctgcgctcg   6960

gtcgttcggc tgcggcgagc ggtatcagct cactcaaagg cggtaatacg gttatccaca   7020

gaatcagggg ataacgcagg aaagaacatg tgagcaaaag gccagcaaaa ggccaggaac   7080

cgtaaaaagg ccgcgttgct ggcgtttttc cataggctcc gcccccctga cgagcatcac   7140

aaaaatcgac gctcaagtca gaggtggcga aacccgacag gactataaag ataccaggcg   7200

tttccccctg gaagctccct cgtgcgctct cctgttccga ccctgccgct taccggatac   7260

ctgtccgcct ttctcccttc gggaagcgtg gcgctttctc atagctcacg ctgtaggtat   7320

ctcagttcgg tgtaggtcgt tcgctccaag ctgggctgtg tgcacgaacc ccccgttcag   7380

cccgaccgct gcgccttatc cggtaactat cgtcttgagt ccaacccggt aagacacgac   7440

ttatcgccac tggcagcagc cactggtaac aggattagca gagcgaggta tgtaggcggt   7500

gctacagagt tcttgaagtg gtggcctaac tacggctaca ctagaagaac agtatttggt   7560

atctgcgctc tgctgaagcc agttaccttc ggaaaaagag ttggtagctc ttgatccggc   7620

aaacaaacca ccgctggtag cggtggtttt tttgtttgca agcagcagat tacgcgcaga   7680

aaaaaaggat ctcaagaaga tcctttgatc ttttctacgg ggtctgacgc tcagtggaac   7740

gaaaactcac gttaagggat tttggtcatg agattatcaa aaaggatctt cacctagatc   7800

cttttaaatt aaaaatgaag ttttaaatca atctaaagta tatatgagta aacttggtct   7860

gacagttacc aatgcttaat cagtgaggca cctatctcag cgatctgtct atttcgttca   7920

tccatagttg cctgactc                                                 7938
```

<210> SEQ ID NO 2
<211> LENGTH: 3733
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 2

```
gcggccgcgg atctgcagga attcggcacg agagtagtag actccgcacg aagaagcaaa     60

cactgaataa aggatataca gaatggtggg ctgggtgtgc atcttcctgg tggtgctgac    120

caccgccaca gccggcctga cccggaacct gtacgagctg aagatcgagt gcccccacac    180

cgtgggcctg ggccagggct acgtgaccgg cagcgtggag acaaccccca tcctgctgac    240

ccaggtggcc gacctgaaga ttgagagcag ctgcaacttc gacctgcacg tgcccgccac    300

caccacccag aaatacaacc aggtggactg gaccaagaag agcagcacca ccgagagcac    360

caacgccgga gccaccacct tcgaggccaa gaccaaagaa gtgaacctga agggcacctg    420

caacatcccc cccaccacat ttgaggccgc ctacaagagc agaaagaccg tgatctgcta    480

cgacctggcc tgcaaccaga cccactgcct gcccaccgtg cacctgatcg cccccgtgca    540

gacctgcatg agcgtgcgga gctgcatgat cggcctgctg tccagccgga tccaggtgat    600
```

-continued

```
ctacgagaaa acctactgcg tgaccggcca gctgatcgag ggcctgtgct tcatccccac    660
ccacacaatc gccctgaccc agcccggcca cacctacgac accatgaccc tgcccgtgac    720
ctgctttctg gtggccaaga agctgggcac ccagctgaag ctggccgtgg agctggaaaa    780
gctgatcacc ggcgtgagct gcaccgagaa cagcttccag ggctactaca tctgcttcat    840
cggcaagcac agcgagcccc tgttcgtgcc caccatggaa gattacagaa gcgccgagct    900
gttcacccgg atggtgctga accccagggg cgaggaccac gaccccgacc agaacggcca    960
gggcctgatg cggatcgccg gacccgtgac cgccaaggtg cccagcaccg agacaaccga   1020
aaccatgcag ggcattgcct tcgccggagc cccccatgtac agcagcttca gcaccctggt   1080
gcggaaggcc gaccccgagt acgtgttcag ccccggcatc attgccgaga gcaaccacag   1140
cgtgtgcgac aagaaaaccg tgcccctgac ctggaccggc ttcctggccg tgagcggcga   1200
gatcgagcgg atcaccggct gcaccgtgtt ctgcaccctg gccggacctg gcgccagctg   1260
cgaggcctac agcgagacag gcatcttcaa catcagcagc cccacctgcc tggtgaacaa   1320
ggtgcagaag ttccggggca gcgagcagcg gatcaacttc atgtgccagc gggtggacca   1380
ggacgtggtg gtgtactgca acggccagaa aaaagtgatc ctgaccaaga ccctggtgat   1440
cggccagtgc atctacacct tcaccagcct gttcagcctg atccctggcg tggctcatag   1500
cctggcagtc gaactgtgcg tgcctggcct gcacggatgg gccaccaccg ccctgctgat   1560
caccttctgc ttcggctggc tgctgatccc cacagtgacc ctgatcatcc tgaagatcct   1620
gcggctgctg accttcagct gcagccacta cagcaccgag tccaagttca aagtgattct   1680
ggaacgcgtg aaggtggagt accagaaaac catgggcagc atggtgtgcg acatctgcca   1740
ccacgagtgc gagacagcca aagagctgga aacccacaag aagagctgcc ccgagggcca   1800
gtgcccctac tgcatgacca tcacagagag caccgagagc gccctgcagg cccacttcag   1860
catctgcaag ctgaccaacc ggttccagga aaacctgaag aagagcctga agcggcccga   1920
agtgcggaag ggctgctacc ggaccctggg cgtgttccgg tacaagagcc ggtgctatgt   1980
gggcctggtg tggggcattc tgctgaccac agagctgatc atctgggccg ccagcgccga   2040
caccccccctg atggaaagcg ggtggagcga caccgctcat ggcgtgggaa tcgtgcccat   2100
gaaaaccgac ctggaactgg acttcgccct ggccagcagc agcagctaca gctaccggcg   2160
gaagctggtg aaccccgcca accaggaaga gacactgccc ttccacttcc aactggacaa   2220
gcaggtggtg cacgccgaga tccagaacct gggccactgg atggacggca ccttcaatat   2280
caagaccgcc ttccactgct acggcgagtg caagaagtac gcctacccct ggcagaccgc   2340
caagtgcttc ttcgagaagg actaccagta cgagacaagc tggggctgca acccccccga   2400
ctgtcctggc gtgggcaccg gctgtaccgc ctgcggcgtg tacctggaca agctgcggag   2460
cgtgggcaag gcctacaaga tcgtgtccct gaagtacacc cggaaagtgt gcatccagct   2520
gggcacagag cagacatgca agcacatcga cgtgaacgat tgcctggtga cccccagcgt   2580
gaaagtctgt atgattggca ccatcagcaa gctgcagccc ggcgataccc tgctgttcct   2640
gggcccccctg gaacagggcg gcatcattct gaagcagtgg tgtaccacct cctgcgtgtt   2700
cggcgacccc ggcgacatca tgagcaccac ctccggcatg cggtgccccg agcacaccgg   2760
cagcttccgg aagatttgtg gcttcgccac cacccctacc tgcgagtacc agggcaacac   2820
cgtgtccggc ttccagcgga tgatggccac ccgggatagc ttccagagct tcaacgtgac   2880
cgagccccac atcaccagca accggctgga atggatcgac cccgacagca gcatcaagga   2940
ccacatcaac atggtgctca atcgggacgt gagcttccag gacctgagcg acaacccctg   3000
```

```
caaggtggac ctgcacaccc agagcatcga cggcgcctgg ggcagcggcg tgggcttcac   3060

actggtgtgc acagtgggcc tgaccgagtg cgccaacttc atcacctcca tcaaggcctg   3120

cgacagcgcc atgtgctacg gcgccaccgt gaccaacctg ctgcggggct ccaacacagt   3180

gaaggtggtg ggcaagggcg gccacagcgg cagcctgttt aagtgctgcc acgacaccga   3240

ctgcaccgag gaaggcctgg ccgccagccc ccctcacctg gacagagtga ccggctacaa   3300

ccagatcgac agcgacaagg tgtacgacga tggcgcccct ccctgcacca tcaagtgctg   3360

gttcaccaag agcggcgagt ggctgctggg catcctgaac ggcaactggg tcgtcgtggc   3420

cgtgctgatc gtgatcctga tcctgtctat cctgctgttc agcttcttct gccccgtgcg   3480

gaaccggaag aacaaggcca actagcaaac atatatgtaa gtaagggtat gatcatatta   3540

tatcattatg cgtatactct tatatctata atatctatgt atccttatac tctaactatt   3600

tatattaatt tttactttta tacaagtatt aactaaccca ttaccagcta aaaaaaacaa   3660

acccttaaca cctatataat cccatttgct tattacgagg cttttgttcc tgcggagtct   3720

actactaaga tct                                                      3733
```

<210> SEQ ID NO 3
<211> LENGTH: 3423
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

```
atggtgggct gggtgtgcat cttcctggtg gtgctgacca ccgccacagc cggcctgacc     60

cggaacctgt acgagctgaa gatcgagtgc ccccacaccg tgggcctggg ccagggctac    120

gtgaccggca gcgtggagac aaccccccatc ctgctgaccc aggtggccga cctgaagatt    180

gagagcagct gcaacttcga cctgcacgtg cccgccacca ccacccagaa atacaaccag    240

gtggactgga ccaagaagag cagcaccacc gagagcacca acgccggagc caccaccttc    300

gaggccaaga ccaaagaagt gaacctgaag ggcacctgca acatcccccc caccacattt    360

gaggccgcct acaagagcag aaagaccgtg atctgctacg acctggcctg caaccagacc    420

cactgcctgc ccaccgtgca cctgatcgcc cccgtgcaga cctgcatgag cgtgcggagc    480

tgcatgatcg gcctgctgtc cagccggatc caggtgatct acgagaaaac ctactgcgtg    540

accggccagc tgatcgaggg cctgtgcttc atccccaccc acacaatcgc cctgacccag    600

cccggccaca cctacgacac catgaccctg cccgtgacct gctttctggt ggccaagaag    660

ctgggcaccc agctgaagct ggccgtggag ctggaaaagc tgatcaccgg cgtgagctgc    720

accgagaaca gcttccaggg ctactacatc tgcttcatcg gcaagcacag cgagcccctg    780

ttcgtgccca ccatggaaga ttacagaagc gccgagctgt tcacccggat ggtgctgaac    840

cccaggggcg aggaccacga ccccgaccag aacggccagg gcctgatgcg gatcgccgga    900

cccgtgaccg ccaaggtgcc cagcaccgag acaaccgaaa ccatgcaggg cattgccttc    960

gccggagccc ccatgtacag cagcttcagc accctggtgc ggaaggccga ccccgagtac   1020

gtgttcagcc ccggcatcat tgccgagagc aaccacagcg tgtgcgacaa gaaaaccgtg   1080

cccctgacct ggaccggctt cctggccgtg agcggcgaga tcgagcggat caccggctgc   1140

accgtgttct gcaccctggc cggacctggc gccagctgcg aggcctacag cgagacaggc   1200

atcttcaaca tcagcagccc cacctgcctg gtgaacaagg tgcagaagtt ccggggcagc   1260
```

-continued gagcagcgga tcaacttcat gtgccagcgg gtggaccagg acgtggtggt gtactgcaac 1320
ggccagaaaa aagtgatcct gaccaagacc ctggtgatcg gccagtgcat ctacaccttc 1380
accagcctgt tcagcctgat ccctggcgtg gctcatagcc tggcagtcga actgtgcgtg 1440
cctggcctgc acggatgggc caccaccgcc ctgctgatca ccttctgctt cggctggctg 1500
ctgatcccca cagtgaccct gatcatcctg aagatcctgc ggctgctgac cttcagctgc 1560
agccactaca gcaccgagtc caagttcaaa gtgattctgg aacgcgtgaa ggtggagtac 1620
cagaaaacca tgggcagcat ggtgtgcgac atctgccacc acgagtgcga gacagccaaa 1680
gagctggaaa cccacaagaa gagctgcccc gagggccagt gcccctactg catgaccatc 1740
acagagagca ccgagagcgc cctgcaggcc cacttcagca tctgcaagct gaccaaccgg 1800
ttccaggaaa acctgaagaa gagcctgaag cggcccgaag tgcggaaggg ctgctaccgg 1860
accctgggcg tgttccggta caagagccgg tgctatgtgg gcctggtgtg gggcattctg 1920
ctgaccacag agctgatcat ctgggccgcc agcgccgaca ccccccctgat ggaaagcggg 1980 tggagcgaca ccgctcatgg cgtgggaatc gtgcccatga aaaccgacct ggaactggac 2040
ttcgccctgg ccagcagcag cagctacagc taccggcgga agctggtgaa ccccgccaac 2100
caggaagaga cactgccctt ccacttccaa ctggacaagc aggtggtgca cgccgagatc 2160
cagaacctgg gccactggat ggacggcacc ttcaatatca agaccgcctt ccactgctac 2220
ggcgagtgca agaagtacgc ctacccctgg cagaccgcca agtgcttctt cgagaaggac 2280
taccagtacg agacaagctg gggctgcaac ccccccgact gtcctggcgt gggcaccggc 2340
tgtaccgcct gcggcgtgta cctggacaag ctgcggagcg tgggcaaggc ctacaagatc 2400
gtgtccctga agtacacccg gaaagtgtgc atccagctgg gcacagagca gacatgcaag 2460
cacatcgacg tgaacgattg cctggtgacc cccagcgtga aagtctgtat gattggcacc 2520
atcagcaagc tgcagcccgg cgataccctg ctgttcctgg gccccctgga acagggcggc 2580
atcattctga agcagtggtg taccacctcc tgcgtgttcg gcgaccccgg cgacatcatg 2640
agcaccacct ccggcatgcg gtgccccgag cacaccggca gcttccggaa gatttgtggc 2700
ttcgccacca cccctacctg cgagtaccag ggcaacaccg tgtccggctt ccagcggatg 2760
atggccaccc gggatagctt ccagagcttc aacgtgaccg agccccacat caccagcaac 2820
cggctggaat ggatcgaccc cgacagcagc atcaaggacc acatcaacat ggtgctcaat 2880
cgggacgtga gcttccagga cctgagcgac aaccccctgca aggtggacct gcacacccag 2940
agcatcgacg gcgcctgggg cagcggcgtg ggcttcacac tggtgtgcac agtgggcctg 3000
accgagtgcg ccaacttcat cacctccatc aaggcctgcg acagcgccat gtgctacggc 3060
gccaccgtga ccaacctgct gcggggctcc aacacagtga aggtggtggg caagggcggc 3120
cacagcggca gcctgtttaa gtgctgccac gacaccgact gcaccgagga aggcctggcc 3180
gccagccccc ctcacctgga cagagtgacc ggctacaacc agatcgacag cgacaaggtg 3240
tacgacgatg gcgcccctcc ctgcaccatc aagtgctggt tcaccaagag cggcgagtgg 3300
ctgctgggca tcctgaacgg caactgggtc gtcgtggccg tgctgatcgt gatcctgatc 3360
ctgtctatcc tgctgttcag cttcttctgc cccgtgcgga accggaagaa caaggccaac 3420
tag 3423

<210> SEQ ID NO 4
<211> LENGTH: 1140
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 4

Met Val Gly Trp Val Cys Ile Phe Leu Val Val Leu Thr Thr Ala Thr
1               5                   10                  15

Ala Gly Leu Thr Arg Asn Leu Tyr Glu Leu Lys Ile Glu Cys Pro His
            20                  25                  30

Thr Val Gly Leu Gly Gln Gly Tyr Val Thr Gly Ser Val Glu Thr Thr
        35                  40                  45

Pro Ile Leu Leu Thr Gln Val Ala Asp Leu Lys Ile Glu Ser Ser Cys
    50                  55                  60

Asn Phe Asp Leu His Val Pro Ala Thr Thr Thr Gln Lys Tyr Asn Gln
65                  70                  75                  80

Val Asp Trp Thr Lys Lys Ser Ser Thr Thr Glu Ser Thr Asn Ala Gly
                85                  90                  95

Ala Thr Thr Phe Glu Ala Lys Thr Lys Glu Val Asn Leu Lys Gly Thr
            100                 105                 110

Cys Asn Ile Pro Pro Thr Thr Phe Glu Ala Ala Tyr Lys Ser Arg Lys
        115                 120                 125

Thr Val Ile Cys Tyr Asp Leu Ala Cys Asn Gln Thr His Cys Leu Pro
    130                 135                 140

Thr Val His Leu Ile Ala Pro Val Gln Thr Cys Met Ser Val Arg Ser
145                 150                 155                 160

Cys Met Ile Gly Leu Leu Ser Ser Arg Ile Gln Val Ile Tyr Glu Lys
                165                 170                 175

Thr Tyr Cys Val Thr Gly Gln Leu Ile Glu Gly Leu Cys Phe Ile Pro
            180                 185                 190

Thr His Thr Ile Ala Leu Thr Gln Pro Gly His Thr Tyr Asp Thr Met
        195                 200                 205

Thr Leu Pro Val Thr Cys Phe Leu Val Ala Lys Lys Leu Gly Thr Gln
    210                 215                 220

Leu Lys Leu Ala Val Glu Leu Glu Lys Leu Ile Thr Gly Val Ser Cys
225                 230                 235                 240

Thr Glu Asn Ser Phe Gln Gly Tyr Tyr Ile Cys Phe Ile Gly Lys His
                245                 250                 255

Ser Glu Pro Leu Phe Val Pro Thr Met Glu Asp Tyr Arg Ser Ala Glu
            260                 265                 270

Leu Phe Thr Arg Met Val Leu Asn Pro Arg Gly Glu Asp His Asp Pro
        275                 280                 285

Asp Gln Asn Gly Gln Gly Leu Met Arg Ile Ala Gly Pro Val Thr Ala
    290                 295                 300

Lys Val Pro Ser Thr Glu Thr Thr Glu Thr Met Gln Gly Ile Ala Phe
305                 310                 315                 320

Ala Gly Ala Pro Met Tyr Ser Ser Phe Ser Thr Leu Val Arg Lys Ala
                325                 330                 335

Asp Pro Glu Tyr Val Phe Ser Pro Gly Ile Ile Ala Glu Ser Asn His
            340                 345                 350

Ser Val Cys Asp Lys Lys Thr Val Pro Leu Thr Trp Thr Gly Phe Leu
        355                 360                 365

Ala Val Ser Gly Glu Ile Glu Arg Ile Thr Gly Cys Thr Val Phe Cys
    370                 375                 380
```

-continued

```
Thr Leu Ala Gly Pro Gly Ala Ser Cys Glu Ala Tyr Ser Glu Thr Gly
385                 390                 395                 400

Ile Phe Asn Ile Ser Ser Pro Thr Cys Leu Val Asn Lys Val Gln Lys
                405                 410                 415

Phe Arg Gly Ser Glu Gln Arg Ile Asn Phe Met Cys Gln Arg Val Asp
            420                 425                 430

Gln Asp Val Val Val Tyr Cys Asn Gly Gln Lys Lys Val Ile Leu Thr
        435                 440                 445

Lys Thr Leu Val Ile Gly Gln Cys Ile Tyr Thr Phe Thr Ser Leu Phe
    450                 455                 460

Ser Leu Ile Pro Gly Val Ala His Ser Leu Ala Val Glu Leu Cys Val
465                 470                 475                 480

Pro Gly Leu His Gly Trp Ala Thr Thr Ala Leu Leu Ile Thr Phe Cys
                485                 490                 495

Phe Gly Trp Leu Leu Ile Pro Thr Val Thr Leu Ile Ile Leu Lys Ile
            500                 505                 510

Leu Arg Leu Leu Thr Phe Ser Cys Ser His Tyr Ser Thr Glu Ser Lys
        515                 520                 525

Phe Lys Val Ile Leu Glu Arg Val Lys Val Glu Tyr Gln Lys Thr Met
    530                 535                 540

Gly Ser Met Val Cys Asp Ile Cys His His Glu Cys Glu Thr Ala Lys
545                 550                 555                 560

Glu Leu Glu Thr His Lys Lys Ser Cys Pro Glu Gly Gln Cys Pro Tyr
                565                 570                 575

Cys Met Thr Ile Thr Glu Ser Thr Glu Ser Ala Leu Gln Ala His Phe
            580                 585                 590

Ser Ile Cys Lys Leu Thr Asn Arg Phe Gln Glu Asn Leu Lys Lys Ser
        595                 600                 605

Leu Lys Arg Pro Glu Val Arg Lys Gly Cys Tyr Arg Thr Leu Gly Val
    610                 615                 620

Phe Arg Tyr Lys Ser Arg Cys Tyr Val Gly Leu Val Trp Gly Ile Leu
625                 630                 635                 640

Leu Thr Thr Glu Leu Ile Ile Trp Ala Ala Ser Ala Asp Thr Pro Leu
                645                 650                 655

Met Glu Ser Gly Trp Ser Asp Thr Ala His Gly Val Gly Ile Val Pro
            660                 665                 670

Met Lys Thr Asp Leu Glu Leu Asp Phe Ala Leu Ala Ser Ser Ser Ser
        675                 680                 685

Tyr Ser Tyr Arg Arg Lys Leu Val Asn Pro Ala Asn Gln Glu Glu Thr
    690                 695                 700

Leu Pro Phe His Phe Gln Leu Asp Lys Gln Val Val His Ala Glu Ile
705                 710                 715                 720

Gln Asn Leu Gly His Trp Met Asp Gly Thr Phe Asn Ile Lys Thr Ala
                725                 730                 735

Phe His Cys Tyr Gly Glu Cys Lys Lys Tyr Ala Tyr Pro Trp Gln Thr
            740                 745                 750

Ala Lys Cys Phe Phe Glu Lys Asp Tyr Gln Tyr Glu Thr Ser Trp Gly
        755                 760                 765

Cys Asn Pro Pro Asp Cys Pro Gly Val Gly Thr Gly Cys Thr Ala Cys
    770                 775                 780

Gly Val Tyr Leu Asp Lys Leu Arg Ser Val Gly Lys Ala Tyr Lys Ile
785                 790                 795                 800

Val Ser Leu Lys Tyr Thr Arg Lys Val Cys Ile Gln Leu Gly Thr Glu
```

```
                805                 810                 815

Gln Thr Cys Lys His Ile Asp Val Asn Asp Cys Leu Val Thr Pro Ser
            820                 825                 830

Val Lys Val Cys Met Ile Gly Thr Ile Ser Lys Leu Gln Pro Gly Asp
        835                 840                 845

Thr Leu Leu Phe Leu Gly Pro Leu Glu Gln Gly Gly Ile Ile Leu Lys
    850                 855                 860

Gln Trp Cys Thr Thr Ser Cys Val Phe Gly Asp Pro Gly Asp Ile Met
865                 870                 875                 880

Ser Thr Thr Ser Gly Met Arg Cys Pro Glu His Thr Gly Ser Phe Arg
                885                 890                 895

Lys Ile Cys Gly Phe Ala Thr Thr Pro Thr Cys Glu Tyr Gln Gly Asn
            900                 905                 910

Thr Val Ser Gly Phe Gln Arg Met Met Ala Thr Arg Asp Ser Phe Gln
        915                 920                 925

Ser Phe Asn Val Thr Glu Pro His Ile Thr Ser Asn Arg Leu Glu Trp
    930                 935                 940

Ile Asp Pro Asp Ser Ser Ile Lys Asp His Ile Asn Met Val Leu Asn
945                 950                 955                 960

Arg Asp Val Ser Phe Gln Asp Leu Ser Asp Asn Pro Cys Lys Val Asp
                965                 970                 975

Leu His Thr Gln Ser Ile Asp Gly Ala Trp Gly Ser Gly Val Gly Phe
            980                 985                 990

Thr Leu Val Cys Thr Val Gly Leu  Thr Glu Cys Ala Asn  Phe Ile Thr
        995                 1000                1005

Ser Ile  Lys Ala Cys Asp Ser  Ala Met Cys Tyr Gly  Ala Thr Val
    1010                 1015                 1020

Thr Asn  Leu Leu Arg Gly Ser  Asn Thr Val Lys Val  Val Gly Lys
    1025                 1030                 1035

Gly Gly  His Ser Gly Ser Leu  Phe Lys Cys Cys His  Asp Thr Asp
    1040                 1045                 1050

Cys Thr  Glu Glu Gly Leu Ala  Ala Ser Pro Pro His  Leu Asp Arg
    1055                 1060                 1065

Val Thr  Gly Tyr Asn Gln Ile  Asp Ser Asp Lys Val  Tyr Asp Asp
    1070                 1075                 1080

Gly Ala  Pro Pro Cys Thr Ile  Lys Cys Trp Phe Thr  Lys Ser Gly
    1085                 1090                 1095

Glu Trp  Leu Leu Gly Ile Leu  Asn Gly Asn Trp Val  Val Val Ala
    1100                 1105                 1110

Val Leu  Ile Val Ile Leu Ile  Leu Ser Ile Leu Leu  Phe Ser Phe
    1115                 1120                 1125

Phe Cys  Pro Val Arg Asn Arg  Lys Asn Lys Ala Asn
    1130                 1135                 1140
```

<210> SEQ ID NO 5
<211> LENGTH: 72
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 5
atctgcagga attcggcacg agagtagtag actccgcacg aagaagcaaa cactgaataa 60
aggatataca ga 72

<210> SEQ ID NO 6
<211> LENGTH: 223
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 6
caaacatata tgtaagtaag ggtatgatca tattatatca ttatgcgtat actcttatat 60
ctataatatc tatgtatcct tatactctaa ctatttatat taatttttac ttttatacaa 120
gtattaacta acccattacc agctaaaaaa aacaaaccct taacacctat ataatcccat 180
ttgcttatta cgaggctttt gttcctgcgg agtctactac taa 223

<210> SEQ ID NO 7
<211> LENGTH: 10
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 7
gcggccgcgg 10

<210> SEQ ID NO 8
<211> LENGTH: 5
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 8 gatct 5

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 9
atctgcagga attcggcacg ag 22

<210> SEQ ID NO 10
<211> LENGTH: 7913
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 10
gggggggggg ggcgctgagg tctgcctcgt gaagaaggtg ttgctgactc ataccaggcc 60
tgaatcgccc catcatccag ccagaaagtg agggagccac ggttgatgag agctttgttg 120
taggtggacc agttggtgat tttgaacttt tgctttgcca cggaacggtc tgcgttgtcg 180
ggaagatgcg tgatctgatc cttcaactca gcaaaagttc gatttattca acaaagccgc 240
cgtcccgtca agtcagcgta atgctctgcc agtgttacaa ccaattaacc aattctgatt 300

```
agaaaaactc atcgagcatc aaatgaaact gcaatttatt catatcagga ttatcaatac    360
catatttttg aaaaagccgt ttctgtaatg aaggagaaaa ctcaccgagg cagttccata    420
ggatggcaag atcctggtat cggtctgcga ttccgactcg tccaacatca atacaaccta    480
ttaatttccc ctcgtcaaaa ataaggttat caagtgagaa atcaccatga gtgacgactg    540
aatccggtga gaatggcaaa agcttatgca tttctttcca gacttgttca acaggccagc    600
cattacgctc gtcatcaaaa tcactcgcat caaccaaacc gttattcatt cgtgattgcg    660
cctgagcgag acgaaatacg cgatcgctgt taaaaggaca attacaaaca ggaatcgaat    720
gcaaccggcg caggaacact gccagcgcat caacaatatt ttcacctgaa tcaggatatt    780
cttctaatac ctggaatgct gttttcccgg ggatcgcagt ggtgagtaac catgcatcat    840
caggagtacg gataaaatgc ttgatggtcg gaagaggcat aaattccgtc agccagttta    900
gtctgaccat ctcatctgta acatcattgg caacgctacc tttgccatgt ttcagaaaca    960
actctggcgc atcgggcttc ccatacaatc gatagattgt cgcacctgat tgcccgacat   1020
tatcgcgagc ccatttatac ccatataaat cagcatccat gttggaattt aatcgcggcc   1080
tcgagcaaga cgtttcccgt tgaatatggc tcataacacc ccttgtatta ctgtttatgt   1140
aagcagacag ttttattgtt catgatgata tatttttatc ttgtgcaatg taacatcaga   1200
gattttgaga cacaacgtgg ctttcccccc ccccccggca tgcctgcagg tcgacaatat   1260
tggctattgg ccattgcata cgttgtatct atatcataat atgtacattt atattggctc   1320
atgtccaata tgaccgccat gttgacattg attattgact agttattaat agtaatcaat   1380
tacggggtca ttagttcata gcccatatat ggagttccgc gttacataac ttacggtaaa   1440
tggcccgcct ggctgaccgc ccaacgaccc ccgcccattg acgtcaataa tgacgtatgt   1500
tcccatagta acgccaatag ggactttcca ttgacgtcaa tgggtggagt atttacggta   1560
aactgcccac ttggcagtac atcaagtgta tcatatgcca agtccgcccc ctattgacgt   1620
caatgacggt aaatggcccg cctggcatta tgcccagtac atgaccttac gggactttcc   1680
tacttggcag tacatctacg tattagtcat cgctattacc atggtgatgc ggttttggca   1740
gtacaccaat gggcgtggat agcggtttga ctcacgggga tttccaagtc tccaccccat   1800
tgacgtcaat gggagtttgt tttggcacca aaatcaacgg gactttccaa aatgtcgtaa   1860
taaccccgcc ccgttgacgc aaatgggcgg taggcgtgta cggtgggagg tctatataag   1920
cagagctcgt ttagtgaacc gtcagatcgc ctggagacgc catccacgct gttttgacct   1980
ccatagaaga caccgggacc gatccagcct ccgcggccgg gaacggtgca ttggaacgcg   2040
gattccccgt gccaagagtg acgtaagtac cgcctataga ctctataggc acaccccttt   2100
ggctcttatg catgctatac tgtttttggc ttggggccta tacacccccg cttccttatg   2160
ctataggtga tggtatagct tagcctatag gtgtgggtta ttgaccatta ttgaccactc   2220
ccctattggt gacgatactt tccattacta atccataaca tggctctttg ccacaactat   2280
ctctattggc tatatgccaa tactctgtcc ttcagagact gacacggact ctgtattttt   2340
acaggatggg gtcccattta ttatttacaa attcacatat acaacaacgc cgtcccccgt   2400
gcccgcagtt tttattaaac atagcgtggg atctccacgc gaatctcggg tacgtgttcc   2460
ggacatgggc tcttctccgg tagcggcgga gcttccacat ccgagccctg gtcccatgcc   2520
tccagcggct catggtcgct cggcagctcc ttgctcctaa cagtggaggc cagacttagg   2580
cacagcacaa tgcccaccac caccagtgtg ccgcacaagg ccgtggcggt agggtatgtg   2640
```

-continued

```
tctgaaaatg agctcggaga ttgggctcgc accgctgacg cagatggaag acttaaggca   2700

gcggcagaag aagatgcagg cagctgagtt gttgtattct gataagagtc agaggtaact   2760

cccgttgcgg tgctgttaac ggtggagggc agtgtagtct gagcagtact cgttgctgcc   2820

gcgcgcgcca ccagacataa tagctgacag actaacagac tgttcctttc catgggtctt   2880

ttctgcagtc agggtccaag cttgcggccg cggatctgca ggaattcggc acgagagtag   2940

tagactccgc acgaagaagc aaaaaattaa agaagtgagt ttaaaatgga agggtggtat   3000

ctggttgttc ttggagtctg ctatacgctg acactggcaa tgcccaagac catttatgag   3060

cttaaaatgg aatgcccgca cactgtgggt ctcggtcaag gttacatcat tggctcaaca   3120

gaactaggtt tgatctcaat tgaggctgca tctgatataa agctcgagag ctcttgcaat   3180

tttgatcttc atacaacatc tatggcccag aagagtttca cccaagttga atggagaaag   3240

aaaagtgaca caactgatac cacaaatgct gcgtccacta cctttgaagc acaaactaaa   3300

actgttaacc ttagagggac ttgtatactg gcacctgaac tctatgatac attgaagaaa   3360

gtaaaaaaga cagtcctgtg ctatgatcta acatgtaatc aaacacattg tcagccaact   3420

gtctatctga ttgcacctgt attgacatgc atgtcaataa gaagttgtat ggctagtgtg   3480

tttacaagca ggattcaggt gatttatgaa aagacacatt gtgtaacagg tcagctgatt   3540

gagggtcagt gtttcaaccc agcacacaca ttgacattat ctcagcctgc tcacacttat   3600

gatactgtca cccttcctat ctcttgtttt ttcacaccaa agaagtcgga gcaactaaaa   3660

gttataaaaa catttgaagg aattctgacg aagacaggtt gcacggagaa tgcattgcag   3720

ggttattatg tgtgtttttt agggagtcat tcagaacctt taattgttcc gagtttggag   3780

gacatacggt ctgctgaagt tgttagtagg atgcttgtac accctagggg agaagaccat   3840

gatgccatac agaattcaca aagtcactta agaatagtgg gacctatcac agcaaaagtg   3900

ccatcaacta gttccacaga taccctaaag ggacagcct ttgcaggcgt cccaatgtat   3960

agctctttat ctacactagt cagaaatgca gacccagaat ttgtattttc tccaggtata   4020

gtacctgaat ctaatcacag tacatgtgat aagaagacag tacctatcac atggacaggc   4080

tacctaccaa tatcaggtga gatggaaaaa gtgactggat gtacagtttt ttgtacacta   4140

gcaggacctg gtgctagttg tgaggcctat tctgaaaatg gtatatttaa catcagttct   4200

ccaacatgtc ttgtaaacaa agtccaaaga tttcgtggat ctgaacagaa aataaatttt   4260

atctgtcagc gggtagatca ggatgttgtt gtatactgca atgggcaaaa gaaagtcata   4320

ttaaccaaaa ctttggttat tggcagtgt atttatacat tcacaagcct attttcattg   4380

atgcctgatg tagcccactc attggctgta gaattatgtg tcccgggatt acatgggtgg   4440

gccactgtca tgcttctatc aacattctgc tttgggtggg tcttgattcc tgcggtcaca   4500

ttaataatat taaagtgtct aagggttttg acgttttctt gttcccatta cactaatgag   4560

tcaaaattta aattcatcct ggaaaaagtt aaaattgaat accaaaagac tatgggatca   4620

atggtgtgcg atgtatgtca tcatgagtgt gaaacagcaa aagaacttga atcacataga   4680

cagagttgta tcaatggaca atgtccttat tgcatgacaa taactgaagc aactgaaagt   4740

gccttgcaag cccattattc catttgtaaa ttggcaggaa gatttcagga ggcactgaaa   4800

aagtcactta aaaagccaga ggtaaaaaaa ggttgttaca gaacactcgg ggtatttaga   4860

tataaaagta gatgttatgt gggtttggta tggtgcctat tgttgacatg tgaaattgtt   4920

atttgggccg caagtgcaga gactccacta atggagtcag gctggtcaga tacggctcat   4980

ggtgttggtg agattccaat gaagacagac ctcgagctgg acttttcact gccttcttca   5040
```

```
tcctcttaca gttataggag aaagctcaca aacccagcca ataaagaaga gtctattccc   5100
ttccacttcc agatggaaaa acaagtaatt catgctgaaa tccaacccct gggtcattgg   5160
atggatgcga catttaatat taagactgca tttcattgtt atggtgcatg ccagaaatac   5220
tcttatccat ggcagacatc taagtgcttc tttgaaaagg actaccagta tgaaacaggc   5280
tggggctgta atcctggtga ctgcccaggg gttgggactg gatgcactgc ttgtggtgtt   5340
tatctcgata aactaaaatc tgttgggaag gcctataaga taatttcttt aaaatatacc   5400
agaaaggttt gtattcagtt aggaacagaa caaacttgca agcatattga tgcaaatgat   5460
tgtttagtga caccatctgt gaaagtttgc atagtgggca cagtttcaaa acttcaacca   5520
tctgatactc ttttgttctt aggtccacta gaacaagggg gaatcattct taagcaatgg   5580
tgcacaacat catgtgcatt tggggaccct ggtgatatca tgtccactcc cagtggtatg   5640
aggtgtccag agcacactgg atcatttagg aaaatttgcg gttttgctac tacaccagtt   5700
tgtgaatatc aaggaaatac catttctgga tataaaagaa tgatggcaac aaaagattca   5760
ttccaatcat ttaacttaac agaacctcac atcacaacaa acaagcttga atggatcgac   5820
ccagatggga atacaagaga ccacgtaaac cttgtcttaa atagagatgt ctcatttcag   5880
gatttaagtg ataacccctg taaagtagac ctacacacac aagcaataga aggggcatgg   5940
ggttctggtg tagggtttac actcacatgt actgtcggat taacagagtg cccaagtttt   6000
atgacatcaa ttaaggcatg tgacctagct atgtgttatg gatcaacagt aacaaacctt   6060
gccaggggct ctaatacagt gaaagtagtt ggtaaaggag gccattcagg gtcctcattt   6120
aaatgctgtc atgatacaga ttgctcctct gaaggtttac ttgcatcagc ccctcatctt   6180
gagagggtaa caggattcaa tcaaattgat tcagataagg tttatgatga tggtgcacca   6240
ccttgcacat tcaaatgctg gttcactaag tcaggtgagt ggcttcttgg gatcttaaac   6300
gggaattgga ttgttgttgt agtgcttgtt gtgatactca ttctctctat cataatgttc   6360
agtgttttgt gtcccaggag agggcacaag aaaactgtct aagcattgac ctcaactcct   6420
acattagatc atatacattt atgcacttcc tcatatttag ctgcactaag atattaataa   6480
actctagtta ttgactttat aagattatta tggaactaac ctcacttaaa aaaaacaaat   6540
actttactca tatataactc catattctct taccgaggat tttgttcctg cggagcatac   6600
tactaggatc tacgtatgat cagcctcgac tgtgccttct agttgccagc catctgttgt   6660
ttgcccctcc cccgtgcctt ccttgaccct ggaaggtgcc actcccactg tcctttccta   6720
ataaaatgag gaaattgcat cgcattgtct gagtaggtgt cattctattc tggggggtgg   6780
ggtggggcag gacagcaagg gggaggattg ggaagacaat agcaggcatg ctggggatgc   6840
ggtgggctct atggcttctg aggcggaaag aaccagctgg ggctcgacag ctcgactcta   6900
gaattgcttc ctcgctcact gactcgctgc gctcggtcgt tcggctgcgg cgagcggtat   6960
cagctcactc aaaggcggta atacggttat ccacagaatc aggggataac gcaggaaaga   7020
acatgtgagc aaaaggccag caaaaggcca ggaaccgtaa aaaggccgcg ttgctggcgt   7080
ttttccatag gctccgcccc cctgacgagc atcacaaaaa tcgacgctca agtcagaggt   7140
ggcgaaaccc gacaggacta taaagatacc aggcgtttcc ccctggaagc tccctcgtgc   7200
gctctcctgt tccgaccctg ccgcttaccg gatacctgtc cgcctttctc ccttcgggaa   7260
gcgtggcgct ttctcatagc tcacgctgta ggtatctcag ttcggtgtag gtcgttcgct   7320
ccaagctggg ctgtgtgcac gaaccccccg ttcagcccga ccgctgcgcc ttatccggta   7380
```

actatcgtct tgagtccaac ccggtaagac acgacttatc gccactggca gcagccactg 7440
gtaacaggat tagcagagcg aggtatgtag gcggtgctac agagttcttg aagtggtggc 7500
ctaactacgg ctacactaga agaacagtat ttggtatctg cgctctgctg aagccagtta 7560
ccttcgaaaa aagagttggt agctcttgat ccggcaaaca aaccaccgct ggtagcggtg 7620
gtttttttgt ttgcaagcag cagattacgc gcagaaaaaa aggatctcaa gaagatcctt 7680
tgatcttttc tacggggtct gacgctcagt ggaacgaaaa ctcacgttaa gggattttgg 7740
tcatgagatt atcaaaaagg atcttcacct agatcctttt aaattaaaaa tgaagtttta 7800
aatcaatcta aagtatatat gagtaaactt ggtctgacag ttaccaatgc ttaatcagtg 7860
aggcacctat ctcagcgatc tgtctatttc gttcatccat agttgcctga ctc 7913

<210> SEQ ID NO 11
<211> LENGTH: 7924
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 11
gggggggggg ggcgctgagg tctgcctcgt gaagaaggtg ttgctgactc ataccaggcc 60
tgaatcgccc catcatccag ccagaaagtg agggagccac ggttgatgag agctttgttg 120
taggtggacc agttggtgat tttgaacttt tgctttgcca cggaacggtc tgcgttgtcg 180
ggaagatgcg tgatctgatc cttcaactca gcaaaagttc gatttattca acaaagccgc 240
cgtcccgtca agtcagcgta atgctctgcc agtgttacaa ccaattaacc aattctgatt 300
agaaaaactc atcgagcatc aaatgaaact gcaatttatt catatcagga ttatcaatac 360
catatttttg aaaaagccgt ttctgtaatg aaggagaaaa ctcaccgagg cagttccata 420
ggatggcaag atcctggtat cggtctgcga ttccgactcg tccaacatca atacaaccta 480
ttaatttccc ctcgtcaaaa ataaggttat caagtgagaa atcaccatga gtgacgactg 540
aatccggtga gaatggcaaa agcttatgca tttctttcca gacttgttca acaggccagc 600
cattacgctc gtcatcaaaa tcactcgcat caaccaaacc gttattcatt cgtgattgcg 660
cctgagcgag acgaaatacg cgatcgctgt taaaaggaca attacaaaca ggaatcgaat 720
gcaaccggcg caggaacact gccagcgcat caacaatatt ttcacctgaa tcaggatatt 780
cttctaatac ctggaatgct gttttcccgg ggatcgcagt ggtgagtaac catgcatcat 840
caggagtacg gataaaatgc ttgatggtcg gaagaggcat aaattccgtc agccagttta 900
gtctgaccat ctcatctgta acatcattgg caacgctacc tttgccatgt ttcagaaaca 960
actctggcgc atcgggcttc ccatacaatc gatagattgt cgcacctgat tgcccgacat 1020
tatcgcgagc ccatttatac ccatataaat cagcatccat gttggaattt aatcgcggcc 1080
tcgagcaaga cgtttcccgt tgaatatggc tcataacacc ccttgtatta ctgtttatgt 1140
aagcagacag ttttattgtt catgatgata tatttttatc ttgtgcaatg taacatcaga 1200
gattttgaga cacaacgtgg ctttcccccc ccccccggca tgcctgcagg tcgacaatat 1260
tggctattgg ccattgcata cgttgtatct atatcataat atgtacattt atattggctc 1320
atgtccaata tgaccgccat gttgacattg attattgact agttattaat agtaatcaat 1380
tacggggtca ttagttcata gcccatatat ggagttccgc gttacataac ttacggtaaa 1440
tggcccgcct ggctgaccgc ccaacgaccc ccgcccattg acgtcaataa tgacgtatgt 1500

-continued

```
tcccatagta acgccaatag ggactttcca ttgacgtcaa tgggtggagt atttacggta   1560
aactgcccac ttggcagtac atcaagtgta tcatatgcca agtccgcccc ctattgacgt   1620
caatgacggt aaatggcccg cctggcatta tgcccagtac atgaccttac gggactttcc   1680
tacttggcag tacatctacg tattagtcat cgctattacc atggtgatgc ggttttggca   1740
gtacaccaat gggcgtggat agcggtttga ctcacgggga tttccaagtc tccaccccat   1800
tgacgtcaat gggagtttgt tttggcacca aaatcaacgg gactttccaa aatgtcgtaa   1860
taaccccgcc ccgttgacgc aaatgggcgg taggcgtgta cggtgggagg tctatataag   1920
cagagctcgt ttagtgaacc gtcagatcgc ctggagacgc catccacgct gttttgacct   1980
ccatagaaga caccgggacc gatccagcct ccgcggccgg gaacggtgca ttggaacgcg   2040
gattccccgt gccaagagtg acgtaagtac cgcctataga ctctataggc acacccctt   2100
ggctcttatg catgctatac tgtttttggc ttggggccta tacacccccg cttccttatg   2160
ctataggtga tggtatagct tagcctatag gtgtgggtta ttgaccatta ttgaccactc   2220
ccctattggt gacgatactt tccattacta atccataaca tggctctttg ccacaactat   2280
ctctattggc tatatgccaa tactctgtcc ttcagagact gacacggact ctgtattttt   2340
acaggatggg gtcccattta ttatttacaa attcacatat acaacaacgc cgtcccccgt   2400
gcccgcagtt tttattaaac atagcgtggg atctccacgc gaatctcggg tacgtgttcc   2460
ggacatgggc tcttctccgg tagcggcgga gcttccacat ccgagccctg gtcccatgcc   2520
tccagcggct catggtcgct cggcagctcc ttgctcctaa cagtggaggc cagacttagg   2580
cacagcacaa tgcccaccac caccagtgtg ccgcacaagg ccgtggcggt agggtatgtg   2640
tctgaaaatg agctcggaga ttgggctcgc accgctgacg cagatggaag acttaaggca   2700
gcggcagaag aagatgcagg cagctgagtt gttgtattct gataagagtc agaggtaact   2760
cccgttgcgg tgctgttaac ggtggagggc agtgtagtct gagcagtact cgttgctgcc   2820
gcgcgcgcca ccagacataa tagctgacag actaacagac tgttcctttc catgggtctt   2880
ttctgcagtc accgtccaag cttgcggccg cggatctgca ggaattcggc acgagagtag   2940
tagactccgc aagaaacagc aaacacagat aaatatgggc gagctgtccc ctgtgtgcct   3000
gtacctgctg ctgcagggcc tgctgctgtg taacaccgga gccgccagga acctgaacga   3060
gctgaagatg gagtgccccc acaccatcag actgggccag ggcctggtgg tgggcagcgt   3120
ggagctgccc agcctgccca tccagcaggt ggagaccctg aagctggaga gcagctgtaa   3180
cttcgacctg cacaccagca cagccggcca gcagagcttc accaagtgga cctgggagat   3240
caagggcgac ctggccgaga acacccaggc cagcagcacc agcttccaga ccaagagcag   3300
cgaggtgaac ctgagaggcc tgtgcctgat ccccacactg gtggtggaga ccgccgccag   3360
aatgagaaag accatcgcct gctacgacct gagctgtaac cagaccgtgt gtcagcctac   3420
cgtgtacctg atgggcccta tccagacctg tatcaccacc aagagctgcc tgctgtccct   3480
gggcgatcag agaatccagg tgaactacga gaaaacctac tgtgtgagcg gccagctggt   3540
ggagggcatc tgcttcaacc ccatccacac catggccctg agccagccta gccacaccta   3600
cgacatcatg accatgatgg tgagatgctt tctggtgatc aagaaggtga ccagcggcga   3660
cagcatgaag atcgagaaga acttcgagac cctggtgcag aagaatggct gtaccgccaa   3720
caacttccag ggctactaca tctgcctgat cggcagcagc agcgagcccc tgtacgtgcc   3780
cgccctggac gactacagaa gcgccgaggt gctgtccaga atggccttcg ccccccacgg   3840
cgaggaccac gacatcgaga aaaacgccgt gtccgccatg agaatcgccg gcaaggtgac   3900
```

```
cggcaaggcc cccagcaccg agtccagcga caccgtgcag ggcatcgcct tcagcggcag   3960
ccccctgtac acctccaccg gcgtgctgac cagcaaggac gaccccgtgt acatctgggc   4020
ccctggcatc atcatggagg gcaaccacag catctgtgag aagaaaaccc tgcccctgac   4080
ctggaccggc ttcatcagcc tgcccggcga gatcgagaaa accacccagt gtaccgtgtt   4140
ctgtaccctg gccggacctg gcgccgactg tgaggcctac agcgagaccg gcatcttcaa   4200
catcagcagc cccacctgcc tgatcaaccg ggtgcagagg ttcagaggca gcgagcagca   4260
gatcaagttt gtgtgccagc gggtggacat ggacatcacc gtgtactgta acggcatgaa   4320
gaaggtgatc ctgaccaaga cactggtgat cggccagtgt atctacacct tcaccagcat   4380
cttctccctg atccccggcg tggcccacag cctggccgtg gagctgtgtg tgcccggcct   4440
gcacggctgg gccaccatgc tgctgctgct gaccttctgc ttcggctggg tgctgatccc   4500
taccatcacc atgatcctgc tgaagatcct gatcgccttc gcctacctgt gctccaagta   4560
caacaccgac agcaagttca gaatcctgat cgagaaagtg aagcgggagt accagaaaac   4620
catgggcagc atggtgtgtg aagtgtgcca gtacgagtgt gagaccgcca aggagctgga   4680
gtcccacaga aagagctgct ccatcggcag ctgcccctac tgcctgaacc ccagcgaggc   4740
caccacctcc gccctgcagg cccacttcaa agtgtgtaag ctgaccagcc ggttccagga   4800
gaacctgagg aagtccctga ccgtgtacga gcccatgcag ggctgctaca gaaccctgag   4860
cctgttccgg tacaggagcc ggttctttgt gggcctggtg tggtgtgtgc tgctggtgct   4920
ggagctgatt gtgtgggccg ccagcgccga gacccagaac ctgaatgccg gctggaccga   4980
caccgcccac ggcagcggca tcatccccat gaaaaccgac ctggagctgg acttcagcct   5040
gcctagcagc gcctcctaca cctacaggcg gcagctgcag aatcctgcca acgagcagga   5100
gaagatcccc ttccacctgc agctgtccaa gcaggtgatc cacgccgaga ttcagcacct   5160
gggccactgg atggacgcca ccttcaacct gaaaaccgcc ttccactgct acggcagctg   5220
tgagaagtac gcctaccctt ggcagaccgc cggctgcttc atcgagaagg actacgagta   5280
cgagaccggc tggggctgta atcctcctga ttgccccgga gtgggcaccg gctgtactgc   5340
atgtggcgtg tacctggaca agctgaagtc tgtgggcaag gtgttcaaga tcgtgtccct   5400
gaggtacacc cggaaagtgt gtatccagct gggcaccgag cagacctgta agaccgtgga   5460
cagcaacgat tgcctgatca caaccagcgt gaaagtgtgt ctgatcggca ccatcagcaa   5520
gttccagccc agcgataccc tgctgtttct gggcccccctg cagcagggcg gcctgatctt   5580
caagcagtgg tgtaccacca cctgccagtt cggcgatccc ggcgatatca tgagcacccc   5640
caccggcatg aagtgccctg agctgaacgg cagcttccgg aagaagtgtg ccttcgccac   5700
cacccctgtg tgtcagttcg acggcaacac catcagcggc tacaagcgga tgatcgccac   5760
caaggacagc ttccagtcct tcaacgtgac cgagccccac atcagcacca gcgccctgga   5820
gtggatcgat cccgacagca gcctgaggga ccacatcaac gtgatcgtgt ccagggacct   5880
gagcttccag gacctgagcg agacccccctg ccagatcgac ctggccaccg ccagcatcga   5940
tggcgcctgg ggcagcggag tgggcttcaa cctggtgtgt acagtgagcc tgaccgagtg   6000
tagcgccttc ctgaccagca tcaaagcctg tgacgccgcc atgtgttacg gcagcaccac   6060
cgccaacctg gtgagaggcc agaacaccat ccacattgtg ggcaaaggcg gccacagcgg   6120
cagcaagttt atgtgctgcc acgacaccaa gtgtagcagc accggcctgg tggccgctgc   6180
cccccacctg gacagagtga ccggctacaa ccaggccgac agcgacaaga ttttcgacga   6240
```

cggagcccct gagtgtggca tgagttgctg gttcaagaag agcggcgagt ggattctggg 6300
cgtgctgaac gggaattgga tggtggtggc cgtgctggtc gtgctgctga tcctgagcat 6360
cctgctgttc accctgtgct gccctaggag acccagctac cggaaggagc acaagccctg 6420
agttttgctt actaacataa ttattgtatt ctgtttattg acacaattac catatgatta 6480
actgtattcc cccatcttat atcttatata atattcttta tttaatcact atatagaaaa 6540
aaaactagca ctttactaat taaattaccc cataccgatt atgcctggac ttttgttcct 6600
gcggagcata ctactaggat ctacgtatga tcagcctcga ctgtgccttc tagttgccag 6660
ccatctgttg tttgcccctc ccccgtgcct tccttgaccc tggaaggtgc cactcccact 6720
gtcctttcct aataaaatga ggaaattgca tcgcattgtc tgagtaggtg tcattctatt 6780
ctggggggtg gggtggggca ggacagcaag ggggaggatt gggaagacaa tagcaggcat 6840
gctggggatg cggtgggctc tatggcttct gaggcggaaa gaaccagctg gggctcgaca 6900
gctcgactct agaattgctt cctcgctcac tgactcgctg cgctcggtcg ttcggctgcg 6960
gcgagcggta tcagctcact caaaggcggt aatacggtta tccacagaat caggggataa 7020
cgcaggaaag aacatgtgag caaaaggcca gcaaaaggcc aggaaccgta aaaaggccgc 7080
gttgctggcg tttttccata ggctccgccc ccctgacgag catcacaaaa atcgacgctc 7140
aagtcagagg tggcgaaacc cgacaggact ataaagatac caggcgtttc cccctggaag 7200
ctccctcgtg cgctctcctg ttccgaccct gccgcttacc ggatacctgt ccgcctttct 7260
cccttcggga agcgtggcgc tttctcatag ctcacgctgt aggtatctca gttcggtgta 7320
ggtcgttcgc tccaagctgg gctgtgtgca cgaacccccc gttcagcccg accgctgcgc 7380
cttatccggt aactatcgtc ttgagtccaa cccggtaaga cacgacttat cgccactggc 7440
agcagccact ggtaacagga ttagcagagc gaggtatgta ggcggtgcta cagagttctt 7500
gaagtggtgg cctaactacg gctacactag aagaacagta tttggtatct gcgctctgct 7560
gaagccagtt accttcggaa aaagagttgg tagctcttga tccggcaaac aaaccaccgc 7620
tggtagcggt ggtttttttg tttgcaagca gcagattacg cgcagaaaaa aaggatctca 7680
agaagatcct ttgatctttt ctacggggtc tgacgctcag tggaacgaaa actcacgtta 7740
agggattttg gtcatgagat tatcaaaaag gatcttcacc tagatccttt taaattaaaa 7800
atgaagtttt aaatcaatct aaagtatata tgagtaaact tggtctgaca gttaccaatg 7860
cttaatcagt gaggcaccta tctcagcgat ctgtctattt cgttcatcca tagttgcctg 7920
actc 7924

<210> SEQ ID NO 12
<211> LENGTH: 7800
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 12
gggggggggg ggcgctgagg tctgcctcgt gaagaaggtg ttgctgactc ataccaggcc 60
tgaatcgccc catcatccag ccagaaagtg agggagccac ggttgatgag agctttgttg 120
taggtggacc agttggtgat tttgaacttt tgctttgcca cggaacggtc tgcgttgtcg 180
ggaagatgcg tgatctgatc cttcaactca gcaaaagttc gatttattca acaaagccgc 240
cgtcccgtca agtcagcgta atgctctgcc agtgttacaa ccaattaacc aattctgatt 300

-continued

```
agaaaaactc atcgagcatc aaatgaaact gcaatttatt catatcagga ttatcaatac    360
catatttttg aaaaagccgt ttctgtaatg aaggagaaaa ctcaccgagg cagttccata    420
ggatggcaag atcctggtat cggtctgcga ttccgactcg tccaacatca atacaaccta    480
ttaatttccc ctcgtcaaaa ataaggttat caagtgagaa atcaccatga gtgacgactg    540
aatccggtga gaatggcaaa agcttatgca tttctttcca gacttgttca acaggccagc    600
cattacgctc gtcatcaaaa tcactcgcat caaccaaacc gttattcatt cgtgattgcg    660
cctgagcgag acgaaatacg cgatcgctgt taaaaggaca attacaaaca ggaatcgaat    720
gcaaccggcg caggaacact gccagcgcat caacaatatt ttcacctgaa tcaggatatt    780
cttctaatac ctggaatgct gttttcccgg ggatcgcagt ggtgagtaac catgcatcat    840
caggagtacg gataaaatgc ttgatggtcg gaagaggcat aaattccgtc agccagttta    900
gtctgaccat ctcatctgta acatcattgg caacgctacc tttgccatgt ttcagaaaca    960
actctggcgc atcgggcttc ccatacaatc gatagattgt cgcacctgat tgcccgacat   1020
tatcgcgagc ccatttatac ccatataaat cagcatccat gttggaattt aatcgcggcc   1080
tcgagcaaga cgtttcccgt tgaatatggc tcataacacc ccttgtatta ctgtttatgt   1140
aagcagacag ttttattgtt catgatgata tatttttatc ttgtgcaatg taacatcaga   1200
gattttgaga cacaacgtgg ctttcccccc ccccccggca tgcctgcagg tcgacaatat   1260
tggctattgg ccattgcata cgttgtatct atatcataat atgtacattt atattggctc   1320
atgtccaata tgaccgccat gttgacattg attattgact agttattaat agtaatcaat   1380
tacggggtca ttagttcata gcccatatat ggagttccgc gttacataac ttacggtaaa   1440
tggcccgcct ggctgaccgc ccaacgaccc ccgcccattg acgtcaataa tgacgtatgt   1500
tcccatagta acgccaatag ggactttcca ttgacgtcaa tgggtggagt atttacggta   1560
aactgcccac ttggcagtac atcaagtgta tcatatgcca agtccgcccc ctattgacgt   1620
caatgacggt aaatggcccg cctggcatta tgcccagtac atgaccttac gggactttcc   1680
tacttggcag tacatctacg tattagtcat cgctattacc atggtgatgc ggttttggca   1740
gtacaccaat gggcgtggat agcggtttga ctcacgggga tttccaagtc tccaccccat   1800
tgacgtcaat gggagtttgt tttggcacca aaatcaacgg gactttccaa aatgtcgtaa   1860
taaccccgcc ccgttgacgc aaatgggcgg taggcgtgta cggtgggagg tctatataag   1920
cagagctcgt ttagtgaacc gtcagatcgc ctggagacgc catccacgct gttttgacct   1980
gcatcgaaga caccgggacc gatccagcct ccgcggccgg gaacggtgca ttggaacgcg   2040
gattccccgt gccaagagtg acgtaagtac cgcctataga ctctataggc acaccccttt   2100
ggctcttatg catgctatac tgtttttggc ttggggccta tacacccccg cttccttatg   2160
ctataggtga tggtatagct tagcctatag gtgtgggtta ttgaccatta ttgaccactc   2220
ccctattggt gacgatactt tccattacta atccataaca tggctctttg ccacaactat   2280
ctctattggc tatatgccaa tactctgtcc ttcagagact gacacggact ctgtattttt   2340
acaggatggg gtcccattta ttatttacaa attcacatat acaacaacgc cgtcccccgt   2400
gcccgcagtt tttattaaac atagcgtggg atctccacgc gaatctcggg tacgtgttcc   2460
ggacatgggc tcttctccgg tagcggcgga gcttccacat ccgagccctg gtcccatgcc   2520
tccagcggct catggtcgct cggcagctcc ttgctcctaa cagtggaggc cagacttagg   2580
cacagcacaa tgcccaccac caccagtgtg ccgcacaagg ccgtggcggt agggtatgtg   2640
tctgaaaatg agctcggaga ttgggctcgc accgctgacg cagatggaag acttaaggca   2700
```

-continued

```
gcggcagaag aagatgcagg cagctgagtt gttgtattct gataagagtc agaggtaact   2760
cccgttgcgg tgctgttaac ggtggagggc agtgtagtct gagcagtact cgttgctgcc   2820
gcgcgcgcca ccagacataa tagctgacag actaacagac tgttcctttc catgggtctt   2880
ttctgcagtc accgtccaag cttgcggccg cggatctgca ggaattcggc acgagagtag   2940
tagactccgc aagaaacagc agtcaatcag caacatgggg atatggaagt ggctagtgat   3000
ggccagttta gtatggcctg ttttgacact gagaaatgtc tatgacatga aaattgagtg   3060
cccccataca gtaagttttg gggaaaacag tgtgataggt tatgtagaat taccccccgt   3120
gccattggcc gacacagcac agatggtgcc tgagagttct tgtagcatgg ataatcacca   3180
atcgttgaat acaataacaa aatataccca agtaagttgg agaggaaagg ctgatcagtc   3240
acagtctagt caaaattcat ttgagacagt gtccactgaa gttgacttga aaggaacatg   3300
tgctctaaaa cacaaaatgg tggaagaatc ataccgtagt aggaaatcag taacctgtta   3360
cgacctgtct tgcaatagca cttactgcaa gccaacacta tacatgattg taccaattca   3420
tgcatgcaat atgatgaaaa gctgtttgat tgcattggga ccatacagag tacaggtggt   3480
ttatgagaga tcttattgca tgacaggagt cctgattgaa gggaaatgct ttgtcccaga   3540
tcaaagtgtg gtcagtatta tcaagcatgg gatctttgat attgcaagtg ttcatattgt   3600
atgtttcttt gttgcagtta aagggaatac ttataaaatt tttgaacagg ttaagaaatc   3660
ctttgaatca acatgcaatg atacagagaa taaagtgcaa ggatattata tttgtattgt   3720
agggggaaac tctgcaccaa tatatgttcc aacacttgat gatttcagat ccatggaagc   3780
atttacagga atcttcagat caccacatgg ggaagatcat gatctggctg gagaagaaat   3840
tgcatcttat tctatagtcg gacctgccaa tgcaaaagtt cctcatagtg ctagctcaga   3900
tacattgagc ttgattgcct attcaggtat accatcttat tcttccctta gcatcctaac   3960
aagttcaaca gaagctaagc atgtattcag ccctgggttg ttcccaaaac ttaatcacac   4020
aaattgtgat aaaagtgcca taccactcat atggactggg atgattgatt tacctggata   4080
ctacgaagct gtccaccctt gtacagtttt ttgcgtatta tcaggtcctg ggcatcatg    4140
tgaagccttt tctgaaggcg ggattttcaa cataacctct cccatgtgct tagtgtcaaa   4200
acaaaatcga ttccggttaa cagaacagca agtgaatttt gtgtgtcagc gagtggacat   4260
ggacattgtt gtgtactgca acgggcagag gaaagtaata ttaacaaaaa ctctagttat   4320
tggacagtgt atatatacta taacaagctt attctcatta ctacctggag tagcacattc   4380
tattgctgtt gaattgtgtg tacctgggtt ccatggttgg gccacagctg ctctgcttgt   4440
tacattctgt ttcggatggg ttcttatacc agcaattaca tttatcatac taacagtcct   4500
aaagttcatt gctaatattt ttcacacaag taatcaagag aataggctaa aatcagtact   4560
tagaaagata aaggaagagt ttgaaaaaac aaaaggctca atggtatgtg atgtctgcaa   4620
gtatgagtgt gaaacctata aagaattaaa ggcacacggg gtatcatgcc cccaatctca   4680
atgtccttac tgttttactc attgtgaacc cacagaagca gcattccaag ctcattacaa   4740
ggtatgccaa gttactcaca gattcaggga tgatctaaag aaaactgtta ctcctcaaaa   4800
ttttacacca ggatgttacc ggacactaaa tttatttaga tacaaaagca ggtgctacat   4860
ctttacaatg tggatatttc ttcttgtctt agaatccata ctgtgggctg caagtgcatc   4920
agagacacca ttaactcctg tctggaatga caatgcccat ggggtaggtt ctgttcctat   4980
gcatacagat ttagagcttg atttctcttt aacatccagt tccaagtata cataccgtag   5040
```

-continued

```
gaggttaaca aacccacttg aggaagcaca atccattgac ctacatattg aaatagaaga   5100
acagacaatt ggtgttgatg tgcatgctct aggacactgg tttgatggtc gtcttaacct   5160
taaaacatcc tttcactgtt atggtgcttg tacaaagtat gaataccctt ggcatactgc   5220
aaagtgccac tatgaaagag attaccaata tgagacgagc tggggttgta atccatcaga   5280
ttgtcctggg gtgggcacag gctgtacagc atgtggttta tacctagatc aactgaaacc   5340
agttggtagt gcttataaaa ttatcacaat aaggtacagc aggagagtct gtgttcagtt   5400
tggggaggaa aacctttgta agataataga catgaatgat tgttttgtat ctaggcatgt   5460
taaggtctgc ataattggta cagtatctaa attctctcag ggtgatacct tattgttttt   5520
tggaccgctt gaaggtggtg gtctaatatt taaacactgg tgtacatcca catgtcaatt   5580
tggtgaccca ggagatatca tgagtccaag agacaaaggt tttttatgcc ctgagtttcc   5640
aggtagtttc aggaagaaat gcaactttgc tactacccct atttgtgagt atgatggaaa   5700
tatggtctca ggttacaaga aagtgatggc cacaattgat tccttccaat cttttaatac   5760
aagcactatg cacttcactg atgaaaggat agagtggaaa gaccctgatg gaatgctaag   5820
ggaccatata aacattttag taacgaagga cattgacttt gataaccttg gtgaaaatcc   5880
ttgcaaaatt ggcctacaaa catcttctat tgagggggcc tggggttctg gtgtggggtt   5940
cacattaaca tgtctggtat cactaacaga atgtcctacc tttttgacct caataaaggc   6000
ttgtgataag gctatctgtt atggtgcaga gagtgtaaca ttgacaagag gacaaaatac   6060
agtcaaggta tcagggaaag gtggccatag tggttcaaca tttaggtgtt gccatgggga   6120
ggactgttca caaattggac tccatgctgc tgcacctcac cttgacaagg taaatgggat   6180
ttctgagata gaaaatagta aagtatatga tgatggggca ccgcaatgtg ggataaaatg   6240
ttggtttgtt aaatcagggg aatggatttc agggatattc agtggtaatt ggattgtact   6300
cattgtcctc tgtgtatttc tattgttctc cttggtttta ctaagcattc tctgtcccgt   6360
aaggaagcat aaaaaatcat agctaaattc tgtgactatc ctgttcttat gtatagcttt   6420
aacatatata ctaattttta tattccagta tactctatct aacacactaa aaaaaatagt   6480
agctttctaa ccacaaaacg gatctacgta tgatcagcct cgactgtgcc ttctagttgc   6540
cagccatctg ttgtttgccc ctcccccgtg ccttccttga ccctggaagg tgccactccc   6600
actgtccttt cctaataaaa tgaggaaatt gcatcgcatt gtctgagtag gtgtcattct   6660
attctggggg gtggggtggg gcaggacagc aagggggagg attgggaaga caatagcagg   6720
catgctgggg atgcggtggg ctctatggct tctgaggcgg aaagaaccag ctggggctcg   6780
acagctcgac tctagaattg cttcctcgct cactgactcg ctgcgctcgg tcgttcggct   6840
gcggcgagcg gtatcagctc actcaaaggc ggtaatacgg ttatccacag aatcagggga   6900
taacgcagga aagaacatgt gagcaaaagg ccagcaaaag gccaggaacc gtaaaaaggc   6960
cgcgttgctg gcgtttttcc ataggctccg cccccctgac gagcatcaca aaaatcgacg   7020
ctcaagtcag aggtggcgaa acccgacagg actataaaga taccaggcgt ttccccctgg   7080
aagctccctc gtgcgctctc ctgttccgac cctgccgctt accggatacc tgtccgcctt   7140
tctcccttcg ggaagcgtgg cgctttctca tagctcacgc tgtaggtatc tcagttcggt   7200
gtaggtcgtt cgctccaagc tgggctgtgt gcacgaaccc cccgttcagc ccgaccgctg   7260
cgccttatcc ggtaactatc gtcttgagtc caacccggta agacacgact tatcgccact   7320
ggcagcagcc actggtaaca ggattagcag agcgaggtat gtaggcggtg ctacagagtt   7380
cttgaagtgg tggcctaact acggctacac tagaagaaca gtatttggta tctgcgctct   7440
```

gctgaagcca gttaccttcg gaaaaagagt tggtagctct tgatccggca aacaaaccac 7500
cgctggtagc ggtggttttt ttgtttgcaa gcagcagatt acgcgcagaa aaaaaggatc 7560
tcaagaagat cctttgatct tttctacggg gtctgacgct cagtggaacg aaaactcacg 7620
ttaagggatt ttggtcatga gattatcaaa aaggatcttc acctagatcc ttttaaatta 7680
aaaatgaagt tttaaatcaa tctaaagtat atatgagtaa acttggtctg acagttacca 7740
atgcttaatc agtgaggcac ctatctcagc gatctgtcta tttcgttcat ccatagttgc 7800

<210> SEQ ID NO 13
<211> LENGTH: 8001
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 13
gggggggggg ggcgctgagg tctgcctcgt gaagaaggtg ttgctgactc ataccaggcc 60
tgaatcgccc catcatccag ccagaaagtg agggagccac ggttgatgag agctttgttg 120
taggtggacc agttggtgat tttgaacttt tgctttgcca cggaacggtc tgcgttgtcg 180
ggaagatgcg tgatctgatc cttcaactca gcaaaagttc gatttattca acaaagccga 240
cgtcccgtca agtcagcgta atgctctgcc agtgttacaa ccaattaacc aattctgatt 300
agaaaaactc atcgagcatc aaatgaaact gcaatttatt catatcagga ttatcaatac 360
catatttttg aaaaagccgt ttctgtaatg aaggagaaaa ctcaccgagg cagttccata 420
ggatggcaag atcctggtat cggtctgcga ttccgactcg tccaacatca atacaaccta 480
ttaatttccc ctcgtcaaaa ataaggttat caagtgagaa atcaccatga gtgacgactg 540
aatccggtga gaatggcaaa agcttatgca tttctttcca gacttgttca acaggccagc 600
cattacgctc gtcatcaaaa tcactcgcat caaccaaacc gttattcatt cgtgattgcg 660
cctgagcgag acgaaatacg cgatcgctgt taaaaggaca attacaaaca ggaatcgaat 720
gcaaccggcg caggaacact gccagcgcat caacaatatt ttcacctgaa tcaggatatt 780
cttctaatac ctggaatgct gttttcccgg ggatcgcagt ggtgagtaac catgcatcat 840
caggagtacg gataaaatgc ttgatggtcg gaagaggcat aaattccgtc agccagttta 900
gtctgaccat ctcatctgta acatcattgg caacgctacc tttgccatgt ttcagaaaca 960
actctggcgc atcgggcttc ccatacaatc gatagattgt cgcacctgat tgccccacat 1020
tatcgcgagc ccatttatac ccatataaat cagcatccat gttggaattt aatcgcggcc 1080
tcgagcaaga cgtttcccgt tgaatatggc tcataacacc ccttgtatta ctgtttatgt 1140
aagcagacag ttttattgtt catgatgata tatttttatc ttgtgcaatg taacatcaga 1200
gattttgaga cacaacgtgg ctttcccccc ccccccggca tgcctgcagg tcgacataaa 1260
tcaatattgg ctattggcca ttgcatacgt tgtatctata tcataatatg tacatttata 1320
ttggctcatg tccaatatga ccgccatgtt gacattgatt attgactagt tattaatagt 1380
aatcaattac ggggtcatta gttcatagcc catatatgga gttccgcgtt acataactta 1440
cggtaaatgg cccgcctcgt gaccgcccaa cgacccccgc ccattgacgt caataatgac 1500
gtatgttccc atagtaacgc caatagggac tttccattga cgtcaatggg tggagtattt 1560
acggtaaact gcccacttgg cagtacatca agtgtatcat atgccaagtc cggcccccta 1620
ttgacgtcaa tgacggtaaa tggcccgcct ggcattatgc ccagtacatg accttacggg 1680

```
actttcctac ttggcagtac atctacgtat tagtcatcgc tattaccatg gtgatgcggt   1740
tttggcagta caccaatggg cgtggatagc ggtttgactc acggggattt ccaagtctcc   1800
accccattga cgtcaatggg agtttgtttt ggcaccaaaa tcaacgggac tttccaaaat   1860
gtcgtaataa ccccgccccg ttgacgcaaa tgggcggtag gcgtgtacgg tgggaggtct   1920
atataagcag agctcgttta gtgaaccgtc agatcgcctg gagacgccat ccacgctgtt   1980
ttgacctcca tagaagacac cgggaccgat ccagcctccg cggccgggaa cggtgcattg   2040
gaacgcggat tccccgtgcc aagagtgacg taagtaccgc ctatagactc tataggcaca   2100
cccctttggc tcttatgcat gctatactgt ttttggcttg gggcctatac acccccgctc   2160
cttatgctat aggtgatggt atagcttagc ctataggtgt gggttattga ccattattga   2220
ccactcccct attggtgacg atactttcca ttactaatcc ataacatggc tctttgccac   2280
aactatctct attggctata tgccaatact ctgtccttca gagactgaca cggactctgt   2340
atttttacag gatggggtcc catttattat ttacaaattc acatatacaa caacgccgtc   2400
ccccgtgccc gcagttttta ttaaacatag cgtgggatct ccacgcgaat ctcgggtacg   2460
tgttccggac atgggctctt ctccggtagc ggcggagctt ccacatccga gccctggtcc   2520
catgcctcca gcggctcatg gtcgctcggc agctccttgc tcctaacagt ggaggccaga   2580
cttaggcaca gcacaatgcc caccaccacc agtgtgccgc acaaggccgt ggcggtaggg   2640
tatgtgtctg aaaatgagct cggagattgg gctcgcaccg tgacgcagat ggaagactta   2700
aggcagcggc agaagaagat gcaggcagct gagttgttgt attctgataa gagtcagagg   2760
taactcccgt tgcggtgctg ttaacggtgg agggcagtgt agtctgagca gtactcgttg   2820
ctgccgcgcg cgccaccaga cataatagct gacagactaa cagactgttc ctttccatgg   2880
gtcttttctg cagtcaccgt ccaagcttgc ggccgcggat ctgcaggaat tcggcacgag   2940
agtagtagac tccgcaagaa acagcagtta aagaacaata ggatcatgtg gagtttgcta   3000
ttactggccg ctttagttgg ccaaggcttt gcattaaaaa atgtatttga catgagaatt   3060
cagttgcccc actcagtcaa ctttggggaa acaagtgtgt caggctatac agaatttccc   3120
ccactctcat tacaggaggc agaacagcta gtgccagaga gctcatgcaa catggacaac   3180
caccagtcac tctcaacaat aaataaatta accaaggtca tatggcggaa aaaagcaaat   3240
caggaatcag caaaccagaa ttcatttgaa gttgtggaaa gtgaagtcag ctttaaaggg   3300
ttgtgtatgt taaagcatag aatggttgaa gaatcatata gaaataggag atcagtaatc   3360
tgttatgatc tagcctgtaa tagtacattc tgtaaaccaa ctgtttatat gattgttcct   3420
atacatgctt gcaacatgat gaaaagctgt ttgattggcc ttggccccta cagaatccag   3480
gttgtctatg aaaggacata ctgcactacg ggtatattga cagaaggaaa atgctttgtc   3540
cctgacaagg ctgttgtcag tgcattgaaa agaggcatgt atgctatagc aagcatagag   3600
acaatctgct tttttattca tcagaaaggg aatacatata agatagtgac tgccattaca   3660
tcagcaatgg gctccaaatg taataataca gatactaaag ttcaaggata ttatatctgt   3720
attattggtg gaaactccgc ccctgtatat gcccctgctg gtgaagactt cagagcaatg   3780
gaggtttttt ctgggattat tacatcacca catggagaag accatgacct acccggcgaa   3840
gaaatcgcaa cgtaccagat ttcagggcag atagaggcaa aaatccctca tacagtgagc   3900
tccaaaaact taaaattgac tgcttttgca ggtattccat catactcatc aactagtata   3960
ttggctgctt cagaagatgg tcgtttcata tttagtcctg gtttatttcc taacctaaat   4020
```

-continued

```
cagtcagtct gtgacaacaa tgcactccct ttaatctgga ggggcctaat tgatttaacg   4080
ggatactatg aggcagtcca cccttgcaat gtgttctgtg tcttatcagg accaggtgct   4140
tcatgtgagg ccttttcaga aggaggtatt ttcaatatta cttctccaat gtgtctggtg   4200
tctaagcaaa atagatttag agcagctgag cagcagatta gctttgtctg ccaaagagtt   4260
gatatggata ttatagtgta ctgtaatggt cagaaaaaaa caatcctaac aaaaacatta   4320
gttataggcc aatgtattta tactattaca agtctctttt cactgttacc agggggttgcc  4380
cattctattg ctattgagtt gtgtgttcca gggtttcatg gctgggccac agctgcactt   4440
ttgattacat tctgcttcgg ctgggtattg attcctgcat gtacattagc tattctttta   4500
gtccttaagt tctttgcaaa tatccttcat acaagcaatc aagagaaccg attcaaagcc   4560
attctacgga aaataaagga ggagtttgaa aaaacaaagg gttccatggt ttgtgagatc   4620
tgtaagtatg agtgtgaaac attaaaggaa ttgaaggcac ataacctatc atgtgttcaa   4680
ggagagtgcc catattgctt tacccactgt gaaccgacag aaactgcaat tcaggcacat   4740
tacaaagttt gtcaagccac ccaccgattc agagaagatt taaaaaagac tgtaactcct   4800
caaaatattg ggccaggctg ttaccgaaca ctaaatcttt ttaggtataa aagtaggtgt   4860
tatattctga caatgtggac tcttcttctc attattgaat ccatcctctg ggcagcaagt   4920
gcagcagaaa tcccccttgt ccctctctgg acagataatg ctcatggcgt tgggagtgtt   4980
cctatgcata cggatcttga attagacttc tctttgccat ccagttctaa gtacacatac   5040
aaaagacatc tcacaaaccc agttaatgac caacagagtg tctcattgca tatagaaatt   5100
gaaagtcaag gcattggtgc tgctgttcat catcttggac attggtatga tgcaagattg   5160
aatctaaaaa cctcatttca ttgttatggt gcctgcacaa aatatcaata cccatggcac   5220
actgcaaaat gccattttga gaaagattat gagtatgaaa atagctgggc ttgcaacccc   5280
ccagattgcc caggggttgg tacaggttgt actgcttgtg gattatatct agatcaattg   5340
aagccggtag gaacagcctt taaaattata agtgtaagat acagtagaaa agtgtgcgtg   5400
cagtttggtg aagaacacct ttgtaaaaca attgatatga atgattgctt tgtgactagg   5460
catgccaaaa tatgtataat tgggactgta tctaagtttt ctcaaggtga cactctacta   5520
tttctggggc ccatggaagg aggtggtata atctttaaac actggtgtac atctacctgt   5580
cactttggag accctggtga tgtcatgggt ccaaaagata aaccatttat ttgccctgaa   5640
ttcccagggc aatttaggaa aaaatgtaac tttgccacaa ctccagtttg tgaatatgat   5700
ggaaacatta tatcaggcta taagaaagta cttgcaacaa ttgattcttt ccaatcattt   5760
aacacaagca atatacactt cactgatgag agaattgaat ggagagaccc tgatggcatg   5820
cttcgggatc atattaatat tgttatttct aaagatattg attttgaaaa tttggctgag   5880
aatccttgta aagtagggct ccaggcagca aacatagaag gtgcctgggg ttcaggtgtc   5940
gggtttacac tcacatgcaa ggtgtctctc acagaatgcc caacatttct tacatcaata   6000
aaggcctgtg acatggcaat ttgttatggt gcagaaagtg tgacactctc acgaggacaa   6060
aatactgtca aaattaccgg gaaaggtggc catagtggtt cttcattcaa atgctgtcat   6120
gggaaagaat gttcatcaac tggcctccaa gccagtgcac cacatctgga taaggtaaat   6180
ggtatctctg agttagaaaa cgagaaagtt tatgatgacg gtgcacctga atgtggcatt   6240
acttgttggt ttaaaaaatc aggtgaatgg gttatgggta taatcaatgg gaactgggtt   6300
gtcctaattg tcttgtgtgt actgctgctc ttttctctta tcctgttgag catcttgtgt   6360
cctgttagaa agcataaaaa atcataaatc ccacctaaca atcttcacat catgtatcga   6420
```

ttttcaaaca ctttatcatt tagaacttaa cttggcacta ctatctgata actgactttc 6480
atttttattt ttatatggat taattactaa aaaaaatact ctctcgtgcc gaattcgata 6540
tcaagcttat cgataccgtc gacctcgagg gggggcccgg tacccgggat cctcgcaatc 6600
cctaggagga ttaggcaagg gcttgagctc acgctcttgt gagggacaga aatacaatca 6660
ggggcagtat atgaatactc catggagaaa cccagatcta cgtatgatca gcctcgactg 6720
tgccttctag ttgccagcca tctgttgttt gcccctcccc cgtgccttcc ttgaccctgg 6780
aaggtgccac tcccactgtc ctttcctaat aaaatgagga aattgcatcg cattgtctga 6840
gtaggtgtca ttctattctg gggggtgggg tggggcagga cagcaagggg gaggattggg 6900
aagacaatag caggcatgct ggggatgcgg tgggctctat ggcttctgag gcggaaagaa 6960
ccagctgggg ctcgacagct cgactctaga attgcttcct cgctcactga ctcgctgcgc 7020
tcggtcgttc ggctgcggcg agcggtatca gctcactcaa aggcggtaat acggttatcc 7080
acagaatcag gggataacgc aggaaagaac atgtgagcaa aaggccagca aaaggccagg 7140
aaccgtaaaa aggccgcgtt gctggcgttt ttccataggc tccgcccccc tgacgagcat 7200
cacaaaaatc gacgctcaag tcagaggtgg cgaaacccga caggactata aagataccag 7260
gcgtttcccc ctggaagctc cctcgtgcgc tctcctgttc cgaccctgcc gcttaccgga 7320
tacctgtccg cctttctccc ttcgggaagc gtggcgcttt ctcaatgctc acgctgtagg 7380
tatctcagtt cggtgtaggt cgttcgctcc aagctgggct gtgtgcacga accccccgtt 7440
cagcccgacc gctgcgcctt atccggtaac tatcgtcttg agtccaaccc ggtaagacac 7500
gacttatcgc cactggcagc agccactggt aacaggatta gcagagcgag gtatgtaggc 7560
ggtgctacag agttcttgaa gtggtggcct aactacggct acactagaag gacagtattt 7620
ggtatctgcg ctctgctgaa gccagttacc ttcggaaaaa gagttggtag ctcttgatcc 7680
ggcaaacaaa ccaccgctgg tagcggtggt ttttttgttt gcaagcagca gattacgcgc 7740
agaaaaaaag gatctcaaga agatcctttg atcttttcta cggggtctga cgctcagtgg 7800
aacgaaaact cacgttaagg gattttggtc atcagattat caaaaaggat cttcacctag 7860
atccttttaa attaaaaatg aagttttaaa tcaatctaaa gtatatatga gtaaacttgg 7920
tctgacagtt accaatgctt aatcagtgag gcacctatct cagcgatctg tctatttcgt 7980
tcatccatag ttgcctgact c 8001

<210> SEQ ID NO 14
<211> LENGTH: 3447
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 14
atgggcgagc tgtcccctgt gtgcctgtac ctgctgctgc agggcctgct gctgtgtaac 60
accggagccg ccaggaacct gaacgagctg aagatggagt gcccccacac catcagactg 120
ggccagggcc tggtggtggg cagcgtggag ctgcccagcc tgcccatcca gcaggtggag 180
accctgaagc tggagagcag ctgtaacttc gacctgcaca ccagcacagc cggccagcag 240
agcttcacca agtggacctg ggagatcaag ggcgacctgg ccgagaacac ccaggccagc 300
agcaccagct tccagaccaa gagcagcgag gtgaacctga gaggcctgtg cctgatcccc 360
acactggtgg tggagaccgc cgccagaatg agaaagacca tcgcctgcta cgacctgagc 420

-continued

```
tgtaaccaga ccgtgtgtca gcctaccgtg tacctgatgg gccctatcca gacctgtatc    480
accaccaaga gctgcctgct gtccctgggc gatcagagaa tccaggtgaa ctacgagaaa    540
acctactgtg tgagcggcca gctggtggag ggcatctgct tcaaccccat ccacaccatg    600
gccctgagcc agcctagcca cacctacgac atcatgacca tgatggtgag atgctttctg    660
gtgatcaaga aggtgaccag cggcgacagc atgaagatcg agaagaactt cgagaccctg    720
gtgcagaaga atggctgtac cgccaacaac ttccagggct actacatctg cctgatcggc    780
agcagcagcg agcccctgta cgtgcccgcc ctggacgact acagaagcgc cgaggtgctg    840
tccagaatgg ccttcgcccc ccacggcgag gaccacgaca tcgagaaaaa cgccgtgtcc    900
gccatgagaa tcgccggcaa ggtgaccggc aaggccccca gcaccgagtc cagcgacacc    960
gtgcagggca tcgccttcag cggcagcccc ctgtacacct ccaccggcgt gctgaccagc   1020
aaggacgacc ccgtgtacat ctgggcccct ggcatcatca tggagggcaa ccacagcatc   1080
tgtgagaaga aaaccctgcc cctgacctgg accggcttca tcagcctgcc cggcgagatc   1140
gagaaaacca cccagtgtac cgtgttctgt accctggccg gacctggcgc cgactgtgag   1200
gcctacagcg agaccggcat cttcaacatc agcagcccca cctgcctgat caaccgggtg   1260
cagaggttca gaggcagcga gcagcagatc aagtttgtgt gccagcgggt ggacatggac   1320
atcaccgtgt actgtaacgg catgaagaag gtgatcctga ccaagacact ggtgatcggc   1380
cagtgtatct acaccttcac cagcatcttc tccctgatcc ccggcgtggc ccacagcctg   1440
gccgtggagc tgtgtgtgcc cggcctgcac ggctgggcca ccatgctgct gctgctgacc   1500
ttctgcttcg gctgggtgct gatccctacc atcaccatga tcctgctgaa gatcctgatc   1560
gccttcgcct acctgtgctc caagtacaac accgacagca agttcagaat cctgatcgag   1620
aaagtgaagc gggagtacca gaaaaccatg ggcagcatgg tgtgtgaagt gtgccagtac   1680
gagtgtgaga ccgccaagga gctggagtcc cacagaaaga gctgctccat cggcagctgc   1740
ccctactgcc tgaaccccag cgaggccacc acctccgccc tgcaggccca cttcaaagtg   1800
tgtaagctga ccagccggtt ccaggagaac ctgaggaagt ccctgaccgt gtacgagccc   1860
atgcagggct gctacagaac cctgagcctg ttccggtaca ggagccggtt ctttgtgggc   1920
ctggtgtggt gtgtgctgct ggtgctggag ctgattgtgt gggccgccag cgccgagacc   1980
cagaacctga atgccggctg gaccgacacc gcccacggca gcggcatcat ccccatgaaa   2040
accgacctgg agctggactt cagcctgcct agcagcgcct cctacaccta caggcggcag   2100
ctgcagaatc ctgccaacga gcaggagaag atccccttcc acctgcagct gtccaagcag   2160
gtgatccacg ccgagattca gcacctgggc cactggatgg acgccacctt caacctgaaa   2220
accgccttcc actgctacgg cagctgtgag aagtacgcct acccttggca gaccgccggc   2280
tgcttcatcg agaaggacta cgagtacgag accggctggg gctgtaatcc tcctgattgc   2340
cccggagtgg gcaccggctg tactgcatgt ggcgtgtacc tggacaagct gaagtctgtg   2400
ggcaaggtgt tcaagatcgt gtccctgagg tacacccgga aagtgtgtat ccagctgggc   2460
accgagcaga cctgtaagac cgtggacagc aacgattgcc tgatcacaac cagcgtgaaa   2520
gtgtgtctga tcggcaccat cagcaagttc cagcccagcg ataccctgct gtttctgggc   2580
cccctgcagc agggcggcct gatcttcaag cagtggtgta ccaccacctg ccagttcggc   2640
gatcccggcg atatcatgag cacccccacc ggcatgaagt gccctgagct gaacggcagc   2700
ttccggaaga agtgtgcctt cgccaccacc cctgtgtgtc agttcgacgg caacaccatc   2760
```

-continued

```
agcggctaca agcggatgat cgccaccaag gacagcttcc agtccttcaa cgtgaccgag   2820

ccccacatca gcaccagcgc cctggagtgg atcgatcccg acagcagcct gagggaccac   2880

atcaacgtga tcgtgtccag ggacctgagc ttccaggacc tgagcgagac cccctgccag   2940

atcgacctgg ccaccgccag catcgatggc gcctggggca gcggagtggg cttcaacctg   3000

gtgtgtacag tgagcctgac cgagtgtagc gccttcctga ccagcatcaa agcctgtgac   3060

gccgccatgt gttacggcag caccaccgcc aacctggtga gaggccagaa caccatccac   3120

attgtgggca aaggcggcca cagcggcagc aagtttatgt gctgccacga caccaagtgt   3180

agcagcaccg gcctggtggc cgctgccccc cacctggaca gagtgaccgg ctacaaccag   3240

gccgacagcg acaagatttt cgacgacgga gcccctgagt gtggcatgag ttgctggttc   3300

aagaagagcg gcgagtggat tctgggcgtg ctgaacggga attggatggt ggtggccgtg   3360

ctggtcgtgc tgctgatcct gagcatcctg ctgttcaccc tgtgctgccc taggagaccc   3420

agctaccgga aggagcacaa gccctga                                       3447
```

<210> SEQ ID NO 15
<211> LENGTH: 1140
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 15

```
Met Val Gly Trp Val Cys Ile Phe Leu Val Val Leu Thr Thr Ala Thr
1               5                   10                  15

Ala Gly Leu Thr Arg Asn Leu Tyr Glu Leu Gln Ile Glu Cys Pro His
            20                  25                  30

Thr Val Gly Leu Gly Gln Gly Tyr Val Thr Gly Ser Val Glu Thr Thr
        35                  40                  45

Pro Ile Leu Leu Thr Gln Val Ala Asp Leu Lys Ile Glu Ser Ser Cys
    50                  55                  60

Asn Phe Asp Leu His Val Pro Ala Thr Thr Thr Gln Lys Tyr Asn Gln
65                  70                  75                  80

Val Asp Trp Thr Lys Lys Ser Ser Thr Thr Glu Ser Thr Asn Ala Gly
                85                  90                  95

Ala Thr Thr Phe Glu Ala Lys Thr Lys Glu Val Asn Leu Lys Gly Thr
            100                 105                 110

Cys Asn Ile Pro Pro Thr Thr Phe Glu Ala Ala Tyr Lys Ser Arg Lys
        115                 120                 125

Thr Val Ile Cys Tyr Asp Leu Ala Cys Asn Gln Thr His Cys Leu Pro
    130                 135                 140

Thr Val His Leu Ile Ala Pro Val Gln Thr Cys Met Ser Val Arg Ser
145                 150                 155                 160

Cys Met Ile Gly Leu Leu Ser Ser Arg Ile Gln Val Ile Tyr Glu Lys
                165                 170                 175

Thr Tyr Cys Val Thr Gly Gln Leu Ile Glu Gly Leu Cys Phe Ile Pro
            180                 185                 190

Thr His Thr Ile Ala Leu Thr Gln Pro Gly His Thr Tyr Asp Thr Met
        195                 200                 205

Thr Leu Pro Val Thr Cys Phe Leu Val Ala Lys Lys Leu Gly Thr Gln
    210                 215                 220

Leu Lys Leu Ala Val Glu Leu Glu Lys Leu Ile Thr Gly Val Ser Cys
225                 230                 235                 240
```

-continued

```
Ala Glu Asn Ser Phe Gln Gly Tyr Tyr Ile Cys Phe Ile Gly Lys His
                245                 250                 255

Ser Glu Pro Leu Phe Val Pro Thr Met Glu Asp Tyr Arg Ser Ala Glu
            260                 265                 270

Leu Phe Thr Arg Met Val Leu Asn Pro Arg Gly Glu Asp His Asp Pro
        275                 280                 285

Asp Gln Asn Gly Gln Gly Leu Met Arg Ile Ala Gly Pro Val Thr Ala
    290                 295                 300

Lys Val Pro Ser Thr Glu Thr Thr Glu Thr Met Gln Gly Ile Ala Phe
305                 310                 315                 320

Ala Gly Ala Pro Met Tyr Ser Ser Phe Ser Thr Leu Val Arg Lys Ala
                325                 330                 335

Asp Pro Glu Tyr Val Phe Ser Pro Gly Ile Ile Ala Glu Ser Asn His
            340                 345                 350

Ser Val Cys Asp Lys Lys Thr Val Pro Leu Thr Trp Thr Gly Phe Leu
        355                 360                 365

Ala Val Ser Gly Glu Ile Glu Arg Ile Thr Gly Cys Thr Val Phe Cys
    370                 375                 380

Thr Leu Ala Gly Pro Gly Ala Ser Cys Glu Ala Tyr Ser Glu Thr Gly
385                 390                 395                 400

Ile Phe Asn Ile Ser Ser Pro Thr Cys Leu Val Asn Lys Val Gln Lys
                405                 410                 415

Phe Arg Gly Ser Glu Gln Arg Ile Asn Phe Met Cys Gln Arg Val Asp
            420                 425                 430

Gln Gly Val Val Val Tyr Cys Asn Gly Gln Lys Lys Val Ile Leu Thr
        435                 440                 445

Lys Thr Leu Val Ile Gly Gln Cys Ile Tyr Thr Phe Thr Ser Leu Phe
    450                 455                 460

Ser Leu Ile Pro Gly Val Ala His Ser Leu Ala Val Glu Leu Cys Val
465                 470                 475                 480

Pro Gly Leu His Gly Trp Ala Thr Thr Ala Leu Leu Ile Thr Phe Cys
                485                 490                 495

Phe Gly Trp Leu Leu Ile Pro Thr Val Thr Leu Ile Ile Leu Lys Ile
            500                 505                 510

Leu Arg Leu Leu Thr Phe Pro Cys Ser His Tyr Ser Thr Glu Ser Lys
        515                 520                 525

Phe Lys Val Ile Leu Glu Arg Val Lys Val Glu Tyr Gln Lys Thr Met
    530                 535                 540

Gly Ser Met Val Cys Asp Ile Cys His His Glu Cys Glu Thr Ala Lys
545                 550                 555                 560

Glu Leu Glu Thr His Lys Lys Ser Cys Pro Glu Gly Gln Cys Pro Tyr
                565                 570                 575

Cys Met Thr Ile Thr Glu Ser Thr Glu Ser Ala Leu Gln Ala His Phe
            580                 585                 590

Ser Ile Cys Lys Leu Thr Asn Arg Phe Gln Glu Asn Leu Lys Lys Ser
        595                 600                 605

Leu Lys Arg Pro Glu Val Arg Lys Gly Cys Tyr Arg Thr Leu Gly Val
    610                 615                 620

Phe Arg Tyr Lys Ser Arg Cys Tyr Val Gly Leu Val Trp Gly Ile Leu
625                 630                 635                 640

Leu Thr Thr Glu Leu Ile Ile Trp Ala Ala Ser Ala Asp Thr Pro Leu
                645                 650                 655
```

-continued

```
Met Glu Ser Gly Trp Ser Asp Thr Ala His Gly Val Gly Ile Val Pro
            660                 665                 670

Met Lys Thr Asp Leu Glu Leu Asp Phe Ala Leu Ala Ser Ser Ser Ser
        675                 680                 685

Tyr Ser Tyr Arg Arg Lys Leu Val Asn Pro Ala Asn Gln Glu Glu Thr
    690                 695                 700

Leu Pro Phe His Phe Gln Leu Asp Lys Gln Val Val His Ala Glu Ile
705                 710                 715                 720

Gln Asn Leu Gly His Trp Met Asp Gly Thr Phe Asn Ile Lys Thr Ala
                725                 730                 735

Phe His Cys Tyr Gly Glu Cys Lys Lys Tyr Ala Tyr Pro Trp Gln Thr
            740                 745                 750

Ala Lys Cys Phe Phe Glu Lys Asp Tyr Gln Tyr Glu Thr Ser Trp Gly
        755                 760                 765

Cys Asn Pro Pro Asp Cys Pro Gly Val Gly Thr Gly Cys Thr Ala Cys
    770                 775                 780

Gly Val Tyr Leu Asp Lys Leu Arg Ser Val Gly Lys Ala Tyr Lys Ile
785                 790                 795                 800

Val Ser Leu Lys Tyr Thr Arg Lys Val Cys Ile Gln Leu Gly Thr Glu
                805                 810                 815

Gln Thr Cys Lys His Ile Asp Val Asn Asp Cys Leu Val Thr Pro Ser
            820                 825                 830

Val Lys Val Cys Met Ile Gly Thr Ile Ser Lys Leu Gln Pro Gly Asp
        835                 840                 845

Thr Leu Leu Phe Leu Gly Pro Leu Glu Gln Gly Gly Ile Ile Leu Lys
    850                 855                 860

Gln Trp Cys Thr Thr Ser Cys Val Phe Gly Asp Pro Gly Asp Ile Met
865                 870                 875                 880

Ser Thr Thr Ser Gly Met Arg Cys Pro Glu His Thr Gly Ser Phe Arg
                885                 890                 895

Lys Ile Cys Gly Phe Ala Thr Thr Pro Thr Cys Glu Tyr Gln Gly Asn
            900                 905                 910

Thr Val Ser Gly Phe Gln Arg Met Met Ala Thr Arg Asp Ser Phe Gln
        915                 920                 925

Ser Phe Asn Val Thr Glu Pro His Ile Thr Ser Asn Arg Leu Glu Trp
    930                 935                 940

Ile Asp Pro Asp Ser Ser Ile Lys Asp His Ile Asn Met Val Leu Asn
945                 950                 955                 960

Arg Asp Val Ser Phe Gln Asp Leu Ser Asp Asn Pro Cys Lys Val Asp
                965                 970                 975

Leu His Thr Gln Ser Ile Asp Gly Ala Trp Gly Ser Gly Val Gly Phe
            980                 985                 990

Thr Leu Val Cys Thr Val Gly Leu  Thr Glu Cys Ala Asn  Phe Ile Thr
        995                 1000                 1005

Ser Ile  Lys Ala Cys Asp Ser  Ala Met Cys Tyr Gly  Ala Thr Val
    1010                 1015                 1020

Thr Asn  Leu Leu Arg Gly Ser  Asn Thr Val Lys Val  Val Gly Lys
    1025                 1030                 1035

Gly Gly  His Ser Gly Ser Leu  Phe Lys Cys Cys His  Asp Thr Asp
    1040                 1045                 1050

Cys Thr  Glu Glu Gly Leu Ala  Ala Ser Pro Pro His  Leu Asp Arg
    1055                 1060                 1065

Val Thr  Gly Tyr Asn Gln Ile  Asp Ser Asp Lys Val  Tyr Asp Asp
```

```
    1070                1075                1080

Gly Ala  Pro Pro Cys Thr Ile  Lys Cys Trp Phe Thr  Lys Ser Gly
    1085                1090                1095

Glu Trp  Leu Leu Gly Ile Leu  Asn Gly Asn Trp Val  Val Val Ala
    1100                1105                1110

Val Leu  Ile Val Ile Leu Ile  Leu Ser Ile Leu Leu  Phe Ser Phe
    1115                1120                1125

Phe Cys  Pro Val Arg Asn Arg  Lys Asn Lys Ala Asn
    1130                1135                1140


<210> SEQ ID NO 16
<211> LENGTH: 1140
<212> TYPE: PRT
<213> ORGANISM: Sin Nombre virus
<220> FEATURE:
<223> OTHER INFORMATION: strain Convict Creek 107

<400> SEQUENCE: 16

Met Val Gly Trp Val Cys Ile Phe Leu Val Val Leu Thr Thr Ala Thr
1               5                   10                  15

Ala Gly Leu Thr Arg Asn Leu Tyr Glu Leu Lys Ile Glu Cys Pro His
            20                  25                  30

Thr Val Gly Leu Gly Gln Gly Tyr Val Thr Gly Ser Val Glu Thr Thr
        35                  40                  45

Pro Ile Leu Leu Thr Gln Val Ala Asp Leu Lys Ile Glu Ser Ser Cys
    50                  55                  60

Asn Phe Asp Leu His Val Pro Ala Thr Thr Thr Gln Lys Tyr Asn Gln
65                  70                  75                  80

Val Asp Trp Thr Lys Lys Ser Ser Thr Thr Glu Ser Thr Asn Ala Gly
                85                  90                  95

Ala Thr Thr Phe Glu Ala Lys Thr Lys Glu Val Asn Leu Lys Gly Thr
            100                 105                 110

Cys Asn Ile Pro Pro Thr Thr Phe Glu Ala Ala Tyr Lys Ser Arg Lys
        115                 120                 125

Thr Val Ile Cys Tyr Asp Leu Ala Cys Asn Gln Thr His Cys Leu Pro
    130                 135                 140

Thr Val His Leu Ile Ala Pro Val Gln Thr Cys Met Ser Val Arg Ser
145                 150                 155                 160

Cys Met Ile Gly Leu Leu Ser Ser Arg Ile Gln Val Ile Tyr Glu Lys
                165                 170                 175

Thr Tyr Cys Val Thr Gly Gln Leu Ile Glu Gly Leu Cys Phe Ile Pro
            180                 185                 190

Thr His Thr Ile Ala Leu Thr Gln Pro Gly His Thr Tyr Asp Thr Met
        195                 200                 205

Thr Leu Pro Val Thr Cys Phe Leu Val Ala Lys Lys Leu Gly Thr Gln
    210                 215                 220

Leu Lys Leu Ala Val Glu Leu Glu Lys Leu Ile Thr Gly Val Ser Cys
225                 230                 235                 240

Thr Glu Asn Ser Phe Gln Gly Tyr Tyr Ile Cys Phe Ile Gly Lys His
                245                 250                 255

Ser Glu Pro Leu Phe Val Pro Thr Met Glu Asp Tyr Arg Ser Ala Glu
            260                 265                 270

Leu Phe Thr Arg Met Val Leu Asn Pro Arg Gly Glu Asp His Asp Pro
        275                 280                 285

Asp Gln Asn Gly Gln Gly Leu Met Arg Ile Ala Gly Pro Val Thr Ala
```

-continued

```
    290                 295                 300

Lys Val Pro Ser Thr Glu Thr Thr Glu Thr Met Gln Gly Ile Ala Phe
305                 310                 315                 320

Ala Gly Ala Pro Met Tyr Ser Ser Phe Ser Thr Leu Val Arg Lys Ala
                325                 330                 335

Asp Pro Glu Tyr Val Phe Ser Pro Gly Ile Ile Ala Glu Ser Asn His
            340                 345                 350

Ser Val Cys Asp Lys Lys Thr Val Pro Leu Thr Trp Thr Gly Phe Leu
        355                 360                 365

Ala Val Ser Gly Glu Ile Glu Arg Ile Thr Gly Cys Thr Val Phe Cys
    370                 375                 380

Thr Leu Ala Gly Pro Gly Ala Ser Cys Glu Ala Tyr Ser Glu Thr Gly
385                 390                 395                 400

Ile Phe Asn Ile Ser Ser Pro Thr Cys Leu Val Asn Lys Val Gln Lys
                405                 410                 415

Phe Arg Gly Ser Glu Gln Arg Ile Asn Phe Met Cys Gln Arg Val Asp
            420                 425                 430

Gln Asp Val Val Val Tyr Cys Asn Gly Gln Lys Lys Val Ile Leu Thr
        435                 440                 445

Lys Thr Leu Val Ile Gly Gln Cys Ile Tyr Thr Phe Thr Ser Leu Phe
    450                 455                 460

Ser Leu Ile Pro Gly Val Ala His Ser Leu Ala Val Glu Leu Cys Val
465                 470                 475                 480

Pro Gly Leu His Gly Trp Ala Thr Thr Ala Leu Leu Ile Thr Phe Cys
                485                 490                 495

Phe Gly Trp Leu Leu Ile Pro Thr Val Thr Leu Ile Ile Leu Lys Ile
            500                 505                 510

Leu Arg Leu Leu Thr Phe Ser Cys Ser His Tyr Ser Thr Glu Ser Lys
        515                 520                 525

Phe Lys Val Ile Leu Glu Arg Val Lys Val Glu Tyr Gln Lys Thr Met
    530                 535                 540

Gly Ser Met Val Cys Asp Ile Cys His His Glu Cys Glu Thr Ala Lys
545                 550                 555                 560

Glu Leu Glu Thr His Lys Lys Ser Cys Pro Glu Gly Gln Cys Pro Tyr
                565                 570                 575

Cys Met Thr Ile Thr Glu Ser Thr Glu Ser Ala Leu Gln Ala His Phe
            580                 585                 590

Ser Ile Cys Lys Leu Thr Asn Arg Phe Gln Glu Ile Leu Lys Lys Ser
        595                 600                 605

Leu Lys Arg Pro Glu Val Arg Lys Gly Cys Tyr Arg Thr Leu Gly Val
    610                 615                 620

Phe Arg Tyr Lys Ser Arg Cys Tyr Val Gly Leu Val Trp Gly Ile Leu
625                 630                 635                 640

Leu Thr Thr Glu Leu Ile Ile Trp Ala Ala Ser Ala Asp Thr Pro Leu
                645                 650                 655

Met Glu Ser Gly Trp Ser Asp Thr Ala His Gly Val Gly Ile Val Pro
            660                 665                 670

Met Lys Thr Asp Leu Glu Leu Asp Phe Ala Leu Ala Ser Ser Ser Ser
        675                 680                 685

Tyr Ser Tyr Arg Arg Lys Leu Val Asn Pro Ala Asn Gln Glu Glu Thr
    690                 695                 700

Leu Pro Phe His Phe Gln Leu Asp Lys Gln Val Val His Ala Glu Ile
705                 710                 715                 720
```

```
Gln Asn Leu Gly His Trp Met Asp Gly Thr Phe Asn Ile Lys Thr Ala
                725                 730                 735

Phe His Cys Tyr Gly Glu Cys Lys Lys Tyr Ala Tyr Pro Trp Gln Thr
            740                 745                 750

Ala Lys Cys Phe Phe Glu Lys Asp Tyr Gln Tyr Glu Thr Ser Trp Gly
        755                 760                 765

Cys Asn Pro Pro Asp Cys Pro Gly Val Gly Thr Gly Cys Thr Ala Cys
    770                 775                 780

Gly Val Tyr Leu Asp Lys Leu Arg Ser Val Gly Lys Ala Tyr Lys Ile
785                 790                 795                 800

Val Ser Leu Lys Tyr Thr Arg Lys Val Cys Ile Gln Leu Gly Thr Glu
                805                 810                 815

Gln Thr Cys Lys His Ile Asp Val Asn Asp Cys Leu Val Thr Pro Ser
            820                 825                 830

Val Lys Val Cys Met Ile Gly Thr Ile Ser Lys Leu Gln Pro Gly Asp
        835                 840                 845

Thr Leu Leu Phe Leu Gly Pro Leu Glu Gln Gly Gly Ile Ile Leu Lys
    850                 855                 860

Gln Trp Cys Thr Thr Ser Cys Val Phe Gly Asp Pro Gly Asp Ile Met
865                 870                 875                 880

Ser Thr Thr Ser Gly Met Arg Cys Pro Glu His Thr Gly Ser Phe Arg
                885                 890                 895

Lys Ile Cys Gly Phe Ala Thr Thr Pro Thr Cys Glu Tyr Gln Gly Asn
            900                 905                 910

Thr Val Ser Gly Phe Gln Arg Met Met Ala Thr Arg Asp Ser Phe Gln
        915                 920                 925

Ser Phe Asn Val Thr Glu Pro His Ile Thr Ser Asn Arg Leu Glu Trp
    930                 935                 940

Ile Asp Pro Asp Ser Ser Ile Lys Asp His Ile Asn Met Val Leu Asn
945                 950                 955                 960

Arg Asp Val Ser Phe Gln Asp Leu Ser Asp Asn Pro Cys Lys Val Asp
                965                 970                 975

Leu His Thr Gln Ser Ile Asp Gly Ala Trp Gly Ser Gly Val Gly Phe
            980                 985                 990

Thr Leu Val Cys Thr Val Gly Leu  Thr Glu Cys Ala Asn  Phe Ile Thr
        995                 1000                1005

Ser Ile  Lys Ala Cys Asp Ser  Ala Met Cys Tyr Gly  Ala Thr Val
    1010                1015                1020

Thr Asn  Leu Leu Arg Gly Ser  Asn Thr Val Lys Val  Val Gly Lys
    1025                1030                1035

Gly Gly  His Ser Gly Ser Leu  Phe Lys Cys Cys His  Asp Thr Asp
    1040                1045                1050

Cys Thr  Glu Glu Gly Leu Ala  Ala Ser Pro Pro His  Leu Asp Arg
    1055                1060                1065

Val Thr  Gly Tyr Asn Gln Ile  Asp Ser Asp Lys Val  Tyr Asp Asp
    1070                1075                1080

Gly Ala  Pro Pro Cys Thr Ile  Lys Cys Trp Phe Thr  Arg Ser Gly
    1085                1090                1095

Glu Trp  Leu Leu Gly Ile Leu  Asn Gly Asn Trp Val  Val Val Ala
    1100                1105                1110

Val Leu  Ile Val Ile Leu Ile  Leu Ser Ile Leu Leu  Phe Ser Phe
    1115                1120                1125
```

```
Phe Cys  Pro Val Arg Asn Arg  Lys Asn Lys Ala Asn
    1130                1135                1140


<210> SEQ ID NO 17
<211> LENGTH: 1140
<212> TYPE: PRT
<213> ORGANISM: Sin Nombre virus
<220> FEATURE:
<223> OTHER INFORMATION: strain Convict Creek 107 isolate 74

<400> SEQUENCE: 17

Met Val Gly Trp Val Cys Ile Phe Leu Val Val Leu Thr Thr Ala Thr
1               5                   10                  15

Ala Gly Leu Thr Arg Asn Leu Tyr Glu Leu Lys Ile Glu Cys Pro His
            20                  25                  30

Thr Val Gly Leu Gly Gln Gly Tyr Val Thr Gly Ser Val Glu Thr Thr
        35                  40                  45

Pro Ile Leu Leu Thr Gln Val Ala Asp Leu Lys Ile Glu Ser Ser Cys
    50                  55                  60

Asn Phe Asp Leu His Val Pro Ala Thr Thr Thr Gln Lys Tyr Asn Gln
65                  70                  75                  80

Val Asp Trp Thr Lys Lys Ser Ser Thr Thr Glu Ser Thr Asn Ala Gly
                85                  90                  95

Ala Thr Thr Phe Glu Ala Lys Thr Lys Glu Val Asn Leu Lys Gly Thr
            100                 105                 110

Cys Asn Ile Pro Pro Thr Thr Phe Glu Ala Ala Phe Lys Ser Arg Lys
        115                 120                 125

Thr Val Ile Cys Tyr Asp Leu Ala Cys Asn Gln Thr His Cys Leu Pro
    130                 135                 140

Thr Val His Leu Ile Ala Pro Val Gln Thr Cys Met Ser Val Arg Ser
145                 150                 155                 160

Cys Met Ile Gly Leu Leu Ser Ser Arg Ile Gln Val Ile Tyr Glu Lys
                165                 170                 175

Thr Tyr Cys Val Thr Gly Gln Leu Ile Glu Gly Leu Cys Phe Ile Pro
            180                 185                 190

Thr His Thr Ile Ala Leu Thr Gln Pro Gly His Thr Tyr Asp Thr Met
        195                 200                 205

Thr Leu Pro Val Thr Cys Phe Leu Val Ala Lys Lys Leu Gly Thr Gln
    210                 215                 220

Leu Lys Leu Ala Val Glu Leu Glu Lys Leu Ile Thr Gly Val Ser Cys
225                 230                 235                 240

Thr Glu Asn Ser Phe Gln Gly Tyr Tyr Ile Cys Phe Ile Gly Lys His
                245                 250                 255

Ser Glu Pro Leu Phe Val Pro Thr Met Glu Asp Tyr Arg Ser Ala Glu
            260                 265                 270

Leu Phe Thr Arg Met Val Leu Asn Pro Arg Gly Glu Asp His Asp Pro
        275                 280                 285

Asp Gln Asn Gly Gln Gly Leu Met Arg Ile Ala Gly Pro Val Thr Ala
    290                 295                 300

Lys Val Pro Ser Thr Glu Thr Thr Glu Thr Met Gln Gly Ile Ala Phe
305                 310                 315                 320

Ala Gly Ala Pro Met Tyr Ser Ser Phe Ser Thr Leu Val Arg Lys Ala
                325                 330                 335

Asp Pro Glu Tyr Val Phe Ser Pro Gly Ile Ile Ala Glu Ser Asn His
            340                 345                 350
```

-continued

```
Ser Val Cys Asp Lys Lys Thr Val Pro Leu Thr Trp Thr Gly Phe Leu
        355                 360                 365

Ala Val Ser Gly Glu Ile Glu Arg Ile Thr Gly Cys Thr Val Phe Cys
    370                 375                 380

Thr Leu Ala Gly Pro Gly Ala Ser Cys Glu Ala Tyr Ser Glu Thr Gly
385                 390                 395                 400

Ile Phe Asn Ile Ser Ser Pro Thr Cys Leu Val Asn Lys Val Gln Lys
                405                 410                 415

Phe Arg Gly Ser Glu Gln Arg Ile Asn Phe Met Cys Gln Arg Val Asp
            420                 425                 430

Gln Asp Val Val Val Tyr Cys Asn Gly Gln Lys Lys Val Ile Leu Thr
        435                 440                 445

Lys Thr Leu Val Ile Gly Gln Cys Ile Tyr Thr Phe Thr Ser Leu Phe
    450                 455                 460

Ser Leu Ile Pro Gly Val Ala His Ser Leu Ala Val Glu Leu Cys Val
465                 470                 475                 480

Pro Gly Leu His Gly Trp Ala Thr Thr Ala Leu Leu Ile Thr Phe Cys
                485                 490                 495

Phe Gly Trp Leu Leu Ile Pro Thr Val Thr Leu Ile Ile Leu Lys Ile
            500                 505                 510

Leu Arg Leu Leu Thr Phe Ser Cys Ser His Tyr Ser Thr Glu Ser Lys
        515                 520                 525

Phe Lys Val Ile Leu Glu Arg Val Lys Val Glu Tyr Gln Lys Thr Met
    530                 535                 540

Gly Ser Met Val Cys Asp Ile Cys His His Glu Cys Glu Thr Ala Lys
545                 550                 555                 560

Glu Leu Glu Thr His Lys Lys Ser Cys Pro Glu Gly Gln Cys Pro Tyr
                565                 570                 575

Cys Met Thr Ile Thr Glu Ser Thr Glu Ser Ala Leu Gln Ala His Phe
            580                 585                 590

Ser Ile Cys Lys Leu Thr Asn Arg Phe Gln Glu Ile Leu Lys Lys Ser
        595                 600                 605

Leu Lys Arg Pro Glu Val Arg Lys Gly Cys Tyr Arg Thr Leu Gly Val
    610                 615                 620

Phe Arg Tyr Lys Ser Arg Cys Tyr Val Gly Leu Val Trp Gly Ile Leu
625                 630                 635                 640

Leu Thr Thr Glu Leu Ile Ile Trp Ala Ala Ser Ala Asp Thr Pro Leu
                645                 650                 655

Met Glu Ser Gly Trp Ser Asp Thr Ala His Gly Val Gly Ile Val Pro
            660                 665                 670

Met Lys Thr Asp Leu Glu Leu Asp Phe Ala Leu Ala Ser Ser Ser Ser
        675                 680                 685

Tyr Ser Tyr Arg Arg Lys Leu Val Asn Pro Ala Asn Gln Glu Glu Thr
    690                 695                 700

Leu Pro Phe His Phe Gln Leu Asp Lys Gln Val Val His Ala Glu Ile
705                 710                 715                 720

Gln Asn Leu Gly His Trp Met Asp Gly Thr Phe Asn Ile Lys Thr Ala
                725                 730                 735

Phe His Cys Tyr Gly Glu Cys Lys Lys Tyr Ala Tyr Pro Trp Gln Thr
            740                 745                 750

Ala Lys Cys Phe Phe Glu Lys Asp Tyr Gln Tyr Glu Thr Ser Trp Gly
        755                 760                 765

Cys Asn Pro Pro Asp Cys Pro Gly Val Gly Thr Gly Cys Thr Ala Cys
```

770 775 780

Gly Val Tyr Leu Asp Lys Leu Arg Ser Val Gly Lys Ala Tyr Lys Ile
785 790 795 800

Val Ser Leu Lys Tyr Thr Arg Lys Val Cys Ile Gln Leu Gly Thr Glu
805 810 815

Gln Thr Cys Lys His Ile Asp Val Asn Asp Cys Leu Val Thr Pro Ser
820 825 830

Val Lys Val Cys Met Ile Gly Thr Ile Ser Lys Leu Gln Pro Gly Asp
835 840 845

Thr Leu Leu Phe Leu Gly Pro Leu Glu Gln Gly Gly Ile Ile Leu Lys
850 855 860

Gln Trp Cys Thr Thr Ser Cys Val Phe Gly Asp Pro Gly Asp Ile Met
865 870 875 880

Ser Thr Thr Ser Gly Met Arg Cys Pro Glu His Thr Gly Ser Phe Arg
885 890 895

Lys Ile Cys Gly Phe Ala Thr Thr Pro Thr Cys Glu Tyr Gln Gly Asn
900 905 910

Thr Val Ser Gly Phe Gln Arg Met Met Ala Thr Arg Asp Ser Phe Gln
915 920 925

Ser Phe Asn Val Thr Glu Pro His Ile Thr Ser Asn Arg Leu Glu Trp
930 935 940

Ile Asp Pro Asp Ser Ser Ile Lys Asp His Ile Asn Met Val Leu Asn
945 950 955 960

Arg Asp Val Ser Phe Gln Asp Leu Ser Asp Asn Pro Cys Lys Val Asp
965 970 975

Leu His Thr Gln Ser Ile Asp Gly Ala Trp Gly Ser Gly Val Gly Phe
980 985 990

Thr Leu Val Cys Thr Val Gly Leu Thr Glu Cys Ala Asn Phe Ile Thr
995 1000 1005

Ser Ile Lys Ala Cys Asp Ser Ala Met Cys Tyr Gly Ala Thr Val
1010 1015 1020

Thr Asn Leu Leu Arg Gly Ser Asn Thr Val Lys Val Val Gly Lys
1025 1030 1035

Gly Gly His Ser Gly Ser Leu Phe Lys Cys Cys His Asp Thr Asp
1040 1045 1050

Cys Thr Glu Glu Gly Leu Ala Ala Ser Pro Pro His Leu Asp Arg
1055 1060 1065

Val Thr Gly Tyr Asn Gln Ile Asp Ser Asp Lys Val Tyr Asp Asp
1070 1075 1080

Gly Ala Pro Pro Cys Thr Ile Lys Cys Trp Phe Thr Lys Ser Gly
1085 1090 1095

Glu Trp Leu Leu Gly Ile Leu Asn Gly Asn Trp Val Val Val Ala
1100 1105 1110

Val Leu Ile Val Ile Leu Ile Leu Ser Ile Leu Leu Phe Ser Phe
1115 1120 1125

Phe Cys Pro Val Arg Asn Arg Lys Asn Lys Ala Asn
1130 1135 1140

<210> SEQ ID NO 18
<211> LENGTH: 1140
<212> TYPE: PRT
<213> ORGANISM: Sin Nombre virus
<220> FEATURE:
<223> OTHER INFORMATION: strain NMH10

<400> SEQUENCE: 18

Met Val Gly Trp Val Cys Ile Phe Leu Val Val Leu Thr Thr Ala Thr
1 5 10 15

Ala Gly Leu Thr Arg Asn Leu Tyr Glu Leu Lys Ile Glu Cys Pro His
20 25 30

Thr Val Gly Leu Gly Gln Gly Tyr Val Thr Gly Ser Val Glu Ile Thr
35 40 45

Pro Ile Leu Leu Thr Gln Val Ala Asp Leu Lys Ile Glu Ser Ser Cys
50 55 60

Asn Phe Asp Leu His Val Pro Ala Thr Thr Thr Gln Lys Tyr Asn Gln
65 70 75 80

Val Asp Trp Thr Lys Lys Ser Ser Thr Thr Glu Ser Thr Asn Ala Gly
85 90 95

Ala Thr Thr Phe Glu Ala Lys Thr Lys Glu Ile Asn Leu Lys Gly Thr
100 105 110

Cys Asn Ile Pro Pro Thr Thr Phe Glu Ala Ala Tyr Lys Ser Arg Lys
115 120 125

Thr Val Ile Cys Tyr Asp Leu Ala Cys Asn Gln Thr His Cys Leu Pro
130 135 140

Thr Val His Leu Ile Ala Pro Val Gln Thr Cys Met Ser Val Arg Ser
145 150 155 160

Cys Met Ile Gly Leu Leu Ser Ser Arg Ile Gln Val Ile Tyr Glu Lys
165 170 175

Thr Tyr Cys Val Thr Gly Gln Leu Ile Glu Gly Leu Cys Phe Ile Pro
180 185 190

Thr His Thr Ile Ala Leu Thr Gln Pro Gly His Thr Tyr Asp Thr Met
195 200 205

Thr Leu Pro Val Thr Cys Phe Leu Val Ala Lys Lys Leu Gly Thr Gln
210 215 220

Leu Lys Leu Ala Val Glu Leu Glu Lys Leu Ile Thr Gly Val Ser Cys
225 230 235 240

Thr Glu Asn Ser Phe Gln Gly Tyr Tyr Ile Cys Phe Ile Gly Lys His
245 250 255

Ser Glu Pro Leu Phe Val Pro Thr Met Glu Asp Tyr Arg Ser Ala Glu
260 265 270

Leu Phe Thr Arg Met Val Leu Asn Pro Arg Gly Glu Asp His Asp Pro
275 280 285

Asp Gln Asn Gly Gln Gly Leu Met Arg Ile Ala Gly Pro Val Thr Ala
290 295 300

Lys Val Pro Ser Thr Glu Thr Thr Glu Thr Met Gln Gly Ile Ala Phe
305 310 315 320

Ala Gly Ala Pro Met Tyr Ser Ser Phe Ser Thr Leu Val Arg Lys Ala
325 330 335

Asp Pro Glu Tyr Val Phe Ser Pro Gly Ile Ile Ala Glu Ser Asn His
340 345 350

Ser Val Cys Asp Lys Lys Thr Val Pro Leu Thr Trp Thr Gly Phe Leu
355 360 365

Ala Val Ser Gly Glu Ile Glu Lys Ile Thr Gly Cys Thr Val Phe Cys
370 375 380

Thr Leu Ala Gly Pro Gly Ala Ser Cys Glu Ala Tyr Ser Glu Thr Gly
385 390 395 400

Ile Phe Asn Ile Ser Ser Pro Thr Cys Leu Val Asn Lys Val Gln Lys
405 410 415

-continued

```
Phe Arg Gly Ser Glu Gln Arg Ile Asn Phe Met Cys Gln Arg Val Asp
            420                 425                 430

Gln Asp Val Val Val Tyr Cys Asn Gly Gln Lys Lys Val Ile Leu Thr
        435                 440                 445

Lys Thr Leu Val Ile Gly Gln Cys Ile Tyr Thr Phe Thr Ser Leu Phe
    450                 455                 460

Ser Leu Ile Pro Gly Val Ala His Ser Leu Ala Val Glu Leu Cys Val
465                 470                 475                 480

Pro Gly Leu His Gly Trp Ala Thr Thr Ala Leu Leu Ile Thr Phe Cys
                485                 490                 495

Phe Gly Trp Leu Leu Ile Pro Ala Val Thr Leu Ile Ile Leu Lys Ile
            500                 505                 510

Leu Arg Leu Leu Thr Phe Ser Cys Ser His Tyr Ser Thr Glu Ser Lys
        515                 520                 525

Phe Lys Val Ile Leu Glu Arg Val Lys Val Glu Tyr Gln Lys Thr Met
    530                 535                 540

Gly Ser Met Val Cys Asp Ile Cys His His Glu Cys Glu Thr Ala Lys
545                 550                 555                 560

Glu Leu Glu Thr His Lys Lys Ser Cys Pro Glu Gly Gln Cys Pro Tyr
                565                 570                 575

Cys Met Thr Ile Thr Glu Ser Thr Glu Ser Ala Leu Gln Ala His Phe
            580                 585                 590

Ala Ile Cys Lys Leu Thr Asn Arg Phe Gln Glu Asn Leu Lys Lys Ser
        595                 600                 605

Leu Lys Arg Pro Glu Val Arg Lys Gly Cys Tyr Arg Thr Leu Gly Val
    610                 615                 620

Phe Arg Tyr Lys Ser Arg Cys Tyr Val Gly Leu Val Trp Gly Ile Leu
625                 630                 635                 640

Leu Thr Thr Glu Leu Ile Ile Trp Ala Ala Ser Ala Asp Thr Pro Leu
                645                 650                 655

Met Glu Ser Gly Trp Ser Asp Thr Ala His Gly Val Gly Ile Ile Pro
            660                 665                 670

Met Lys Thr Asp Leu Glu Leu Asp Phe Ala Leu Ala Ser Ser Ser Ser
        675                 680                 685

Tyr Ser Tyr Arg Arg Lys Leu Val Asn Pro Ala Asn Gln Glu Glu Thr
    690                 695                 700

Leu Pro Phe His Phe Gln Leu Asp Lys Gln Val Val His Ala Glu Ile
705                 710                 715                 720

Gln Asn Leu Gly His Trp Met Asp Gly Thr Phe Asn Ile Lys Thr Ala
                725                 730                 735

Phe His Cys Tyr Gly Glu Cys Lys Lys Tyr Ala Tyr Pro Trp Gln Thr
            740                 745                 750

Ala Lys Cys Phe Phe Glu Lys Asp Tyr Gln Tyr Glu Thr Ser Trp Gly
        755                 760                 765

Cys Asn Pro Pro Asp Cys Pro Gly Val Gly Thr Gly Cys Thr Ala Cys
    770                 775                 780

Gly Val Tyr Leu Asp Lys Leu Arg Ser Val Gly Lys Ala Tyr Lys Ile
785                 790                 795                 800

Val Ser Leu Lys Tyr Thr Arg Lys Val Cys Ile Gln Leu Gly Thr Glu
                805                 810                 815

Gln Thr Cys Lys His Ile Asp Val Asn Asp Cys Leu Val Thr Pro Ser
            820                 825                 830
```

-continued

```
Val Lys Val Cys Met Ile Gly Thr Ile Ser Lys Leu Gln Pro Gly Asp
        835                 840                 845

Thr Leu Leu Phe Leu Gly Pro Leu Glu Gln Gly Gly Ile Ile Leu Lys
    850                 855                 860

Gln Trp Cys Thr Thr Ser Cys Val Phe Gly Asp Pro Gly Asp Ile Met
865                 870                 875                 880

Ser Thr Thr Ser Gly Met Arg Cys Pro Glu His Thr Gly Ser Phe Arg
                885                 890                 895

Lys Ile Cys Gly Phe Ala Thr Thr Pro Thr Cys Glu Tyr Gln Gly Asn
            900                 905                 910

Thr Val Ser Gly Phe Gln Arg Met Met Ala Thr Arg Asp Ser Phe Gln
        915                 920                 925

Ser Phe Asn Val Thr Glu Pro His Ile Thr Ser Asn Arg Leu Glu Trp
    930                 935                 940

Ile Asp Pro Asp Ser Ser Ile Lys Asp His Ile Asn Met Val Leu Asn
945                 950                 955                 960

Arg Asp Val Ser Phe Gln Asp Leu Ser Asp Asn Pro Cys Lys Val Asp
                965                 970                 975

Leu His Thr Gln Ser Ile Asp Gly Ala Trp Gly Ser Gly Val Gly Phe
            980                 985                 990

Thr Leu Val Cys Thr Val Gly Leu  Thr Glu Cys Ala Asn  Phe Ile Thr
        995                 1000                1005

Ser Ile  Lys Ala Cys Asp Ser  Ala Met Cys Tyr Gly  Ala Thr Val
    1010                 1015                1020

Thr Asn  Leu Leu Arg Gly Ser  Asn Thr Val Lys Val  Val Gly Lys
    1025                 1030                1035

Gly Gly  His Ser Gly Ser Leu  Phe Lys Cys Cys His  Asp Thr Asp
    1040                 1045                1050

Cys Thr  Glu Glu Gly Leu Ala  Ala Ser Pro Pro His  Leu Asp Arg
    1055                 1060                1065

Val Thr  Gly Tyr Asn Gln Ile  Asp Ser Asp Lys Val  Tyr Asp Asp
    1070                 1075                1080

Gly Ala  Pro Pro Cys Thr Ile  Lys Cys Trp Phe Thr  Lys Ser Gly
    1085                 1090                1095

Glu Trp  Leu Leu Gly Ile Leu  Asn Gly Asn Trp Val  Val Val Ala
    1100                 1105                1110

Val Leu  Ile Val Ile Leu Ile  Leu Ser Ile Leu Leu  Phe Ser Phe
    1115                 1120                1125

Phe Cys  Pro Val Arg Ser Arg  Lys Asn Lys Ala Asn
    1130                 1135                1140


<210> SEQ ID NO 19
<211> LENGTH: 1140
<212> TYPE: PRT
<213> ORGANISM: New York virus

<400> SEQUENCE: 19

Met Val Gly Trp Val Cys Ile Ser Leu Val Val Leu Ala Thr Thr Thr
1               5                   10                  15

Ala Gly Leu Thr Arg Asn Leu Tyr Glu Leu Lys Ile Glu Cys Pro His
            20                  25                  30

Thr Val Gly Leu Gly Gln Gly Tyr Val Thr Gly Ser Val Glu Thr Thr
        35                  40                  45

Pro Ile Leu Leu Thr Gln Val Thr Asp Leu Lys Ile Glu Ser Ser Cys
    50                  55                  60
```

```
Asn Phe Asp Leu His Val Pro Ser Thr Ser Ile Gln Lys Tyr Asn Gln
65                  70                  75                  80

Val Glu Trp Ala Lys Lys Ser Ser Thr Thr Glu Ser Thr Ser Ala Gly
                85                  90                  95

Ala Thr Thr Phe Glu Ala Lys Thr Lys Glu Val Ser Leu Lys Gly Thr
            100                 105                 110

Cys Asn Ile Pro Val Thr Thr Phe Glu Ala Ala Tyr Lys Ser Arg Lys
        115                 120                 125

Thr Val Ile Cys Tyr Asp Leu Ala Cys Asn Gln Thr His Cys Leu Pro
    130                 135                 140

Thr Val His Leu Ile Ala Pro Val Gln Thr Cys Met Ser Val Arg Ser
145                 150                 155                 160

Cys Met Ile Gly Leu Leu Ser Ser Arg Ile Gln Val Ile Tyr Glu Lys
                165                 170                 175

Thr Tyr Cys Val Thr Gly Gln Leu Val Glu Gly Leu Cys Phe Ile Pro
            180                 185                 190

Thr His Thr Ile Ala Leu Thr Gln Pro Gly His Thr Tyr Asp Thr Met
        195                 200                 205

Thr Leu Pro Ile Thr Cys Phe Leu Val Ala Lys Lys Leu Gly Thr Gln
    210                 215                 220

Leu Lys Ile Ala Val Glu Leu Glu Lys Leu Ile Thr Ala Ser Gly Cys
225                 230                 235                 240

Thr Glu Asn Ser Phe Gln Gly Tyr Tyr Ile Cys Phe Leu Gly Lys His
                245                 250                 255

Ser Glu Pro Leu Phe Val Pro Met Met Asp Asp Tyr Arg Ser Ala Glu
            260                 265                 270

Leu Phe Thr Arg Met Val Leu Asn Pro Arg Gly Glu Asp His Asp Pro
        275                 280                 285

Asp Gln Asn Gly Gln Gly Leu Met Arg Ile Ala Gly Pro Ile Thr Ala
    290                 295                 300

Lys Val Pro Ser Thr Glu Thr Thr Glu Thr Met Gln Gly Ile Ala Phe
305                 310                 315                 320

Ala Gly Ala Pro Met Tyr Ser Ser Phe Ser Thr Leu Val Arg Lys Ala
                325                 330                 335

Asp Pro Asp Tyr Val Phe Ser Pro Gly Ile Ile Ala Glu Ser Asn His
            340                 345                 350

Ser Val Cys Asp Lys Lys Thr Ile Pro Leu Thr Trp Thr Gly Phe Leu
        355                 360                 365

Ala Val Ser Gly Glu Ile Glu Lys Ile Thr Gly Cys Thr Val Phe Cys
    370                 375                 380

Thr Leu Val Gly Pro Gly Ala Ser Cys Glu Ala Tyr Ser Glu Thr Gly
385                 390                 395                 400

Ile Phe Asn Ile Ser Ser Pro Thr Cys Leu Val Asn Lys Val Gln Lys
                405                 410                 415

Phe Arg Gly Ser Glu Gln Arg Ile Asn Phe Met Cys Gln Arg Val Asp
            420                 425                 430

Gln Asp Val Ile Val Tyr Cys Asn Gly Gln Lys Lys Val Ile Leu Thr
        435                 440                 445

Lys Thr Leu Val Ile Gly Gln Cys Ile Tyr Thr Phe Thr Ser Leu Phe
    450                 455                 460

Ser Leu Ile Pro Gly Val Ala His Ser Leu Ala Val Glu Leu Cys Val
465                 470                 475                 480
```

-continued

```
Pro Gly Leu His Gly Trp Ala Thr Thr Ala Leu Leu Ile Thr Phe Cys
                485                 490                 495

Phe Gly Trp Leu Leu Ile Pro Thr Ile Thr Met Ile Ile Leu Lys Ile
            500                 505                 510

Leu Arg Leu Leu Thr Phe Ser Cys Ser His Tyr Ser Thr Glu Ser Lys
        515                 520                 525

Phe Lys Ala Ile Leu Glu Arg Val Lys Val Glu Tyr Gln Lys Thr Met
    530                 535                 540

Gly Ser Met Val Cys Asp Val Cys His His Glu Cys Glu Thr Ala Lys
545                 550                 555                 560

Glu Leu Glu Thr His Lys Lys Ser Cys Pro Glu Gly Gln Cys Pro Tyr
                565                 570                 575

Cys Met Thr Met Thr Glu Ser Thr Glu Ser Ala Leu Gln Ala His Phe
            580                 585                 590

Ser Ile Cys Lys Leu Thr Asn Arg Phe Gln Glu Asn Leu Lys Lys Ser
        595                 600                 605

Leu Lys Arg Pro Glu Val Lys Gln Gly Cys Tyr Arg Thr Leu Gly Val
    610                 615                 620

Phe Arg Tyr Lys Ser Arg Cys Tyr Val Gly Leu Val Trp Gly Val Leu
625                 630                 635                 640

Leu Thr Thr Glu Leu Ile Val Trp Ala Ala Ser Ala Asp Thr Pro Leu
                645                 650                 655

Met Glu Ser Gly Trp Ser Asp Thr Ala His Gly Val Gly Ile Val Pro
            660                 665                 670

Met Lys Thr Asp Leu Glu Leu Asp Phe Ala Leu Ala Ser Ser Ser Ser
        675                 680                 685

Tyr Ser Tyr Arg Arg Lys Leu Val Asn Pro Ala Asn Lys Glu Glu Thr
    690                 695                 700

Leu Pro Phe His Phe Gln Leu Asp Lys Gln Val Val His Ala Glu Ile
705                 710                 715                 720

Gln Asn Leu Gly His Trp Met Asp Gly Thr Phe Asn Ile Lys Thr Ala
                725                 730                 735

Phe His Cys Tyr Gly Glu Cys Lys Lys Tyr Ala Tyr Pro Trp Gln Thr
            740                 745                 750

Ala Lys Cys Phe Phe Glu Lys Asp Tyr Gln Tyr Glu Thr Ser Trp Gly
        755                 760                 765

Cys Asn Pro Pro Asp Cys Pro Gly Val Gly Thr Gly Cys Thr Ala Cys
    770                 775                 780

Gly Val Tyr Leu Asp Lys Leu Arg Ser Val Gly Lys Ala Tyr Lys Ile
785                 790                 795                 800

Val Ser Leu Lys Phe Thr Arg Lys Val Cys Ile Gln Leu Gly Thr Glu
                805                 810                 815

Gln Thr Cys Lys His Ile Asp Val Asn Asp Cys Leu Val Thr Pro Ser
            820                 825                 830

Val Lys Val Cys Leu Ile Gly Thr Ile Ser Lys Leu Gln Pro Gly Asp
        835                 840                 845

Thr Leu Leu Phe Leu Gly Pro Leu Glu Gln Gly Gly Ile Ile Leu Lys
    850                 855                 860

Gln Trp Cys Thr Thr Ser Cys Val Phe Gly Asp Pro Gly Asp Ile Met
865                 870                 875                 880

Ser Thr Thr Thr Gly Met Lys Cys Pro Glu His Thr Gly Ser Phe Arg
                885                 890                 895

Lys Ile Cys Gly Phe Ala Thr Thr Pro Thr Cys Glu Tyr Gln Gly Asn
```

900 905 910

Thr Ile Ser Gly Phe Gln Arg Met Met Ala Thr Arg Asp Ser Phe Gln
915 920 925

Ser Phe Asn Val Thr Glu Pro His Ile Thr Ser Asn Arg Leu Glu Trp
930 935 940

Ile Asp Pro Asp Ser Ser Ile Lys Asp His Ile Asn Met Val Leu Asn
945 950 955 960

Arg Asp Val Ser Phe Gln Asp Leu Ser Asp Asn Pro Cys Lys Val Asp
965 970 975

Leu His Thr Gln Ser Ile Asp Gly Ala Trp Gly Ser Gly Val Gly Phe
980 985 990

Thr Leu Val Cys Thr Val Gly Leu Thr Glu Cys Ala Asn Phe Ile Thr
995 1000 1005

Ser Ile Lys Ala Cys Asp Ser Ala Met Cys Tyr Gly Ala Thr Val
1010 1015 1020

Thr Asn Leu Leu Arg Gly Ser Asn Thr Val Lys Val Val Gly Lys
1025 1030 1035

Gly Gly His Ser Gly Ser Leu Phe Lys Cys Cys His Asp Thr Asp
1040 1045 1050

Cys Thr Glu Glu Gly Leu Ala Ala Ser Pro Pro His Leu Asp Arg
1055 1060 1065

Val Thr Gly Tyr Asn Gln Ile Asp Ser Asp Lys Val Tyr Asp Asp
1070 1075 1080

Gly Ala Pro Pro Cys Thr Ile Lys Cys Trp Phe Thr Lys Ser Gly
1085 1090 1095

Glu Trp Leu Leu Gly Ile Leu Asn Gly Asn Trp Val Val Val Ala
1100 1105 1110

Val Leu Ile Val Ile Leu Ile Leu Ser Ile Leu Leu Phe Ser Phe
1115 1120 1125

Phe Cys Pro Ile Arg Gly Arg Lys Asn Lys Ser Asn
1130 1135 1140

<210> SEQ ID NO 20
<211> LENGTH: 1140
<212> TYPE: PRT
<213> ORGANISM: New York virus

<400> SEQUENCE: 20

Met Val Gly Phe Val Cys Ile Phe Leu Val Val Leu Ala Thr Thr Thr
1 5 10 15

Ala Gly Leu Thr Arg Asn Leu Tyr Glu Leu Lys Ile Glu Cys Pro His
20 25 30

Thr Val Gly Leu Gly Gln Gly Tyr Val Thr Gly Ser Val Gly Thr Thr
35 40 45

Pro Ile Leu Leu Thr Gln Val Thr Asp Leu Lys Ile Glu Ser Ser Cys
50 55 60

Asn Phe Asp Leu His Val Pro Ser Thr Ser Ile Gln Lys Tyr Asn Gln
65 70 75 80

Val Glu Trp Ala Lys Lys Ser Ser Thr Thr Glu Ser Thr Ser Ala Gly
85 90 95

Ala Thr Thr Phe Glu Ala Lys Thr Lys Glu Val Ser Leu Lys Gly Thr
100 105 110

Cys Asn Ile Pro Val Thr Thr Phe Glu Ala Ala Tyr Lys Ser Arg Lys
115 120 125

```
Thr Val Ile Cys Tyr Asp Leu Ala Cys Asn Gln Thr His Cys Leu Pro
    130                 135                 140

Thr Val His Leu Ile Ala Pro Val Gln Thr Cys Met Ser Val Arg Ser
145                 150                 155                 160

Cys Met Ile Gly Leu Leu Ser Ser Arg Ile Gln Val Ile Tyr Glu Lys
                165                 170                 175

Thr Tyr Cys Val Thr Gly Gln Leu Val Glu Gly Leu Cys Phe Ile Pro
            180                 185                 190

Thr His Thr Ile Ala Leu Thr Gln Pro Gly His Thr Tyr Asp Thr Met
        195                 200                 205

Thr Leu Pro Ile Thr Cys Phe Leu Val Ala Lys Lys Leu Gly Thr Gln
    210                 215                 220

Leu Lys Ile Ala Val Glu Leu Glu Lys Leu Ile Thr Ala Gly Gly Cys
225                 230                 235                 240

Thr Glu Asn Ser Phe Gln Gly Tyr Tyr Ile Cys Phe Leu Gly Lys His
                245                 250                 255

Ser Glu Pro Leu Phe Val Pro Met Met Asp Asp Tyr Arg Ser Ala Glu
            260                 265                 270

Leu Phe Thr Arg Met Val Leu Asn Pro Arg Gly Glu Asp His Asp Pro
        275                 280                 285

Asp Gln Asn Gly Gln Gly Leu Met Arg Ile Ala Gly Pro Ile Thr Ala
    290                 295                 300

Lys Val Pro Ser Thr Glu Thr Thr Glu Ala Met Gln Gly Ile Ala Phe
305                 310                 315                 320

Ala Gly Ala Pro Met Tyr Ser Ser Phe Ser Thr Leu Val Arg Lys Ala
                325                 330                 335

Asp Pro Asp Tyr Val Phe Ser Pro Gly Ile Ile Ala Glu Ser Asn His
            340                 345                 350

Ser Val Cys Asp Lys Lys Thr Ile Pro Leu Thr Trp Thr Gly Phe Leu
        355                 360                 365

Ala Val Ser Gly Glu Ile Glu Lys Ile Thr Gly Cys Thr Val Phe Cys
    370                 375                 380

Thr Leu Val Gly Pro Gly Ala Ser Cys Glu Ala Tyr Ser Glu Thr Gly
385                 390                 395                 400

Ile Phe Asn Ile Ser Ser Pro Thr Cys Leu Val Asn Lys Val Gln Lys
                405                 410                 415

Phe Arg Gly Ser Glu Gln Arg Ile Asn Phe Met Cys Gln Arg Val Asp
            420                 425                 430

Gln Asp Val Ile Val Tyr Cys Asn Gly Gln Lys Lys Val Ile Leu Thr
        435                 440                 445

Lys Thr Leu Val Ile Gly Gln Cys Ile Tyr Thr Phe Thr Ser Leu Phe
    450                 455                 460

Ser Leu Ile Pro Gly Val Ala His Ser Leu Ala Val Glu Leu Cys Val
465                 470                 475                 480

Pro Gly Leu His Gly Trp Ala Thr Thr Ala Leu Leu Ile Thr Phe Cys
                485                 490                 495

Phe Gly Trp Leu Leu Ile Pro Thr Ile Thr Met Ile Ile Leu Lys Ile
            500                 505                 510

Leu Arg Leu Leu Thr Phe Ser Cys Ser His Tyr Ser Thr Glu Ser Lys
        515                 520                 525

Phe Lys Ala Ile Leu Glu Arg Val Lys Val Glu Tyr Gln Lys Thr Met
    530                 535                 540

Gly Ser Met Val Cys Asp Val Cys His His Glu Cys Glu Thr Ala Lys
```

-continued

```
545                 550                 555                 560

Glu Leu Glu Thr His Lys Lys Ser Cys Pro Glu Gly Gln Cys Pro Tyr
                565                 570                 575

Cys Met Thr Met Thr Glu Ser Thr Glu Ser Ala Leu Gln Ala His Phe
            580                 585                 590

Ser Ile Cys Lys Leu Thr Asn Arg Phe Gln Glu Asn Leu Lys Lys Ser
        595                 600                 605

Leu Lys Arg Pro Glu Val Lys Gln Gly Cys Tyr Arg Thr Leu Gly Val
    610                 615                 620

Phe Arg Tyr Lys Ser Arg Cys Tyr Val Gly Leu Val Trp Gly Val Leu
625                 630                 635                 640

Leu Thr Thr Glu Leu Ile Val Trp Ala Ala Ser Ala Asp Thr Pro Leu
                645                 650                 655

Met Glu Ser Gly Trp Ser Asp Thr Ala His Gly Val Gly Ile Val Pro
            660                 665                 670

Met Lys Thr Asp Leu Glu Leu Asp Phe Ala Leu Ala Ser Ser Ser Ser
        675                 680                 685

Tyr Ser Tyr Arg Arg Lys Leu Val Asp Pro Ala Asn Lys Glu Glu Thr
    690                 695                 700

Leu Pro Phe His Phe Gln Leu Asp Lys Gln Val Val His Ala Glu Ile
705                 710                 715                 720

Gln Asn Leu Gly His Trp Met Asp Gly Thr Phe Asn Ile Lys Thr Ala
                725                 730                 735

Phe His Cys Tyr Gly Glu Cys Lys Lys Tyr Ala Tyr Pro Trp Gln Thr
            740                 745                 750

Ala Lys Cys Phe Phe Glu Lys Asp Tyr Gln Tyr Glu Thr Ser Trp Gly
        755                 760                 765

Cys Asn Pro Pro Asp Cys Pro Gly Val Gly Thr Gly Cys Thr Ala Cys
    770                 775                 780

Gly Val Tyr Leu Asp Lys Leu Arg Ser Val Gly Lys Ala Tyr Lys Ile
785                 790                 795                 800

Val Ser Leu Lys Phe Thr Arg Lys Val Cys Ile Gln Leu Gly Thr Glu
                805                 810                 815

Gln Thr Cys Lys His Ile Asp Val Asn Asp Cys Leu Val Thr Pro Ser
            820                 825                 830

Val Lys Val Cys Leu Ile Gly Thr Ile Ser Lys Leu Gln Pro Gly Asp
        835                 840                 845

Thr Leu Leu Phe Leu Gly Pro Leu Glu Gln Gly Gly Ile Ile Leu Lys
    850                 855                 860

Gln Trp Cys Thr Thr Ser Cys Val Phe Gly Asp Pro Gly Asp Ile Met
865                 870                 875                 880

Ser Thr Thr Thr Gly Met Lys Cys Pro Glu His Thr Gly Ser Phe Arg
                885                 890                 895

Lys Ile Cys Gly Phe Ala Thr Thr Pro Thr Cys Glu Tyr Gln Gly Asn
            900                 905                 910

Thr Ile Ser Gly Phe Gln Arg Met Met Ala Thr Arg Asp Ser Phe Gln
        915                 920                 925

Ser Phe Asn Val Thr Glu Pro His Ile Thr Ser Asn Arg Leu Glu Trp
    930                 935                 940

Ile Asp Pro Asp Ser Ser Ile Lys Asp His Ile Asn Met Val Leu Asn
945                 950                 955                 960

Arg Asp Val Ser Phe Gln Asp Leu Ser Asp Asn Pro Cys Lys Val Asp
                965                 970                 975
```

```
Leu His Thr Gln Ser Ile Asp Gly Ala Trp Gly Ser Gly Val Gly Phe
            980                 985                 990

Thr Leu Val Cys Thr Val Gly Leu  Thr Glu Cys Ala Asn  Phe Ile Thr
        995                 1000                1005

Ser Ile  Lys Ala Cys Asp Ser  Ala Met Cys Tyr Gly  Ala Thr Val
    1010                 1015                1020

Thr Asn  Leu Leu Arg Gly Ser  Asn Thr Val Lys Val  Val Gly Lys
    1025                 1030                1035

Gly Gly  His Ser Gly Ser Leu  Phe Lys Cys Cys His  Asp Thr Asp
    1040                 1045                1050

Cys Thr  Glu Glu Gly Leu Ala  Ala Ser Pro Pro His  Leu Asp Arg
    1055                 1060                1065

Val Thr  Gly Tyr Asn Gln Ile  Asp Ser Asp Lys Val  Tyr Asp Asp
    1070                 1075                1080

Gly Ala  Pro Pro Cys Thr Ile  Lys Cys Trp Phe Thr  Lys Ser Gly
    1085                 1090                1095

Glu Trp  Leu Leu Gly Ile Leu  Asn Gly Asn Trp Val  Val Val Ala
    1100                 1105                1110

Val Leu  Ile Val Ile Leu Ile  Leu Ser Ile Leu Leu  Phe Ser Phe
    1115                 1120                1125

Phe Cys  Pro Ile Arg Gly Arg  Lys Asn Lys Ser Asn
    1130                 1135                1140


<210> SEQ ID NO 21
<211> LENGTH: 1140
<212> TYPE: PRT
<213> ORGANISM: New York virus
<220> FEATURE:
<223> OTHER INFORMATION: strain Rhode Island-1

<400> SEQUENCE: 21

Met Val Gly Trp Val Cys Ile Phe Leu Val Val Leu Ala Thr Thr Thr
1               5                   10                  15

Ala Gly Leu Thr Arg Asn Leu Tyr Glu Leu Lys Ile Glu Cys Pro His
            20                  25                  30

Thr Val Gly Leu Gly Gln Gly Tyr Val Thr Gly Ser Val Glu Thr Thr
        35                  40                  45

Pro Ile Leu Leu Thr Gln Val Thr Asp Leu Lys Ile Glu Ser Ser Cys
    50                  55                  60

Asn Phe Asp Leu His Val Pro Ser Thr Ser Ile Gln Lys Tyr Asn Gln
65                  70                  75                  80

Val Glu Trp Ala Lys Lys Ser Ser Thr Thr Glu Ser Thr Ser Ala Gly
                85                  90                  95

Ala Thr Thr Phe Glu Ala Lys Thr Lys Glu Val Ser Leu Lys Gly Thr
            100                 105                 110

Cys Asn Ile Pro Val Thr Thr Phe Glu Ala Ala Tyr Lys Ser Arg Lys
        115                 120                 125

Thr Val Ile Cys Tyr Asp Leu Ala Cys Asn Gln Thr Tyr Cys Leu Pro
    130                 135                 140

Thr Val His Leu Ile Ala Pro Val Gln Thr Cys Met Ser Val Arg Ser
145                 150                 155                 160

Cys Met Ile Gly Leu Leu Ser Ser Arg Ile Gln Val Ile Tyr Glu Lys
                165                 170                 175

Thr Tyr Cys Val Thr Gly Gln Leu Val Glu Gly Leu Cys Phe Ile Pro
            180                 185                 190
```

-continued

```
Thr His Thr Ile Ala Leu Thr Gln Pro Gly His Thr Tyr Asp Thr Met
        195                 200                 205

Thr Leu Pro Ile Thr Cys Phe Leu Val Ala Lys Lys Leu Gly Thr Gln
    210                 215                 220

Leu Lys Ile Ala Val Glu Leu Glu Lys Leu Ile Thr Ala Ser Gly Cys
225                 230                 235                 240

Thr Glu Asn Ser Phe Gln Gly Tyr Tyr Ile Cys Phe Leu Gly Lys His
                245                 250                 255

Ser Glu Pro Leu Ser Val Pro Met Met Asp Asp Tyr Arg Ser Ala Glu
            260                 265                 270

Leu Phe Thr Arg Met Val Leu Asn Pro Arg Gly Glu Asp His Asp Pro
        275                 280                 285

Asp Gln Asn Gly Gln Gly Leu Met Arg Ile Ala Gly Pro Ile Thr Ala
    290                 295                 300

Lys Val Pro Ser Thr Glu Thr Thr Glu Thr Met Gln Gly Ile Ala Phe
305                 310                 315                 320

Ala Gly Ala Pro Thr Tyr Ser Ser Phe Ser Thr Leu Val Arg Lys Ala
                325                 330                 335

Asp Pro Asp Tyr Val Phe Ser Pro Gly Ile Ile Ala Glu Ser Asn His
            340                 345                 350

Ser Val Cys Asp Lys Lys Ala Ile Pro Leu Thr Trp Thr Gly Phe Leu
        355                 360                 365

Ala Val Ser Gly Glu Ile Glu Lys Ile Thr Gly Cys Thr Val Phe Cys
    370                 375                 380

Thr Leu Val Gly Pro Gly Ala Ser Cys Lys Ala Tyr Ser Glu Thr Gly
385                 390                 395                 400

Ile Phe Asn Ile Ser Ser Pro Thr Cys Leu Val Asn Lys Val Gln Lys
                405                 410                 415

Phe Arg Gly Ser Glu Gln Arg Ile Asn Phe Met Cys Gln Arg Val Asp
            420                 425                 430

Gln Asp Val Ile Val Tyr Cys Asn Gly Gln Lys Lys Val Ile Leu Thr
        435                 440                 445

Lys Thr Leu Ile Ile Gly Gln Cys Ile Tyr Thr Phe Thr Ser Leu Phe
    450                 455                 460

Ser Leu Ile Pro Gly Val Ala His Ser Leu Ala Val Glu Leu Cys Val
465                 470                 475                 480

Pro Gly Leu His Gly Trp Ala Thr Ala Ala Leu Leu Ile Thr Phe Cys
                485                 490                 495

Phe Gly Trp Leu Leu Ile Pro Thr Ile Thr Met Ile Ile Leu Lys Ile
            500                 505                 510

Leu Arg Leu Leu Thr Phe Ser Cys Ser His Tyr Ser Thr Glu Ser Lys
        515                 520                 525

Phe Lys Ala Ile Leu Glu Arg Val Lys Val Glu Tyr Gln Lys Thr Met
    530                 535                 540

Gly Ser Met Val Cys Asp Ala Cys His His Glu Cys Glu Thr Ala Lys
545                 550                 555                 560

Glu Leu Glu Thr His Lys Lys Ser Cys Pro Glu Gly Gln Cys Pro Tyr
                565                 570                 575

Cys Met Thr Met Thr Glu Ser Thr Glu Ser Ala Leu Leu Ala His Phe
            580                 585                 590

Ser Ile Cys Lys Leu Thr Asn Arg Phe Gln Glu Asn Leu Lys Lys Ser
        595                 600                 605
```

-continued

```
Leu Lys Arg Pro Glu Val Lys Gln Gly Arg Tyr Arg Thr Leu Gly Val
    610                 615                 620

Phe Arg Tyr Lys Ser Arg Cys Tyr Val Gly Leu Val Trp Gly Val Leu
625                 630                 635                 640

Leu Thr Thr Glu Leu Ile Val Trp Ala Ala Ser Ala Asp Thr Pro Leu
                645                 650                 655

Met Glu Ser Gly Trp Ser Asp Thr Ala His Gly Val Gly Ile Val Pro
            660                 665                 670

Met Lys Thr Asp Leu Glu Leu Asp Phe Ala Leu Ala Ser Ser Ser Ser
        675                 680                 685

Tyr Ser Tyr Arg Arg Lys Leu Val Asn Pro Ala Asn Lys Glu Glu Thr
    690                 695                 700

Leu Pro Phe His Phe Gln Leu Asp Lys Gln Val Val His Ala Glu Ile
705                 710                 715                 720

Gln Asn Leu Gly His Trp Met Asp Gly Thr Phe Asn Ile Lys Thr Ala
                725                 730                 735

Phe His Cys Tyr Gly Glu Cys Lys Lys Tyr Ala Tyr Pro Trp Gln Thr
            740                 745                 750

Ala Lys Cys Phe Phe Glu Lys Asp Tyr Gln Tyr Glu Thr Ser Trp Gly
        755                 760                 765

Cys Asn Pro Pro Asp Cys Pro Gly Val Gly Thr Gly Cys Thr Ala Cys
    770                 775                 780

Gly Val Tyr Leu Asp Lys Leu Arg Ser Gly Gly Lys Ala Tyr Lys Ile
785                 790                 795                 800

Val Ser Leu Lys Phe Thr Arg Lys Val Cys Ile Gln Leu Gly Thr Glu
                805                 810                 815

Gln Thr Cys Lys His Ile Asp Val Asn Asp Cys Leu Val Thr Pro Ser
            820                 825                 830

Val Lys Val Cys Leu Ile Gly Thr Ile Ser Lys Leu Gln Pro Gly Asp
        835                 840                 845

Thr Leu Leu Phe Leu Gly Pro Leu Glu Gln Gly Gly Ile Ile Leu Lys
    850                 855                 860

Gln Trp Cys Thr Thr Ser Cys Val Phe Gly Asp Pro Gly Asp Ile Met
865                 870                 875                 880

Ser Thr Thr Thr Gly Met Lys Cys Pro Glu His Thr Gly Ser Phe Arg
                885                 890                 895

Lys Ile Cys Gly Phe Ala Thr Thr Pro Thr Cys Glu Tyr Gln Gly Asn
            900                 905                 910

Thr Ile Ser Gly Phe Gln Arg Met Met Ala Thr Arg Asp Ser Phe Gln
        915                 920                 925

Ser Phe Asn Val Thr Glu Pro His Ile Thr Ser Asn Arg Leu Glu Trp
    930                 935                 940

Ile Asp Pro Asp Ser Ser Ile Lys Asp His Ile Asn Met Val Leu Asn
945                 950                 955                 960

Arg Asp Val Ser Phe Gln Asp Leu Ser Asp Asn Pro Cys Lys Val Asp
                965                 970                 975

Leu His Thr Gln Ser Ile Asp Gly Ala Trp Gly Ser Gly Val Gly Phe
            980                 985                 990

Thr Leu Val Cys Thr Val Gly Leu  Thr Glu Cys Ala Asn  Phe Ile Thr
        995                 1000                1005

Ser Ile  Lys Ala Cys Asp Ser  Ala Met Cys Tyr Gly  Ala Thr Val
    1010                1015                1020

Thr Asn  Leu Leu Arg Gly Ser  Asn Thr Val Lys Val  Val Gly Lys
```

```
    1025                1030                1035

Gly Gly  His Ser Ser Ser Leu  Phe Lys Cys Cys His  Asp Thr Asp
    1040                1045                1050

Cys Thr  Glu Glu Gly Leu Ala  Ala Ser Pro Pro His  Leu Asp Arg
    1055                1060                1065

Val Thr  Gly Tyr Asn Gln Ile  Asp Ser Asp Lys Val  Tyr Asp Asp
    1070                1075                1080

Gly Ala  Pro Pro Cys Thr Ile  Lys Cys Trp Phe Thr  Lys Ser Gly
    1085                1090                1095

Glu Trp  Leu Leu Gly Ile Leu  Asn Gly Asn Trp Val  Val Val Ala
    1100                1105                1110

Val Leu  Ile Val Ile Leu Ile  Leu Ser Ile Leu Leu  Phe Ser Phe
    1115                1120                1125

Phe Cys  Pro Ile Arg Gly Arg  Lys Asn Lys Ser Asn
    1130                1135                1140


<210> SEQ ID NO 22
<211> LENGTH: 3733
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22

gcggccgcgg atctgcagga attcggcacg agagtagtag actccgcacg aagaagcaaa     60

cactgaataa aggatataca gaatggtagg gtgggtttgc atcttcctcg tggtccttac    120

tactgcaact gctggattga cacggaatct ctatgaatta cagatagaat gtccacatac    180

tgtgggtcta ggtcaaggtt atgtgacagg ttctgtagaa actacaccta ttctcttaac    240

acaggtagct gacctcaaga ttgagagttc ttgcaatttt gacttgcatg tcccagccac    300

tactactcag aaatacaatc aagttgactg gactaaaaaa agttctacta cagaaagcac    360

gaatgcaggt gcaactacat ttgaggctaa aacaaaagag gtaaatttaa aaggcacatg    420

taatattcct ccaactacgt ttgaggctgc atacaagtca aggaagacag tgatttgtta    480

tgatttggcc tgtaatcaaa cacattgtct tcctacagtc catctgattg ctcctgttca    540

aacatgtatg tctgtacgga gctgtatgat aggtctgtta tctagcagga tccaggttat    600

ctacgagaag acatattgtg tcacgggtca gttaatagaa gggctatgtt tcattccaac    660

acatacaatt gcacttacac agcctggtca tacttatgat actatgacat tgcctgtgac    720

ttgtttttta gtagccaaaa agttggggac gcagcttaag ctggctgttg agttagagaa    780

attgattact ggtgtgagct gcgcagagaa tagcttccaa ggttattaca tctgttttat    840

tggaaaacat tcagagccct tatttgtacc aacaatggaa gattatagat cagctgagtt    900

atttactcgt atggttttaa atccaagagg tgaagatcat gaccctgatc aaaatggaca    960

agggttgatg agaatagctg gacctgttac tgccaaggta ccatctacag aaacgactga   1020

aacaatgcaa ggaattgcat ttgctggggc accaatgtat agttcattct caactcttgt   1080

gagaaaagct gatcctgaat atgtcttttc tccaggtata attgcagaat caaatcatag   1140

tgtttgtgat aaaaagacag tgcccctaac atggactggg tttctagcag tttcaggaga   1200

gatagaaagg ataacaggct gtacagtttt ctgtacattg gctggacctg gtgccagttg   1260

tgaagcatac tcagaaacag gaatcttcaa cataagctcc ccaacttgct tggtaaataa   1320

agtccaaaaa tttagaggtt cagaacaaag aattaatttt atgtgtcaaa gggttgatca   1380
```

-continued

```
aggtgttgtg gtttactgta atggacagaa gaaagtcatt cttaccaaaa ccctagtaat   1440
aggtcaatgt atctacacat ttactagtct gttttcactg atccctggag ttgctcattc   1500
ccttgctgtg gagttatgtg ttccaggtct tcatggctgg gctacaacag cactacttat   1560
tactttctgc tttggctggc ttctcatacc aacagttact ttaattatac taaaaatctt   1620
aaggctattg accttcccat gctcgcacta ttctacagaa tcaaaattca aagtcatttt   1680
agaaagagtc aaggtggagt atcaaaagac aatgggttca atggtgtgtg acatttgtca   1740
ccatgaatgt gagacggcaa aagagctcga aacacataag aaaagttgcc cagaaggtca   1800
atgcccatac tgcatgacaa taactgagtc cactgagagt gcattacaag ctcatttttc   1860
aatctgtaag ctaacgaaca ggttccagga aaatctaaaa aaatcattaa aacgtccaga   1920
agtaaggaaa ggttgttaca ggacattagg agtattccgc tacaagagca ggtgctatgt   1980
tggcttagta tgggggatcc tcttgacgac agagctgatt atatgggctg ctagtgcaga   2040
tacccctcta atggagtctg gttggtcaga tacagcacat ggtgtaggta tagtccctat   2100
gaaaacagat ttagagcttg actttgcctt ggcctcatca tcttcttata gttatagaag   2160
aaagcttgta aaccctgcca atcaagagga gacactccct tttcatttcc agttagataa   2220
gcaagtagtg catgcagaaa tacagaacct agggcattgg atggatggca cattcaacat   2280
aaagactgct ttccattgct atggagaatg taaaaaatat gcctatcctt ggcagacagc   2340
caagtgtttc tttgaaaaag attatcagta tgaaacaagc tggggctgta acccaccaga   2400
ttgcccagga gtagggacag gttgtacagc ctgtggggta tacttagaca agctccgttc   2460
agttgggaaa gcctataaaa ttgtatcact caaatacacg cgaaaggtgt gtattcaatt   2520
ggggacagaa caaacctgta aacatataga tgttaatgat tgtttggtca ccccgtctgt   2580
taaagtttgc atgataggta ccatctcgaa gcttcagcca ggtgacacct tattgttttt   2640
gggcccttta gagcaaggtg ggattattct aaaacaatgg tgcacaacat catgtgtgtt   2700
tggagaccct ggtgatatca tgtcaacaac aagtgggatg agatgccctg agcacacagg   2760
gtcttttaga aaaatctgtg gatttgctac aacacctaca tgtgaatatc aaggtaatac   2820
agtgtctgga ttccaacgca tgatggcaac tcgagattct tttcaatcat tcaatgtgac   2880
agaaccacat attaccagca atcgactgga atggattgat ccagatagta gtattaaaga   2940
ccatatcaac atggttttga atagagatgt ttccttccaa gatctaagtg ataatccatg   3000
taaggttgat ttgcatacac aatctattga tggggcttgg ggatcaggag tgggctttac   3060
attagtatgt actgtaggtc ttacagagtg tgcaaatttc ataacttcaa ttaaggcgtg   3120
tgattctgct atgtgttatg gggccacagt tacaaatcta ctcagagggt ctaacacagt   3180
taaagttgtc ggtaaaggtg ggcattctgg gtccttgttc aagtgctgcc atgatactga   3240
ctgtactgaa gaaggtttag cagcatcacc acctcattta gatagggtta ctggttacaa   3300
tcaaatagat tctgataagg tttatgatga cggtgcaccg ccctgtacaa ttaaatgttg   3360
gttcacaaag tcaggtgagt ggttgctagg aattcttaat ggcaattggg tagtagttgc   3420
tgttttgatt gtaattttga tactatcaat actcctgttc agcttctttt gtcctgttag   3480
aaatagaaaa aataaggcca attagcaaac atatatgtaa gtaagggtat gatcatatta   3540
tatcattatg cgtatactct tatatctata atatctatgt atccttatac tctaactatt   3600
tatattaatt tttactttta tacaagtatt aactaaccca ttaccagcta aaaaaaacaa   3660
```

-continued

```
acccttaaca cctatataat cccatttgct tattacgagg cttttgttcc tgcggagtct    3720

actactattc gaa                                                       3733
```